(12) United States Patent
Johannesson et al.

(10) Patent No.: US 7,994,179 B2
(45) Date of Patent: Aug. 9, 2011

(54) CARBAMOYL COMPOUNDS AS DGAT1 INHIBITORS 190

(75) Inventors: Petra Johannesson, Mölndal (SE); Jan Magnus Johansson, Mölndal (SE); Annika Ulrika Petersson, Mölndal (SE); Alan Martin Birch, Cheshire (GB); Roger John Butlin, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 12/339,349

(22) Filed: Dec. 19, 2008

(65) Prior Publication Data

US 2009/0298853 A1    Dec. 3, 2009

Related U.S. Application Data

(60) Provisional application No. 61/015,397, filed on Dec. 20, 2007.

(51) Int. Cl.
*A61K 31/4965* (2006.01)
(52) U.S. Cl. ................. 514/255.06; 544/406
(58) Field of Classification Search ............. 514/255.06; 544/406
See application file for complete search history.

(56) References Cited

U.S. PATENT DOCUMENTS

| | | |
|---|---|---|
| 3,245,989 A | 4/1966 | Palazzo |
| 4,983,731 A | 1/1991 | Wagner et al. |
| 5,491,172 A | 2/1996 | Lee et al. |
| 6,608,185 B1 | 8/2003 | Omura et al. |
| 6,624,185 B2 | 9/2003 | Glombik et al. |
| 7,138,414 B2 | 11/2006 | Schoenafinger et al. |
| 7,453,010 B2 | 11/2008 | Bovy et al. |
| 7,749,997 B2 | 7/2010 | Birch et al. |
| 7,795,283 B2 | 9/2010 | Birch et al. |
| 2002/0183384 A1 | 12/2002 | Cornicelli et al. |
| 2003/0072757 A1 | 4/2003 | Farese et al. |
| 2004/0102432 A1 | 5/2004 | Sanganee et al. |
| 2005/0070545 A1 | 3/2005 | Fox et al. |
| 2007/0123504 A1 | 5/2007 | Bolin et al. |
| 2007/0155832 A1 | 7/2007 | Haeberlein et al. |
| 2007/0249620 A1 | 10/2007 | Kurata et al. |
| 2008/0090876 A1 | 4/2008 | Cheng et al. |
| 2008/0096874 A1 | 4/2008 | Birch et al. |
| 2008/0306059 A1 | 12/2008 | Birch et al. |
| 2008/0312282 A1 | 12/2008 | Judd et al. |
| 2009/0048258 A1 | 2/2009 | Ogino et al. |
| 2009/0093497 A1 | 4/2009 | Bolin et al. |
| 2009/0197926 A1 | 8/2009 | Birch et al. |
| 2009/0209602 A1 | 8/2009 | Butlin et al. |
| 2009/0215779 A1 | 8/2009 | Butlin et al. |
| 2009/0275620 A1 | 11/2009 | Butlin et al. |
| 2010/0029727 A1 | 2/2010 | Johnstone et al. |
| 2010/0160397 A1 | 6/2010 | Birch et al. |
| 2010/0173958 A1 | 7/2010 | Bennett et al. |
| 2010/0184813 A1 | 7/2010 | Birch et al. |
| 2010/0311737 A1 | 12/2010 | Birch et al. |

FOREIGN PATENT DOCUMENTS

| | | |
|---|---|---|
| DE | 10223273 | 12/2003 |
| EP | 1236468 | 9/2002 |
| EP | 1541563 | 6/2005 |
| EP | 1661889 | 5/2006 |
| EP | 1760071 | 3/2007 |
| JP | 2002284741 | 3/2002 |
| JP | 2004/067635 | 3/2004 |
| JP | 2005/206492 | 8/2005 |
| JP | 2007/131584 | 5/2007 |
| JP | 2007/191471 | 8/2007 |
| JP | 2010132590 | 6/2010 |
| WO | WO 94/26702 | 11/1994 |
| WO | WO 00/58491 | 10/2000 |
| WO | WO 00/72832 | 12/2000 |
| WO | WO 02/20484 | 3/2002 |
| WO | WO 03/099772 | 12/2003 |
| WO | WO 2004/007455 | 1/2004 |
| WO | WO 2004/017920 | 3/2004 |
| WO | WO 2004/032882 | 4/2004 |

(Continued)

OTHER PUBLICATIONS

Jordan, V. C. Nature Reviews: Drug Discovery, 2, 2003, 205.*

(Continued)

*Primary Examiner* — James O Wilson
*Assistant Examiner* — Douglas M Willis
(74) *Attorney, Agent, or Firm* — Morgan Lewis & Bockius LLP

(57) ABSTRACT

DGAT-1 inhibitor compounds of formula (I), pharmaceutically-acceptable salts and pro-drugs thereof are described, together with pharmaceutical compositions, processes for making them and their use in treating, for example, obesity

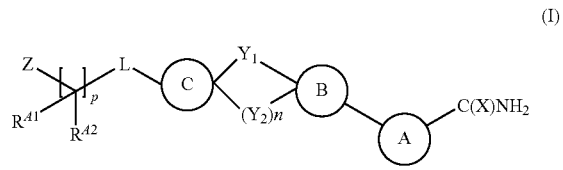

(I)

wherein, for example,
Ring A is optionally substituted 2,6-pyrazindiyl;
X is =O;
Ring B is optionally substituted 1,4-phenylene;
$Y_1$ is a direct bond or —O—;
$Y_2$ is —(CH$_2$)$_r$— wherein r is 2 or 3;
n is 0 or n is 1 when $Y_1$ is a direct bond between Ring B and Ring C and when Ring B is 1,4-phenylene and Ring C is (4-6C)cycloalkane;
Ring C is optionally substituted (4-6C)cycloalkane, (7-10C)bicycloalkane, (8-12C)tricycloalkane, phenylene or pryidindiyl;
L is a direct bond or —O—;
p is 0, 1 or 2 and when p is 1 or 2 $R^{41}$ and $R^{42}$ are each independently hydrogen or (1-4C)alkyl;
Z is carboxy or a mimic or bioisostere thereof.

10 Claims, No Drawings

FOREIGN PATENT DOCUMENTS

| | | |
|---|---|---|
| WO | WO 2004/047755 | 6/2004 |
| WO | WO 2004/062601 | 7/2004 |
| WO | WO 2004/089927 | 10/2004 |
| WO | WO 2004/100881 | 11/2004 |
| WO | WO 2004/110350 | 12/2004 |
| WO | WO 2005/013907 | 2/2005 |
| WO | WO 2005/027892 | 3/2005 |
| WO | WO 2005/037826 | 4/2005 |
| WO | WO 2005/044250 | 5/2005 |
| WO | WO 2005/046670 | 5/2005 |
| WO | WO 2005/072740 | 8/2005 |
| WO | WO 2006/004200 | 1/2006 |
| WO | WO 2006/019020 | 2/2006 |
| WO | WO 2006/044775 | 4/2006 |
| WO | WO 2006/054370 | 5/2006 |
| WO | WO 2006/064189 | 6/2006 |
| WO | WO 2006/082010 | 8/2006 |
| WO | WO 2006/082952 | 8/2006 |
| WO | WO 2006/113919 | 10/2006 |
| WO | WO 2006/120125 | 11/2006 |
| WO | WO 2006/134317 | 12/2006 |
| WO | WO 2007/007588 | 1/2007 |
| WO | WO 2007/016538 | 2/2007 |
| WO | WO 2007/060140 | 5/2007 |
| WO | WO 2007/071966 | 6/2007 |
| WO | WO 2007/074753 | 7/2007 |
| WO | WO 2007/124337 | 11/2007 |
| WO | WO 2007/126957 | 11/2007 |
| WO | WO 2007/137103 | 11/2007 |
| WO | WO 2007/137107 | 11/2007 |
| WO | WO 2007/138304 | 12/2007 |
| WO | WO 2007/138311 | 12/2007 |
| WO | WO 2007/141502 | 12/2007 |
| WO | WO 2007/141517 | 12/2007 |
| WO | WO 2007/141538 | 12/2007 |
| WO | WO 2007/141545 | 12/2007 |
| WO | WO 2007/144571 | 12/2007 |
| WO | WO 2008/011130 | 1/2008 |
| WO | WO 2008/011131 | 1/2008 |
| WO | WO 2008/039007 | 4/2008 |
| WO | WO 2008/039008 | 4/2008 |
| WO | WO 2008/040651 | 4/2008 |
| WO | WO 2008/046216 | 4/2008 |
| WO | WO 2008/048991 | 4/2008 |
| WO | WO 2008/058402 | 5/2008 |
| WO | WO 2008/067257 | 6/2008 |
| WO | WO 2008/073865 | 6/2008 |
| WO | WO 2008/099221 | 8/2008 |
| WO | WO 2008/129319 | 10/2008 |
| WO | WO 2008/134690 | 11/2008 |
| WO | WO 2008/134693 | 11/2008 |
| WO | WO 2008/141976 | 11/2008 |
| WO | WO 2008/148840 | 12/2008 |
| WO | WO 2008/148849 | 12/2008 |
| WO | WO 2008/148851 | 12/2008 |
| WO | WO 2008/148868 | 12/2008 |
| WO | WO 2008/154642 | 12/2008 |
| WO | WO 2009/009041 | 1/2009 |
| WO | WO 2009/011285 | 1/2009 |
| WO | WO 2009/016462 | 2/2009 |
| WO | WO 2009/024821 | 2/2009 |
| WO | WO 2009/037222 | 3/2009 |
| WO | WO 2009/040410 | 4/2009 |
| WO | WO 2009/071483 | 6/2009 |
| WO | WO 2009/081195 | 7/2009 |
| WO | WO 2009/112445 | 9/2009 |
| WO | WO 2009/119534 | 10/2009 |
| WO | WO 2009/126624 | 10/2009 |
| WO | WO 2009/126861 | 10/2009 |
| WO | WO 2009/137938 | 11/2009 |
| WO | WO 2010/007046 | 1/2010 |
| WO | WO 2010/017040 | 2/2010 |
| WO | WO 2010/023609 | 3/2010 |
| WO | WO 2010/048149 | 4/2010 |
| WO | WO 2010/056496 | 5/2010 |
| WO | WO 2010/056506 | 5/2010 |
| WO | WO 2010/059602 | 5/2010 |
| WO | WO 2010/059606 | 5/2010 |
| WO | WO 2010/059611 | 5/2010 |
| WO | WO 2010/065310 | 6/2010 |
| WO | WO 2010/070343 | 6/2010 |
| WO | WO 2010/077861 | 7/2010 |
| WO | WO 2010/083280 | 7/2010 |
| WO | WO 2010/084979 | 7/2010 |
| WO | WO 2010/86820 | 8/2010 |
| WO | WO 2010/089685 | 8/2010 |
| WO | WO 2010/089686 | 8/2010 |
| WO | WO 2010/091041 | 8/2010 |
| WO | WO 2010/095766 | 8/2010 |
| WO | WO 2010/107765 | 9/2010 |
| WO | WO 2010/107768 | 9/2010 |
| WO | WO 2010/108051 | 9/2010 |
| WO | WO 2010/122968 | 10/2010 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Adcock et al., "Electronic effect of the tricyanomethyl group by carbon-13 and fluorine-19 NMR: nature of aryl fluorine-19 NMR polar field effects in the benzene and naphthalene ring systems" Journal of Organic Chemistry 44 (17): 3004-3017 (1979).

Anderson et al. "Identification of a Form of Acyl-CoA:Cholesterol Acyltransferase Specific to Liver and Intestine in Nonhuman Primates" J Biol Chem 273(41):26747-26754 (1998).

Birch et al. "Discovery of a Potent, Selective, and Orally Efficacious Pyrimidinooxazinyl Bicyclooctaneacetic Acid Diacylglycerol Acyltransferase-1 Inhibitor" J. Med. Chem. 52(6):1558-1568 (2009).

Brown and Goldstein "Lipoprotein metabolism in the macrophage: implications for cholesterol deposition in atherosclerosis" Annu Rev Biochem. 52:223-261 (1983).

Burnett and Huff "Avasimibe Pfizer " Curr Opin Investig Drugs 3(9):1328-1333 (2002).

CAPLUS RN 404032-15-1, retrieved from CAPLUS on Jul. 17, 2009.

Cases et al. "ACAT-2, A Second Mammalian Acyl-CoA:Cholesterol Acyltransferase" J Biol Chem 273(41):26755-26764 (1998).

Cases et al. "Cloning of DGAT2, a Second Mammalian Diacylglycerol Acyltransferase, and Related Family Members" J. Biol. Chem. 276(42):38870-38876 (2001).

Cases et al. "Identification of a gene encoding an acyl CoA:diacylglycerol acyltransferase, a key enzyme in triacylglycerol synthesis" Proc Natl Acad Sci U S A. 95(22):13018-13023 (1998).

Chang et al. "Molecular cloning and functional expression of human acyl-coenzyme A:cholesterol acyltransferase cDNA in mutant Chinese hamster ovary cells" J. Biol. Chem. 268(28):20747-20755 (1993).

Chen et al. "Increased Insulin and Leptin Sensitivity in Mice Lacking ACYL COA: Diacylglycerol Acyltransferase 1" Journal of Clinical Investigation 109(8):1049-1055 (2002).

Chen et al. "Inhibition of Triglyceride Synthesis as a Treatment Strategy for Obesity: Lessons From DGAT1-Deficient Mice" Arteriosclerosis, Thrombosis, and Vascular Biology 25(3): 482-486 (2005).

Chen et al. "Obesity resistance and enhanced glucose metabolismin mice transplanted with white adipose tissue lacking acyl CoA:diacylglycerol acyltransferase 1" J. Clin. Invest. 111(11):1715-1722 (2003).

Coleman "Diacylglycerol acyltransferase and monoacylglycerol acyltransferase from liver and intestine" Methods in Enzymology 209:98-104 (1992).

Field and Salome "Effect of dietary fat saturation, cholesterol and cholestyramine on acyl-CoA: cholesterol acyltransferase activity in rabbit intestinal microsomes" Biochimica et Biophysica Acta 712(3):557-570 (1982).

Hoffman et al. "Synthesis and evaluation of 2-pyridinone derivatives as HIV-1-specific reverse transcriptase inhibitors. 4. 3-[2-(Benzoxazol-2-yl)ethyl]-5-ethyl-6-methylpyridin-2(1H)-one and analogs" Journal of Medicinal Chemistry 36(8):953-966 (1993).

Hubbard et al. "Antisense and small-molecule modulation of diacylglycerol acyltransferase" Expert Opinion on Therapeutic Patents 17(11): 1331-1339 (2007).

Insull Jr. et al. "Efficacy and short-term safety of a new ACAT inhibitor, avasimibe, on lipids, lipoproteins, and apolipoproteins, in patients with combined hyperlipidemia" Atherosclerosis 157(1):137-144 (2001).

Lehner and Kuksis "Biosynthesis of triacylglycerols" Prog Lipid Res. 35(2):169-201 (1996).

Oelkers et al. "Characterization of Two Human Genes Encoding Acyl Coenzyme A:Cholesterol Acyltransferase-related Enzymes" J Biol Chem 273(41):26765-26771 (1998).

Robertson et al. "Preclinical Safety Evaluation of Avasimibe in Beagle Dogs: An ACAT Inhibitor with Minimal Adrenal Effects" Toxicological Sciences 2001 US, 59(2):324-334 (2001).

Sawhney et al. "Synthesis of some 2-(5-substituted 1,3,4-oxadiazol-2-yl)-, 2-(5-substituted 1,3,4-thiadiazol-2-yl)- and 2-(3-mercapto-4-substituted-4H-1,2,4-triazol-5 -yl)- benzimidazoles as potential antiinflammatory agents" Indian Journal of Chemistry Section B, 30B:407-412 (1991).

Smith et al. "Obesity resistance and multiple mechanisms of triglyceride synthesis in mice lacking Dgat" Nature Genetics 25:87-90 (2000).

Yen et al. "Identification of a gene encoding MGAT1, a monoacylglycerol acyltransferase" Proc Natl Acad Sci U S A. 99(13):8512-8517 (2002).

Yen et al. "Thematic Review Series: Glycerolipids. DGAT enzymes and triacylglycerol biosynthesis" Journal of Lipid Research 49: 2283-2301 (2008).

Zammit et al. "Diacylglycerol acyltransferases: Potential roles as pharmacological targets" Pharmacology & Therapeutics 118(3):295-302 (2008).

Zhao et al. "Validation of diacyl glycerolacyltransferase I as a novel target for the treatment of obesity and dyslipidemia using a potent and selective small molecule inhibitor" J. Med. Chem. 51:380-383 (2008).

International Search Report and Written Opinion for PCT/GB2008/051199, dated Mar. 31, 2009.

W. Adcock et al., "Electronic Effect of the Tricyanomethyl Group by 13C and 19F NMR: Nature of Aryl 19F NMR Polar Field Effects in the Benzene and Naphthalene Ring Systems", J. Org. Chem. 44(17): 3004-3017 (1979).

A.M. Birch et al., "DGAT1 Inhibitors as anti-obesity and anti-diabetic agents", Curr. Opinion in Drug Discovery & Development 13(4): 489-496 (2010).

S. Birtles et at, "Pharmacological effect of DGAT1 inhibition on food intake and post-prandial-lipaemia-determination of the mechanism of action", Poster, Cheshire, UK, Mar. 24-26, 2010.

S. Birtles et al., "Pharmacological effect of DGAT1 inhibition on food intake and post-prandial lipaemia-determination of the mechanism of action", Abstract, Cheshire, UK, Mar. 24-26, 2010.

B.M. Fox et al., "Discovery of pyrrolopyridazines as novel DGAT1 inhibitors", Bioorg. Med. Chem. Lett, 20: 6030-6033 (2010).

W. Langhans et al., "Fatty acid oxidation in the energostatic control of eating—a new idea", Appetite 51: 446-451 (2008).

Y. Nakada at al., "Novel acyl coenzyme A (CoA): Diacylglycerol acyltransferase-1 inhibitors: Synthesis and biological activities of diacylethylenediamine derivatives", Bioorg, Med. Chem. 18: 2785-2795 (2010).

* cited by examiner

CARBAMOYL COMPOUNDS AS DGAT1 INHIBITORS 190

This application claims the benefit of U.S. Provisional Application No. 61/015,397, filed Dec. 20, 2007, which is herein incorporated by reference in its entirety.

The present invention relates to compounds which inhibit acetyl CoA(acetyl coenzyme A):diacylglycerol acyltransferase (DGAT1) activity, processes for their preparation, pharmaceutical compositions containing them as the active ingredient, methods for the treatment of disease states associated with DGAT1 activity, to their use as medicaments and to their use in the manufacture of medicaments for use in the inhibition of DGAT1 in warm-blooded animals such as humans. In particular this invention relates to compounds useful for the treatment of type II diabetes, insulin resistance, impaired glucose tolerance and obesity in warm-blooded animals such as humans, more particularly to the use of these compounds in the manufacture of medicaments for use in the treatment of type II diabetes, insulin resistance, impaired glucose tolerance and obesity in warm-blooded animals such as humans.

Acyl CoA:diacylglycerol acyltransferase (DGAT) is found in the microsomal fraction of cells. It catalyzes the final reaction in the glycerol phosphate pathway, considered to be the main pathway of triglyceride synthesis in cells by facilitating the joining of a diacylglycerol with a fatty acyl CoA, resulting in the formation of triglyceride. Although it is unclear whether DGAT is rate-limiting for triglyceride synthesis, it catalyzes the only step in the pathway that is committed to producing this type of molecule [Lehner & Kuksis (1996) Biosynthesis of triacylglycerols. Prog. Lipid Res. 35: 169-201].

Two DGAT genes have been cloned and characterised. Both of the encoded proteins catalyse the same reaction although they share no sequence homology. The DGAT1 gene was identified from sequence database searches because of its similarity to acyl CoA:cholesterol acyltransferase (ACAT) genes. [Cases et al (1998) Identification of a gene encoding an acyl CoA:diacylglycerol acyltransferase, a key enzyme in triacylglycerol synthesis. Proc. Natl. Acad. Sci. USA 95: 13018-13023]. DGAT1 activity has been found in many mammalian tissues, including adipocytes.

Because of the previous lack of molecular probes, little is known about the regulation of DGAT1. DGAT1 is known to be significantly up-regulated during adipocyte differentiation.

Studies in gene knockout mice has indicated that modulators of the activity of DGAT1 would be of value in the treatment of type II diabetes and obesity. DGAT1 knockout (Dgat1$^{-/-}$) mice, are viable and capable of synthesizing triglycerides, as evidenced by normal fasting serum triglyceride levels and normal adipose tissue composition. Dgat1$^{-/-}$ mice have less adipose tissue than wild-type mice at baseline and are resistant to diet-induced obesity. Metabolic rate is ~20% higher in Dgat1$^{-/-}$ mice than in wild-type mice on both regular and high-fat diets [Smith et al (2000) Obesity resistance and multiple mechanisms of triglyceride synthesis in mice lacking DGAT. Nature Genetics 25: 87-90]. Increased physical activity in Dgat1$^{-/-}$ mice partially accounts for their increased energy expenditure. The Dgat1$^{-/-}$ mice also exhibit increased insulin sensitivity and a 20% increase in glucose disposal rate. Leptin levels are 50% decreased in the Dgat1$^{-/-}$ mice in line with the 50% decrease in fat mass.

When Dgat1$^{-/-}$ mice are crossed with ob/ob mice, these mice exhibit the ob/ob phenotype [Chen et al (2002) Increased insulin and leptin sensitivity in mice lacking acyl CoA:diacylglycerol acyltransferase J. Clin. Invest. 109:1049-1055] indicating that the Dgat1$^{-/-}$ phenotype requires an intact leptin pathway. When Dgat1$^{-/-}$ mice are crossed with Agouti mice a decrease in body weight is seen with normal glucose levels and 70% reduced insulin levels compared to wild type, agouti or ob/ob/Dgat1$^{-/-}$ mice.

Transplantation of adipose tissue from Dgat1$^{-/-}$ mice to wild type mice confers resistance to diet-induced obesity and improved glucose metabolism in these mice [Chen et al (2003) Obesity resistance and enhanced glucose metabolism in mice transplanted with white adipose tissue lacking acyl CoA:diacylglycerol acyltransferase J. Clin. Invest. 111: 1715-1722].

International Application WO 2006/064189 describes certain oxadiazole compounds which inhibit DGAT-1. However, there remains a need for further DGAT-1 inhibitors possessing desirable properties, such as, for example, pharmacokinetic/dynamic and/or physico-chemical and/or toxicological profiles.

Accordingly, the present invention provides a compound of formula (I), or a pharmaceutically-acceptable salt, or prodrug thereof,

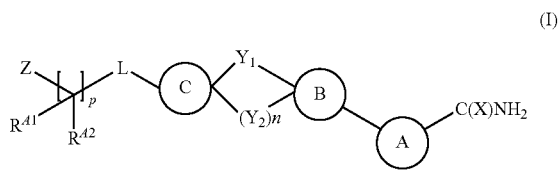

(I)

wherein
Ring A is 2,6-pyrazindiyl, 3,5-pyridindiyl or 2,6-pyridindiyl, each optionally substituted on an available carbon atom by one or two substituents independently selected from linear (1-3C)alkyl, (2-3C)alkenyl, (2-3C)alkynyl, (1-2C)alkoxy, methoxymethyl, amino and cyano;
X is =O or =S;
Ring B is 1,4-phenylene or Ring B is a di-linked (excluding links via the same or adjacent atoms) ring selected from pyridindiyl, furandiyl, thiophendiyl, pyrroldiyl, oxazoldiyl, thiazoldiyl, imidazoldiyl, isoxazoldiyl, isothiazoldiyl and pyrazoldiyl; each optionally substituted on an available carbon atom by one or two substituents independently selected from halo, amino, cyano, (1-4C)alkyl, (2-3C)alkenyl, (2-3C)alkynyl, (1-4C)alkoxy and (1-4C)alkoxy-(1-4C)alkyl;
$Y_1$ is a direct bond between Ring B and Ring C or $Y_1$ is —O—, —S— or —NRa— wherein Ra is hydrogen or (1-4C)alkyl;
$Y_2$ is —(CH$_2$)$_r$— wherein r is 2 or 3, and $Y_2$ is linked at the same carbon atom as $Y_1$ in Ring C and $Y_2$ is linked at an adjacent carbon atom to $Y_1$ in Ring B;
n is 0 or n is 1 when $Y_1$ is a direct bond between Ring B and Ring C and when Ring B is 1,4-phenylene and Ring C is (4-6C)cycloalkane, so that a 5- or 6-membered spiro-ring system is formed and Ring C is tri-linked;
Ring C is a di-linked (excluding links via the same or adjacent atoms) ring or ring system chosen from (4-6C)cycloalkane, (7-10C)bicycloalkane and (8-12C)tricycloalkane each optionally substituted on an available carbon atom, including the ring carbon atom bearing the Z-containing group, by one substituent selected from hydroxy, (1-4C)alkyl, (1-4C)alkoxy and (1-4C)alkoxy(1-4C)alkyl;
or Ring C is a di-linked (excluding links via the same or adjacent atoms) ring selected from phenylene, pryidindiyl, piperidinediyl N-linked to $Y_1$, piperazinediyl, furandiyl, thiophendiyl, pyrroldiyl, oxazoldiyl, thiazoldiyl, imidazoldiyl, isoxazoldiyl, isothiazoldiyl, pyrazoldiyl and azabicyclo[3.1.0]hexanediyl;

each optionally substituted on an available carbon atom by up to four substituents independently selected from fluoro, chloro, bromo, cyano, (1-4C)alkyl, (1-4C)alkoxy and (1-4C)alkoxy(1-4C)alkyl;

L is a direct bond to Ring C, —O—, —S— or —NH—;

p is 0 (when L is a direct bond), 1 or 2 and when p is 1 or 2 $R^{41}$ and $R^{42}$ are each independently hydrogen or (1-4C)alkyl or $R^{41}$ and $R^{42}$ are linked together to form a (3-6C)spiroalkyl ring;

Z is carboxy or a mimic or bioisostere thereof, hydroxy or —CONRbRc wherein Rb and Rc are independently selected from hydrogen and (1-4C)alkyl, which (1-4C)alkyl group may be optionally substituted by carboxy or a mimic or bioisostere thereof;

and wherein any carbon atom in a linear (1-3C)alkyl, (1-2C)alkoxy, (1-4C)alkyl or (1-4C)alkoxy containing group defined above may be optionally substituted by up to 3 fluoro atoms; with the proviso that the compound (4-(4-(6-Carbamoyl-pyridin-2-yl)phenyl)cyclohexyl)acetic acid is excluded.

In one embodiment there is provided a compound of formula (I), or a pharmaceutically-acceptable salt, or pro-drug thereof,

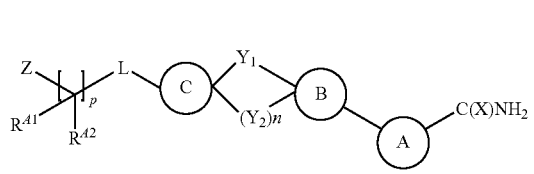

(I)

wherein

Ring A is 2,6-pyrazindiyl, 3,5-pyridindiyl or 2,6-pyridindiyl, each optionally substituted on an available carbon atom by one or two substituents independently selected from linear (1-3C)alkyl, (2-3C)alkenyl, (2-3C)alkynyl, (1-2C)alkoxy, methoxymethyl, amino and cyano;

X is =O or =S;

Ring B is 1,4-phenylene or Ring B is a di-linked (excluding links via the same or adjacent atoms) ring selected from pyridindiyl, furandiyl, thiophendiyl, pyrroldiyl, oxazoldiyl, thiazoldiyl, imidazoldiyl, isoxazoldiyl, isothiazoldiyl and pyrazoldiyl; each optionally substituted on an available carbon atom by one or two substituents independently selected from halo, amino, cyano, (1-4C)alkyl, (2-3C)alkenyl, (2-3C)alkynyl, (1-4C)alkoxy and (1-4C)alkoxy-(1-4C)alkyl;

$Y_1$ is a direct bond between Ring B and Ring C or $Y_1$ is —O—, —S— or —NRa— wherein Ra is hydrogen or (1-4C)alkyl;

$Y_2$ is —(CH$_2$)$_r$— wherein r is 2 or 3, and $Y_2$ is linked at the same carbon atom as $Y_1$ in Ring C and $Y_2$ is linked at an adjacent carbon atom to $Y_1$ in Ring B;

n is 0 or n is 1 when $Y_1$ is a direct bond between Ring B and Ring C and when Ring B is 1,4-phenylene and Ring C is (4-6C)cycloalkane, so that a 5- or 6-membered spiro-ring system is formed;

Ring C is a di-linked (excluding links via the same or adjacent atoms) ring or ring system chosen from (4-6C)cycloalkane, (7-10C)bicycloalkane and (8-12C)tricycloalkane each optionally substituted on an available carbon atom, including the ring carbon atom bearing the Z-containing group, by one substituent selected from hydroxy, (1-4C)alkyl, (1-4C)alkoxy and (1-4C)alkoxy(1-4C)alkyl;

or Ring C is a di-linked (excluding links via the same or adjacent atoms) ring selected from phenylene, pryidindiyl, piperidinediyl N-linked to $Y_1$, furandiyl, thiophendiyl, pyrroldiyl, oxazoldiyl, thiazoldiyl, imidazoldiyl, isoxazoldiyl, isothiazoldiyl and pyrazoldiyl; each optionally substituted on an available carbon atom by up to four substituents independently selected from fluoro, chloro, bromo, cyano, (1-4C)alkyl, (1-4C)alkoxy and (1-4C)alkoxy(1-4C)alkyl;

L is a direct bond to Ring C, —O—, —S— or —NH—;

p is 0, 1 or 2 and when p is 1 $R^{41}$ and $R^{42}$ are each independently hydrogen or (1-4C)alkyl or $R^{41}$ and $R^{42}$ are linked together to form a (3-6C)spiroalkyl ring;

Z is carboxy or a mimic or bioisostere thereof, hydroxy or —CONRbRc wherein Rb and Rc are independently selected from hydrogen and (1-4C)alkyl, which (1-4C)alkyl group may be optionally substituted by carboxy or a mimic or bioisostere thereof;

and wherein any carbon atom in a linear (1-3C)alkyl, (1-2C)alkoxy, (1-4C)alkyl or (1-4C)alkoxy containing group defined above may be optionally substituted by up to 3 fluoro atoms.

In a further embodiment there is provided a compound of formula (I), or a pharmaceutically-acceptable salt, or pro-drug thereof, as in any embodiment hereinbefore or hereinafter, with the proviso that the compound (4-(4-(6-carbamoyl-pyridin-2-yl)phenyl)cyclohexyl)acetic acid is excluded.

A further feature is any of the above three embodiments with the proviso that any of the specific Examples herein are individually disclaimed. For example, a further feature is any of the above embodiments with the proviso that any of the compounds selected from the following are individually disclaimed, {trans-4-[4-(6-Carbamoyl-3,5-dimethylpyrazin-2-yl)phenyl]cyclohexyl}acetic acid;

3,5-Dimethyl-6-[4-(trans-4-{2-[(methylsulfonyl)amino]-2-oxoethyl}cyclohexyl)-phenyl]pyrazine-2-carboxamide;

6-{4-[trans-4-(2-Amino-2-oxoethyl)cyclohexyl]phenyl}-3,5-dimethylpyrazine-2-carboxamide;

N-({trans-4-[4-(6-Carbamoyl-3,5-dimethylpyrazin-2-yl)phenyl]cyclohexyl}acetyl)-2-methylalanine;

6-{4-[trans-4-(2-Hydroxyethyl)cyclohexyl]phenyl}-3,5-dimethylpyrazine-2-carboxamide; (trans-4-{4-[6-Carbamoyl-5-(difluoromethyl)-3-methylpyrazin-2-yl]phenyl}cyclohexyl)acetic acid;

{trans-4-[4-(6-Carbamoyl-3-ethyl-5-methylpyrazin-2-yl)phenyl]cyclohexyl}acetic acid;

{trans-4-[4-(6-Carbamoyl-5-ethyl-3-methylpyrazin-2-yl)phenyl]cyclohexyl}acetic acid and {trans-4-[4-(6-Carbamoyl-3-methylpyrazin-2-yl)phenyl]cyclohexyl}acetic acid; or a pharmaceutically-acceptable salt of any of these.

It will be understood that Ring B and Ring C as a di-linked ring or ring system excludes links to $Y_1$ and L via the same or adjacent atoms (i.e. −1,1- and −1,2-links are excluded).

It will be understood that Ring B is numbered clockwise towards Ring C from the dominant heteroatom in Ring B.

When p is 0 the group Z is connected directly to direct bond L (i.e. Z is connected directly to Ring C and L is not —O—, —S— or —NH—); when p is 2 the group Z is connected as follows to L;

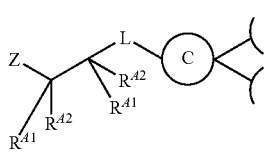

As used herein, the reference to carboxylic acid mimic or bioisostere includes groups as defined in The Practice of Medicinal Chemistry, Wermuth C. G. Ed.: Academic Press: New York, 1996, p 203. Particular examples of such groups include —SO$_3$H, —S(O)$_2$NHR$^{13}$, S(O)$_2$NHC(O)R$^{13}$, —CH$_2$S(O)$_2$R$^{13}$, —C(O)NHS(O)$_2$R$^{13}$, —C(O)NHOH, —C(O)NHCN, —CH(CF$_3$)OH, C(CF$_3$)$_2$OH, —P(O)(OH)$_2$ and groups of sub-formula (a)-(i') below

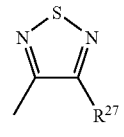 (a)

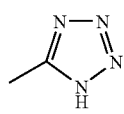 (b)

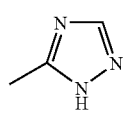 (c)

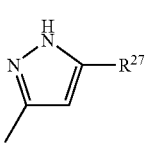 (d)

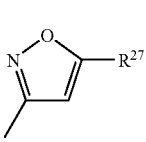 (e)

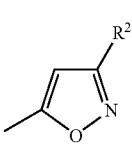 (f)

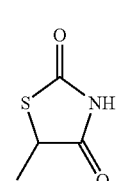 (g)

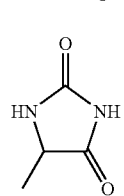 (h)

-continued

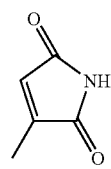 (i)

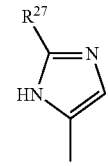 (j)

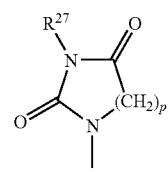 (k)

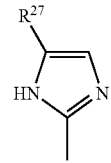 (l)

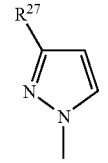 (m)

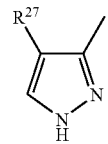 (n)

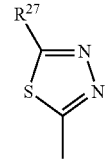 (o)

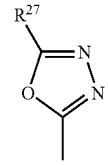 (p)

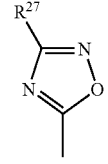 (q)

-continued
(r) 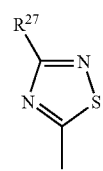
(s) 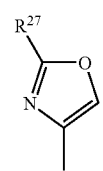
(t) 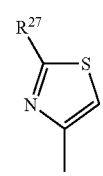
(u) 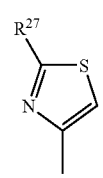
(v) 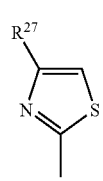
(w) 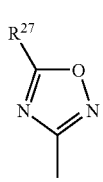
(x) 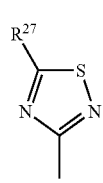
(y) 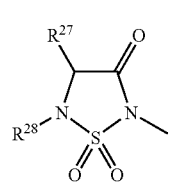
(z) 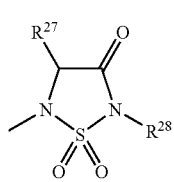
-continued
(a') 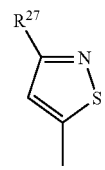
(b') 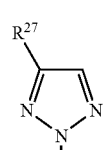
(c') 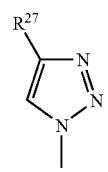
(d') 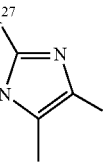
(e') 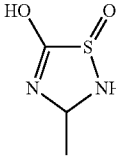
(f') 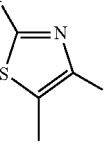
(g') 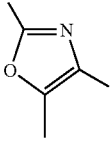
(h') 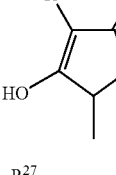
(i') 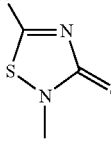
where p in sub-formula (k) is 1 or 2, $R^{27}$ and $R^{28}$ are independently selected from hydrogen, hydroxy, (1-6C)alkoxy, thiol, (1-6C)alkylthio, —C(O)$R^{29}$, —S(O)$R^{30}$, —SO$_2 R^{31}$, —$NR^{32}R^{33}$, —NHCN, halogen and trihalomethyl, where $R^{29}$, $R^{30}$ and $R^{31}$ are —$OR^{34}$, (1-6C)alkyl, —$NR^{32}R^{33}$ or trihalomethyl, $R^{32}$ and $R^{33}$ are independently selected from hydrogen, (1-6C)alkyl, —$SO_2R^{34}$ and —$COR^{35}$, where $R^{35}$ is (1-6C)alkyl or trihalomethyl, and $R^{34}$ is hydrogen, (1-6C) alkyl or trihalomethyl and $R^{13}$ is selected from hydrogen, (1-6C)alkyl, hydroxy, halo, amino, cyano, ((1-3C)alkyl) CONH—, carboxy, (1-6C)alkoxy, (1-6C)alkoxycarbonyl, carbamoyl, N-((1-6C)alkyl)carbamoyl, halo((1-6C)alkyl) (such as trifluoromethyl), (1-6C)alkylsulphonyl or (1-6C) alkylsulphinyl. Particular examples of $R^{27}$ or $R^{28}$ are hydroxy.

Particular carboxylic acid mimic or bioisosteres are a tetrazole group of sub-formula (b) and —C(O)NHS(O)$_2$Me.

In this specification the term "alkyl" includes both straight and branched chain alkyl groups, unless otherwise stated, and references to individual alkyl groups such as "propyl" are specific for the straight chain version only. An analogous convention applies to other generic terms. Unless otherwise stated the term "alkyl" advantageously refers to chains with 1-10 carbon atoms, suitably from 1-6 carbon atoms, preferably 1-4 carbon atoms.

In this specification the term "alkoxy" means an alkyl group as defined hereinbefore linked to an oxygen atom.

Particular values include for linear (1-3C)alkyl, methyl, ethyl and propyl; for (1-4C)alkyl, methyl, ethyl, propyl and butyl; for (2-3C)alkenyl, ethenyl; for (2-3C)alkynyl, ethynyl; for (1-2C)alkoxy, methoxy and ethoxy; for (1-4C)alkoxy, methoxy, ethoxy and propoxy; for —CONRbRc, —CONH$_2$ and —CONHMe.

Particular values include for any carbon atom in a linear (1-3C)alkyl, (1-2C)alkoxy, (1-4C)alkyl or (1-4C)alkoxy group that may be optionally substituted by up to 3 fluoro atoms, a group such as, for example, trifluoromethyl, difluoromethyl, difluoromethoxy or trifluoromethoxy.

When p in formula (I) is 1 and $R^{41}$ and $R^{42}$ are linked together to form a (3-6C)spiroalkyl ring, such a ring may be, for example, a spiro-linked cyclopropyl or cyclobutyl.

When p in formula (I) is 2 and $R^{41}$ and $R^{42}$ are linked together to form a (3-6C)spiroalkyl ring, such a ring may be, for example, a spiro-linked cyclopropyl or cyclobutyl.

When Ring C is a di-linked (excluding links via the same or adjacent atoms) (4-6C)cycloalkane ring this includes 1,4-cyclohexane, 1,3-cyclopentane and 1,3-cyclobutane.

When Ring C is (7-10C)bicycloalkanediyl this includes bicyclo[2.2.1]heptanediyl, 1,4-bicyclo[2.2.2]octanediyl, 1,5-bicyclo[3.2.1]octanediyl, 1,5-bicyclo[3.2.2]nonanediyl and 1,5-bicyclo[3.3.2]decanediyl.

When Ring C is (8-12C)tricycloalkanediyl this includes adamantanediyl.

For the avoidance of doubt it is to be understood that where in this specification a group is qualified by 'hereinbefore defined' or 'defined hereinbefore' the said group encompasses the first occurring and broadest definition as well as each and all of the particular definitions for that group.

If not stated elsewhere, suitable optional substituents for a particular group are those as stated for similar groups herein.

A compound of formula (I) may form stable acid or basic salts, and in such cases administration of a compound as a salt may be appropriate, and pharmaceutically acceptable salts may be made by conventional methods such as those described following.

Suitable pharmaceutically-acceptable salts include acid addition salts such as methanesulfonate, tosylate, α-glycerophosphate, fumarate, hydrochloride, citrate, maleate, tartrate and (less preferably) hydrobromide. Also suitable are salts formed with phosphoric and sulfuric acid. In another aspect suitable salts are base salts such as Group (I) (alkali metal) salt, Group (II) (alkaline earth) metal salt, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions.

Other suitable pharmaceutically-acceptable salts are mentioned in, for example, Berge et al. (J. Pharm. Sci., 1977, 66, 1-19) and/or Handbook of Pharmaceutical Salts: Properties, Selection and Use by Stahl and Wermuth (Wiley-VCH, 2002).

A feature of the invention relates to a compound of the invention, such as any one of the Examples, in the free acid or free base form or as a pharmaceutically acceptable salt thereof. Such forms may be prepared by standard techniques.

However, to facilitate isolation of the salt during preparation, salts which are less soluble in the chosen solvent may be preferred whether pharmaceutically-acceptable or not.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which inhibits DGAT1 activity and is not to be limited merely to any one tautomeric form utilised within the formulae drawings.

Pro-drugs of compounds of formula (I), and salts thereof, are also within the scope of the invention.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

Examples of such prodrugs are in vivo cleavable esters of a compound of the invention. An in vivo cleavable ester of a compound of the invention containing a carboxy group is, for example, a pharmaceutically-acceptable ester which is cleaved in the human or animal body to produce the parent acid. Suitable pharmaceutically-acceptable esters for carboxy include (1-6C)alkyl esters, for example methyl or ethyl; (1-6C)alkoxymethyl esters, for example methoxymethyl; (1-6C)alkanoyloxymethyl esters, for example pivaloyloxymethyl; phthalidyl esters; (3-8C)cycloalkoxycarbonyloxy(1-6C)alkyl esters, for example 1-cyclohexylcarbonyloxyethyl; 1,3-dioxolan-2-ylmethyl esters, for example 5-methyl-1,3-dioxolan-2-ylmethyl; (1-6C)alkoxycarbonyloxyethyl esters, for example 1-methoxycarbonyloxyethyl; aminocarbonylmethyl esters and mono- or di-N-((1-6C)alkyl) versions thereof, for example N,N-dimethylaminocarbonylmethyl esters and N-ethylaminocarbonylmethyl esters; and may be formed at any carboxy group in the compounds of this invention. An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include (1-6C)alkanoyl esters, for example acetyl esters; and benzoyl esters wherein the phenyl group may be substituted with aminomethyl or N-substituted mono- or di-(1-6C)alkyl aminomethyl, for example 4-aminomethylbenzoyl esters and 4-N,N-dimethylaminomethylbenzoyl esters.

Particular prodrugs are (1-4C)alkyl esters of the carboxylic acid in compounds of formula (I), (IA) and/or (IB).

It will be appreciated by those skilled in the art that certain compounds of formula (I) contain asymmetrically substituted carbon and/or sulfur atoms, and accordingly may exist in, and be isolated in, optically-active and racemic forms. Some compounds of formula (I) may exhibit polymorphism. It is to be understood that the present invention encompasses any racemic, optically-active, polymorphic or stereoisomeric form, or mixtures thereof, which form possesses properties useful in the inhibition of DGAT1 activity, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy for the inhibition of DGAT1 activity by the standard tests described hereinafter.

It is also to be understood that certain compounds of the formula (I) and salts thereof can exist in solvated as well as unsolvated forms such as, for example, hydrated forms. It is to be understood that the invention encompasses all such solvated forms which inhibit DGAT1 activity.

As stated before, a range of compounds are provided that have good DGAT1 inhibitory activity. They have good physical and/or pharmacokinetic properties in general.

Thus, in one embodiment there is provided a compound of formula (I), or a pharmaceutically-acceptable salt thereof,

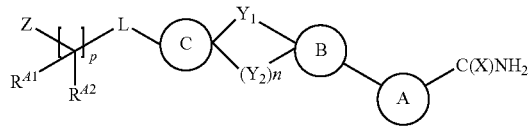

(I)

wherein
Ring A is 2,6-pyrazindiyl, 3,5-pyridindiyl or 2,6-pyridindiyl, each optionally substituted on an available carbon atom by one or two substituents independently selected from linear (1-3C)alkyl, (2-3C)alkenyl, (2-3C)alkynyl, (1-2C)alkoxy, methoxymethyl, amino and cyano;
X is =O or =S;
Ring B is 1,4-phenylene or Ring B is a di-linked (excluding links via the same or adjacent atoms) ring selected from pyridindiyl, furandiyl, thiophendiyl, pyrroldiyl, oxazoldiyl, thiazoldiyl, imidazoldiyl, isoxazoldiyl, isothiazoldiyl and pyrazoldiyl; each optionally substituted on an available carbon atom by one or two substituents independently selected from halo, amino, cyano, (1-4C)alkyl, (2-3C)alkenyl, (2-3C)alkynyl, (1-4C)alkoxy and (1-4C)alkoxy-(1-4C)alkyl;
$Y_1$ is a direct bond between Ring B and Ring C or $Y_1$ is —O—, —S— or —NRa— wherein Ra is hydrogen or (1-4C)alkyl;
$Y_2$ is —(CH$_2$)$_r$— wherein r is 2 or 3, and $Y_2$ is linked at the same carbon atom as $Y_1$ in Ring C and $Y_2$ is linked at an adjacent carbon atom to $Y_1$ in Ring B;
n is 0 or n is 1 when $Y_1$ is a direct bond between Ring B and Ring C and when Ring B is 1,4-phenylene and Ring C is (4-6C)cycloalkane, so that a 5- or 6-membered spiro-ring system is formed and Ring C is tri-linked;
Ring C is a di-linked (excluding links via the same or adjacent atoms) ring or ring system chosen from (4-6C)cycloalkane, (7-10C)bicycloalkane and (8-12C)tricycloalkane each optionally substituted on an available carbon atom, including the ring carbon atom bearing the Z-containing group, by one substituent selected from hydroxy, (1-4C)alkyl, (1-4C)alkoxy and (1-4C)alkoxy(1-4C)alkyl;
or Ring C is a di-linked (excluding links via the same or adjacent atoms) ring selected from phenylene, pryidindiyl, piperidinediyl N-linked to $Y_1$, piperazinediyl, furandiyl, thiophendiyl, pyrroldiyl, oxazoldiyl, thiazoldiyl, imidazoldiyl, isoxazoldiyl, isothiazoldiyl, pyrazoldiyl and azabicyclo[3.1.0]hexanediyl;
each optionally substituted on an available carbon atom by up to four substituents independently selected from fluoro, chloro, bromo, cyano, (1-4C)alkyl, (1-4C)alkoxy and (1-4C)alkoxy(1-4C)alkyl;
L is a direct bond to Ring C, —O—, —S— or —NH—;
p is 0, 1 or 2 and when p is 1 $R^{A1}$ and $R^{A2}$ are each independently hydrogen or (1-4C)alkyl or $R^{A1}$ and $R^{A2}$ are linked together to form a (3-6C)spiroalkyl ring;
Z is carboxy or a mimic or bioisostere thereof, hydroxy or —CONRbRc wherein Rb and Rc are independently selected from hydrogen and (1-4C)alkyl, which (1-4C)alkyl group may be optionally substituted by carboxy or a mimic or bioisostere thereof;
and wherein any carbon atom in a linear (1-3C)alkyl, (1-2C)alkoxy, (1-4C)alkyl or (1-4C)alkoxy containing group defined above may be optionally substituted by up to 3 fluoro atoms; with the proviso that the compound (4-(4-(6-Carbamoyl-pyridin-2-yl)phenyl)cyclohexyl)acetic acid is excluded.

In another embodiment there is provided a compound of formula (I), or a pharmaceutically-acceptable salt, or prodrug thereof wherein
Ring A is 2,6-pyrazindiyl, 3,5-pyridindiyl or 2,6-pyridindiyl, each optionally substituted on an available carbon atom by one or two substituents independently selected from linear (1-3C)alkyl, (2-3C)alkenyl, (2-3C)alkynyl, (1-2C)alkoxy, methoxymethyl, amino and cyano;
X is =O or =S;
Ring B is 1,4-phenylene or Ring B is a di-linked (excluding links via the same or adjacent atoms) ring selected from pyridindiyl, furandiyl, thiophendiyl, pyrroldiyl, oxazoldiyl, thiazoldiyl, imidazoldiyl, isoxazoldiyl, isothiazoldiyl and pyrazoldiyl; each optionally substituted on an available carbon atom by one or two substituents independently selected from halo, amino, cyano, (1-4C)alkyl, (2-3C)alkenyl, (2-3C)alkynyl, (1-4C)alkoxy and (1-4C)alkoxy-(1-4C)alkyl;
$Y_1$ is a direct bond between Ring B and Ring C or $Y_1$ is —O—, —S— or —NRa— wherein Ra is hydrogen or (1-4C)alkyl;
$Y_2$ is —(CH$_2$)$_r$— wherein r is 2 or 3, and $Y_2$ is linked at the same carbon atom as $Y_1$ in Ring C and $Y_2$ is linked at an adjacent carbon atom to $Y_1$ in Ring B;
n is 0 or n is 1 when $Y_1$ is a direct bond between Ring B and Ring C and when Ring B is 1,4-phenylene and Ring C is (4-6C)cycloalkane, so that a 5- or 6-membered spiro-ring system is formed;
Ring C is a di-linked (excluding links via the same or adjacent atoms) ring or ring system chosen from (4-6C)cycloalkane, (7-10C)bicycloalkane and (8-12C)tricycloalkane each optionally substituted on an available carbon atom, including the ring carbon atom bearing the Z-containing group, by one substituent selected from hydroxy, (1-4C)alkyl, (1-4C)alkoxy and (1-4C)alkoxy(1-4C)alkyl;

or Ring C is a di-linked (excluding links via the same or adjacent atoms) ring selected from phenylene, pryidindiyl, piperidinediyl N-linked to $Y_1$, furandiyl, thiophendiyl, pyrroldiyl, oxazoldiyl, thiazoldiyl, imidazoldiyl, isoxazoldiyl, isothiazoldiyl and pyrazoldiyl; each optionally substituted on an available carbon atom by up to four substituents independently selected from fluoro, chloro, bromo, cyano, (1-4C)alkyl, (1-4C)alkoxy and (1-4C)alkoxy(1-4C)alkyl;

L is a direct bond to Ring C, —O—, —S— or —NH—;

p is 0, 1 or 2 and when p is 1 $R^{41}$ and $R^{42}$ are each independently hydrogen or (1-4C)alkyl or $R^{41}$ and $R^{42}$ are linked together to form a (3-6C)spiroalkyl ring;

Z is carboxy or a mimic or bioisostere thereof, hydroxy or —CONRbRc wherein Rb and Rc are independently selected from hydrogen and (1-4C)alkyl, which (1-4C)alkyl group may be optionally substituted by carboxy or a mimic or bioisostere thereof;

and wherein any carbon atom in a linear (1-3C)alkyl, (1-2C)alkoxy, (1-4C)alkyl or (1-4C)alkoxy containing group defined above may be optionally substituted by up to 3 fluoro atoms.

In another embodiment there is provided a compound of formula (IA), or a pharmaceutically-acceptable salt, or pro-drug thereof,

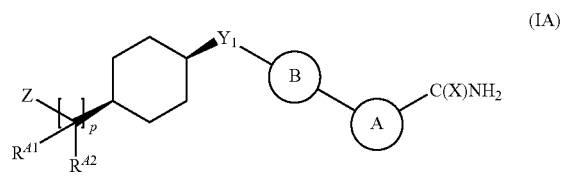

(IA)

wherein X, Ring A, Ring B, $Y_1$, p, $R^{41}$, $R^{42}$ and Z are as defined in Claim 1 or 2.

In another embodiment there is provided a compound of formula (IB), or a pharmaceutically-acceptable salt, or pro-drug thereof,

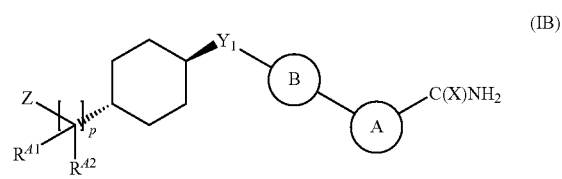

(IB)

wherein X, Ring A, Ring B, $Y_1$, p, $R^{41}$, $R^{42}$ and Z are as defined in Claim 1 or 2.

In another embodiment there is provided a compound as claimed in any one of Claims 1 to 4, or a pharmaceutically-acceptable salt, or pro-drug thereof, wherein X is =O;

Ring A is 2,6-pyrazindiyl optionally substituted on an available carbon atom by one or two substituents independently selected from linear (1-3C)alkyl, (2-3C)alkenyl, (2-3C)alkynyl, (1-2C)alkoxy, methoxymethyl, amino and cyano;

Ring B is 1,4-phenylene optionally substituted on an available carbon atom by one or two substituents independently selected from halo, amino, cyano, (1-4C)alkyl, (2-3C)alkenyl, (2-3C)alkynyl, (1-4C)alkoxy and (1-4C)alkoxy-(1-4C)alkyl;

Ring C is 1,4-cyclohexane;

n is 0 and $Y_1$ is a direct bond or $Y_1$ is —O—;

L is a direct bond;

p is 1 and $R^{41}$ and $R^{42}$ are each hydrogen;

Z is carboxy, a tetrazole group, —C(O)NHS(O)$_2$Me, hydroxy or —CONRbRc wherein Rb and Rc are independently selected from hydrogen and (1-4C)alkyl, which (1-4C)alkyl group may be optionally substituted by carboxy; and wherein any carbon atom in a linear (1-3C)alkyl, (1-2C)alkoxy, (1-4C)alkyl or (1-4C)alkoxy containing group defined above may be optionally substituted by up to 3 fluoro atoms.

In another embodiment there is provided a compound as claimed in any one of Claims 1 to 5, or a pharmaceutically-acceptable salt, or pro-drug thereof, wherein Ring A is 2,6-pyrazindiyl optionally substituted on an available carbon atom by one or two linear (1-3C)alkyl substituents.

The following compounds possess particular, desirable pharmaceutical and/or physical and/or pharmacokinetic/dynamic and/or toxicological properties and/or selective activity for DGAT1.

A compound of formula (I), or a pharmaceutically-acceptable salt, or pro-drug thereof,

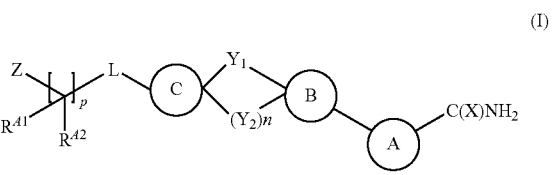

(I)

wherein

Ring A is 2,6-pyrazindiyl, 3,5-pyridindiyl or 2,6-pyridindiyl, each optionally substituted on an available carbon atom by one or two substituents independently selected from linear (1-3C)alkyl, (2-3C)alkenyl, (2-3C)alkynyl, (1-2C)alkoxy, methoxymethyl, amino and cyano;

X is =O or =S;

Ring B is 1,4-phenylene or Ring B is a di-linked (excluding links via the same or adjacent atoms) pyridindiyl ring; each optionally substituted on an available carbon atom by one or two substituents independently selected from halo, amino, cyano, (1-4C)alkyl, (2-3C)alkenyl, (2-3C)alkynyl, (1-4C)alkoxy and (1-4C)alkoxy-(1-4C)alkyl;

$Y_1$ is a direct bond between Ring B and Ring C or $Y_1$ is —O—, —S— or —NRa— wherein Ra is hydrogen or (1-4C)alkyl;

n is 0;

Ring C is a di-linked (excluding links via the same or adjacent atoms) (4-6C)cycloalkane ring, optionally substituted on an available carbon atom, including the ring carbon atom bearing the Z-containing group, by one substituent selected from hydroxy, (1-4C)alkyl, (1-4C)alkoxy and (1-4C)alkoxy(1-4C)alkyl;

L is a direct bond to Ring C or —O—;

p is 0, 1 or 2 and when p is 1 $R^{41}$ and $R^{42}$ are each independently hydrogen or (1-4C)alkyl;

Z is carboxy or a mimic or bioisostere thereof, hydroxy or —CONRbRc wherein Rb and Rc are independently selected from hydrogen and (1-4C)alkyl, which (1-4C)alkyl group may be optionally substituted by carboxy or a mimic or bioisostere thereof;

and wherein any carbon atom in a linear (1-3C)alkyl, (1-2C)alkoxy, (1-4C)alkyl or (1-4C)alkoxy containing group defined above may be optionally substituted by up to 3 fluoro atoms.

In one aspect, it will be appreciated that in certain compounds of formula (I) the Ring C substituent bearing the Z group (or suitable replacement thereof) and the —$Y_1$-link are in either a cis- or a trans-arrangement across the ring, in relation to each other. Where appropriate the invention encompasses both the cis- and trans-isomers. Techniques for separation of such isomers are well known in the art.

Thus, in one aspect, when Ring C is cyclohexyl the Z containing group and —$Y_1$-link are in a cis-configuration across the cyclohexyl ring, to give a compound of formula (IA), wherein the variables are as defined hereinbefore or hereinafter:

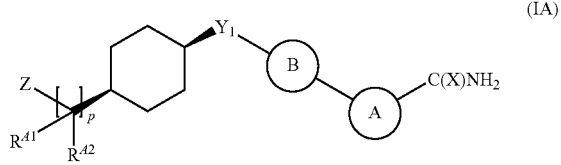

Thus, in one aspect, when Ring C is cyclohexyl the Z containing group and —$Y_1$-link are in a trans-configuration across the cyclohexyl ring, to give a compound of formula (IB), wherein the variables are as defined hereinbefore or hereinafter:

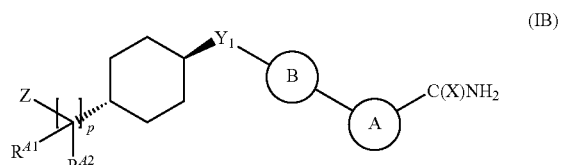

References hereinbefore or hereinafter to a compound of formula (I) are taken to apply also to compounds of formulae (IA) and (IB).

In one embodiment of the invention there are provided compounds of formulae (I), (IA) and (IB), in an alternative embodiment there are provided salts, particularly pharmaceutically-acceptable salts of compounds of formulae (I), (IA) and (IB). In a further embodiment, there are provided pro-drugs, particularly in-vivo cleavable esters, of compounds of formulae (I), (IA) and (IB). In a further embodiment, there are provided salts, particularly pharmaceutically-acceptable salts of pro-drugs of compounds of formulae (I), (IA) and (IB).

Particular values of substituents in compounds of formulae (I), (IA) and (IB) are as follows (such values may be used where appropriate with any of the other values, definitions, claims or embodiments defined hereinbefore or hereinafter) . . . .

1) X is =O;
2) X is =S;
3) Ring A is 2,6-pyrazindiyl;
4) Ring A is 2,6-pyrazindiyl substituted with any of the substituents in the Examples;
5) Ring A is 2,6-pyrazindiyl substituted with one or two (1-3C)alkyl;
6) Ring B is 1,4-phenylene;
7) Ring B is 2,5-pyridindiyl or 3,6-pyridindiyl;
8) Ring B is optionally substituted on an available carbon atom by one or two halo substituents;
9) Ring C is 1,4-cyclohexane (i.e. 1,4-cyclohexyl);
10) n is 0 and $Y_1$ is a direct bond between Ring B and Ring C or $Y_1$ is —O—;
11) Ring B and Ring C are particularly 2,4- or 2,5-furandiyl, 2,4- or 2,5-thiophendiyl, 2,4- or 2,5-pyr-roldiyl, 2,4- or 2,5-oxazoldiyl, 2,4- or 2,5-thiazoldiyl, 2,4- or 2,5-imidazoldiyl, 3,4- or 3,5-isoxazoldiyl, 3,4- or 3,5-isothiazoldiyl, 3,4- or 3,5-pyrazoldiyl;
12) L is a direct bond;
13) p is 0;
14) p is 1 and $R^{41}$ and $R^{42}$ are each hydrogen;
15) p is 2 and $R^{41}$ and $R^{42}$ are each hydrogen;
16) Z is carboxy, —CONRbRc (wherein Rb and Rc are independently selected from hydrogen and (1-4C)alkyl (which (1-4C)alkyl group may be optionally substituted by carboxy), a tetrazole group or —C(O)NHS(O)$_2$Me;
17) Z is carboxy;
18) a pro-drug for Z as carboxy is a (1-6C)alkyl ester.

Thus, for example, in one embodiment there is provided a compound of formula (I), or a pharmaceutically-acceptable salt thereof, wherein X=O; Ring A is 2,6-pyrazindiyl optionally substituted on an available carbon atom by one or two substituents independently selected from linear (1-3C)alkyl, (2-3C)alkenyl, (2-3C)alkynyl, (1-2C)alkoxy, methoxymethyl, amino and cyano; Ring B is 1,4-phenylene (optionally substituted on an available carbon atom by one or two halo substituents); n is 0 and $Y_1$ is a direct bond between Ring B and Ring C; p is 0 or p is 1 and $R^{41}$ and $R^{42}$ are each hydrogen; L is a direct bond and Z is carboxy, —CONRbRc (wherein Rb and Rc are independently selected from hydrogen and (1-4C) alkyl (which (1-4C)alkyl group may be optionally substituted by carboxy), a tetrazole group or —C(O)NHS(O)$_2$Me; i.e. a compound of formula (IC), or a pharmaceutically-acceptable salt thereof, wherein the 2,6-pyrazindiyl ring is optionally substituted on an available carbon atom by one or two substituents independently selected from linear (1-3C)alkyl, (2-3C)alkenyl, (2-3C)alkynyl, (1-2C)alkoxy, methoxymethyl, amino and cyano and other values are as defined immediately above.

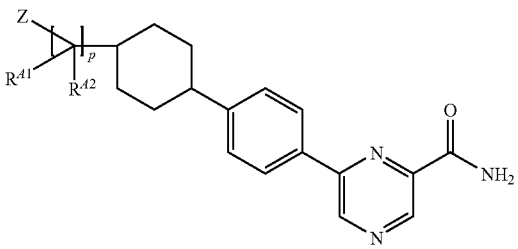

In another embodiment there is provided a compound of formula (I), or a pharmaceutically-acceptable salt thereof, wherein X=O; Ring A is 2,6-pyrazindiyl optionally substituted on an available carbon atom by one or two substituents independently selected from linear (1-3C)alkyl, (2-3C)alkenyl, (2-3C)alkynyl, (1-2C)alkoxy, methoxymethyl, amino and cyano; Ring B is 1,4-phenylene (optionally substituted on an available carbon atom by one or two halo substituents); n is 0 and $Y_1$ is a direct bond between Ring B and Ring C; p is 1 and $R^{41}$ and $R^{42}$ are each hydrogen; L is a direct bond and Z is carboxy or a tetrazole group.

In another embodiment there is provided a compound of formula (I), or a pharmaceutically-acceptable salt thereof, wherein X=O; Ring A is 2,6-pyrazindiyl optionally substituted on an available carbon atom by one or two substituents independently selected from linear (1-3C)alkyl; Ring B is 1,4-phenylene (optionally substituted on an available carbon atom by one or two fluoro substituents); n is 0 and $Y_1$ is a direct bond between Ring B and Ring C; p is 1 and $R^{A1}$ and $R^{A2}$ are each hydrogen; L is a direct bond and Z is carboxy or a tetrazole group.

In another embodiment there is provided a compound of formula (I), or a pharmaceutically-acceptable salt thereof, wherein X=O; Ring A is 2,6-pyrazindiyl optionally substituted on an available carbon atom by one or two methyl substituents; Ring B is 1,4-phenylene (optionally substituted on an available carbon atom by one or two fluoro substituents); n is 0 and $Y_1$ is a direct bond between Ring B and Ring C; p is 1 and $R^{A1}$ and $R^{A2}$ are each hydrogen; L is a direct bond and Z is carboxy or a tetrazole group.

In another embodiment there is provided a compound of formula (I), or a pharmaceutically-acceptable salt thereof, wherein X=O; Ring A is 2,6-pyrazindiyl optionally substituted on an available carbon atom by one or two methyl substituents; Ring B is 1,4-phenylene; n is 0 and $Y_1$ is a direct bond between Ring B and Ring C; p is 1 and $R^{A1}$ and $R^{A2}$ are each hydrogen; L is a direct bond and Z is carboxy or a tetrazole group.

In another embodiment there is provided a compound of formula (I), or a pharmaceutically-acceptable salt thereof, wherein X=O; Ring A is 2,6-pyrazindiyl optionally substituted on an available carbon atom by one or two methyl substituents; Ring B is 1,4-phenylene; n is 0 and $Y_1$ is a direct bond between Ring B and Ring C; p is 1 and $R^{A1}$ and $R^{A2}$ are each hydrogen; L is a direct bond and Z is carboxy.

In another embodiment there is provided a compound of formula (I), wherein X=O; Ring A is 2,6-pyrazindiyl optionally substituted on an available carbon atom by one or two methyl substituents; Ring B is 1,4-phenylene; n is 0 and $Y_1$ is a direct bond between Ring B and Ring C; p is 1 and $R^{A1}$ and $R^{A2}$ are each hydrogen; L is a direct bond and Z is carboxy.

In another embodiment there is provided a compound of formula (I) as defined in any of the seven embodiments immediately above, wherein the Z containing group and the —$Y_1$-link are in either a cis- or a trans-arrangement across the ring, in relation to each other.

In another embodiment there is provided a compound of formula (I) as defined in any of the eight embodiments immediately above wherein a pro-drug for Z as carboxy is a (1-6C) alkyl ester.

A further feature is any of the scopes defined herein with the proviso that specific Examples, such as Example 1, 2, 3, 4 etc. are individually disclaimed.

Further particular compounds of the invention are each of the Examples, each of which provides a further independent aspect of the invention. In further aspects, the present invention also comprises any particular compounds of the Examples or a pharmaceutically-acceptable salt thereof (such as, for example, a sodium, magnesium, tert-butylammonium, tris(hydroxymethyl)methylammonium, triethanolammonium, diethanolammonium, ethanolammonium, methylethanolammonium, diethylammonium or nicotinamide salt).

For example, a further feature is any of the particular compounds of the Examples or a pharmaceutically-acceptable salt thereof, such as any compound selected from
{trans-4-[4-(6-Carbamoyl-3,5-dimethylpyrazin-2-yl)phenyl]cyclohexyl}acetic acid;
3,5-Dimethyl-6-[4-(trans-4-{2-[(methylsulfonyl)amino]-2-oxoethyl}cyclohexyl)-phenyl]pyrazine-2-carboxamide;
6-{4-[trans-4-(2-Amino-2-oxoethyl)cyclohexyl]phenyl}-3,5-dimethylpyrazine-2-carboxamide;
N-({trans-4-[4-(6-Carbamoyl-3,5-dimethylpyrazin-2-yl)phenyl]cyclohexyl}acetyl)-2-methylalanine;
6-{4-[trans-4-(2-Hydroxyethyl)cyclohexyl]phenyl}-3,5-dimethylpyrazine-2-carboxamide; (trans-4-{4-[6-Carbamoyl-5-(difluoromethyl)-3-methylpyrazin-2-yl]phenyl}cyclohexyl)acetic acid;
{trans-4-[4-(6-Carbamoyl-3-ethyl-5-methylpyrazin-2-yl)phenyl]cyclohexyl}acetic acid;
{trans-4-[4-(6-Carbamoyl-5-ethyl-3-methylpyrazin-2-yl)phenyl]cyclohexyl}acetic acid;
{trans-4-[4-(6-Carbamoyl-3-methylpyrazin-2-yl)phenyl]cyclohexyl}acetic acid;
2-((1r,4s)-5'-(6-Carbamoyl-3,5-dimethylpyrazin-2-yl)-2',3'-dihydrospiro[cyclohexane-1,1'-indene]-4-yl)acetic acid;
(1r,4s)-5'-(6-Carbamoyl-3,5-dimethylpyrazin-2-yl)-2',3'-dihydrospiro[cyclohexane-1,1'-indene]-4-carboxylic acid;
2-((1r,4r)-4-(4-(6-Carbamoyl-3,5-dimethylpyrazin-2-yl)phenyl)cyclohexyl)-2-methylpropanoic acid
2-(1-(4-(6-Carbamoyl-3,5-dimethylpyrazin-2-yl)phenyl)pyrrolidin-3-yl)acetic acid;
(1R,5S,6r)-3-(4-(6-Carbamoyl-3,5-dimethylpyrazin-2-yl)phenyl)-3-azabicyclo[3.1.0]hexane-6-carboxylic acid;
6-(4-((1r,4r)-4-((1H-Tetrazol-5-yl)methyl)cyclohexyl)phenyl)-3,5-dimethylpyrazine-2-carboxamide;
4'-(6-Carbamoyl-3,5-dimethylpyrazin-2-yl)biphenyl-4-carboxylic acid;
Methyl trans-4-{4-[6-(aminocarbonyl)-3-methylpyrazin-2-yl]phenyl}-cyclohexanecarboxylate;
trans-4-{4-[6-(Aminocarbonyl)-3-methylpyrazin-2-yl]phenyl}cyclo-hexanecarboxylic acid; or a pharmaceutically-acceptable salt of any of these.

In a further aspect, the present invention also comprises any particular isomers of compounds of the Examples, such as the cis-isomer of compounds such as Examples 1 or 2, i.e. {cis-4-[4-(6-carbamoyl-3,5-dimethylpyrazin-2-yl)phenyl]cyclohexyl}acetic acid or 3,5-dimethyl-6-[4-(cis-4-{2-[(methylsulfonyl)amino]-2-oxoethylcyclohexyl)phenyl]-pyrazine-2-carboxamide or a pharmaceutically-acceptable salt of either of these; or compounds such as 6-{4-[cis-4-(2-Amino-2-oxoethyl)cyclohexyl]phenyl}-3,5-dimethylpyrazine-2-carboxamide;
N-({cis-4-[4-(6-Carbamoyl-3,5-dimethylpyrazin-2-yl)phenyl]cyclohexyl}acetyl)-2-methylalanine;
6-{4-[cis-4-(2-Hydroxyethyl)cyclohexyl]phenyl}-3,5-dimethylpyrazine-2-carboxamide;
(cis-4-{4-[6-Carbamoyl-5-(difluoromethyl)-3-methylpyrazin-2-yl]phenyl}cyclohexyl)acetic acid;
{cis-4-[4-(6-Carbamoyl-3-ethyl-5-methylpyrazin-2-yl)phenyl]cyclohexyl}acetic acid;
{cis-4-[4-(6-Carbamoyl-5-ethyl-3-methylpyrazin-2-yl)phenyl]cyclohexyl}acetic acid;
{cis-4-[4-(6-Carbamoyl-3-methylpyrazin-2-yl)phenyl]cyclohexyl}acetic acid; or a pharmaceutically-acceptable salt of any of these.

A compound of formula (I) and its salts may be prepared by any process known to be applicable to the preparation of chemically related compounds. Such processes, when used to prepare a compound of the formula (I), or a pharmaceutically-acceptable salt thereof, are provided as a further feature of the invention.

In a further aspect the present invention also provides that the compounds of the formula (I) and salts thereof, can be prepared by the following processes, the processes of the Examples and analogous processes (wherein all variables are as hereinbefore defined for a compound of formula (I) unless otherwise stated) and thereafter if necessary any protecting groups can be removed and/or an appropriate salt formed. Any defined carboxylic acid groups may be replaced as appropriate by a mimic or bioisostere thereof.

Variables shown in the schemes are defined or can be interpreted in the context of the variants described herein for the compounds of the invention. Analogous chemistry to that shown in the schemes and Examples may be used to prepare other ring variants and linking group options within the scope of the invention.

Also included as an aspect of the invention are the compounds obtainable by any of the processes or Examples described herein.

Process a)

By modifying a substituent in, or introducing a substituent into, another compound of formula (I). Suitable methods for converting substituents into other substituents are known in the art. For example, an acid group may be converted into an amide group or reduced to an alcohol group.

An amide in Ring A may be converted into a thioamide by use of Lawesson's reagent or $P_2S_5$.

Compounds of formula (I) where, for example, Z is an acylsulfonamide group or Z is a tetrazole may be prepared from the corresponding carboxylic acid. The tetrazole may be introduced early in the synthetic route via an amide (which, for primary amides, may be converted to the nitrile by standard methods) which is then in turn converted into a tetrazole by reaction with azide. The tetrazole may be carried through the rest of the synthesis in protected form, e.g. N-benzylated or N-(2-cyanoethyl)ated.

Process b)

Suzuki coupling of an appropriate iodo-, bromo- or chloro-substituted Ring A derivative (e.g. pyrazine ester (III)) with a suitably substituted intermediate boronate compound of formula (II) followed by conversion of the ring A ester group to the corresponding acid by basic hydrolysis and thence to the corresponding primary carboxamide by reaction with ammonia in the presence of a coupling agent, for example PyBOP.

A protecting group can be removed, for example, by acid catalysed hydrolysis of a tert-butyl ester to give a compound of formula (I) where $Z=CO_2H$.

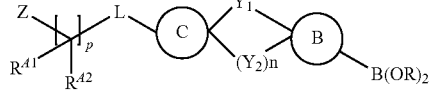
(II)

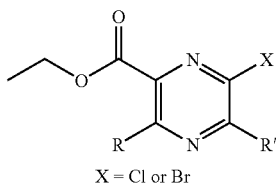
(III)

X = Cl or Br

R and R' may represent any of the variables defined herein at such positions.

Analogous chemistry may be used to prepare other Ring A derivatives (e.g. pyridine compounds).

Alternatively a Suzuki coupling of an appropriate iodo-, bromo- or chloro-pyrazine amide (IV), particularly bromo- or chloro-pyrazine amide (IV), can be used followed by removal of the protecting group by basic hydrolysis of a methyl or ethyl ester.

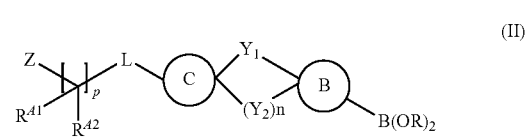
(II)

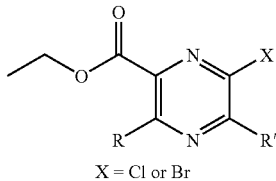
(III)

X = Cl or Br

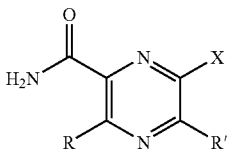
(IV)

Preparation of Formula (III) Compound Types (Ring A)

The following schemes illustrate how certain Ring A variants may be prepared. Variables shown in the schemes are defined or can be interpreted in the context of the variants described herein for the compounds of the invention. Analogous chemistry to that shown in the schemes and Examples may be used to prepare other Ring variants and linking group options within the scope of the invention.

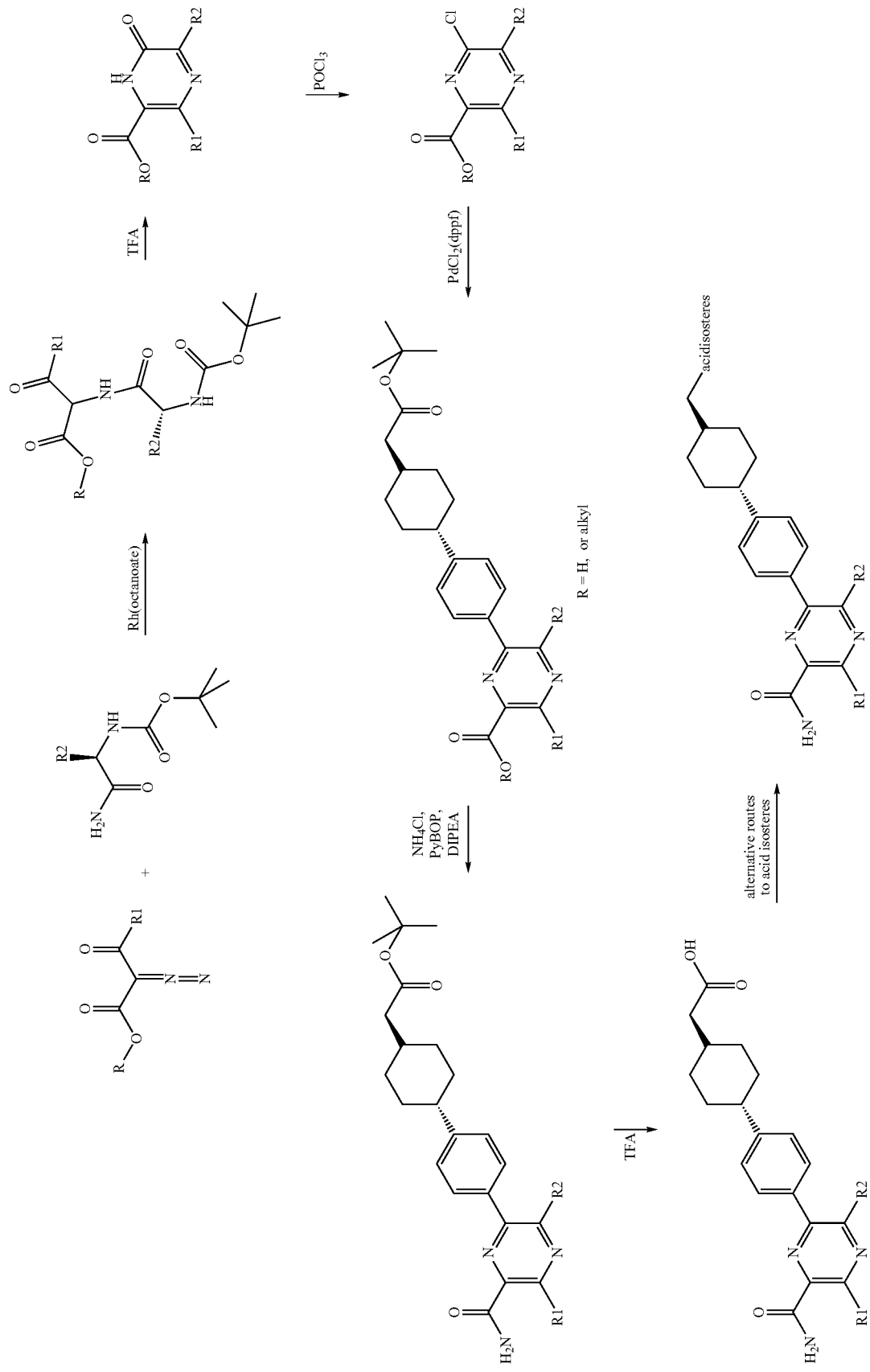
Scheme A1: Reaction scheme for dimethylpyrazine and derivatives

Scheme A2: Reaction scheme for mono-methylpyrazine and derivatives
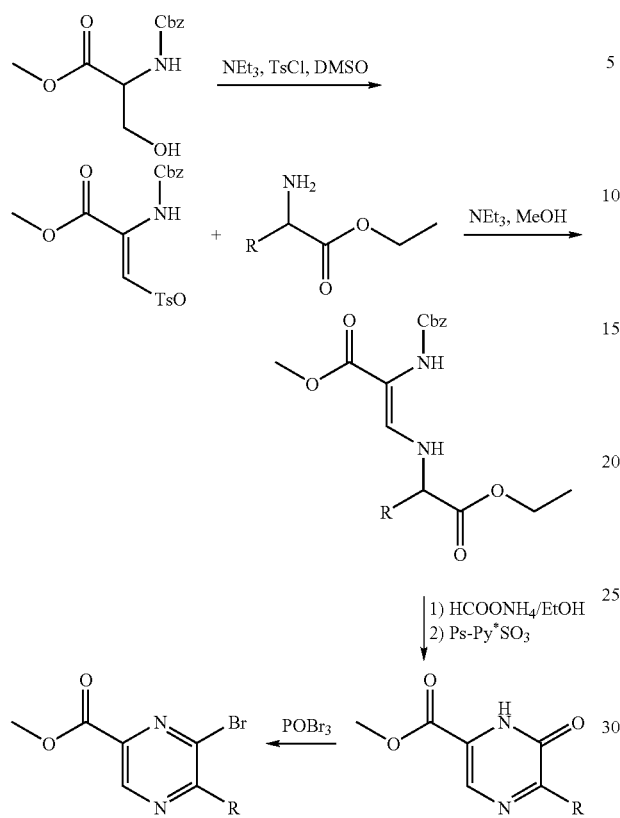
Scheme A3: Reaction scheme for condensation procedure
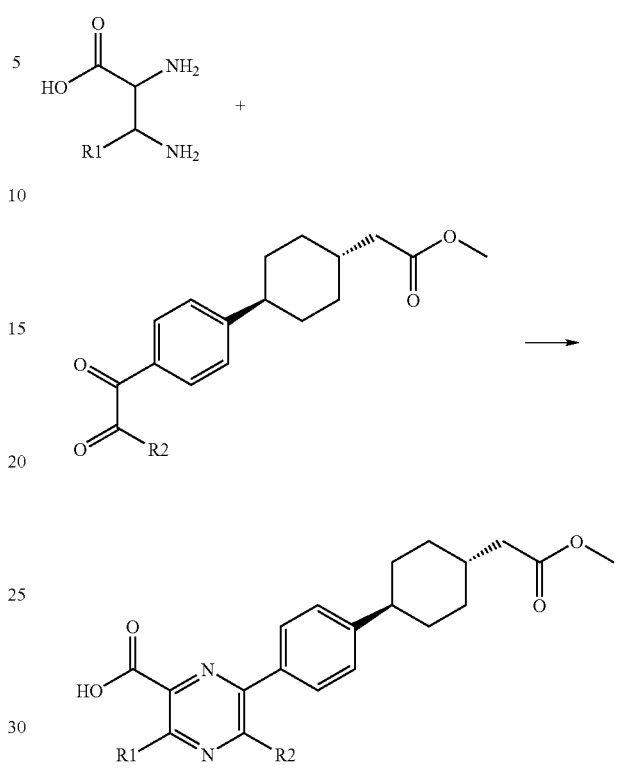
Preparation of Formula (III) and (IV) Compound Types (Ring A)
Scheme A4: Reaction scheme for dimethylpyrazine and derivatives
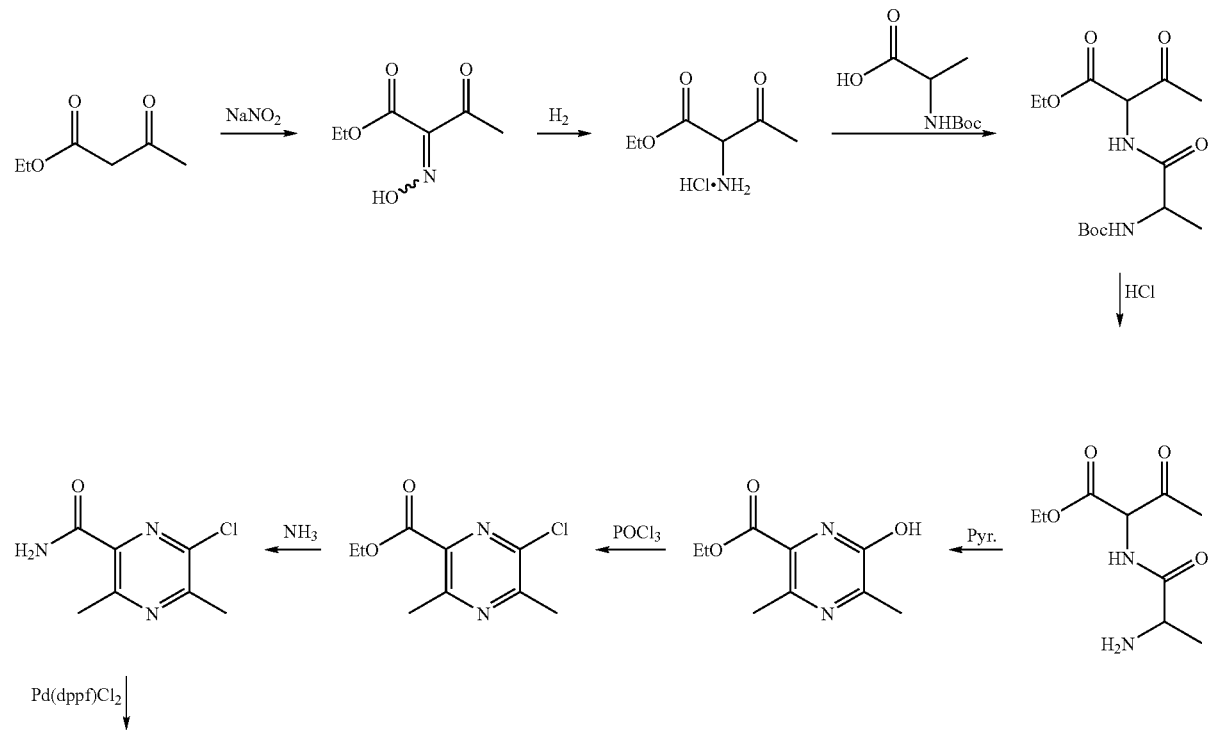

25

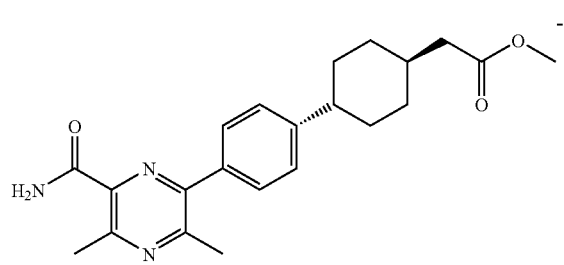

-continued

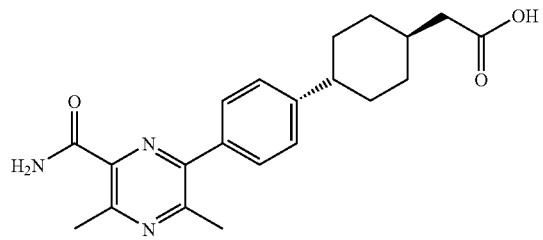

Analogues of pyrazine can be prepared using the procedure described by C. Christensen, C. W. Tornoe and M. Meldal, *QSAR & Combinatorial Science*, 2004, 23, (2-3), 109-116, for example, 3-methylpyrazine . . . . variants described herein for the compounds of the invention. Analogous chemistry to that shown in the schemes and Examples may be used to prepare other ring variants and linking group options within the scope of the invention.

Scheme A5: Reaction scheme for 3 mono-methylpyrazine and derivatives

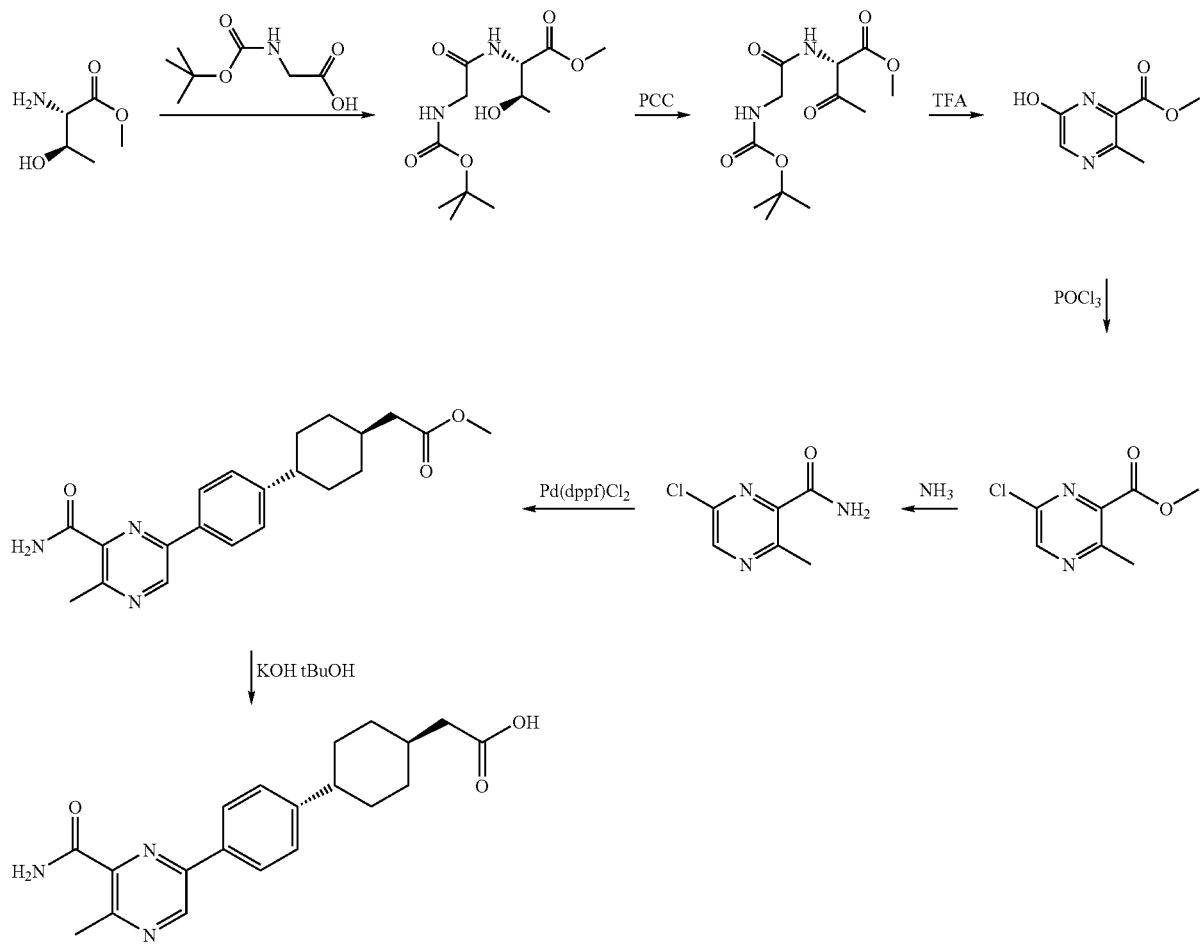

Preparation of Formula (II) Compound Types (Ring C and Ring B)

The following schemes illustrate how certain Ring C and Ring B variants may be prepared. Variables shown in the schemes are defined or can be interpreted in the context of the (i) Compounds of formula (II) in which Ring C is cyclohexane (p is 2 in structure C1) and Ring B is phenyl are described in the literature or can be made by analogy. These may be brominated to (C2) and then converted into the boronate esters (C3) using standard procedures. Alternative leaving groups to bromo in (C2) are iodo and triflate (see Scheme C1-B).

Scheme C1-A: Reaction scheme for cyclohexane variants

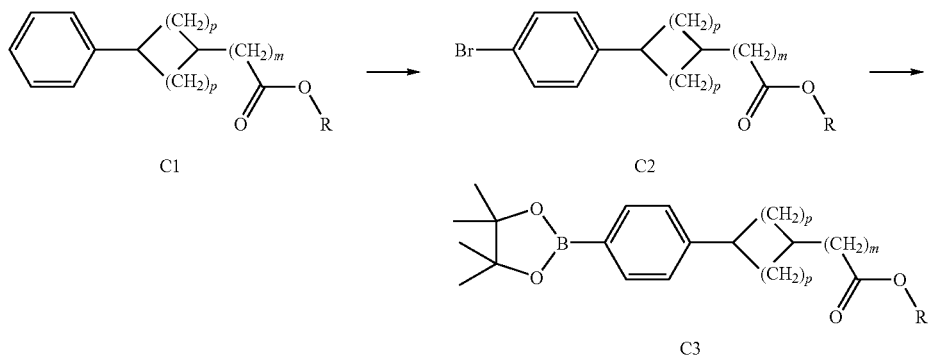

Scheme C1-B: Reaction scheme for synthesis of boronic acid ester intermediate

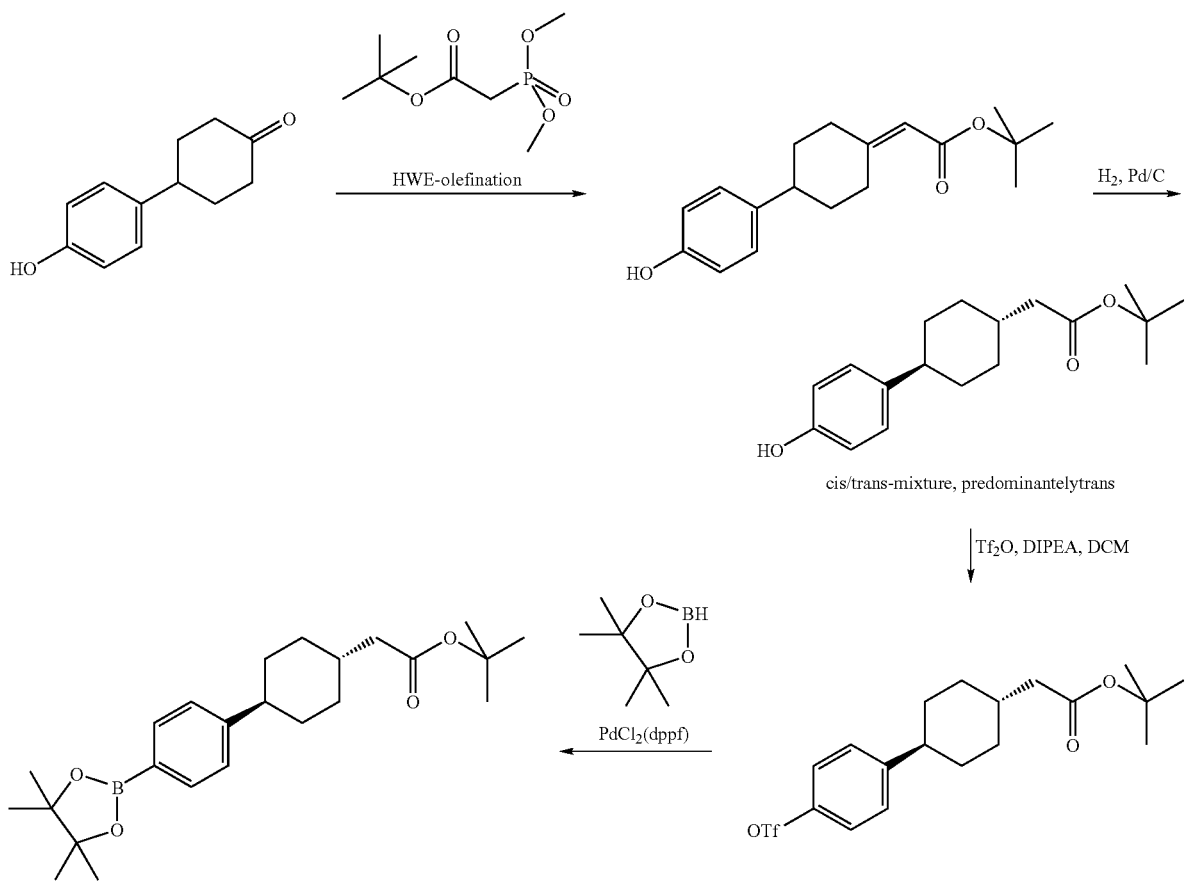

Scheme C1-B methyl ester has been described in WO 2004/047755.

Compounds in which a bromo-heteroaryl compound is required may not be directly obtainable via the unsubstituted heteroaryl compound. The bromo group, or other suitable alternative, may be introduced at an earlier stage in the synthetic route.

(ii) For compounds of formula (II) in which Ring C is phenyl and Ring B is phenyl many appropriate intermediates are in the literature, or can be made by analogy, and introduction of various substitution patterns may be achieved through biaryl Suzuki coupling:

Scheme C2: Reaction scheme for biaryl variants

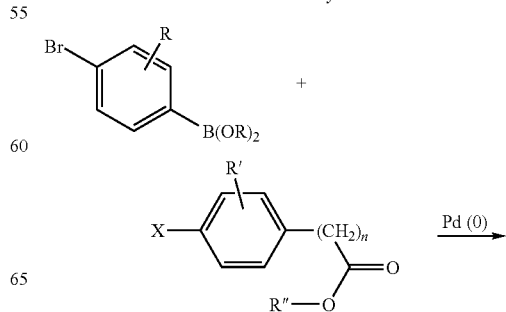

-continued

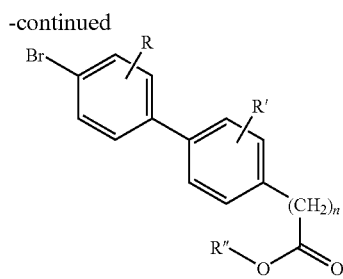

In Scheme C2, R and R' are any of the claimed aromatic substituents which are compatible with the reaction conditions, X is a suitable leaving group such as bromo, iodo or triflate. The bromobiaryl is then converted into the corresponding boronate derivative by standard methods.

For both Scheme C1 and C2, introduction of α-alkyl and dialkyl groups is possible at the intermediate C1 or C2 stage through standard alkylation methodology, for example by deprotonation α-to the ester group using a lithium base such as LDA followed by quenching with an appropriate alkyl halide.

Preparation of Formula (V) Compound Types (Ring A and Ring B)

(i) In an alternative sequence of Suzuki couplings a cyano-heterocyclylphenylboronic ester of type V is generated as a key intermediate, as illustrated by the scheme below. This intermediate is then used in further coupling reactions to generate biaryl compounds of the formula I.

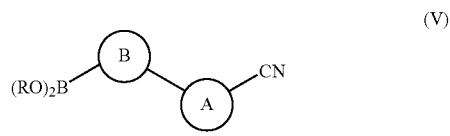

Scheme C2-A: Reaction scheme for biaryl variants

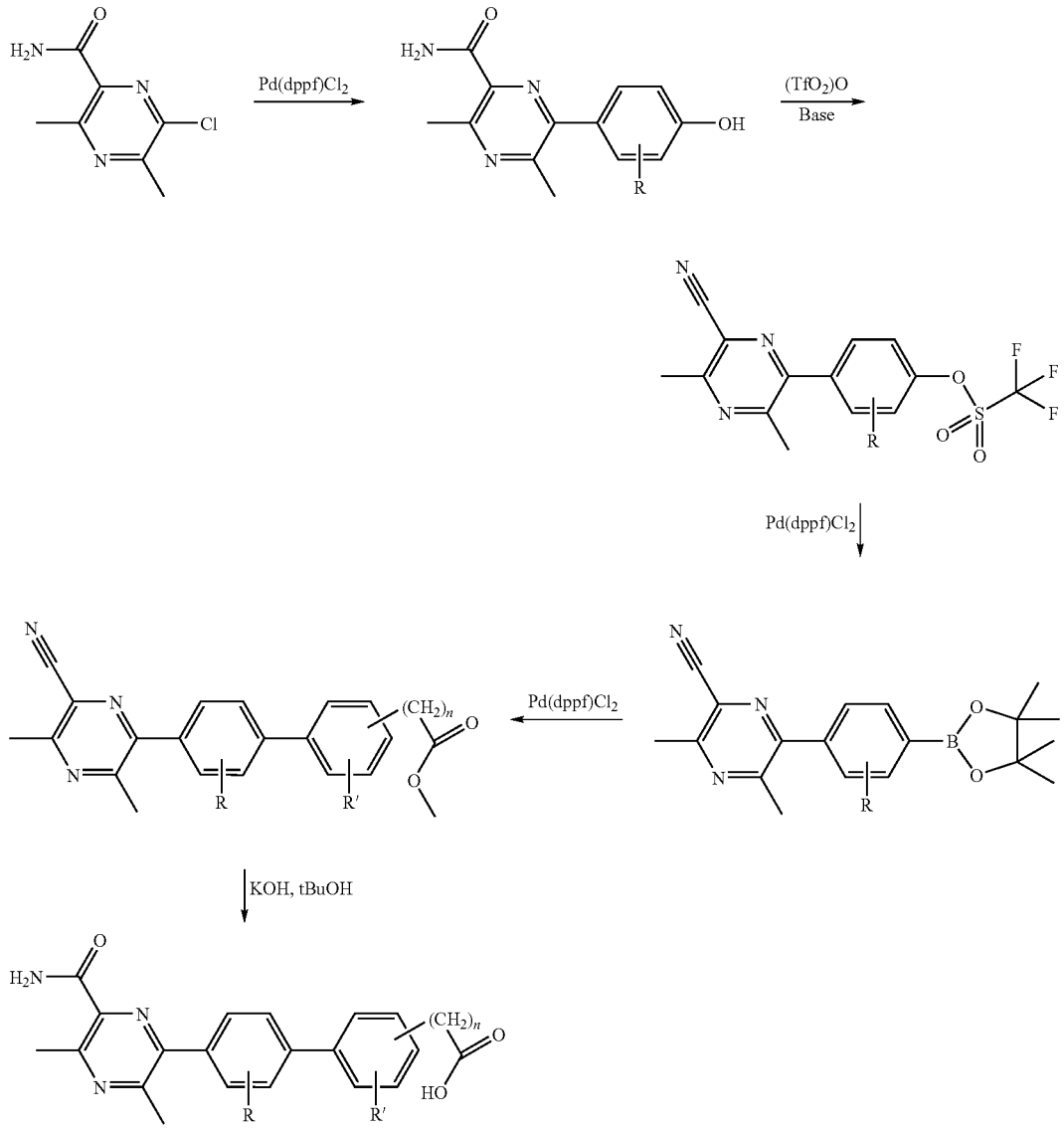

In Scheme C2, R and R' are any of the claimed aromatic substituents which are compatible with the reaction conditions. The phenol is converted into the corresponding triflate with trifluoromethanesulfonic anhydride and a suitable base, such as triethylamine, which also results in dehydration of the amide to the nitrile. The aryltriflate is converted to the corresponding boronate derivative followed by subsequent Suzuki reaction under standard methods with a suitable palladium catalyst, such as 1,1'-bis(diphenylphosphino)-ferrocene-dichloropalladium(II). Base hydrolysis, for example with potassium hydroxide in tert-butanol results in hydrolysis of the ester and nitrile.

Scheme C2-B: Reaction scheme for biaryl variants

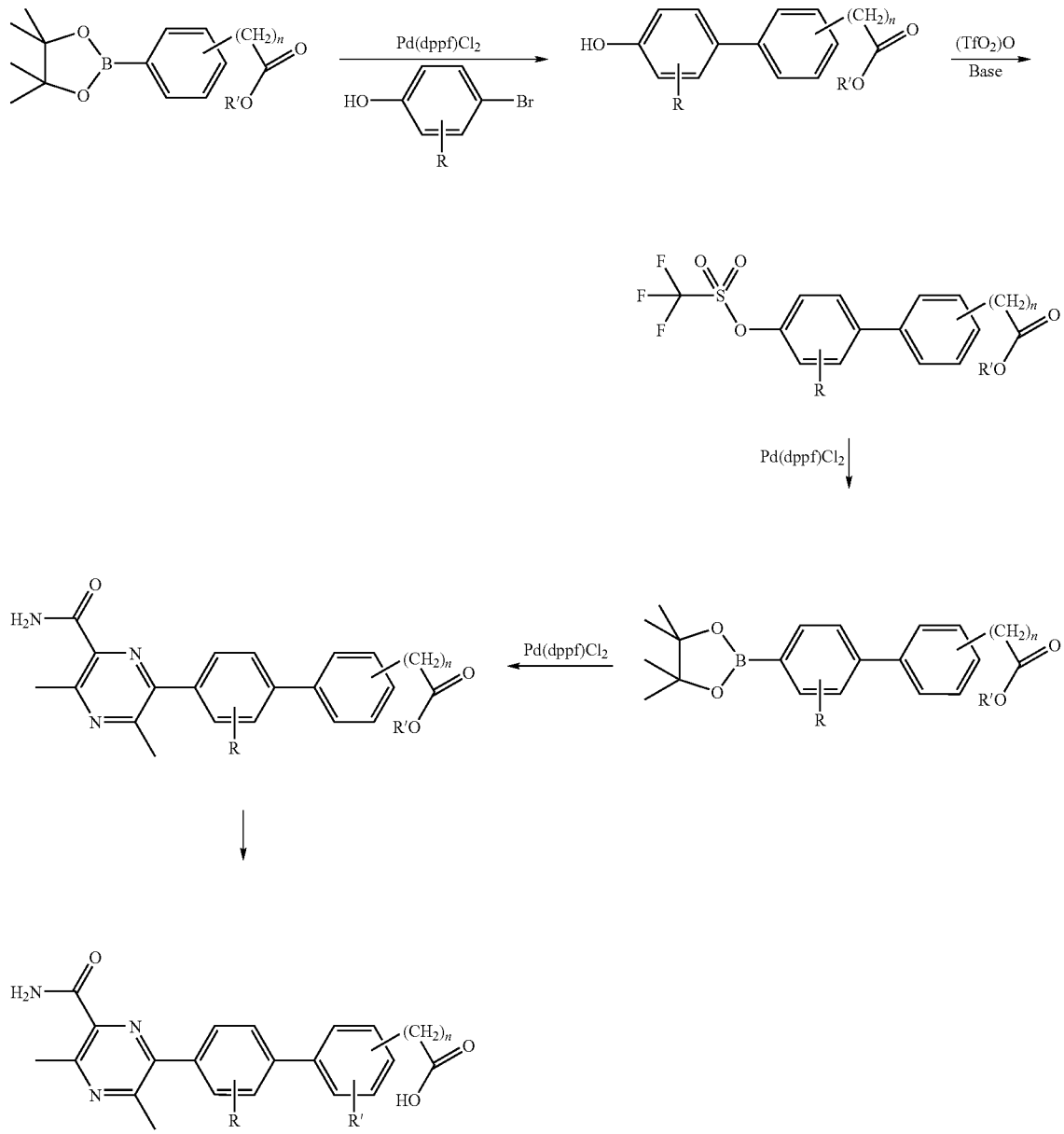

In Scheme C2-B, R and R' are any of the claimed aromatic substituents which are compatible with the reaction conditions.

(ii) Spirocyclic compounds of formula (II) may be prepared by analogy with preparations involving the intermediates in Scheme C4 below (see WO 2004/047755-relevant sections of which are hereby incorporated by reference).

Scheme C4: Reaction scheme for spirocyclic compounds

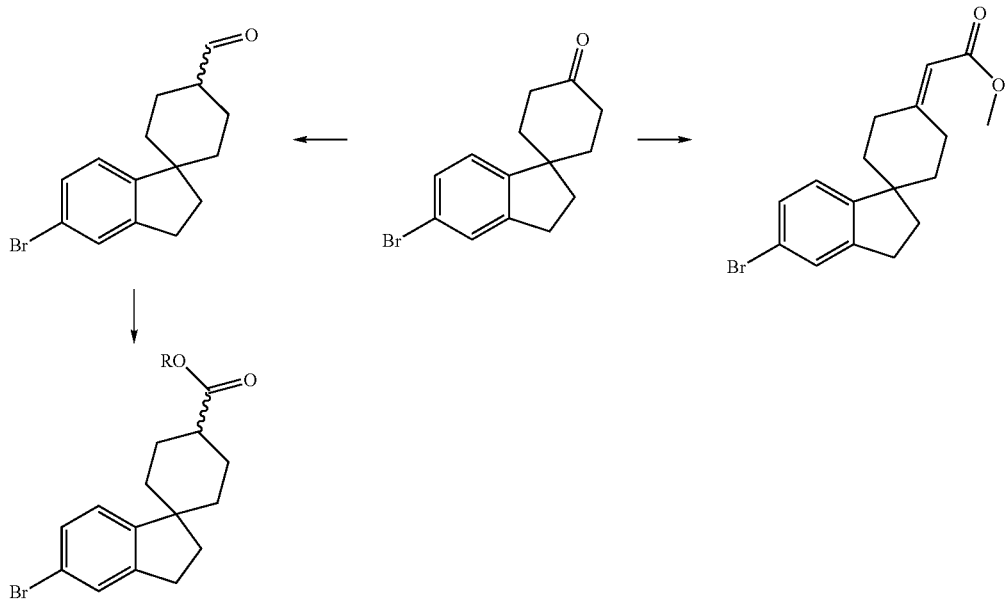

The double bond may be reduced at a suitable stage in the synthesis and the resultant cis- and trans-isomers separated chromatographically. As above, this route may proceed by conversion of the bromo into the boronate for coupling to the appropriate Ring A (e.g. pyrazine) compound.

The cyclohexanone may be converted to the unsaturated ketone and the double bond reduced at a suitable stage in the synthesis and the cis- and trans-isomers separated chromatographically. Alternatively the cyclohexane may be converted to the aldehyde which can be oxidised to the acid, for example with oxone and the acid converted to an ester, for example a tert-butyl and the cis- and trans-isomers separated chromatographically. As above, this route may proceed by conversion of the bromo into the boronate for coupling to the appropriate Ring A (e.g. pyrazine) compound.

For compounds of the formula (V) in which Ring B is Phenyl and Ring C is a cyclic amine, introduction of the amine maybe achieved through transition metal coupling.

Scheme C5: Reaction scheme for cyclic amine variants

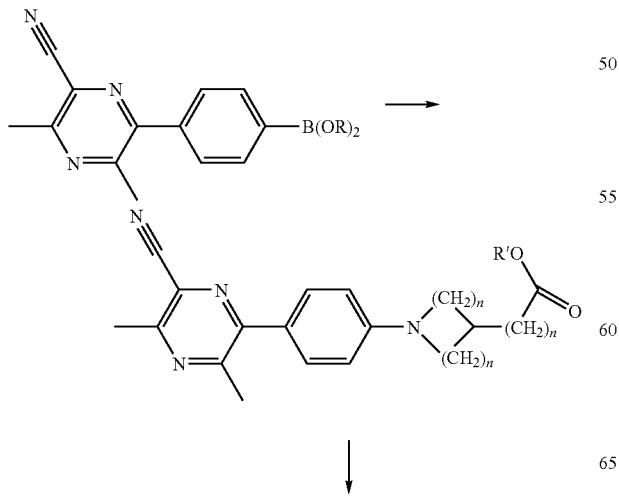

-continued

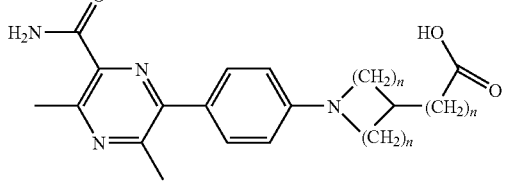

In Scheme C5 the amines may be introduced using boronic acids or esters using copper acetate as in the procedure described by D. M. T. Chan, K. L Monaco, R. Li, D. Bonne, C. G. Clark, P. Y. S Lam, *Tet. Lett.,* 2003, 44(19), 3863-3865.

(iii) Bicyclooctane derivatives of formula (II) may be prepared by analogy with preparations involving the phenyl Intermediate C5 below (see WO 2007/071966—relevant sections of which are hereby incorporated by reference), which is brominated and converted into the boronate for coupling to the appropriate Ring A (e.g. pyrazine) compound.

Intermediate C5

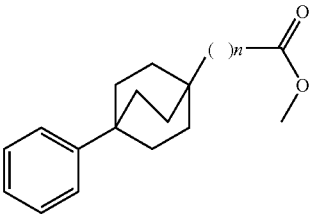

Compounds of formula C5 may be made as their ester derivative according to the process shown below in Scheme C3, or analogously thereto.

Scheme C3: Bicyclooctane variants

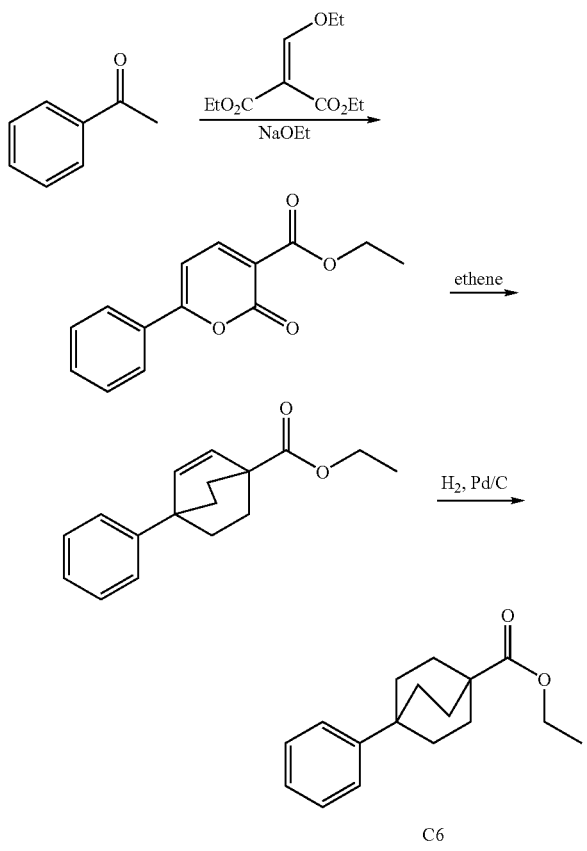

C6

Compounds such as C6 may be homologated by standard procedures such as reduction of the ester to the corresponding alcohol, conversion of this to a leaving group such as tosylate, displacing this with cyanide followed by hydrolysis and esterification, all by standard methods, to compounds such as C5 wherein n=1.

Compounds in which Ring C is other than bicyclo[2.2.2]octane-1,4-diyl may be prepared by analogous processes.

Adamantyl derivatives of formula (II) may be prepared by analogy with preparations involving the phenyl Intermediate C7 below (see WO 2007/071966—relevant sections are hereby incorporated by reference), which is iodinated and converted to the boronate for coupling to the appropriate Ring A (e.g. pyrazine).

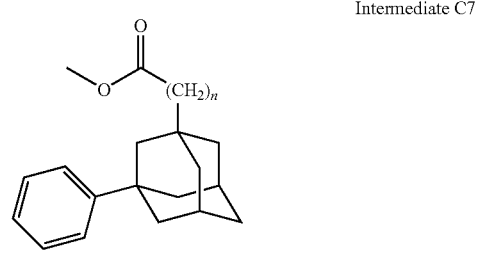

Intermediate C7

If not commercially available, the necessary starting materials for the procedures such as those described above may be made by procedures which are selected from standard organic chemical techniques, techniques which are analogous to the synthesis of known, structurally similar compounds, techniques which are described or illustrated in the references given above, or techniques which are analogous to the above described procedure or the procedures described in the examples. The reader is further referred to Advanced Organic Chemistry, 5$^{th}$ Edition, by Jerry March and Michael Smith, published by John Wiley & Sons 2001, for general guidance on reaction conditions and reagents.

It will be appreciated that some intermediates to compounds of the formula (I) are also novel and these are provided as separate independent aspects of the invention. In particular, certain compounds of formula (IV) may form a further independent aspect of the invention. Furthermore, ester derivatives of compounds of formula (I) form a further aspect of the invention.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T. W. Greene, Protective Groups in Organic Synthesis, John Wiley and Sons, 1991).

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl or SEM may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art, or they may be removed during a later reaction step or work-up.

The skilled organic chemist will be able to use and adapt the information contained and referenced within the above references, and accompanying Examples therein and also the examples herein, to obtain necessary starting materials, and products.

The removal of any protecting groups and the formation of a pharmaceutically-acceptable salt are within the skill of an ordinary organic chemist using standard techniques. Furthermore, details on the these steps has been provided hereinbefore.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

According to a further aspect of the invention there is provided a pharmaceutical composition which comprises a compound of formula (I), (IA) or (IB) as defined hereinbefore or a pharmaceutically-acceptable salt thereof, in association with a pharmaceutically-acceptable excipient or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

According to a further aspect of the present invention there is provided a compound of formula (I), (IA) and/or (IB), or a pharmaceutically acceptable salt, or a pro-drug thereof as defined hereinbefore for use in a method of treatment of the human or animal body by therapy.

We have found that compounds of the present invention inhibit DGAT1 activity and are therefore of interest for their blood glucose-lowering effects.

A further feature of the present invention is a compound of formula (I), (IA) and/or (IB), or a pharmaceutically-acceptable salt, or a pro-drug thereof for use as a medicament.

Conveniently this is a compound of formula (I), (IA) and/or (IB), or a pharmaceutically-acceptable salt, or a pro-drug thereof, for (use as a medicament for) producing an inhibition of DGAT1 activity in a warm-blooded animal such as a human being.

Particularly this is a compound of formula (I), (IA) and/or (IB), or a pharmaceutically-acceptable salt, or a pro-drug thereof, for (use as a medicament for) treating diabetes mellitus and/or obesity in a warm-blooded animal such as a human being.

Thus according to a further aspect of the invention there is provided the use of a compound of formula (I), (IA) and/or (IB), or a pharmaceutically-acceptable salt, or a pro-drug thereof in the manufacture of a medicament for use in the production of an inhibition of DGAT1 activity in a warm-blooded animal such as a human being.

Thus according to a further aspect of the invention there is provided the use of a compound of formula (I), (IA) and/or (IB), or a pharmaceutically-acceptable salt, or a pro-drug thereof in the manufacture of a medicament for use in the treatment of diabetes mellitus and/or obesity in a warm-blooded animal such as a human being.

According to a further aspect of the invention there is provided a pharmaceutical composition which comprises a compound of formula (I), (IA) and/or (IB) as defined hereinbefore, or a pharmaceutically-acceptable salt, or a pro-drug thereof, in association with a pharmaceutically-acceptable excipient or carrier for use in producing an inhibition of DGAT1 activity in an warm-blooded animal, such as a human being.

According to a further aspect of the invention there is provided a pharmaceutical composition which comprises a compound of formula (I), (IA) and/or (IB) as defined hereinbefore, or a pharmaceutically-acceptable salt, or a pro-drug thereof, in association with a pharmaceutically-acceptable excipient or carrier for use in the treatment of diabetes mellitus and/or obesity in an warm-blooded animal, such as a human being.

According to a further feature of the invention there is provided a method for producing an inhibition of DGAT1 activity in a warm-blooded animal, such as a human being, in need of such treatment which comprises administering to said animal an effective amount of a compound of formula (I), (IA) and/or (IB), or a pharmaceutically-acceptable salt, or a pro-drug thereof as defined hereinbefore.

According to a further feature of the invention there is provided a method of treating diabetes mellitus and/or obesity in a warm-blooded animal, such as a human being, in need of such treatment which comprises administering to said animal an effective amount of a compound of formula (I), (IA) and/or (IB), or a pharmaceutically-acceptable salt, or a pro-drug thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1-50 mg/kg is employed. In another embodiment a daily dose is in the range of 0.01-50 mg/kg, particularly 0.01-10 mg/kg, 0.01-1 mg/kg or 0.01-0.1 mg/kg. However the daily dose will necessarily be varied depending upon the host treated, the particular route of administration, and the severity of the illness being treated. Accordingly the optimum dosage may be determined by the practitioner who is treating any particular patient.

As stated above compounds defined in the present invention are of interest for their ability to inhibit the activity of DGAT1. A compound of the invention may therefore be useful for the prevention, delay or treatment of a range of disease states including diabetes mellitus, more specifically type 2 diabetes mellitus (T2DM) and complications arising there from (for example retinopathy, neuropathy and nephropathy), impaired glucose tolerance (IGT), conditions of impaired fasting glucose, metabolic acidosis, ketosis, dysmetabolic syndrome, arthritis, osteoporosis, obesity and obesity related disorders, (which include peripheral vascular disease, (including intermittent claudication), cardiac failure and certain cardiac myopathies, myocardial ischaemia, cerebral ischaemia and reperfusion, hyperlipidaemias, atherosclerosis, infertility and polycystic ovary syndrome); the compounds of the invention may also be useful for muscle weakness, diseases of the skin such as acne, various immunomodulatory diseases (such as psoriasis), HIV infection, inflammatory bowel syndrome and inflammatory bowel disease such as Crohn's disease and ulcerative colitis.

In particular, the compounds of the present invention are of interest for the prevention, delay or treatment of diabetes mellitus and/or obesity and/or obesity related disorders. In one aspect, the compounds of the invention are used for prevention, delay or treatment of diabetes mellitus. In another aspect, the compounds of the invention are used for prevention, delay or treatment of obesity. In a further aspect, the compounds of the invention are used for prevention, delay or treatment of obesity related disorders.

The inhibition of DGAT1 activity described herein may be applied as a sole therapy or in combination with one or more other substances and/or treatments for the indication being treated. Such conjoint treatment may be achieved by way of the simultaneous, sequential or separate administration of the individual components of the treatment. Simultaneous treatment may be in a single tablet or in separate tablets. For example such conjoint treatment may be beneficial in the treatment of metabolic syndrome [defined as abdominal obesity (as measured by waist circumference against ethnic and gender specific cut-points) plus any two of the following: hypertriglyceridemia (>150 mg/dl; 1.7 mmol/l); low HDLc (<40 mg/dl or <1.03 mmol/l for men and <50 mg/dl or 1.29 mmol/l for women) or on treatment for low HDL (high density lipoprotein); hypertension (SBP≧130 mmHg DBP≧85 mmHg) or on treatment for hypertension; and hyperglycemia (fasting plasma glucose≧100 mg/dl or 5.6 mmol/l or impaired glucose tolerance or pre-existing diabetes mellitus)-International Diabetes Federation & input from IAS/NCEP].

Such conjoint treatments may include the following main categories:

1) Anti-obesity therapies such as those that cause weight loss by effects on food intake, nutrient absorption or energy expenditure, such as orlistat, sibutramine and the like.
2) Insulin secretagogues including sulphonylureas (for example glibenclamide, glipizide), prandial glucose regulators (for example repaglinide, nateglinide);
3) Agents that improve incretin action (for example dipeptidyl peptidase IV inhibitors, and GLP-1 agonists);
4) Insulin sensitising agents including PPARgamma agonists (for example pioglitazone and rosiglitazone), and agents with combined PPARalpha and gamma activity;
5) Agents that modulate hepatic glucose balance (for example metformin, fructose 1, 6 bisphosphatase inhibitors, glycogen phopsphorylase inhibitors, glycogen synthase kinase inhibitors, glucokinase activators);
6) Agents designed to reduce the absorption of glucose from the intestine (for example acarbose);
7) Agents that prevent the reabsorption of glucose by the kidney (SGLT inhibitors);
8) Agents designed to treat the complications of prolonged hyperglycaemia (for example aldose reductase inhibitors);
9) Anti-dyslipidaemia agents such as, HMG-CoA reductase inhibitors (eg statins); PPAR α-agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
10) Antihypertensive agents such as β-blockers (eg atenolol, inderal); ACE inhibitors (eg lisinopril); Calcium antagonists (eg. nifedipine); Angiotensin receptor antagonists (eg candesartan), α-antagonists and diuretic agents (eg. furosemide, benzthiazide);
11) Haemostasis modulators such as, antithrombotics, activators of fibrinolysis and antiplatelet agents; thrombin antagonists; factor Xa inhibitors; factor VIIa inhibitors); anti-platelet agents (eg. aspirin, clopidogrel); anticoagulants (heparin and Low molecular weight analogues, hirudin) and warfarin;
12) Agents which antagonise the actions of glucagon; and
13) Anti-inflammatory agents, such as non-steroidal anti-inflammatory drugs (eg. aspirin) and steroidal anti-inflammatory agents (eg. cortisone).

In addition to their use in therapeutic medicine, compounds of formula (I) and their pharmaceutically-acceptable salts are also useful as pharmacological tools in the development and standardisation of in vitro and in vivo test systems for the evaluation of the effects of inhibitors of DGAT1 activity in laboratory animals such as cats, dogs, rabbits, monkeys, rats and mice, as part of the search for new therapeutic agents.

In the above other pharmaceutical composition, process, method, use and medicament manufacture features, the alternative, particular and preferred embodiments of the compounds of the invention described herein also apply. The alternative, particular and preferred embodiments of the invention described herein also apply to a compound of formula (I), or a pharmaceutically-acceptable salt, or a pro-drug thereof.

As indicated above, all of the compounds, and their corresponding pharmaceutically-acceptable salts, are useful in inhibiting DGAT1. The ability of the compounds of formula (I), and their corresponding pharmaceutically-acceptable (acid addition) salts, to inhibit DGAT1 may be demonstrated employing the following enzyme assay:

Human Enzyme Assay

See, for example, International Application WO 2005/044250.

The in vitro assay to identify DGAT1 inhibitors uses human DGAT1 expressed in insect cell membranes as the enzyme source (Proc. Natl. Acad. Sci. 1998, 95, 13018-13023). Briefly, sf9 cells were infected with recombinant baculovirus containing human DGAT1 coding sequences and harvested after 48 h. Cells were lysed by sonication and membranes isolated by centrifuging at 28000 rpm for 1 h at 4° C. on a 41% sucrose gradient. The membrane fraction at the interphase was collected, washed, and stored in liquid nitrogen.

DGAT1 activity was assayed by a modification of the method described by Coleman (Methods in Enzymology 1992, 209, 98-102). Compound at 0.0000256 µM (or 0.003 µM)-33 µM (final conc.) (typically 10 µM) was incubated with 4 µg/ml (final conc) membrane protein, 5 mM $MgCl_2$, and 100 µM 1,2 dioleoyl-sn-glycerol (dissolved in acetone with a final assay conc. of acetone of 1.8%; other acetone concentrations may be used as appropriate, for example 10%) in a total assay volume of 200 µl in a 96 well plate. The reaction was started by adding $^{14}C$ oleoyl coenzyme A (30 µM final concentration) and incubated at room temperature for 30 minutes. The reaction was stopped by adding 200 µl 2-propanol:heptane 7:1. Radioactive triolein product was separated into the organic phase by adding 300 µl heptane and 100 µl 0.1 M carbonate buffer pH 9.5. DGAT1 activity was quantified by counting aliquots of the upper heptane layer by liquid scintillography.

Using this assay the compounds generally show activity with an $IC_{50}$ around or below 10 µM, preferably below 10 µM (i.e. $IC_{50}$<10 µM), preferably <1 µM, more preferably <0.1 µM, particularly, <0.05 µM, and more particularly <0.01 µM. Stated figures are usually a mean of a number of measurements (usually 2 measurements) according to standard practice.

In some cases % inhibition data may have been provided at a particular concentration (10 μM)

Example 1 showed an IC$_{50}$=0.016 μM (using an assay acetone concentration of 1.8%) and 0.079 μM (using an assay acetone concentration of 10%).

Examples 2 to 20 showed respectively IC$_{50}$=0.071 μM; 0.023 μM; 0.042 μM; 0.018 μM; 5.71 μM; 5.09 μM; 0.233 μM; 0.674 μM; 1.34 μM; 0.102 μM; 0.025 μM; 0.428 μM; 0.159 μM; 0.157 μM; 1.23 μM; 0.418 μM; 2.85 μM; 1.55 μM and 6.31 μM.

Examples 21 to 54 showed respectively IC$_{50}$=0.27 μM; 0.067 μM; 0.096 μM; 1 μM; 0.1 μM; 1.5 μM; 0.31 μM; 0.038 μM; 0.1 μM; 0.032 μM; 0.17 μM; 0.27 μM; 1.3 μM; 3 μM; 0.96 μM; Example 36=46-67% inhibition at 10 μM; Example 37=47-50% inhibition at 10 μM; 2.4 μM; 3 μM; 1.2 μM; 0.95 μM; 0.21 μM; 0.066 μM; 0.093 μM; 0.035 μM; 0.047 μM; 0.056 μM; 4.4 μM; 0.57 μM; 0.6 μM; 3.4 μM; 4.6 μM; 4.6 μM; 1.3 μM.

Examples 55 to 64 showed respectively IC$_{50}$=7 μM; Example 56=15-31% inhibition at 10 μM; 6.7 μM; (Example 58-no data); 0.12 μM; 0.09 μM; 0.15 μM; 8 μM; 0.18 μM; 0.67 μM.

Example 65 showed an IC$_{50}$=7.8 μM and Example 66 an IC$_{50}$=0.88 μM.

Example 67 showed IC$_{50}$=0.18 μM; Example 68=25% inhibition at 10 μM.

Examples 69 and 70 showed respectively IC$_{50}$=0.4 μM and IC$_{50}$=4.9 μM.

The ability of the compounds of formula (I), and their corresponding pharmaceutically-acceptable (acid) salts, to inhibit DGAT1 may further be demonstrated employing the following whole cell assay.

Measurement of Triglyceride Synthesis in HuTu 80 Cells

HuTu80 cells were cultured to confluency in 6 well plates in minimum essential media containing foetal calf serum. For the experiment, the medium was changed to serum-free medium and the cells pre-incubated with compound solubilised in DMSO (final concentration 0.1%) for 30 minutes. De novo lipogenesis was measured by the addition of 0.12 mM sodium oleate plus 1 μCi/mL $^{14}$C-sodium oleate complexed to 0.03 mM BSA to each well for a further 2 h. The cells were washed in phosphate buffered saline and solubilised in 1% sodium dodecyl sulfate. An aliquot was removed for protein determination using a protein estimation kit (Perbio) based on the method of Lowry (J. Biol. Chem., 1951, 193, 265-275). The lipids were extracted into the organic phase using a heptane:propan-2-ol:water (80:20:2) mixture followed by aliquots of water and heptane according to the method of Coleman (Methods in Enzymology, 1992, 209, 98-104). The organic phase was collected and the solvent evaporated under a stream of nitrogen. The extracts solubilised in iso-hexane: acetic acid (99:1) and lipids separated via normal phase high performance liquid chromatography (HPLC) using a Lichrospher diol-5, 4×250 mm column and a gradient solvent system of iso-hexane:acetic acid (99:1) and iso-hexane:propan-2-ol:acetic acid (85:15:1), flow rate of 1 mL/minute according to the method of Silversand and Haux (1997). Incorporation of radiolabel into the triglyceride fraction was analysed using a Radiomatic Flo-one Detector (Packard) connected to the HPLC machine.

EXAMPLES

The following examples are for illustration purposes and are not intended to limit the scope of this application. Each exemplified compound represents a particular and independent aspect of the invention. In the following non-limiting Examples, unless otherwise stated:

(i) evaporations were carried out by rotary evaporation under reduced pressure and work-up procedures were carried out after removal of residual solids such as drying agents by filtration;

(ii) operations were carried out at room temperature, that is in the range 18-25° C. and generally under an atmosphere of an inert gas such as argon or nitrogen;

(iii) yields are given for illustration only and are not necessarily the maximum attainable;

(iv) the structures of the end-products of the Formula (I) were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) flash chromatography was carried out on silica unless otherwise stated with flash chromatography purifications run on Biotage SP1 or SP4 instruments using Biotage Silica columns;

(vii) mass spectra were recorded on a Finnigan LCQ Duo ion trap mass spectrometer equipped with an electrospray interface (LC-MS) or LC-MS system consisting of a Waters ZQ using a LC-Agilent 1100 LC system;

(viii) $^1$H NMR measurements were performed on a Varian Mercury VXR 300 and 400 spectrometer, operating at a 1H frequency of 300 and 400 and Varian UNITY plus 400, 500 and 600 spectrometers, operating at 1H frequencies of 400, 500 and 600 respectively. Chemical shifts are given in ppm with the solvent as internal standard. Protons on heteroatoms such as NH and OH protons are only reported when detected in NMR and can therefore be missing.

(ix) HPLC separations were performed on a Waters YMC-ODS AQS-3 120 Angstrom 3×500 mm or on a Waters Delta Prep Systems using Kromasil C8, 10 μm columns. Acidic HPLC was carried out using gradients of mobilephase A: 100% ACN and mobilephase B: 5% ACN+95% H$_2$O+0.2% FA. Neutral HPLC was carried out using gradients of mobilephase A: 100% ACN and mobilephase B: 5% ACN+95% 0.1 M NH$_4$OAc.

(x) Reactions performed in a microwave oven were run in a Biotage Initiator Instrument.

(xi) A number of chemical nomenclature software packages, such as ACDName; ACDLabs Name: Release 9:00, product version 9.04 and Struc=Name/CambridgeSoft ELN, have been used in the naming of compounds.

LIST OF ABBREVIATIONS HEREIN

ACN Acetonitrile
aq Aqueous
Boc tert-butyloxycarbonyl
Brine Saturated solution of sodium chloride in water
BSA Bovine Serum Albumine
DCE 1,2-dichloroethane
DCM Dichloromethane
DEE Diethylether
DIPEA N,N-Diisopropylethylamine
DMAP Dimethylaminopyridine
DMF N,N-dimethylformamide
DMSO Dimethylsulphoxide Dppf 1,1'-bis(Diphenylphosphino)ferrocene
EDCI 1-Ethyl-3-(3-dimethylaminopropyl)carbodiimide hydrochloride
EDTA Ethylenediaminetetraacetic acid
EtOAc Ethyl acetate
EtOH Ethanol
FA Formic acid
HOAc Acetic acid
HPLC High-performance liquid chromatography
HWE Horner-Wadsworth-Emmons
Hz Hertz
IPA Isopropylalcohol
iPr isopropyl
LC Liquid chromatography
m-CPBA meta-chloroperoxybenzoicacid
MeOH Methanol
MHz Megahertz
ML Milliliter
MS Mass spectra
NMM N-methylmorpholine
NMP N-methylpiperazine
NMR Nuclear magnetic resonance
OAc acetate
Ph Phenyl
PyBOP Benzotriazol-1-yl-oxytri-pyrrolidinophosphonium hexafluorophosphate
PyBROP Bromo-tris-pyrrolidino-phosphonium hexafluorophosphate
RT Room temperature
sat saturated
TEA Triethylamine
Tf trifluoromethylsulfonyl
TFA Trifluoroacetic acid
THF Tetrahydrofurane
TLC Thin layer chromatography
Ts p-toluenesulfonyl

Example 1

{trans-4-[4-(6-Carbamoyl-3,5-dimethylpyrazin-2-yl)phenyl]cyclohexyl}acetic acid

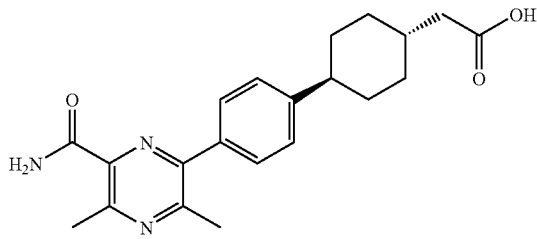

To a solution of Intermediate 1-1 (363 mg, 0.86 mmol) in DCM (30 mL) was added TFA (3 mL) dropwise. The colorless solution gradually turned into pale yellow clear solution. The reaction mixture was stirred under $N_2$ at RT overnight. The solvent was evaporated to give the title compound (100%).

$^1$H NMR (600 MHz, CD$_3$OD) δ 1.22 (q, 2H), 1.59 (q, 2H), 1.85 (s, 1H), 1.94 (d, 4H), 2.23 (d, 2H), 2.58 (t, 1H), 2.62 (s, 3H), 2.84 (s, 3H), 7.37 (d, 2H), 7.58 (d, 2H); m/z 368 (M+H)$^+$.

Intermediate 1-1: tert-Butyl {trans-4-[4-(6-carbamoyl-3,5-dimethylpyrazin-2-yl)phenyl]cyclohexyl}acetate

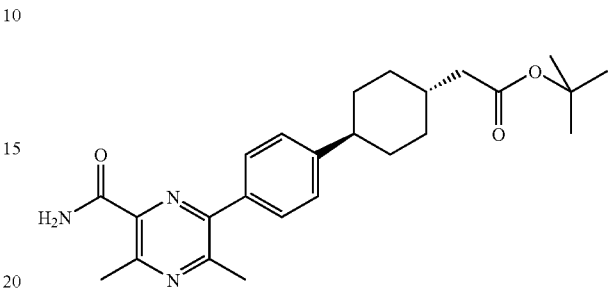

To a solution of PyBOP (717 mg, 1.38 mmol) and NH$_4$Cl (196.6 mg, 3.68 mmol) in DMF (50 mL) was added Intermediate 1-2 (390.0 mg, 0.92 mmol) and finally DIPEA (0.80 mL, 4.59 mmol) to initiate the reaction. The solution was stirred for 5 h at RT. The reaction was quenched by the addition of sat Na$_2$CO$_3$ and extracted with toluene (3×100 mL). The combined organics were washed with brine and water, dried over Na$_2$SO$_4$, filtered and concentrated under reduced pressure. The crude material was purified by flash chromatography using EtOAc (20-60%) in petroleum ether. Evaporation of pure product fractions gave title compound (376 mg, 96%) as white solid.

$^1$H NMR (400 MHz, CDCl$_3$) δ 1.20 (q, 2H), 1.47 (s, 9H), 1.50-1.64 (m, 2H), 1.80-2.00 (m, 5H), 2.17 (d, 2H), 2.56 (t, 1H), 2.67 (t, 3H), 2.98 (t, 3H), 5.43 (s, 1H), 7.33 (d, 2H), 7.52 (d, 2H), 7.81 (d, 2H); m/z 424 (M+H)$^+$.

Intermediate 1-2: 6-{4-[trans-4-(2-tert-Butoxy-2-oxoethyl)cyclohexyl]phenyl}-3,5-dimethylpyrazine-2-carboxylic acid

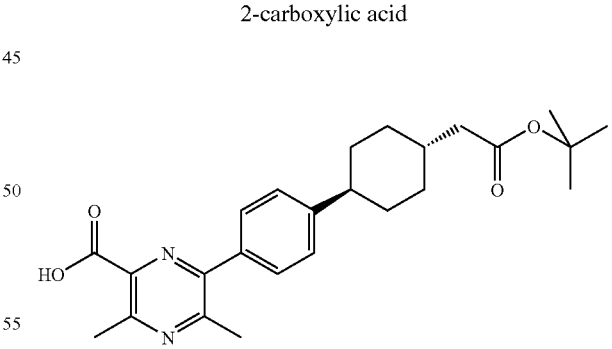

To a solution of Intermediate 1-3 (0.530 g, 1.17 mmol) in THF (10 mL) was added LiOH (1M, 15 mL). The reaction was stirred at room temperature for 5 h. THF was removed under vacuum and the aqueous residue was acidified with 1M HCl and extracted with EtOAc. The organic layer was dried through a phase separator and concentrated to give the title compound (0.5 g, 100%).

$^1$H NMR (500 MHz, CDCl$_3$) δ 1.12-1.21 (m, 2H), 1.45 (s, 9H), 1.49-1.57 (m, 2H), 1.79-1.96 (m, 5H), 2.15 (d, 2H), 2.51-2.57 (m, 1H), 2.70 (s, 3H), 2.97 (s, 3H), 7.33 (d, 2H), 7.48 (d, 2H); m/z 425 (M+H)+.

Intermediate 1-3: Ethyl 6-{4-[trans-4-(2-tert-butoxy-2-oxoethyl)cyclohexyl]phenyl}-3,5-dimethylpyrazine-2-carboxylate

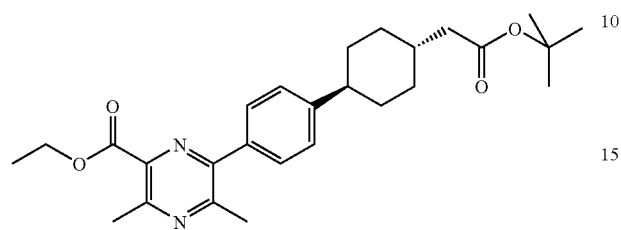

To a solution of Intermediate 1-4 (0.580 g, 2.70 mmol) in DME (22 mL), EtOH (12 mL) and water (5 mL) was added Intermediate D (see after Intermediate 1-7; 1.244 g, 3.11 mmol), potassium phosphate, tribasic (0.688 g, 3.24 mmol) and PdCl$_2$(dppf) (0.119 g, 0.16 mmol). The solutions degassed with nitrogen for 10 min and then heated in the microwave oven at 140° C. for 20 min. Additional amounts of Intermediate D and PdCl$_2$(dppf) was added to drive the reaction. The microwave heating was continued at 140° C. for an additional 30 min.

(The ethyl ester can be hydrolyzed here by prolonging the heating time and adding 3 extra equivalents of potassium phosphate, to give Intermediate 1-2.)

The mixtures were combined, filtered through a glass filter funnel and evaporated. The remaining black residue was dissolved in EtOAc, washed with 0.5M HCl and extracted with 2×EtOAc. The combined organics were dried through a phase separator and concentrated. The crude was purified by flash chromatography using EtOAc (0-50%) in heptane as eluent. Evaporation gave title compound (1.063 g, 80%) as oil.

$^1$H NMR (500 MHz, CDCl$_3$) δ 1.13-1.22 (m, 2H), 1.42 (t, 3H), 1.47 (s, 9H), 1.49-1.58 (m, 2H), 1.80-1.95 (m, 5H), 2.16 (d, 2H), 2.49-2.56 (m, 1H), 2.66 (s, 3H), 2.81 (s, 3H), 4.45 (q, 2H), 7.30 (d, 2H), 7.53 (d, 2H); m/z 453 (M+H)+.

Intermediate 1-4: Ethyl 6-chloro-3,5-dimethylpyrazine-2-carboxylate

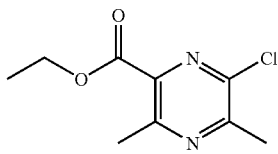

To a suspension of Intermediate 1-5 (0.23 g, 1.17 mmol) in butyronitrile (4 mL) was added POCl$_3$ (0.27 mL, 2.93 mmol). The reaction was heated to 150° C. for 10 min in the microwave oven and cooled to RT. To the reaction mixture was added water (2 mL) and the phases were separated. The organic layer was concentrated under reduced pressure. The crude product was purified by flash chromatography using 0.5% HOAc in DCM as eluent to afford the title compound (0.18 g, 73%).

$^1$H NMR (500 MHz, CDCl$_3$) δ 1.43 (t, 3H), 2.68 (s, 3H), 2.78 (s, 3H), 4.46 (q, 2H); m/z 215 (M+H)+.

Intermediate 1-5: Ethyl 3,5-dimethyl-6-oxo-1,6-dihydropyrazine-2-carboxylate

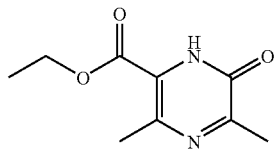

To a solution of Intermediate 1-6 (800 mg, 2.53 mmol) in dry DCE (40 mL) was added TFA (1.95 mL, 25.3 mmol). The reaction mixture was heated to reflux for 4 h. The solvent was evaporated and the crude product was purified by flash chromatography using EtOAc (20-80%) in heptane as eluent. Concentration of pure fractions gave title compound (160 mg, 32%) as white-yellow powder. The crude from this reaction can optionally be used directly in the next step without purification.

$^1$H NMR (400 Mhz, CDCl$_3$) δ 4.42 (q, 2H), 2.61 (s, 3H), 2.52 (s, 3H), 1.41 (t, 3H); m/z 197 (M+H)+.

Intermediate 1-6: Ethyl 2-{[N-(tert-butoxycarbonyl)-L-alanyl]amino}-3-oxobutanoate

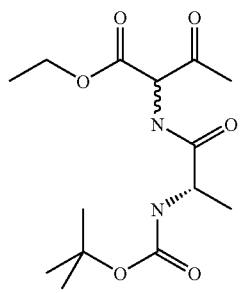

Intermediate 1-7 (500 mg, 3.2 mmol) and BOC-Ala-NH$_2$ (843.8 mg, 4.5 mmol, CAS 85642-13-3) were added to a round bottomed flask, sealed and backfilled with argon. Dry toluene (30 mL) was added via syringe and the resulting heterogeneous mixture was stirred at 90° C. for 10 min to get a homogeneous solution. Meanwhile, the rhodium (II) octanoate dimer (62.3 mg, 0.080 mmol, CAS 73482-96-9) was dissolved in toluene (5 mL) and put on an ultrasound bath for 5 min, to get a fine Rh-dispersion. This dispersion was then added dropwise to the reaction mixture at 80° C. (a violent N$_2$ effervescence was observed). After stirring another 20 min at elevated temperature the reaction mixture was concentrated under reduced pressure to give a black pasty solid. The N—H insertion product could here be purified or taken directly to the next step. The crude was purified by flash chromatography using EtOAc (20-80%) in heptane to afford the title compound (850 mg, 84%) (diastereomeric mixture) as a yellow oil. m/z 317 (M+H)+.

Intermediate 1-7: Ethyl 2-diazo-3-oxobutanoate

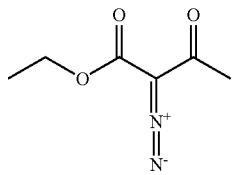

Polymer-bound tosylazide (11 g, 15.4 mmol) (typical loading 1.4 mmol/g, prepared according to Merz et al *J. Org. Chem.* 2001, 66, 2509-2511) was swollen in dry DCM (40 mL). Ethyl acetoacetate (1.0 g, 7.7 mmol, CAS 141-97-9) and TEA (3.2 mL, 23.1 mmol) were dissolved in DCM (10 mL) and added to the polymer containing solution. The resulting mixture was then shaken at RT under nitrogen until the reaction was judged completed by TLC, typically 6 h. The supernatant was filtered off, then the resin was washed with DCM (3×30 mL) to rinse out residual product. The reaction mixture was then evaporated to dryness to afford the title compound (1.1 g, 92%) as yellow oil.

$^1$H NMR (400 MHz, CDCl$_3$) δ 4.28 (q, 2H), 2.45 (s, 3H), 1.33 (t, 3H).

Typically these intermediates were not characterized due to their high-energetic properties (Clark et al, *Thermochimica Acta*, 386, 2002, 73-79), but carried through to the next step as crude products.

Preparation of Intermediate D

Intermediate A: tert-Butyl [4-(4-hydroxyphenyl)cyclohexylidene]acetate

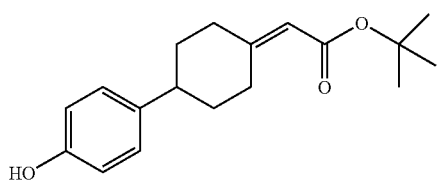

To an ice-cold solution of 4-(4-hydroxy-phenyl)-cyclohexanone (15.22 g, 78.4 mmol, CAS 105640-07-1) in THF (375 mL) under N$_2$ was added NaH in mineral oil (3.28 g, 79.3 mmol) to give a thick suspension.

In a separate flask NaH in mineral oil (4.06 g, 98.0 mmol) was suspended in dry THF (375 mL) under N$_2$. The suspension was cooled to 0° C. and tert-butyl P,P-dimethyl phosphonoacetate (16.82 mL, 82.32 mmol, CAS 62327-21-3) was added carefully. Both mixtures were stirred for ~15 min before the ice-baths were removed. After 2 h at RT the ketone solution was transferred to the ylide solution via syringe. The combined mixture was stirred under N$_2$ overnight. The reaction was quenched by the addition of water (~100 mL) and THF was then removed under vacuum. More water was added (150 mL) and the aqueous solution was extracted with EtOAc (3×200 mL). The combined organic layer was washed with brine (2×200 mL) and dried through a phase separator. Concentration gave product as colorless oil (24.6 g, 99%).

$^1$H NMR (500 MHz, CDCl$_3$) δ 1.51 (s, 9H), 1.55-1.65 (m, 2H), 1.97-2.07 (m, 3H), 2.29-2.40 (m, 2H), 2.70-2.78 (m, 1H), 3.90-3.96 (m, 1H), 4.60 (s, 1H), 5.62 (s, 1H), 6.77 (d, 2H), 7.09 (d, 2H). m/z 287 (M–H)$^-$.

Intermediate B: tert-Butyl [trans-4-(4-hydroxyphenyl)cyclohexyl]acetate

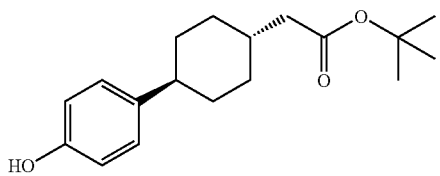

To a solution of Intermediate A (4.2 g, 14.56 mmol) in EtOAc (120 mL) was added 10% Pd/C (390 mg). The reaction was hydrogenated for 3 h (5 Bar). The catalyst was filtered off through Celite and the organic filtrate was washed with water, dried through a phase separator and concentrated to a colorless oil (4.02 g of cis:trans mixture). The crude mixture was purified by chiral HPLC (neutral) using a Chiralpak AD (250×50 mm) column and 100% ACN as mobile phase. Purification gave pure trans phenol (2.88 g, 68%) as white solid and also pure cis phenol. NMR analysis of both isomers confirmed that the wanted (major) isomer was trans.

$^1$H NMR (500 MHz, CDCl$_3$) δ 1.10-1.20 (m, 2H), 1.42-1.52 (m, 2H), 1.48 (s, 9H), 1.77-1.92 (m, 5H), 2.17 (d, 2H), 2.38-2.45 (m, 1H), 4.7-4.9 (m, 1H), 6.78 (d, 2H), 7.09 (d, 2H); m/z 289 (M–H)$^-$.

Intermediate C: tert-Butyl [trans-4-(4-{[(trifluoromethyl)sulfonyl]oxy}phenyl)cyclohexyl]acetate

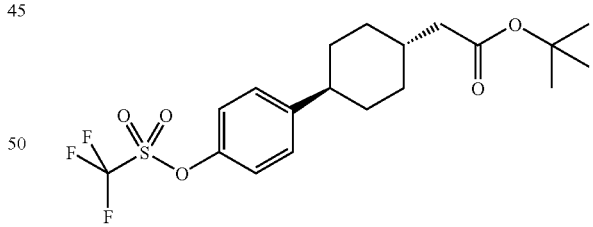

To a solution of Intermediate B (2.86 g, 9.85 mmol) in DCM (75 mL) was added pyridine (1.59 mL, 19.7 mmol). The solution was cooled on an ice-bath and trifluoromethanesulfonic anhydride (1.99 mL, 11.82 mmol, CAS 358-23-6) was added dropwise. The ice-bath was removed and the reaction was stirred for 10 min. The reaction was quenched with 1M HCl, diluted with DCM and washed with saturated NaHCO$_3$ and brine. The organic layer was dried through a phase separator and concentrated. The crude product was filtered through silica using 8% EtOAc in heptane as eluent. Concentration of pure product fractions gave title compound (4.06 g, 98%) as white crystalline solid.

¹H NMR (500 MHz, CDCl₃) δ 1.12-1.22 (m, 2H), 1.45-1.54 (m, 2H), 1.48 (s, 9H), 1.79-1.88 (m, 1H), 1.89-1.95 (m, 4H), 2.17 (d, 2H), 2.48-2.56 (m, 1H), 7.20 (d, 2H), 7.28 (d, 2H); m/z 421 (M–H)⁻.

Intermediate D: tert-Butyl {trans-4-[4-(4,4,5,5-tetramethyl-1,3,2-dioxaborolan-2-yl)phenyl]cyclohexyl}acetate

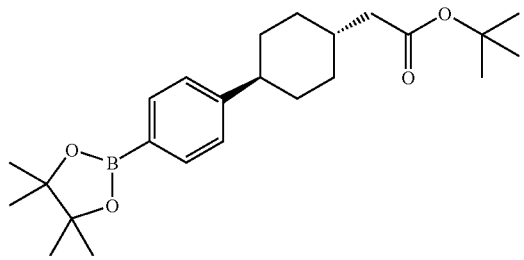

To a suspension of PdCl₂(dppf) (0.93 g, 1.27 mmol, CAS 72287-26-4) in dioxane (135 mL) under N₂ was added Intermediate C (17.9 g, 42.4 mmol), TEA (17.7 mL, 127 mmol) and finally a 1M solution of 4,4,5,5-tetramethyl-1,3,2-dioxaborolane in THF (72 mL, 72 mmol, CAS 25015-63-8). The mixture was refluxed for 7 h, cooled to 10° C. and quenched carefully with H₂O. The aqueous solution was extracted with 2×DCM and the combined organics were dried through a phase separator and concentrated to a black oil. Flash chromatography using 6% EtOAc in heptane as eluent gave title compound (12.1 g, 71%) as white powder.

¹H NMR (500 MHz, CDCl₃) δ 1.12-1.22 (m, 2H), 1.36 (s, 12H), 1.49 (s, 9H), 1.48-1.61 (m, 2H), 1.80-1.95 (m, 5H), 2.17 (d, 2H), 2.46-2.54 (m, 1H), 7.25 (d, 2H), 7.78 (d, 2H). m/z no ionization.

Example 2

3,5-Dimethyl-6-[4-(trans-4-{2-[(methylsulfonyl)amino]-2-oxoethyl}cyclohexyl)phenyl]pyrazine-2-carboxamide

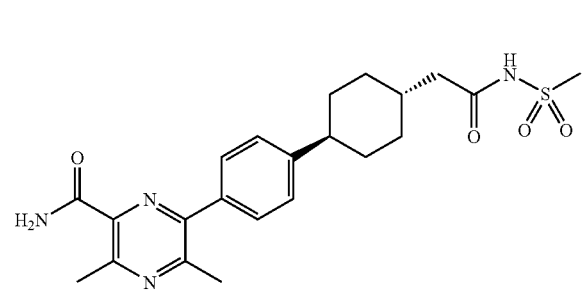

To a solution of Example 1 (30 mg, 0.082 mmol) in DCM was added DMAP (2 mg, 0.02 mmol), TEA (16 μL, 0.122 mmol), EDCI (20 mg, 0.11 mmol) and finally methanesulfonamide (11 mg, 0.11 mmol, CAS 3144-09-0). The solution was stirred at RT overnight. The crude was concentrated and purified by HPLC (acidic). Evaporation and co-evaporation with toluene gave title compound (22 mg, 60%).

¹H NMR (500 MHz, CDCl₃) δ 1.08-1.18 (m, 2H), 1.45-1.56 (m, 2H), 1.76-1.86 (m, 5H), 2.20 (d, 2H), 2.42-2.52 (m, 1H), 2.57 (s, 3H), 2.72 (s, 3H), 3.22 (s, 3H), 7.35 (d, 2H), 7.59 (s, 1H), 7.64 (d, 2H), 7.99 (s, 1H), 11.67 (s, 1H); m/z 445 (M+H)⁺.

Example 3

6-{4-[trans-4-(2-Amino-2-oxoethyl)cyclohexyl]phenyl}-3,5-dimethylpyrazine-2-carboxamide

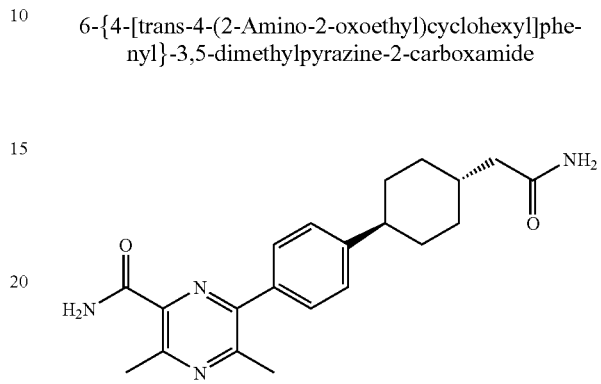

This compound was synthesised from Example 1 using similar conditions as described in Intermediate 1-1 to afford title compound (40 mg, 38%) as white solid.

¹H NMR (500 MHz, DMSO) δ 1.05-1.15 (m, 2H), 1.43-1.53 (m, 2H), 1.69-1.86 (m, 5H), 1.97 (d, 2H), 2.47-2.55 (m, 1H), 2.58 (s, 3H), 2.72 (s, 3H), 6.71 (s, 1H), 7.24 (s, 1H), 7.35 (d, 2H), 7.59 (s, 1H), 7.64 (d, 2H), 7.99 (s, 1H); m/z 367 (M+H)⁺.

Example 4

N-({trans-4-[4-(6-Carbamoyl-3,5-dimethylpyrazin-2-yl)phenyl]cyclohexyl}acetyl)-2-methylalanine

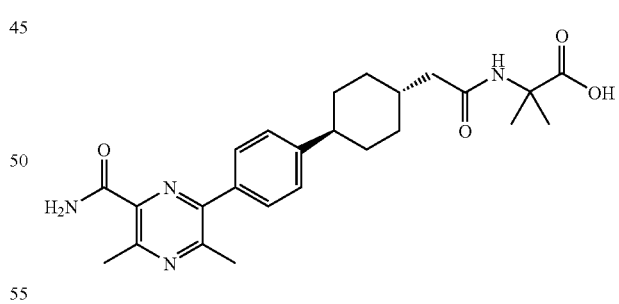

This compound was synthesised from Example 1 and alpha-aminoisobutyric acid methyl ester hydrochloride (CAS 15028-41-8) using similar conditions as in Intermediate 1-1. The intermediate methyl ester was hydrolysed to the corresponding acid using similar protocol as described in Intermediate 1-2.

¹H NMR (500 MHz, DMSO) δ 1.04-1.14 (m, 2H), 1.31 (s, 6H), 1.43-1.53 (m, 2H), 1.67-1.75 (m, 1H), 1.77-1.85 (m, 4H), 1.96 (d, 2H), 2.48-2.56 (m, 1H), 2.57 (s, 3H), 2.72 (s,

3H), 7.35 (d, 2H), 7.59 (br s, 1H), 7.64 (d, 2H), 7.77-7.82 (m, 1H), 8.00 (br s, 1H); m/z 453 (M+H)⁺.

Example 5

6-{4-[trans-4-(2-Hydroxyethyl)cyclohexyl]phenyl}-3,5-dimethylpyrazine-2-carboxamide

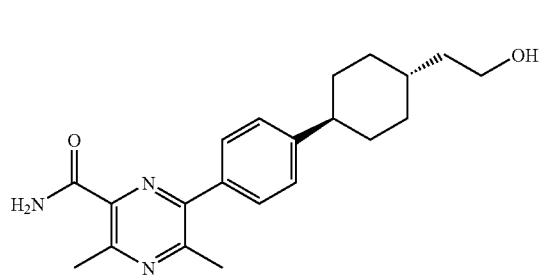

To a suspension of Example 1 (50 mg, 0.14 mmol) and NMM (71 µL, 0.64 mmol) in THF (1 mL) at 0° C. was added a solution of ethyl chloroformate (61 µL, 0.64 mmol) in THF (0.5 mL). The reaction was stirred at 0° C. for ~3 h, but additional equivalents of NMM and ethyl chloroformate were needed during this time to drive the reaction. The reaction mixture was added dropwise to a solution of NaBH₄ in water at 0-5° C. and the combined mixture was stirred for 30 min. The mixture was partitioned between EtOAc and 1M HCl and the organic layer was washed with water, dried through a phase separator and concentrated. The crude was dissolved in DMSO and purified by HPLC (neutral). Freeze-drying of pure fractions gave the title compound (8 mg, 17%) as white powder.

$^1$H NMR (500 MHz, DMSO) δ 1.02-1.14 (m, 2H), 1.34-1.54 (m, 5H), 1.80-1.87 (m, 4H), 2.47-2.57 (m, 1H), 2.58 (s, 3H), 2.73 (s, 3H), 3.43-3.51 (m, 2H), 4.30-4.35 (m, 1H), 7.35 (d, 2H), 7.60 (br s, 1H), 7.65 (d, 2H), 7.99 (br s, 1H); m/z 354 (M+H)⁺.

Example 6 cis-4-{[5-(6-Carbamoyl-3,5-dimethylpyrazin-2-yl)pyridin-2-yl]oxy}cyclohexanecarboxylic acid

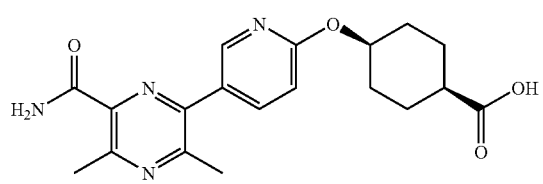

A solution of Intermediate 6-1 (0.0243 g, 0.06 mmol) in 10 mL of a 4.0 M solution of HCl in 1,4-dioxane and a few drops of water was stirred at 40° C. for 5 h. The solvent was evaporated and the remaining solid was purified by HPLC (acidic) to afford the title compound (8.7 mg, 42%) as a dry film.

$^1$H NMR (500 MHz, CD₃OD) δ 1.72-1.83 (m, 4H), 1.90-2.07 (m, 4H), 2.47 (m, 1H), 2.67 (s, 3H), 2.85 (s, 3H), 5.27 (s, 1H), 6.92 (d, 1H), 8.03 (dd, 1H), 8.45 (s, 1H); m/z 371 (M+H)⁺.

Intermediate 6-1: tert-Butyl cis-4-{[5-(6-carbamoyl-3,5-dimethylpyrazin-2-yl)pyridin-2-yl]oxy}cyclohexanecarboxylate

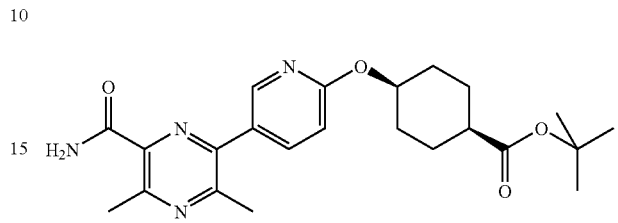

This compound was synthesised from Intermediate 6-2 using similar procedure as described in Intermediate 1-1. Purification gave title product (24.3 mg, 68%) as white solid.

$^1$H NMR (500 MHz, CDCl₃) δ 1.45 (s, 9H), 1.67-1.79 (m, 4H), 1.85-2.07 (m, 4H), 2.34 (m, 1H), 2.68 (s, 3H), 2.96 (s, 3H), 5.28 (s, 1H), 5.77 (s, 1H), 6.84 (d, 1H), 7.76 (s, 1H), 7.82 (dd, 1H), 8.39 (s, 1H); m/z 427 (M+H)⁺.

Intermediate 6-2: 6-(6-{[cis-4-(tert-Butoxycarbonyl)cyclohexyl]oxy}pyridin-3-yl)-3,5-dimethylpyrazine-2-carboxylic acid

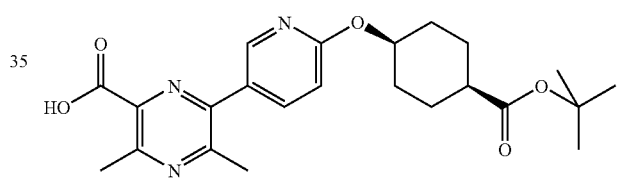

This compound was synthesised from Intermediate 6-3 and Intermediate 1-4 using similar Suzuki conditions as in Intermediate 1-3 to afford the title compound (36 mg, 45%) as white solid.

$^1$H NMR (500 MHz, CDCl₃) δ 1.44 (s, 9H), 1.67-1.79 (m, 4H), 1.84-2.05 (m, 4H), 2.34 (m, 1H), 2.72 (s, 3H), 2.97 (s, 3H), 5.27 (s, 1H), 6.85 (d, 1H), 7.80 (d, 1H), 8.37 (s, 1H); m/z 428 (M+H)⁺.

Intermediate 6-3: tert-Butyl cis-4-{[5-(4,4,5,5-tetramethyl-1,3,2-dioxaborolan-2-yl)pyridin-2-yl]oxy}cyclohexanecarboxylate

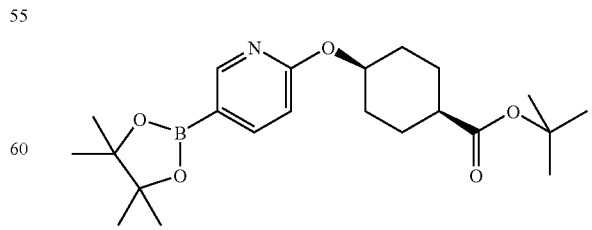

Intermediate 6-4 (0.124 g, 0.35 mmol), 4,4,4',4',5,5,5',5'-octamethyl-2,2'-bi(1,3,2-dioxaborolane) (0.121 g, 0.48 mmol, CAS 73183-34-3) and potassium acetate (0.139 g, 1.41 mmol) in 1,4-dioxane (10 mL) was degassed prior to addition of PdCl$_2$(dppf) (0.013 g, 0.02 mmol) under N$_2$. The reaction was heated at 85° C. for 16 h. The solvent was evaporated and the crude was dissolved in EtOAc, washed with water (2×25 mL), organics dried over Na$_2$SO$_4$, filtered and evaporated. The brownish oil was purified by flash chromatography using 5-50% EtOAc in heptane to afford the title compound (74 mg, 52%) as a dry film.

$^1$H NMR (500 MHz, CDCl$_3$) δ 1.30 (s, 12H), 1.43 (s, 9H), 1.59-1.77 (m, 4H), 1.80-2.00 (m, 4H), 2.29 (m, 1H), 5.25 (m, 1H), 6.67 (d, 1H), 7.88 (dd, 1H), 8.48 (d, 1H).

Intermediate 6-4: tert-Butyl cis-4-[(5-bromopyridin-2-yl)oxy]cyclohexane carboxylate

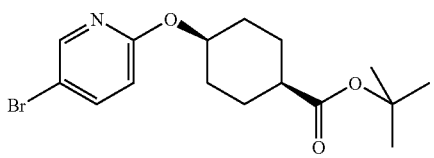

A solution of Intermediate 6-5 (0.224 g, 0.75 mmol) in 1,1-di-tert-butoxy-N,N-dimethylmethaneamine (0.893 mL, 3.72 mmol, CAS 36805-97-7) were heated at 120° C. in a microwave oven for 45 min. The crude was purified by flash chromatography using EtOAc (5-70%) in heptane to afford the title compound (124 mg, 46%) as white solid.

$^1$H NMR (500 MHz, CDCl$_3$) δ 1.43 (s, 9H), 1.58-1.75 (m, 4H), 1.82-2.00 (m, 4H), 2.3 (m, 1H), 5.13 (m, 1H), 6.61 (d, 1H), 7.59 (dd, 1H), 8.12 (d, 1H); m/z 357 (M+H)$^+$.

Intermediate 6-5: cis-4-[(5-Bromopyridin-2-yl)oxy]cyclohexanecarboxylic acid

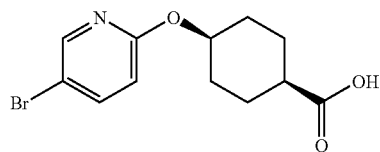

A solution of (1S,4S)-4-hydroxycyclohexanecarboxylic acid (2.14 g, 14.9 mmol) in DMA (10 mL) was added to a stirred suspension of NaH (1.32 g, 30.2 mmol) in DMA (15 mL) at 0° C. where it was stirred for 10 min. The suspension was taken off the cooling bath and 5-bromo-2-fluoropyridine (1.53 mL, 14.87 mmol, CAS 766-11-0) was added followed by DMA (10 mL). The reaction was heated at 100° C. for 2.5 h. The solvent was evaporated and DCM and 2M HCl were added, the phases separated and the aqueous phase was extracted with DCM (2×50 mL). The combined organics were dried over MgSO$_4$, filtered and evaporated. The remaining crude was purified by flash chromatography using 5-75% EtOAc (1% HOAc) in heptane to afford the title compound (1.86 g, 42%) as solid.

$^1$H NMR (500 MHz, CDCl$_3$) δ 1.70 (t, 2H), 1.75-1.86 (m, 2H), 1.90-2.06 (m, 4H), 2.49 (m, 1H), 5.18 (m, 1H), 6.64 (d, 1H), 7.62 (dd, 1H), 8.16 (d, 1H); m/z 301 (M+H)$^+$.

Example 7

(cis-4-{[5-(6-Carbamoyl-3,5-dimethylpyrazin-2-yl)pyridin-2-yl]oxy}cyclohexyl)acetic acid

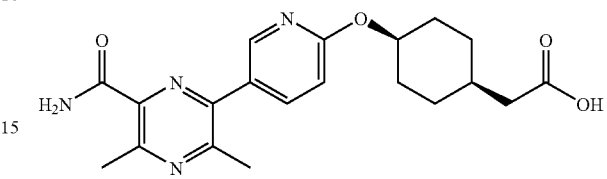

This compound was synthesised from Intermediate 7-1 using similar conditions as described in Example 1 to give the title compound (15 mg, 42%) as white solid.

$^1$H NMR (500 MHz, CD$_3$OD) δ 1.51 (t, 2H), 1.61-1.75 (m, 4H), 1.91 (m, 1H), 2.05 (d, 2H), 2.25 (d, 2H), 2.66 (s, 3H), 2.84 (s, 3H), 5.29 (s, 1H), 6.91 (d, 1H), 8.02 (dd, 1H), 8.44 (s, 1H); m/z 385 (M+H)$^+$.

Intermediate 7-1: tert-Butyl (cis-4-{[5-(6-carbamoyl-3,5-dimethylpyrazin-2-yl)pyridin-2-yl]oxy}cyclohexyl)acetate

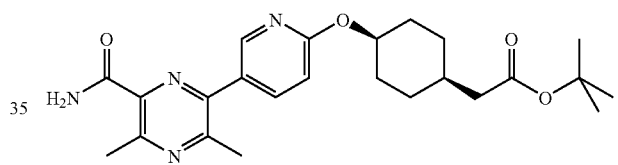

This compound was synthesised from Intermediate 7-2 using similar conditions as described in Intermediate 1-1 to afford the title compound (42 mg, 66%) as white solid.

$^1$H NMR (500 MHz, CDCl$_3$) δ 1.39-1.50 (m, 11H), 1.55-1.69 (m, 4H), 1.87 (m, 1H), 2.02-2.06 (m, 2H), 2.16 (d, 2H), 2.66 (s, 3H), 2.93 (s, 3H), 5.29 (s, 1H), 6.40 (s, 1H), 6.80 (d, 1H), 7.75-7.82 (m, 2H), 8.37 (d, 1H); m/z 441 (M+H)$^+$.

Intermediate 7-2: 6-(6-{[cis-4-(2-tert-Butoxy-2-oxoethyl)cyclohexyl]oxy}pyridin-3-yl)-3,5-dimethylpyrazine-2-carboxylic acid

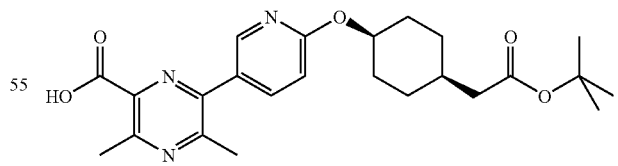

This compound was synthesised from Intermediate 7-3 and Intermediate 1-4 using similar conditions as described in Intermediate 1-3 to afford the title compound (64 mg, 44%) as white solid.

$^1$H NMR (500 MHz, CDCl$_3$) δ 1.38-1.51 (m, 11H), 1.56-1.69 (m, 4H), 1.88 (m, 1H), 2.03 (d, 2H), 2.17 (d, 2H), 2.71 (s, 3H), 2.94 (s, 3H), 5.29 (s, 1H), 6.82 (d, 1H), 7.80 (d, 1H), 8.37 (s, 1H), 9.94 (s, 1H); m/z 442 (M+H)$^+$.

Intermediate 7-3: tert-Butyl (cis-4-{[5-(4,4,5,5-tetramethyl-1,3,2-dioxaborolan-2-yl)pyridin-2-yl]oxy}cyclohexyl)acetate

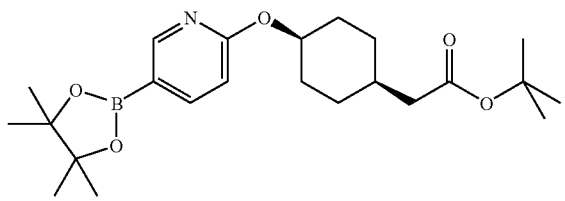

This compound was synthesised from Intermediate 7-4 using similar conditions as described in Intermediate 6-3 to afford the title compound (0.149 g, 43%) as white solid.

$^1$H NMR (500 MHz, CDCl$_3$) δ 1.43 (s, 12H), 1.39-1.50 (m, 11H), 1.53-1.67 (m, 4H), 1.87 (m, 1H), 2.00 (d, 2H), 2.16 (d, 2H), 5.30 (s, 1H), 6.67 (d, 1H), 7.89 (dd, 1H), 8.50 (d, 1H).

Intermediate 7-4: tert-Butyl{cis-4-[(5-bromopyridin-2-yl)oxy]cyclohexyl}acetate

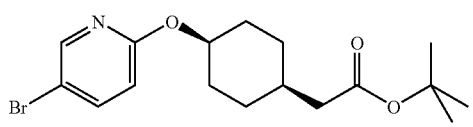

This compound was synthesised from Intermediate 7-5 using similar conditions as described in Intermediate 6-4 to afford the title compound (0.303 g, 43%) as white solid.

$^1$H NMR (500 MHz, CDCl$_3$) δ 1.35-1.46 (m, 11H), 1.52-1.63 (m, 4H), 1.85 (m, 1H), 1.96 (d, 2H), 2.14 (d, 2H), 5.16 (s, 1H), 6.59 (d, 1H), 7.58 (dd, 1H), 8.13 (d, 1H); m/z 372 (M+H)$^+$.

Intermediate 7-5: {cis-4-[(5-Bromopyridin-2-yl)oxy]cyclohexyl}acetic acid

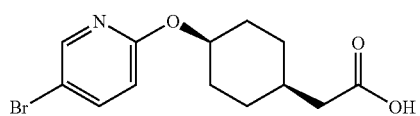

This compound was synthesised from Intermediate 7-6 using similar conditions as described in Intermediate 6-5 to afford the title compound (1.287 g, 68%) as white solid.

$^1$H NMR (400 MHz, CDCl$_3$) δ 1.44-1.52 (m, 2H), 1.58-1.68 (m, 4H), 1.93 (m, 1H), 2.00 (d, 2H), 2.31 (d, 2H), 5.19 (s, 1H), 6.63 (d, 1H), 7.62 (dd, 1H), 8.16 (d, 1H); m/z 316 (M+H)$^+$.

Intermediate 7-6: (cis-4-Hydroxycyclohexyl)acetic acid

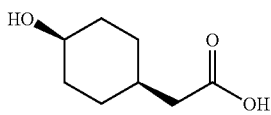

This compound was synthesised from Intermediate 7-7 using similar conditions as described in Intermediate 1-2 to afford the title compound (0.943 g, 100%) as white solid.

$^1$H NMR (500 MHz, CD$_3$OD) δ 1.39-1.60 (m, 6H), 1.65-1.73 (m, 2H), 1.83 (m, 1H), 2.10 (d, 2H), 3.85 (m, 1H).

Intermediate 7-7: Methyl (cis-4-hydroxycyclohexyl)acetate

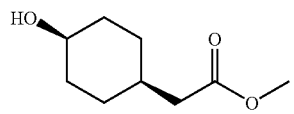

A solution of methyl 4-hydroxyphenylacetate (10.01 g, 60.2 mmol, CAS 14199-15-6), rhodium (5% on Alumina) (0.073 g, 0.71 mmol) in MeOH (30 mL) was hydrogenated at 8 bar. The crude was filtered through Celite and concentrated at reduced pressure. The remaining colorless oil was dissolved in isohexane and EtOAc and purified by flash chromatography using EtOAc (20-50%) in isohexane to afford the title cis compound (4.31 g, 42%) as colorless oil. NMR analysis of both trans and cis isomers were compared to make sure that the right isomer was used in subsequent steps.

$^1$H NMR (500 MHz, CDCl$_3$) δ 1.40-1.48 (m, 2H), 1.48-1.62 (m, 4H), 1.66-1.74 (m, 2H), 1.86 (m, 1H), 2.24 (d, 2H), 3.66 (s, 3H), 3.97 (s, 1H).

Example 8

(trans-4-{4-[6-Carbamoyl-5-(difluoromethyl)-3-methylpyrazin-2-yl]phenyl}cyclohexyl)acetic acid

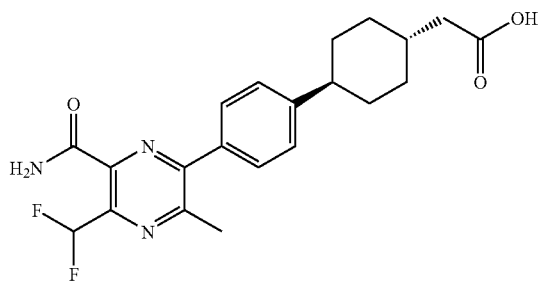

This compound was synthesised from Intermediate 8-1 using similar conditions as described in Example 1 to give the title compound (3.8 mg, 31%).

$^1$H NMR (500 MHz, CD$_3$OD) δ 1.17-1.30 (m, 2H), 1.54-1.67 (m, 2H), 1.80-2.00 (m, 5H), 2.24 (d, 2H), 2.56-2.65 (m, 1H), 2.74 (s, 3H), 7.42 (m, 2H), 7.67 (m, 2H), 7.79 (t, 1H); m/z 404 (M+H)$^+$.

Intermediate 8-1: tert-Butyl (trans-4-{4-[6-carbamoyl-5-(difluoromethyl)-3-methylpyrazin-2-yl]phenyl}cyclohexyl)acetate

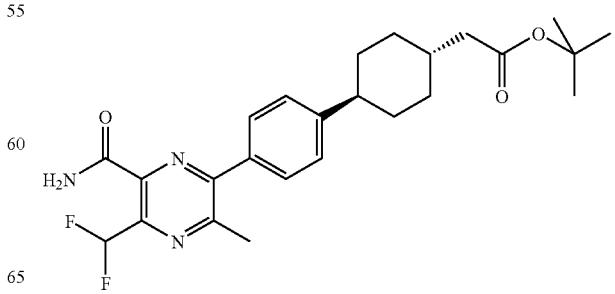

This compound was synthesised from Intermediate 8-2 using similar conditions as described in Intermediate 1-1 to give the title compound (11 mg, 44%).
$^1$H NMR (500 MHz, CDCl$_3$) δ 1.14-1.24 (m, 2H), 1.47 (s, 9H), 1.51-1.63 (m, 2H), 1.80-2.01 (m, 5H), 2.18 (d, 2H), 2.53-2.62 (m, 1H), 2.81 (s, 3H), 5.72 (s, 1H), 7.37 (m, 2H), 7.56 (m, 2H), 7.84 (s, 1H), 7.97 (t, 1H); m/z 460 (M+H)$^+$.

Intermediate 8-2: 6-{4-[trans-4-(2-tert-Butoxy-2-oxoethyl)cyclohexyl]phenyl}-3-(difluoromethyl)-5-methylpyrazine-2-carboxylic acid

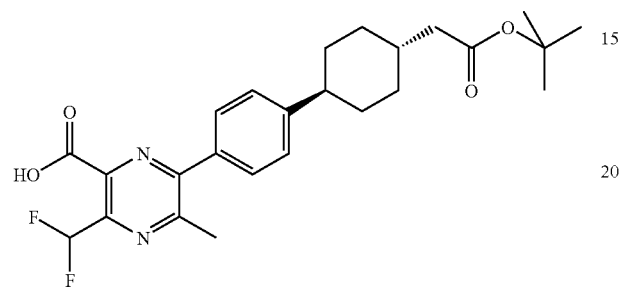

This compound was synthesised from Intermediate 8-3 using similar conditions as described in Intermediate 1-3 to give the title compound (25 mg, 44%).
$^1$H NMR (500 MHz, CDCl$_3$) δ 1.14-1.25 (m, 2H), 1.47 (s, 9H), 1.51-1.61 (m, 2H), 1.80-2.01 (m, 5H), 2.14-2.21 (m, 2H), 2.53-2.63 (m, 1H), 2.86 (s, 3H), 7.35-7.60 (m, 4H), 7.83 (t, 1H); m/z 461 (M+H)$^+$.

Intermediate 8-3: Ethyl 6-bromo-3-(difluoromethyl)-5-methylpyrazine-2-carboxylate

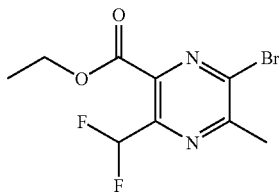

This compound was synthesised from Intermediate 8-4 using similar procedure as described in Intermediate 9-3 to afford the title compound (36 mg, 37%).
$^1$H NMR (500 MHz, CDCl$_3$) δ 1.45 (t, 3H), 2.83 (s, 3H), 4.50 (q, 2H), 7.24 (t, J=55 Hz, 1H); m/z 295 (M+H)$^+$.

Intermediate 8-4: Ethyl 3-(difluoromethyl)-5-methyl-6-oxo-1,6-dihydropyrazine-2-carboxylate

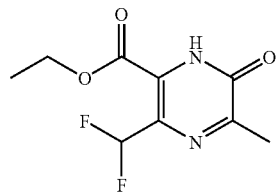

This compound was synthesised from Intermediate 8-5 using similar procedure as described in Intermediate 1-5. The cyclized intermediate product was oxidized by heating at 120° C. for 20 min in a microwave oven with Pd/C in HOAc to afford the title compound (280 mg, 38.6%).
$^1$H NMR (500 MHz, CDCl$_3$) δ 1.46 (t, 3H), 2.59 (s, 3H), 4.51 (q, 2H), 7.36 (t, 1H, J=56 Hz); m/z 233 (M+H)$^+$.

Intermediate 8-5: Ethyl 2-{[N-(tert-butoxycarbonyl)-L-alanyl]amino}-4,4-difluoro-3-oxobutanoate

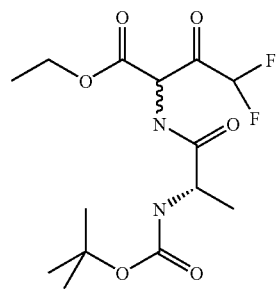

This compound was synthesised from Intermediate 8-6 using similar procedure as described in Intermediate 1-6. The crude was used directly in next step.

Intermediate 8-6: Ethyl 2-diazo-4,4-difluoro-3-oxobutanoate

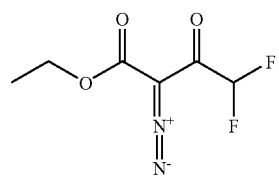

This compound was synthesised from 4,4-difluoro-3-oxo-butyric acid ethyl ester (CAS 352-24-9) and polymer-bound tosylazide using similar conditions as described in Intermediate 1-7. The crude was used directly in next step.
$^1$H NMR (400 MHz, CDCl$_3$) δ 1.35 (t, 3H), 4.35 (q, 2H), 6.59 (t, J=56 Hz, 1H).

Example 9

{trans-4-[4-(6-Carbamoyl-3-ethyl-5-methylpyrazin-2-yl)phenyl]cyclohexyl}acetic acid

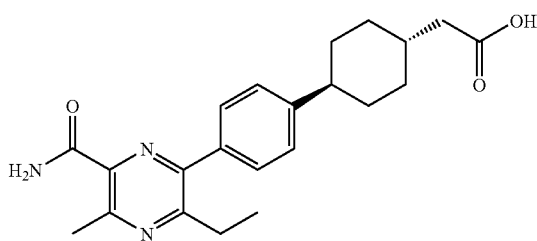

This compound was synthesised from Intermediate 9-1 using similar conditions as described in Example 1 to afford the title compound (5 mg, 29%) as white solid.

¹H NMR (500 MHz, CDCl₃) δ 1.17 (q, 2H), 1.21 (t, 3H), 1.52 (q, 2H), 1.75-1.88 (m, 1H), 1.92 (d, 4H), 2.22 (d, 2H), 2.52 (t, 1H), 2.88 (q, 2H), 2.9 (s, 3H), 6.12 (br s, 1H), 7.28 (d, 2H), 7.42 (d, 2H), 7.80 (br s, 1H); m/z 382 (M+H)⁺.

Intermediate 9-1: tert-Butyl {trans-4-[4-(6-carbamoyl-3-ethyl-5-methylpyrazin-2-yl)phenyl]cyclohexyl}acetate

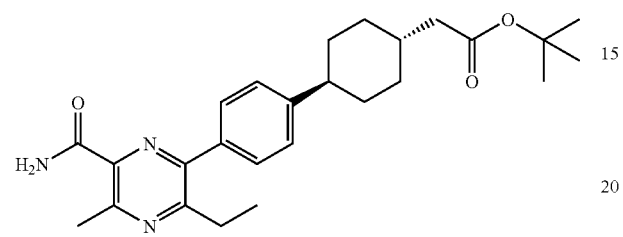

This compound was synthesised from Intermediate 9-2 using similar conditions as described in Intermediate 1-1 to afford the title compound (20 mg, 30%) as white solid.

¹H NMR (400 MHz, CDCl₃) δ 1.18 (q, 2H), 1.26 (t, 3H), 1.46 (s, 9H), 1.48-1.62 (m, 2H), 1.78-1.87 (m, 1H), 1.94 (t, 4H), 2.16 (d, 2H), 2.55 (t, 1H), 2.93 (q, 2H), 2.98 (s, 3H), 5.65 (br s, 1H), 7.31 (d, 2H), 7.46 (d, 2H), 7.80 (s, 1H); m/z 438 (M+H)⁺.

Intermediate 9-2: 6-{4-[trans-4-(2-tert-Butoxy-2-oxoethyl)cyclohexyl]phenyl}-5-ethyl-3-methylpyrazine-2-carboxylic acid

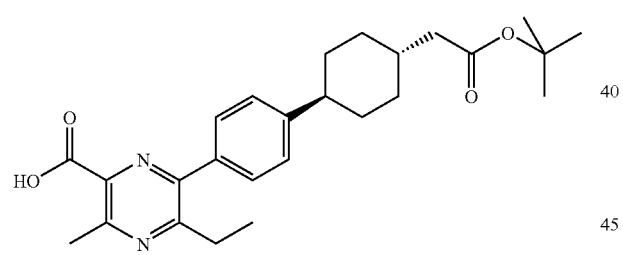

This compound was synthesised from Intermediate 9-3 and Intermediate D using similar Suzuki conditions as described in Intermediate 1-2 to afford the title compound (65.7 mg, 67% yield) as white solid.

¹H NMR (500 MHz, CDCl₃) δ 1.14-1.23 (m, 2H), 1.28 (t, 3H), 1.47 (s, 9H), 1.55 (q, 2H), 1.78-1.98 (m, 6H), 2.17 (d, 2H), 2.55 (t, 1H), 2.93-3.01 (m, 5H), 7.29-7.36 (m, 2H), 7.40-7.47 (m, 2H); m/z 439 (M+H)⁺.

Intermediate 9-3: Ethyl 6-bromo-5-ethyl-3-methylpyrazine-2-carboxylate

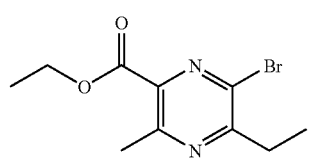

To a solution of POBr₃ (0.307 mL, 3.02 mmol, CAS 7789-59-5) in DCE (10 mL) was added Intermediate 9-4 (0.160 g, 0.76 mmol). The mixture was heated at 100° C. for 19 h. The reaction was cooled to RT. Saturated NaHCO₃ was added carefully and the mixture was extracted with DCM. The extracts were combined, dried over Na₂SO₄, filtered and concentrated. The remaining crude was purified by flash chromatography using EtOAc (0-25%) in heptane to afford the title compound (60.4 mg, 29%) as pale yellow solid.

¹H NMR (500 MHz, CDCl₃) δ 1.30 (t, 3H), 1.41 (t, 3H), 2.74 (s, 3H), 2.98 (q, 2H), 4.43 (q, 2H).

Intermediate 9-4: Ethyl 5-ethyl-3-methyl-6-oxo-1,6-dihydropyrazine-2-carboxylate

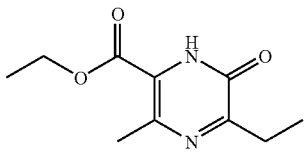

This compound was synthesised from Intermediate 9-5 using similar conditions as described in Intermediate 1-5 to afford the title compound (160 mg, 21%) as white solid.

¹H NMR (500 MHz, CDCl₃) δ 1.23 (t, 3H), 1.39 (t, 3H), 2.61 (s, 3H), 2.85 (q, 2H), 4.40 (q, 2H).

Intermediate 9-5: Ethyl 2-({(2S)-2-[(tert-butoxycarbonyl)amino]butanoyl}amino)-3-oxobutanoate

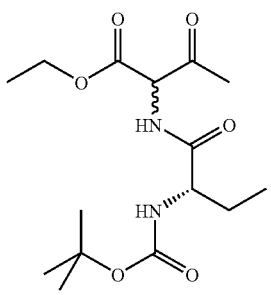

This compound was synthesised from Intermediate 9-6 and Intermediate 1-7 using similar conditions as in Intermediate 1-6. Crude residue was taken directly to next step.

Intermediate 9-6: tert-Butyl [(1S)-1-carbamoylpropyl]carbamate

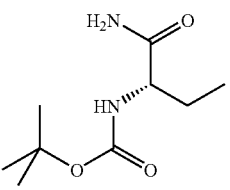

To a solution of (2S)-2-[(tert-butoxycarbonyl)amino]butanoic acid (1.01 g, 4.99 mmol) in DMF (5 mL) at −20° C. was added NMM (1.10 mL, 9.99 mmol) and isobutyl chloroformate (1.30 mL, 9.99 mmol). The reaction was stirred for 10 min at −20° C. The precipitate was removed by filtration. 26% NH₄OH (aq) solution (0.39 mL, 9.99 mmol) was added and the reaction was stirred at −20° C. for 3 h. The volume was reduced under vacuum and hexane was added. A white precipitate was formed after a few minutes. The precipitate was collected in a filter and washed with additional hexane. The precipitate was recrystallised from EtOAc and hexane to give the title compound (0.811 g, 80%) as white solid.

¹H NMR (500 MHz, CD₃OD) δ 0.96 (t, 3H), 1.45 (s, 9H), 1.61 (m, 1H), 1.78 (m, 1H), 3.93 (t, 1H), 6.63 (s, 1H), 6.96 (s, 1H), 7.51 (s, 1H).

Example 10

{trans-4-[4-(6-Carbamoyl-5-ethyl-3-methylpyrazin-2-yl)phenyl]cyclohexyl}acetic acid

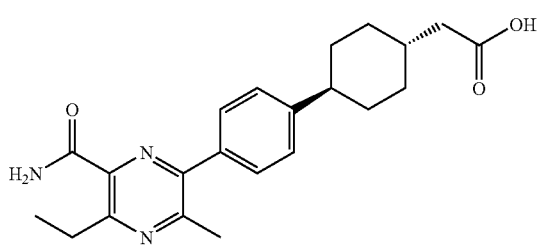

This compound was synthesised from Intermediate 10-1 using similar conditions as described in Example 1 to give title compound (13 mg, 95%).

¹H NMR (500 MHz, CDCl₃) δ 1.19-1.30 (2H, m), 1.36 (3H, t), 1.52-1.65 (2H, m), 1.84-2.04 (5H, m), 2.35 (2H, d), 2.54-2.64 (1H, m), 2.73 (3H, s), 3.39 (2H, q), 7.29 (1H, s), 7.36 (2H, m), 7.52 (2H, m), 8.10 (1H, s), 8.50 (1H, br s); m/z 382 (M+H)⁺.

Intermediate 10-1: tert-Butyl {trans-4-[4-(6-carbamoyl-5-ethyl-3-methylpyrazin-2-yl)phenyl]cyclohexyl}acetate

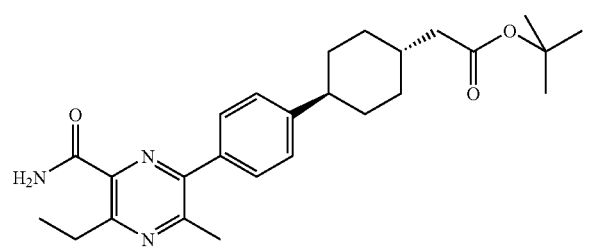

This compound was synthesised from Intermediate 10-2 using similar procedure as described in Intermediate 1-1 to give title compound (15 mg, 50%).

¹H NMR (500 MHz, CDCl₃) δ 1.13-1.25 (m, 2H), 1.36 (t, 3H), 1.47 (s, 9H), 1.52-1.62 (m, 2H), 1.80-2.00 (m, 5H), 2.18 (d, 2H), 2.52-2.60 (m, 1H), 2.68 (s, 3H), 3.39 (q, 2H), 5.48 (br s, 1H), 7.33 (d, 2H), 7.52 (d, 2H), 7.81 (br s, 1H); m/z 438 (M+H)⁺.

Intermediate 10-2: 6-{4-[trans-4-(2-tert-Butoxy-2-oxoethyl)cyclohexyl]phenyl}-3-ethyl-5-methylpyrazine-2-carboxylic acid

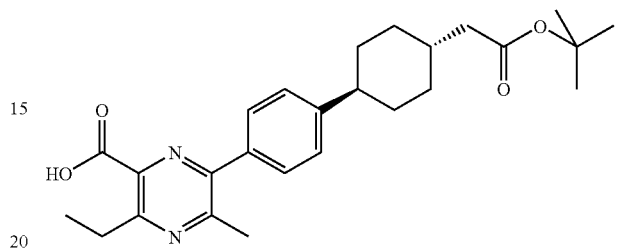

This compound was synthesised from Intermediate 10-3 and Intermediate D using similar Suzuki conditions as described in Intermediate 1-3. Purification gave title product (30 mg, 62%).

¹H NMR (500 MHz, CDCl₃) δ 1.13-1.25 (m, 2H), 1.37 (t, 3H), 1.47 (s, 9H), 1.52-1.62 (m, 2H), 1.80-2.00 (m, 5H), 2.18 (d, 2H), 2.53-2.61 (m, 1H), 2.74 (s, 3H), 3.42 (q, 2H), 7.36 (d, 2H), 7.51 (d, 2H), 11.21 (br s, 1H); m/z 439 (M+H)⁺.

Intermediate 10-3: Ethyl 6-bromo-3-ethyl-5-methylpyrazine-2-carboxylate

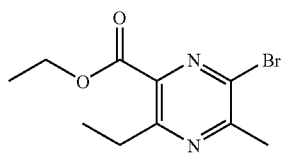

This compound was synthesised from Intermediate 10-4 using similar protocol as described in Intermediate 9-3 to give title compound (30 mg, 8%).

¹H NMR (500 MHz, CDCl₃) δ 1.30 (t, 3H), 1.42 (t, 3H), 2.71 (s, 3H), 3.06 (q, 2H), 4.45 (q, 2H); m/z 275 (M+H)⁺.

Intermediate 10-4: Ethyl 3-ethyl-5-methyl-6-oxo-1,6-dihydropyrazine-2-carboxylate

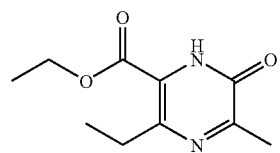

This compound was synthesised from Intermediate 10-5 using similar protocol as described in Intermediate 1-5. Purification gave title compound (0.340 g, 67%) as bright yellow oil.

¹H NMR (500 MHz, CDCl₃) δ 1.23 (t, 3H), 1.43 (t, 3H), 2.54 (s, 3H), 3.02 (q, 2H), 4.44 (q, 2H), 9.20 (br s, 1H); m/z 211 (M+H)⁺.

Intermediate 10-5: ethyl N-(tert-butoxycarbonyl)-L-alanyl-3-oxonorvalinate

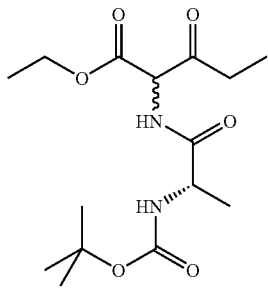

This compound was synthesised from Intermediate 10-6 using similar conditions as described in Intermediate 1-6. Crude product (1 g, 46%) was taken directly to next step. m/z 331 (M+H)⁺.

Intermediate 10-6: Ethyl 2-diazo-3-oxopentanoate

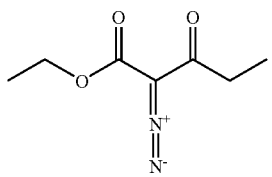

This compound was synthesised from ethyl propionylacetate (CAS 4949-44-4) and polymer-bound tosylazide using similar protocol as described in Intermediate 1-7. Crude material (0.9 g, 95%) was taken directly to next step.

Example 11

{trans-4-[4-(6-Carbamoyl-3-methylpyrazin-2-yl)phenyl]cyclohexyl}acetic acid

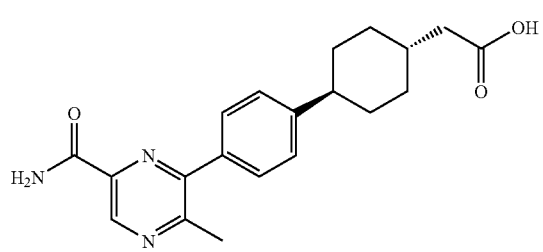

This compound was synthesised from Intermediate 11-1 using similar conditions as described in Example 1 to give title compound (16 mg, 53%).

¹H NMR (500 MHz, CDCl₃) δ 1.15-1.25 (m, 2H), 1.51-1.61 (m, 2H), 1.83-2.00 (m, 5H), 2.26 (d, 2H), 2.53-2.61 (m, 1H), 2.71 (s, 3H), 7.34 (d, 2H), 7.51 (d, 2H), 9.18 (s, 1H); m/z 354 (M+H)⁺.

Intermediate 11-1: tert-Butyl {trans-4-[4-(6-carbamoyl-3-methylpyrazin-2-yl)phenyl]cyclohexyl}acetate

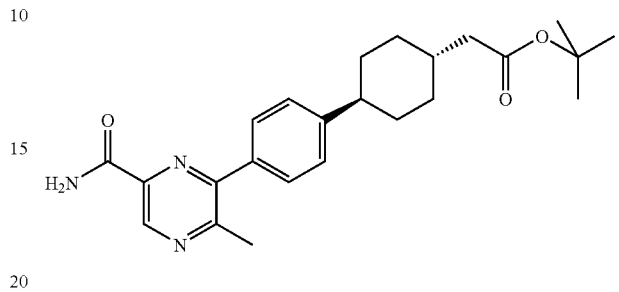

This compound was synthesised from Intermediate 11-2 using similar conditions as described in Intermediate 1-1. The crude was taken directly to next step.
m/z 410 (M+H)⁺.

Intermediate 11-2: 6-{4-[trans-4-(2-tert-Butoxy-2-oxoethyl)cyclohexyl]phenyl}-5-methylpyrazine-2-carboxylic acid

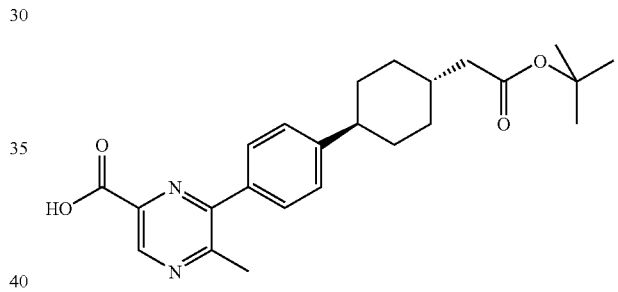

This compound was synthesised from Intermediate 11-3 and Intermediate D using similar Suzuki conditions as described in Intermediate 1-3. Purification gave title compound (410 mg, 66%).
¹H NMR (500 MHz, CDCl₃) δ 1.15-1.26 (m, 2H), 1.48 (s, 9H), 1.52-1.62 (m, 2H), 1.81-2.00 (m, 5H), 2.19 (d, 2H), 2.54-2.61 (m, 1H), 2.78 (s, 3H), 7.37 (d, 2H), 7.53 (d, 2H), 9.26 (s, 1H); m/z 411 (M+H)⁺.

Intermediate 11-3: Methyl 6-bromo-5-methylpyrazine-2-carboxylate

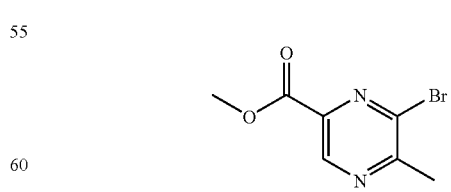

This compound was synthesised from Intermediate 11-4 using similar conditions as described in Intermediate 9-3 to give the title compound (0.493 mg, 54%).
¹H NMR (500 MHz, CDCl₃) δ 2.78 (s, 3H), 4.02 (s, 3H), 9.10 (s, 1H); m/z 233 (M+H)⁺.

Intermediate 11-4: Methyl 5-methyl-6-oxo-1,6-dihydropyrazine-2-carboxylate

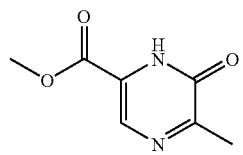

To a solution of intermediate 11-5 (0.98 g, 5.76 mmol) in DCM (180 mL) was added polymer-bound sulfurtrioxide (7.3 g, 3 eq, CAS 26412-87-3). The mixture was stirred at RT for 4 days. The polymer was filtered off and washed with portions of DCM. Concentration of filtrate gave title compound (0.8 g, 80%) as yellow solid.
$^1$H NMR (500 MHz, CDCl$_3$) δ 2.56 (s, 3H), 4.00 (s, 3H), 7.94 (s, 1H); m/z 169 (M+H)$^+$.

Intermediate 11-5: Methyl 5-methyl-6-oxo-1,4,5,6-tetrahydropyrazine-2-carboxylate

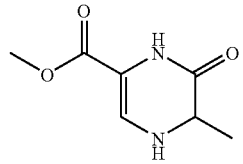

To a solution of Intermediate 11-6 (3.0 g, 8.56 mmol) in EtOH (250 mL) under N$_2$ was added 10% Pd/C (1.35 g) and ammonium formate (2.43 g, 38.5 mmol). The solution was stirred at RT for 90 min. The alcohol was removed under vacuum and the black residue was dissolved in EtOAc and filtered through Celite. Concentration of filtrate gave the title compound (1.2 g, 80%). m/z 171 (M+H)$^+$.

Intermediate 11-6: Ethyl N-[(1Z)-2-{[(benzyloxy)carbonyl]amino}-3-methoxy-3-oxoprop-1-en-1-yl]-L-alaninate

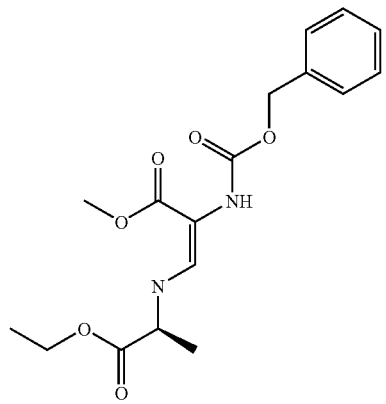

A solution of Intermediate 11-7 (0.450 g, 0.78 mmol), L-alanine ethyl ester hydrochloride (0.179, 1.17 mmol, CAS 1115-59-9) and TEA (0.33 mL, 2.33 mmol) in MeOH (10 mL) was stirred at RT overnight. The residue was concentrated, dissolved in EtOAc (50 mL) and washed with brine (2×25 mL). The organic layer was dried through a phase separator and concentrated. The crude residue was purified by flash chromatography using a gradient of EtOAc (30-50%) in heptane as eluent. Pure product fractions were concentrated to give the title compound (230 mg, 85%) as colorless oil.
$^1$H NMR (500 MHz, CDCl$_3$) δ 1.24-1.33 (m, 6H), 3.70 (s, 3H), 3.94-4.02 (m, 1H), 4.22 (q, 2H), 5.16 (s, 2H), 5.75 (br s, 1H), 6.13 (br s, 1H), 7.25 (d, 1H), 7.30-7.45 (m, 5H); m/z 351 (M+H)$^+$.

Intermediate 11-7: Methyl (2Z)-2-{[(benzyloxy)carbonyl]amino}-3-{[(4-methylphenyl)sulfonyl]oxy}acrylate

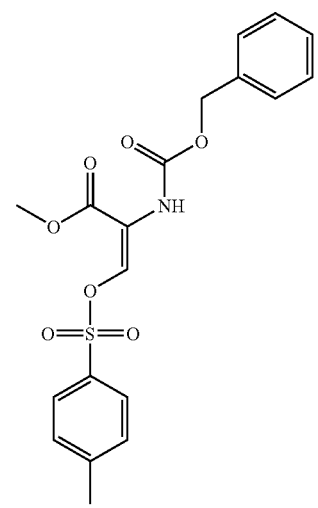

To a pre-cooled (−30° C.) solution of DMF:DMSO (1:1, 200 mL) under nitrogen was added TsCl (76.3 g, 0.4 mol) in small portions over 30 min. NOTE: This reaction is highly exothermic and careful temperature control is essential! The solution was stirred at −10° C. for 10 min, then again taken to −30° C. A solution of cbz-L-serine methyl ester (20.3 g, 0.08 mol, CAS 1676-81-9) in DMF was added dropwise, again with careful temperature control. After stirring for 10 min at −30° C. triethylamine (110 mL, 0.79 mol) was added and the reaction was slowly taken to 0° C. and kept at this temperature for 2 h. The reaction was quenched by addition of ice-cold water. The solution was extracted with 3×EtOAc, then the combined organic layer was washed extensively with brine and water. Drying and evaporation gave product as yellow oil (30 g, 94%).
$^1$H NMR (500 MHz, CDCl$_3$) δ 2.47 (s, 3H), 3.77 (s, 3H), 5.11 (s, 2H), 6.01 (br s, 1H), 7.32-7.41 (m, 7H), 7.48 (s, 1H), 7.84 (d, 2H); m/z 406 (M+H)$^+$.

Example 12

(trans-4-{4-[6-(Aminocarbonothioyl)-3-methylpyrazin-2-yl]phenyl}cyclohexyl)acetic acid

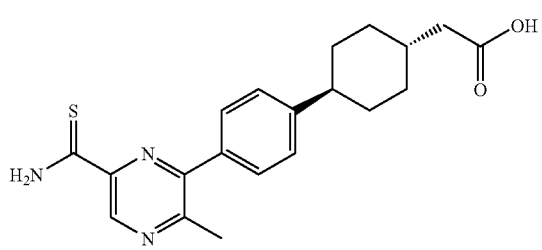

This compound was synthesised from Intermediate 12-1 using similar procedure as in Example 1 to afford the title compound (46 mg, 100%).

¹H NMR (400 MHz, CDCl₃) δ 1.20-1.34 (m, 2H), 1.50-1.67 (m, 2H), 1.92 (s, 1H), 2.0 (d, 4H), 2.37 (d, 2H), 2.60 (t, 1H), 2.78 (s, 3H), 7.38 (d, 2H), 7.53 (d, 2H), 7.83 (s, 1H), 9.18 (s, 1H), 9.67 (s, 1H); m/z 370 (M+H)⁺.

Intermediate 12-1: tert-Butyl (trans-4-{4-[6-(aminocarbonothioyl)-3-methylpyrazin-2-yl]phenyl}cyclohexyl)acetate

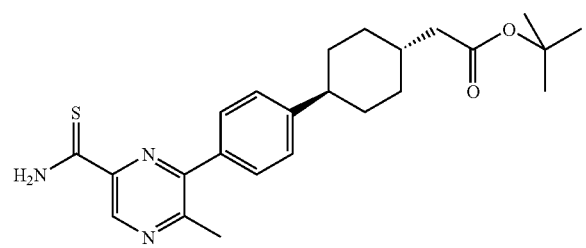

A solution of Example 11 (40 mg, 0.10 mmol) and Lawesson's reagent (39.5 mg, 0.10 mmol) in toluene:THF (3:1 mL) was heated at 80° C. overnight. An additional amount (0.5 eq) of Lawesson's reagent was added followed by continued heating for another 1 h. The reaction mixture was concentrated and purified by flash chromatography using EtOAc (10-30%) in petroleum ether as eluent to give the title compound (37 mg, 89%) as slightly yellowish powder.

¹H NMR (400 MHz, CDCl₃) δ 1.12-1.25 (m, 3H), 1.45 (s, 9H), 1.50-1.60 (m, 1H), 1.83 (s, 1H), 1.93 (t, 4H), 2.15 (d, 2H), 2.54 (t, 1H), 2.70 (s, 3H), 7.33 (d, 2H), 7.50 (d, 2H), 7.54 (s, 1H), 9.21 (s, 1H), 9.64 (s, 1H); m/z 426 (M+H)⁺.

Example 13

{trans-4-[4-(6-Carbamoylpyrazin-2-yl)phenyl]cyclohexyl}acetic acid

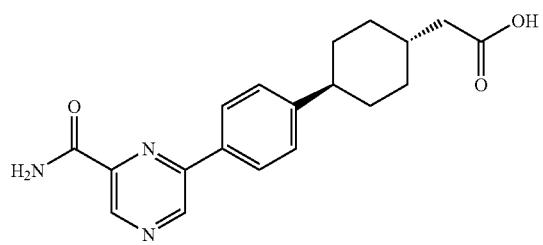

This compound was synthesised from Intermediate 13-1 using similar procedure as described in Example 1 to afford the title compound (0.5 g, 95%).

¹H NMR (500 MHz, DMSO) δ 1.08-1.19 (m, 2H), 1.47-1.57 (m, 2H), 1.71-1.87 (m, 5H), 2.15 (d, 2H), 2.52-2.58 (m, 1H), 7.40 (d, 2H), 8.27 (d, 2H), 9.06 (s, 1H), 9.40 (s, 1H); m/z 340 (M+H)⁺.

Intermediate 13-1: tert-Butyl {trans-4-[4-(6-carbamoylpyrazin-2-yl)phenyl]cyclohexyl}acetate

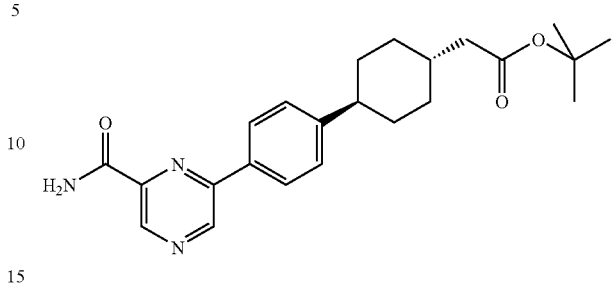

This compound was synthesised from Intermediate 13-2 and Intermediate D using similar Suzuki conditions as described in Intermediate 1-3. This gave the title compound (570 mg, 45%) as light-yellow solid.

¹H NMR (500 MHz, CDCl₃) δ 1.14-1.24 (m, 2H), 1.47 (s, 9H), 1.51-1.61 (m, 2H), 1.81-1.98 (m, 5H), 2.18 (d, 2H), 2.53-2.61 (m, 1H), 5.67 (br s, 1H), 7.39 (d, 2H), 7.77 (br s, 1H), 7.96 (d, 2H), 9.18 (s, 1H), 9.32 (s, 1H); m/z 396 (M+H)⁺.

Intermediate 13-2: 6-chloropyrazine-2-carboxamide

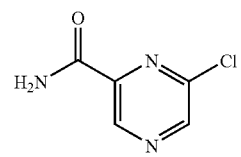

A solution of 6-chloro-pyrazine carboxylic acid (2.00 g, 12.62 mmol) in DMF (7 mL) was cooled to −40° C. NMP (2.77 mL, 25.23 mmol) and isobutyl chloroformate 3.27 mL, 25.23 mmol) were added. The temperature was allowed to increase to −20° C. during 20 min and then NH₄OH was added. A precipitate was rapidly formed and after 15 min it was filtered off and washed with water. Crystallization from EtOH gave the title compound (670 mg, 34%) as light-brown needles.

¹H NMR (500 MHz, DMSO) δ 7.93 (br s, 1H), 8.24 (br s, 1H), 8.99 (s, 1H), 9.12 (s, 1H).

Example 14

6-{4-[trans-4-(2-Amino-2-oxoethyl)cyclohexyl]phenyl}pyrazine-2-carboxamide

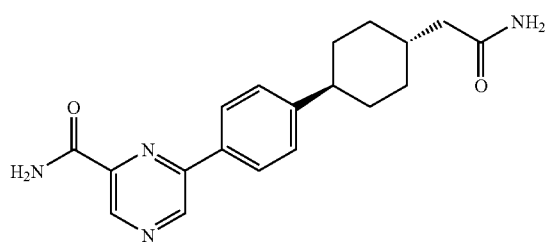

This compound was synthesised from Example 13 using similar conditions as described in Intermediate 1-1. Aqueous work-up gave low yield and is not recommended here (4 mg, 10%).

¹H NMR (500 MHz, DMSO) δ 1.05-1.17 (m, 2H), 1.45-1.56 (m, 2H), 1.71-1.87 (m, 5H), 1.99 (d, 2H), 2.50-2.59 (m, 1H), 6.71 (s, 1H), 7.25 (s, 1H), 7.39 (d, 2H), 7.88 (s, 1H), 8.26 (d, 2H), 8.40 (s, 1H), 9.07 (s, 1H), 9.39 (s, 1H); m/z 339 (M+H)⁺.

Example 15

6-{4-[trans-4-(2-Hydroxyethyl)cyclohexyl]phenyl}pyrazine-2-carboxamide

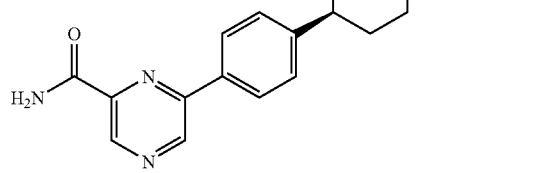

This compound was synthesised from Example 13 using similar conditions as in Example 5 to afford the title compound (3 mg, 11%) as white solid.

¹H NMR (500 MHz, THF) δ 1.11-1.21 (m, 2H), 1.47 (q, 2H), 1.52-1.63 (m, 3H), 1.90-1.98 (m, 4H), 2.55-2.64 (m, 1H), 3.33 (br s, 1H), 3.56-3.63 (m, 2H), 7.09 (br s, 1H), 7.40 (d, 2H), 7.95 (br s, 1H), 8.15 (d, 2H), 9.18 (s, 1H), 9.26 (s, 1H); m/z 326 (M+H)⁺.

Example 16

Methyl N-({trans-4-[4-(6-carbamoylpyrazin-2-yl)phenyl]cyclohexyl}acetyl)-2-methylalaninate

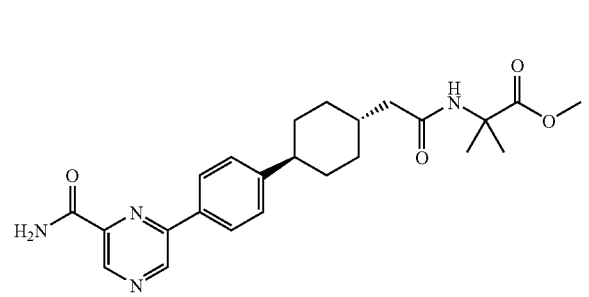

This compound was synthesised from Example 13 and alpha-aminoisobutyric acid methyl ester hydrochloride using similar conditions as in Intermediate 1-1. Purification gave title compound (40 mg, 76%).

¹H NMR (500 MHz, CDCl₃) δ 1.13-1.23 (m, 2H), 1.52-1.62 (m, 2H), 1.58 (s, 6H), 1.86-1.98 (m, 5H), 2.11 (d, 2H), 2.52-2.61 (m, 2H), 3.76 (s, 3H), 5.71 (br s, 1H), 6.02 (br s, 1H), 7.38 (d, 2H), 7.77 (br s, 1H), 7.96 (d, 2H), 9.18 (s, 1H), 9.32 (s, 1H); m/z 439 (M+H)⁺.

Example 17

N-({trans-4-[4-(6-Carbamoylpyrazin-2-yl)phenyl]cyclohexyl}acetyl)-2-methylalanine

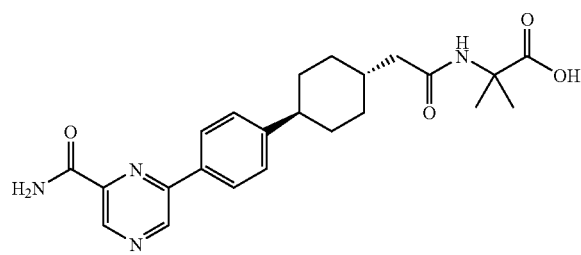

The methyl ester from Example 16 was hydrolysed to the corresponding acid using similar protocol as described in Intermediate 1-2 to afford the title compound (21 mg, 72%) as white solid.

¹H NMR (500 MHz, DMSO) δ 1.04-1.14 (m, 2H), 1.31 (s, 6H), 1.43-1.53 (m, 2H), 1.69-1.85 (m, 5H), 1.99 (d, 2H), 2.48-2.57 (m, 2H), 7.39 (d, 2H), 7.87 (br s, 1H), 7.98 (s, 1H), 8.26 (d, 2H), 8.42 (br s, 1H), 9.06 (s, 1H), 9.39 (s, 1H), 12.0 (s, 1H); m/z 425 (M+H)⁺.

Example 18

3-Carbamoyl-5-{4-[trans-4-(carboxymethyl)cyclohexyl]phenyl}pyrazin-2-aminium chloride

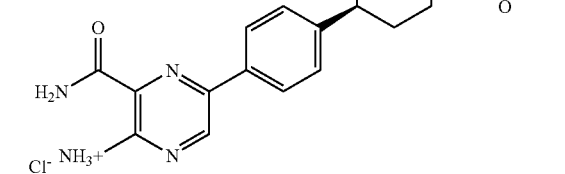

To a solution of Intermediate 18-1 (26 mg, 0.06 mmol) in dioxane (5 mL) was added a solution of 4M HCl in dioxane (0.316 mL) in one portion. A precipitate formed. Water (1 mL) was added to dissolve the precipitate. The reaction mixture was heated in a microwave oven at 120° C. Evaporation gave title compound (25.8 mg, 100%) as yellow solid.

¹H NMR (400 MHz, DMSO) δ 1.05-1.20 (m, 2H), 1.48 (q, 2H), 1.66-1.87 (m, 5H), 2.14 (d, 2H), 2.50 (1H, covered by DMSO), 7.29 (d, 2H), 7.64 (s, 1H), 8.01 (d, 2H), 8.23 (s, 1H), 8.77 (s, 1H); m/z 355 (M+H—HCl)⁺.

Intermediate 18-1: tert-Butyl {trans-4-[4-(5-amino-6-carbamoylpyrazin-2-yl)phenyl]cyclohexyl}acetate

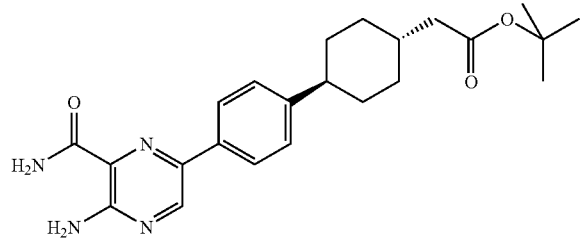

This compound was synthesised from Intermediate 18-2 using similar procedure as described in Intermediate 1-1 to afford the title compound (26 mg, 24%) as white-yellow powder.

$^1$H NMR (400 MHz, CDCl$_3$) δ 1.08-1.32 (m, 4H), 1.46 (s, 9H), 1.84 (m, 1H), 2.16 (d, 2H), 2.52 (t, 1H), 5.46 (s, 1H), 7.31 (d, 2H), 7.78 (d, 2H), 7.83 (s, 1H), 8.63 (s, 1H); m/z 411 (M+H)$^+$.

Intermediate 18-2: 3-amino-6-{4-[trans-4-(2-tert-butoxy-2-oxoethyl)cyclohexyl]phenyl}pyrazine-2-carboxylic acid

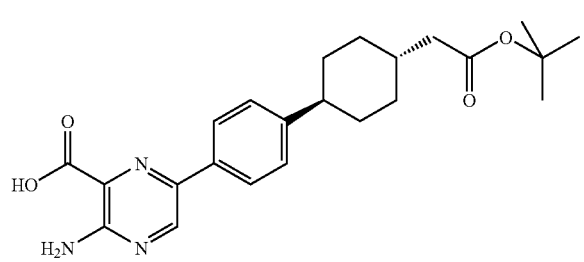

This compound was synthesised from 3-Amino-6-bromo-pyrazine-2-carboxylic acid methyl ester (CAS 6966-01-4) and Intermediate D using similar Suzuki protocol as described in Intermediate 1-3. Crude was not isolated. m/z 412 (M+H)$^+$.

Example 19

3-Carbamoyl-5-{4-[trans-4-(carboxymethyl)cyclohexyl]phenyl}pyridinium trifluoroacetate

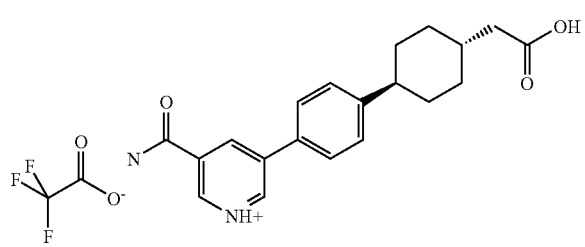

This compound was synthesised from Intermediate 19-1 using similar procedure as described in Example 1. Evaporation yielded the title compound (22 mg, 69%) as white powder.

$^1$H NMR (600 MHz, DMSO) δ 1.12 (2H, q), 1.50 (2H, q), 1.74 (1H, s), 1.82 (4H, d), 2.13 (2H, d), 2.51 (1H, t); m/z 339 (M+H-TFA)$^+$.

Intermediate 19-1: tert-Butyl {trans-4-[4-(5-carbamoylpyridin-3-yl)phenyl]cyclohexyl}acetate

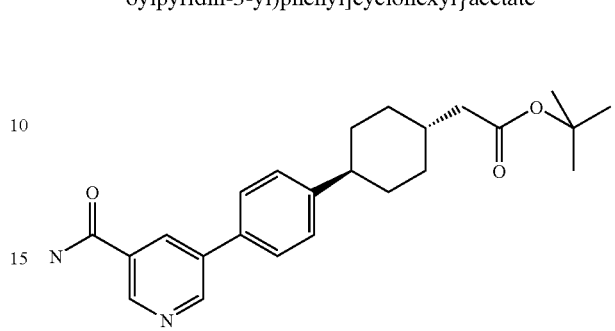

This compound was synthesised from Intermediate 19-2 using similar reaction conditions as described in Intermediate 1-1. Purification gave title compound (40 mg, 37%) as white powder.

$^1$H NMR (400 MHz, CDCl$_3$) δ 0.78-1.70 (13H, m), 1.83 (1H, s), 1.91 (4H, t), 2.15 (2H, d), 2.52 (1H, t), 5.68 (1H, s), 6.28 (1H, s), 7.33 (2H, d), 7.54 (2H, d), 8.39 (1H, t), 8.95 (1H, s), 8.99 (1H, s); m/z 395 (M+H)$^+$.

Intermediate 19-2: 5-{4-[trans-4-(2-tert-Butoxy-2-oxoethyl)cyclohexyl]phenyl}nicotinic acid

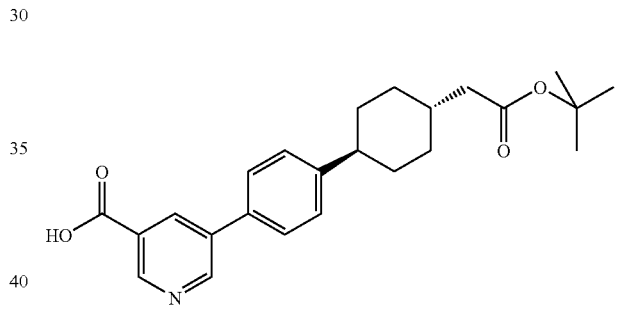

This compound was synthesised from 5-bromonicotinic acid (CAS 20826-04-4) and Intermediate D using similar Suzuki protocol as described in Intermediate 1-3. Purification gave title compound (230 mg, 74%) as white solid.

$^1$H NMR (400 MHz, CD$_3$OD) δ 1.18 (2H, q), 1.44 (9H, s), 1.55 (2H, q), 1.81 (1H, s), 1.89 (4H, t), 2.14 (2H, d), 2.53 (1H, t), 7.34 (2H, d), 7.59 (2H, d), 8.50 (1H, t), 8.76 (1H, d), 8.97 (1H, d); m/z 396 (M+H)$^+$.

Example 20

{trans-4-[4-(6-Carbamoyl-3-methylpyridin-2-yl)phenyl]cyclohexyl}acetic acid

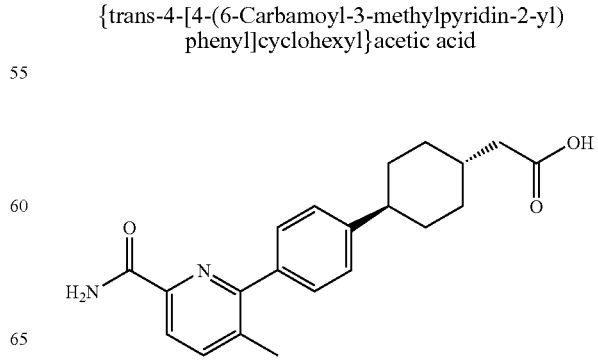

This compound was synthesised from Intermediate 20-1 using similar conditions as described in Example 1 to afford title compound (11 mg, 85%).

¹H NMR (400 MHz, CDCl₃) δ 1.02-1.18 (m, 2H), 1.37-1.51 (m, 2H), 1.62-1.82 (m, 5H), 2.08 (d, 2H), 2.32 (s, 3H), 2.40-2.51 (m, 1H), 7.27 (d, 2H), 7.49 (d, 3H), 7.81 (d, 2H), 7.86 (s, 1H); m/z 353 (M+H)⁺.

Intermediate 20-1: tert-Butyl {trans-4-[4-(6-carbamoyl-3-methylpyridin-2-yl)phenyl]cyclohexyl}acetate

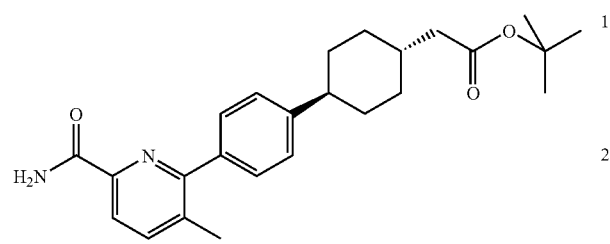

This compound was synthesised from Intermediate 20-2 and Intermediate D using similar Suzuki protocol as in Intermediate 1-3. Purification gave title product (15 mg, 21%).

¹H NMR (400 MHz, CDCl₃) δ 1.09-1.30 (m, 2H), 1.45 (s, 9H), 1.48-1.61 (m, 2H), 1.76-1.98 (m, 5H), 2.15 (d, 2H), 2.41 (s, 3H), 2.48-2.57 (m, 1H), 5.60 (s, 1H), 7.29 (d, 2H), 7.45 (d, 2H), 7.71 (d, 1H), 7.87 (s, 1H), 8.04 (d, 1H).

Intermediate 20-2: 6-chloro-5-methylpyridine-2-carboxamide

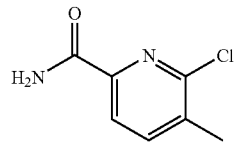

To a solution of Intermediate 20-3 (112 mg, 0.65 mmol) in DCM (5 mL) was added PyBROP (457 mg, 0.98 mmol), NH₄Cl (70 mg, 1.30 mmol) and DIPEA (0.43 mL, 2.61 mmol). The reaction mixture was stirred at RT for 2 h. After dilution with DCM (15 mL) the solution was washed with sat NaHCO₃ (2×15 mL) and water (15 mL), dried through a phase separator and evaporated. The crude product was purified by flash chromatography using EtOAc in heptane as eluent. Pure fractions were evaporated to dryness to afford the title compound (83 mg, 74%).

¹H NMR (400 MHz, DMSO) δ 2.35 (s, 3H), 7.63 (s, 1H), 7.85-7.90 (m, 3H); m/z 171 (M+H)⁺.

Intermediate 20-3: 6-Chloro-5-methylpyridine-2-carboxylic acid

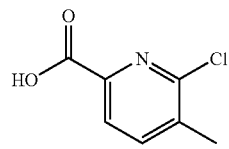

This compound was synthesised from the corresponding Me-ester using similar protocol as described in Intermediate 1-2 to give title compound (0.11 g, 80%); m/z 172 (M+H)⁺.

Intermediate 20-4: Methyl 6-chloro-5-methylpyridine-2-carboxylate

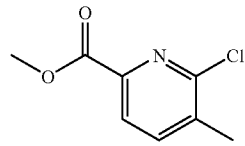

A solution of Intermediate 20-5 (1.67 g, 9.99 mmol) in POCl₃ (15 mL) was heated to reflux for 3 h. After cooling to RT the reaction mixture was added to an ice-water solution, basified with 1M NaOH (aq) and extracted with DCM (3×30 mL). Organic layers were combined, passed through a phase separator and evaporated. The crude product was purified by flash chromatography using EtOAc (15%) in heptane as eluent. Pure fractions were evaporated to dryness to afford the title compound (0.73 g, 39%).

¹H NMR (400 MHz, CDCl₃) δ 2.44 (s, 3H), 3.97 (s, 3H), 7.67 (d, 1H), 7.96 (d, 1H); m/z 186 (M+H)⁺.

Intermediate 20-5: Methyl 5-methylpyridine-2-carboxylate 1-oxide

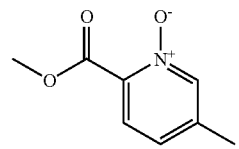

To a solution of Intermediate 20-6 (2.11 g, 14.0 mmol) in DCM (40 mL) was added m-CPBA (4.70 g, 21.0 mmol) and the reaction was stirred at RT for 5 h. Sat Na₂SO₂ (15 mL) was added and the reaction was stirred for 5 min. The two phases were separated and the organic phase was washed with 1M NaHCO₃, passed through a phase separator and evaporated. The crude product was taken to the next step without further purification. m/z 168 (M+H)⁺.

Intermediate 20-6: Methyl 5-methylpyridine-2-carboxylate

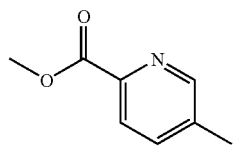

To a solution of 2,5-dimethylpyridine (3.00 g, 28.0 mmol, CAS 589-93-5) in pyridine (15 mL) was added selenium dioxide (4.66 g, 42.0 mmol, CAS 7446-08-4). The reaction mixture was heated at reflux overnight. After cooling to RT a solid was filtered off and washed with water and pyridine (2×5 mL/wash). The filtrate was evaporated and the crude retaken in methanol (100 mL). Sulphuric acid (1.34 mL, 25.0 mmol) was added and the reaction mixture was heated at reflux for 5 h. After cooling to RT the reaction mixture was basified with 20% NaOH (aq). The methanol was evaporated off and water was added (50 mL). This mixture was extracted with DEE (3×100 mL). The combined organics were dried (Na$_2$SO$_4$) and evaporated to afford the title compound (2.11 g, 50%) as light-brown oil.

$^1$H NMR (400 MHz, CDCl$_3$) δ 2.40 (s, 3H), 3.97 (s, 3H), 7.61 (d, 1H), 8.01 (d, 1H), 8.54 (s, 1H).

Example 21

4-(4-(6-Carbamoyl-3,5-dimethylpyrazin-2-yl)phenyl)bicyclo[2.2.2]octane-1-carboxylic acid

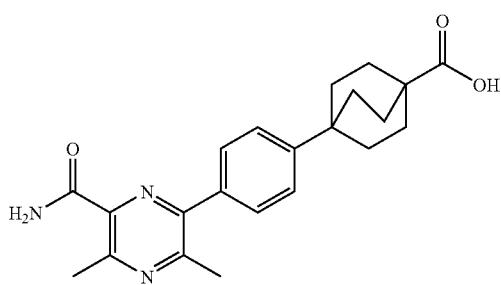

Powdered potassium hydroxide (204 mg, 3.63 mmol) was added in one portion to Intermediate 21-1 (493 mg, 1.21 mmol) in tert-butanol (10 mL) at 40° C. under nitrogen. The resulting suspension was stirred at 45° C. for 5 h, a thick white precipitate suspension slowly formed. Acetic acid (0.346 mL, 6.05 mmol) was added and the resulting solution stirred for a several minutes before being partitioned between EtOAc (100 mL) and 1N citric acid (50 mL). The suspension was filtered and dried to afford of desired product as a white solid (300 mg), the organic phase was separated, dried over MgSO$_4$, filtered and evaporated to afford crude product as a colourless oil which solidified on standing. The filtrate was purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness and combined with the solid to afford the title compound (376 mg, 82%) as a white solid.

$^1$H NMR (400 MHz, DMSO) δ 1.84 (12H, s), 2.58 (3H, s), 2.73 (3H, s), 7.46 (2H, d), 7.57 (1H, s), 7.66 (2H, d), 7.98 (1H, s), 12.08 (1H, s); m/z 380 (M+H)$^+$.

Intermediate 21-1: Ethyl 4-(4-(6-carbamoyl-3,5-dimethylpyrazin-2-yl)phenyl)bicyclo[2.2.2]octane-1-carboxylate

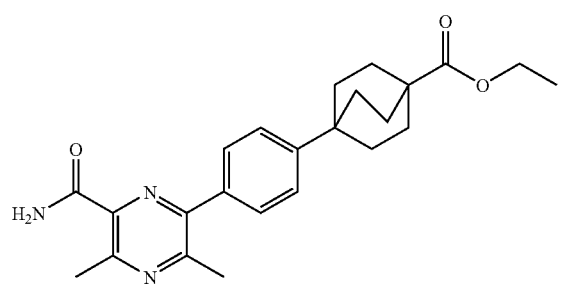

A solution of Intermediate 21-2 (525 mg, 1.37 mmol), Intermediate 21-4 (254 mg, 1.37 mmol), and tripotassium phosphate (348 mg, 1.64 mmol) in DME (15 mL), EtOH (5 mL) and water (2 mL) were degassed before addition of (1,1'-Bis(diphenylphosphino)ferrocene)-dichloropalladium(II) (DCM adduct) (56.2 mg, 0.07 mmol). The reaction mixture was heated to 80° C., under nitrogen, and left to stir at 80° C. for 2 h. The reaction mixture was allowed to cool to room temperature and then evaporated. The crude product was partitioned between EtOAc (100 mL) and water (50 mL), filtered through celite and the organic phase was separated, washed with saturated brine (50 mL). The organic layer was dried over MgSO$_4$, filtered and evaporated to afford crude product. The crude product was purified by flash silica chromatography, elution gradient 20 to 50% EtOAc in isohexane. Pure fractions were evaporated to dryness to afford the title compound (493 mg, 89%) as a white solid.

$^1$H NMR (400 MHz, DMSO) δ 1.18 (3H, t), 1.85 (12H, s), 2.58 (3H, s), 2.73 (3H, s), 4.05 (2H, q), 7.46 (2H, d), 7.57 (1H, s), 7.66 (2H, d), 7.97 (1H, s); m/z 408 (M+H)$^+$.

Intermediate 21-2: Ethyl 4-(4-(4,4,5,5-tetramethyl-1,3,2-dioxaborolan-2-yl)phenyl)bicyclo[2.2.2]octane-1-carboxylate

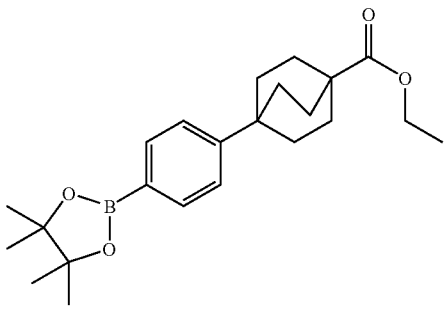

To a degassed solution of Intermediate 21-3 (1.66 g, 4.32 mmol) in DMSO (30 mL) was added potassium acetate (1.272 g, 12.96 mmol) and bis(pinacolato)diboron (1.207 g, 4.75 mmol), the reaction mixture was degassed for a further 20 minutes. (1,1'-Bis(diphenylphosphino)ferrocene)-dichloropalladium(II) (DCM adduct) (0.212 g, 0.26 mmol) was added and the suspension was degassed and then heated, under nitrogen at 80° C. for 3 h. The reaction mixture was allowed to cool, poured onto water (125 mL), the suspension was filtered and the solid was purified by flash silica chromatography, elution gradient 0 to 20% EtOAc in isohexane. Pure fractions were evaporated to dryness to afford the title compound (1.080 g, 65.0%) as a white solid.

$^1$H NMR (400 MHz, CDCl$_3$) δ 1.25 (3H, t), 1.33 (12H, s), 1.84-1.93 (12H, m), 4.12 (2H, q), 7.33 (2H, d), 7.75 (2H, d); m/z (EI+) 384 M$^+$.

Intermediate 21-3: Ethyl 4-(4-iodophenyl)bicyclo[2.2.2]octane-1-carboxylate

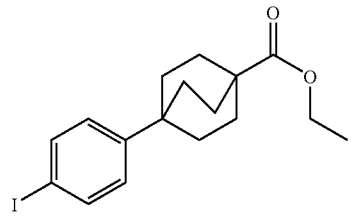

[Bis(trifluoroacetoxy)iodo]benzene (3.78 g, 8.78 mmol) and iodine (1.061 g, 4.18 mmol) were added to a stirred solution of ethyl 4-phenylbicyclo[2.2.2]octane-1-carboxylate (prepared according to the procedure described in WO 2007/071966) (2.16 g, 8.36 mmol, CAS 10207-26-8) in CHCl₃ (50 mL). The resulting solution was stirred at ambient temperature for 90 minutes. The reaction mixture was poured into sodium thiosulfate (100 mL), extracted with DCM (2×100 mL), the organic layer was washed with aqueous sodium thiosulfate (2×80 mL), separated, dried over MgSO₄, filtered and evaporated to afford a yellow oil which solidified on standing. The crude product was purified by flash silica chromatography, elution gradient 0 to 20% EtOAc in isohexane. Pure fractions were evaporated to dryness to afford the title compound (2.78 g, 87%) as a white solid.

¹H NMR (400 MHz, CDCl₃) δ 1.24 (3H, t), 1.79-1.84 (6H, m), 1.88-1.93 (6H, m), 4.11 (2H, q), 7.05 (2H, d), 7.61 (2H, d); m/z 385 (M+H)⁺.

Intermediate 21-4:
6-Chloro-3,5-dimethylpyrazine-2-carboxamide

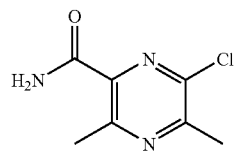

Intermediate 1-4 (227 g, 1057.54 mmol) was stirred in ammonia (7N in MeOH) (1957 mL, 89633.59 mmol) at ambient temperature overnight. The mixture was evaporated to dryness and the residue was triturated with ether and the suspension was filtered and at 40° C. under vacuum to afford the title compound (181 g, 92%) as a light brown solid.

¹H NMR (400 MHz, DMSO) δ 2.59 (3H, s), 2.67 (3H, s), 7.70 (1H, s), 7.99 (1H, s) m/z 186 (M+H)⁺.

Example 22

2-(4-(4-(6-Carbamoyl-3,5-dimethylpyrazin-2-yl)phenyl)bicyclo-[2.2.2]octan-1-yl)acetic acid

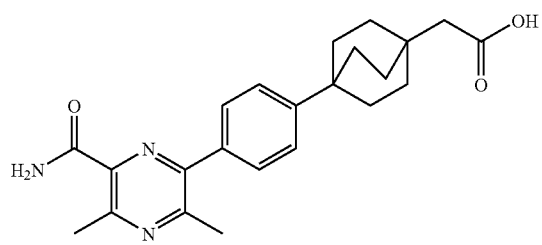

This compound was synthesised from Intermediate 22-1 using similar conditions as described in Example 21 to give the title compound (292 mg, 77%) as a white solid.

¹H NMR (400 MHz, DMSO) δ 1.60-1.65 (6H, m), 1.80-1.84 (6H, m), 2.05 (2H, s), 2.58 (3H, s), 2.72 (3H, s), 7.45 (2H, d), 7.56 (1H, s), 7.64 (2H, d), 7.97 (1H, s), 11.91 (1H, s); m/z 394 (M+H)⁺.

Intermediate 22-1: Methyl 2-(4-(4-(6-carbamoyl-3,5-dimethylpyrazin-2-yl)phenyl)bicyclo[2.2.2]octan-1-yl)acetate

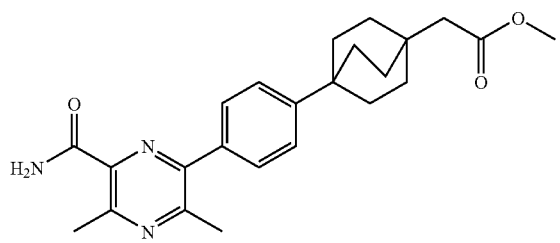

This compound was synthesised from Intermediate 21-4 and Intermediate 22-2 using similar conditions as described in Intermediate 21-1 to give the title compound (392 mg, 96%) as a white solid.

¹H NMR (400 MHz, DMSO) δ 1.57-1.63 (6H, m), 1.80-1.86 (6H, m), 2.15 (2H, s), 2.58 (3H, s), 2.73 (3H, s), 3.58 (3H, s), 7.44 (2H, d), 7.57 (1H, s), 7.64 (2H, d), 7.97 (1H, s); m/z 408 (M+H)⁺.

Intermediate 22-2: Methyl 2-(4-(4-(4,4,5,5-tetramethyl-1,3,2-dioxaborolan-2-yl)phenyl)bicyclo[2.2.2]octan-1-yl)acetate

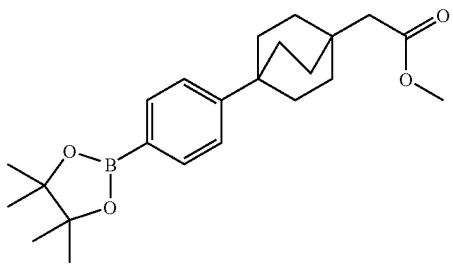

This compound was synthesised from Intermediate 22-3 using similar conditions as described in Intermediate 21-2 to give the title compound (0.701 g, 55.6%) as a white solid.

¹H NMR (400, CDCl₃) δ 1.33 (12H, s), 1.62-1.66 (6H, m), 1.82-1.87 (6H, m), 2.16 (2H, s), 3.65 (3H, s), 7.32 (2H, d), 7.74 (2H, d); m/z (EI+) 384 M⁺.

Intermediate 22-3: Methyl 2-(4-(4-iodophenyl)bicyclo[2.2.2]octan-1-yl)acetate

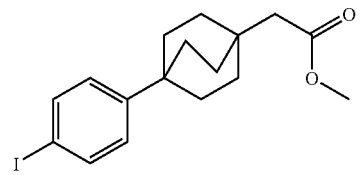

This compound was synthesised from methyl 2-(4-phenyl-bicyclo[2.2.2]octan-1-yl)acetate (prepared according to the procedure described in WO 2007/071966, CAS 70631-58-2) using similar conditions as described in Intermediate 21-3 to give the title compound (1.320 g, 80%) as a white solid.

$^1$H NMR (400 MHz, CDCl$_3$) δ 1.62-1.66 (6H, m), 1.77-1.82 (6H, m), 2.16 (2H, s), 3.66 (3H, s), 7.05 (2H, d), 7.59 (2H, d); m/z (EI+) 384 M$^+$.

Example 23

3-[4-(6-Carbamoyl-3,5-dimethylpyrazin-2-yl)phenyl]adamantane-1-carboxylic acid

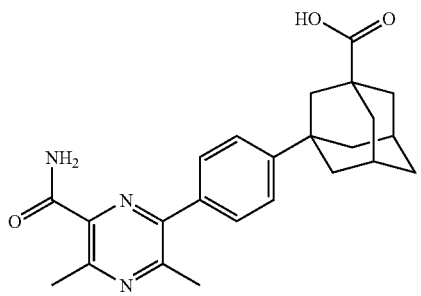

This compound was synthesised from Intermediate 23-1 using similar conditions as described in Example 21. Except after 70 minutes the reaction mixture was allowed to cool and 1N citric acid (15 mL) was added, the precipitate was collected by filtration, washed with 1N citric acid (10 mL), water (10 mL) and dried under vacuum to afford the title compound (360 mg, 90%) as a white solid.

$^1$H NMR (400 MHz, DMSO) δ 1.69-1.73 (2H, m), 1.84-1.89 (8H, m), 1.96 (2H, s), 2.17-2.19 (2H, m), 2.59 (3H, s), 2.74 (3H, s), 7.50 (2H, d), 7.59 (1H, s), 7.68 (2H, d), 7.98 (1H, s), 12.07 (1H, s); m/z 406 (M+H)$^+$.

Intermediate 23-1: Methyl 3-[4-(6-carbamoyl-3,5-dimethylpyrazin-2-yl)phenyl]adamantane-1-carboxylate

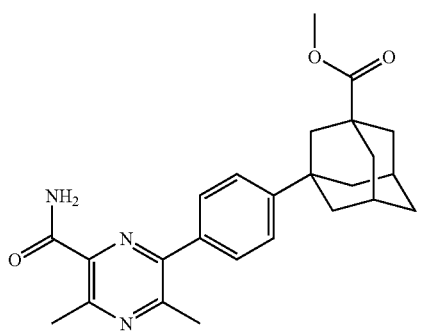

This compound was synthesised from Intermediate 21-4 and Intermediate 23-2 using similar conditions as described in Intermediate 21-1 to give the title compound (412 mg, 74.3%) as a white solid.

$^1$H NMR (400 MHz, DMSO) δ 1.70-1.73 (2H, m), 1.85-1.91 (8H, m), 1.98 (2H, s), 2.18-2.20 (2H, m), 2.58 (3H, s), 2.73 (3H, s), 3.60 (3H, s), 7.49 (2H, d), 7.58 (1H, s), 7.68 (2H, d), 7.97 (1H, s); m/z 420 (M+H)$^+$.

Intermediate 23-2: Methyl 3-[4-(4,4,5,5-tetramethyl-1,3,2-dioxaborolan-2-yl)phenyl]adamantane-1-carboxylate

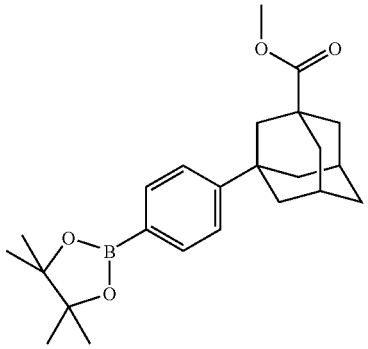

This compound was synthesised from Intermediate 23-3 using similar conditions as described in Intermediate 21-2 to give the title compound (1.758 g, 63.9%) as a white solid.

$^1$H NMR (400 MHz, CDCl$_3$) δ 1.33 (12H, s), 1.73-1.75 (2H, m), 1.88-1.95 (8H, m), 2.05 (2H, s), 2.21-2.25 (2H, m), 3.67 (3H, s), 7.37 (2H, d), 7.77 (2H, d); m/z 396 (EI+) M$^+$.

Intermediate 23-3: Methyl 3-(4-iodophenyl)adamantane-1-carboxylate

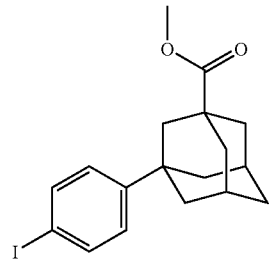

This compound was synthesised from Intermediate 23-4 using similar conditions as described in Intermediate 21-3 to give the title compound (2.75 g, 88%) as a colourless oil.

$^1$H NMR (400 MHz, CDCl$_3$) δ 1.72-1.74 (2H, m), 1.89-1.95 (8H, m), 1.99 (2H, s), 2.22-2.24 (2H, m), 3.67 (3H, s), 7.11 (2H, d), 7.63 (2H, d); m/z 396 (EI+) M$^+$.

Intermediate 23-4: Methyl 3-phenyladamantane-1-carboxylate

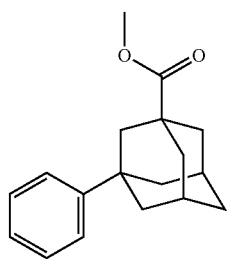

Trimethylsilyldiazomethane 2M solution in hexane (8.15 mL, 16.31 mmol) was added dropwise to a stirred solution of 3-phenyl-1-adamantanecarboxylic acid (2.09 g, 8.15 mmol, CAS 37589-22-3) in toluene (20 mL) and methanol (10 mL) over a period of 2 minutes. The resulting solution was stirred at ambient temperature for 60 minutes. The reaction mixture was evaporated to afford crude product. The crude product was purified by flash silica chromatography, elution gradient 0 to 20% EtOAc in isohexane. Pure fractions were evaporated to dryness to afford the title compound (2.140 g, 97%) as a colourless oil.

$^1$H NMR (400 MHz, CDCl$_3$) δ 1.73-1.75 (2H, m), 1.90-1.93 (8H, m), 2.04 (2H, s), 2.22-2.25 (2H, m), 3.67 (3H, s), 7.17-7.21 (1H, m), 7.30-7.38 (4H, m); m/z 270 (EI+) M$^+$.

Example 24

2-[3-[4-(6-Carbamoyl-3,5-dimethylpyrazin-2-yl)phenyl]-1-adamantyl]acetic acid

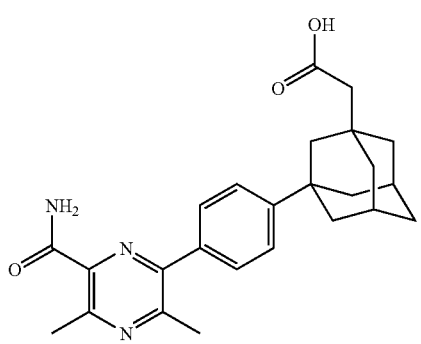

This compound was synthesised from Intermediate 24-1 using similar conditions as described in Example 21 to give the title compound (126 mg, 62.0%) as a white solid.

$^1$H NMR (400 MHz, DMSO) δ 1.62-1.71 (6H, m), 1.75 (2H, s), 1.81-1.88 (4H, m), 2.07 (2H, s), 2.15 (2H, s), 2.59 (3H, s), 2.73 (3H, s), 7.47 (2H, d), 7.58 (1H, s), 7.67 (2H, d), 7.97 (1H, s), 11.89 (1H, s); m/z 420 (M+H)$^+$.

Intermediate 24-1: Methyl 2-[3-[4-(6-carbamoyl-3,5-dimethylpyrazin-2-yl)phenyl]-1-adamantyl]acetate

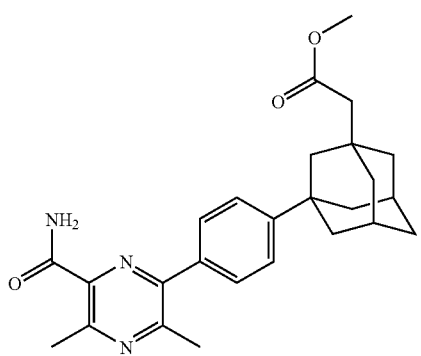

This compound was synthesised from Intermediate 21-4 and Intermediate 24-2 using similar conditions as described in Intermediate 21-1 to give the title compound (210 mg, 48.4%) as a colourless oil which solidified on standing.

$^1$H NMR (400 MHz, DMSO) δ 1.60-1.70 (6H, m), 1.73 (2H, s), 1.81-1.89 (4H, m), 2.14-2.16 (2H, m), 2.16 (2H, s), 2.59 (3H, s), 2.74 (3H, s), 3.57 (3H, s), 7.47 (2H, d), 7.58 (1H, s), 7.68 (2H, d), 7.97 (1H, s); m/z 434 (M+H)$^+$.

Intermediate 24-2: Methyl 2-[3-[4-(4,4,5,5-tetramethyl-1,3,2-dioxaborolan-2-yl)phenyl]-1-adamantyl]acetate

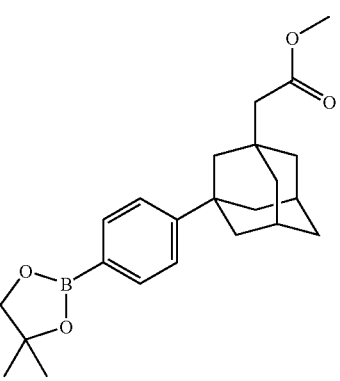

This compound was synthesised from Intermediate 24-3 using similar conditions as described in Intermediate 21-2 to give the title compound (1.240 g, 76%) as a white solid.

$^1$H NMR (400 MHz, CDCl$_3$) δ 1.33 (12H, s), 1.61-1.72 (6H, m), 1.75 (2H, s), 1.82-1.90 (2H, m), 2.17 (2H, s), 2.17-2.20 (4H, m), 3.64 (3H, s), 7.36 (2H, d), 7.77 (2H, d); m/z 410 (EI+) M$^+$.

Intermediate 24-3: Methyl 2-[3-(4-iodophenyl)-1-adamantyl]acetate

This compound was synthesised from methyl 2-(3-phenyl-1-adamantyl)acetate (CAS 175721-57-0, prepared according to the procedure described in WO 2007/071966 using similar conditions as described in Intermediate 21-3 to give the title compound (1.680 g, 81%) as a yellow oil which solidified on standing.

¹H NMR (400 MHz, CDCl₃) δ 1.62-1.71 (8H, m), 1.78-1.84 (4H, m), 2.16 (2H, s), 2.17-2.20 (2H, m), 3.65 (3H, s), 7.09 (2H, d), 7.62 (2H, d); m/z 410 (EI+) M⁺.

Example 25

3-((1r,4r)-4-(4-(6-Carbamoyl-3,5-dimethylpyrazin-2-yl)phenyl)cyclohexyl)propanoic acid

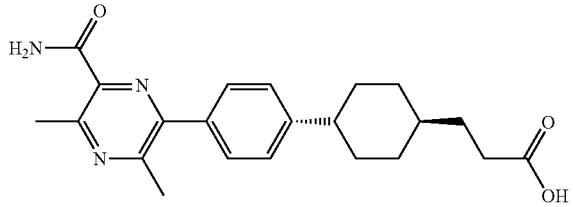

This compound was synthesised from Intermediate 25-1 using similar conditions as described in Example 21. Except the crude product was purified by crystallisation from boiling EtOH (~10 mL) to afford the title compound (180 mg, 65.3%) as a pale red solid.

¹H NMR (400 MHz, DMSO) δ 1.02-1.11 (2H, m), 1.27-1.36 (1H, m), 1.43-1.53 (4H, m), 1.81-1.87 (4H, m), 2.25 (2H, t), 2.51-2.55 (1H, m), 2.58 (3H, s), 2.73 (3H, s), 7.35 (2H, d), 7.57 (1H, s), 7.64 (2H, d), 7.97 (1H, s), 11.97 (1H, s); m/z 382 (M+H)⁺.

Intermediate 25-1: Methyl 3-((1r,4r)-4-(4-(6-carbamoyl-3,5-dimethylpyrazin-2-yl)phenyl)cyclohexyl)propanoate

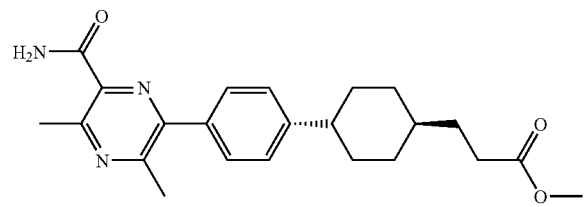

Acetonitrile (4.345 mL) added to 1,1bis(di-tert-butylphosphino)ferrocene palladium dichloride (57.7 mg, 0.10 mmol) and stirred at room temperature for 5 min before addition of potassium carbonate (540 mg, 3.91 mmol), water (4.35 mL) and Intermediate 25-2 (728 mg, 1.96 mmol). After a further 5 minutes Intermediate 21-4 (364 mg, 1.96 mmol) was added and the reaction mixture heated to 80° C. for 5 hours. The reaction mixture was partitioned between EtOAc (100 mL) and water (50 mL) and the mixture was filtered through celite, washing through with EtOAc (50 mL). The organic layer was dried over MgSO₄, filtered and evaporated to afford crude product. The crude product was purified by flash silica chromatography, elution gradient 0 to 50% EtOAc in isohexane. Pure fractions were evaporated to dryness to afford the title compound (286 mg, 37.0%) as a red brown solid.

¹H NMR (400 MHz, DMSO) δ 1.02-1.13 (3H, m), 1.26-1.37 (1H, m), 1.42-1.53 (4H, m), 1.80-1.88 (4H, m), 2.35 (2H, t), 2.58 (3H, s), 2.74 (3H, s), 3.59 (3H, s), 7.34 (2H, d), 7.57 (1H, s), 7.64 (2H, d), 7.96 (1H, s); m/z 396 (M+H)⁺.

Intermediate 25-2: Methyl 3-((1r,4r)-4-(4-(4,4,5,5-tetramethyl-1,3,2-dioxaborolan-2-yl)phenyl)cyclohexyl)propanoate

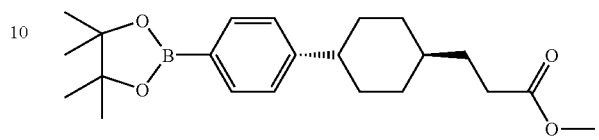

A solution of Intermediate 25-3 (4.40 g, 11.16 mmol) in dioxane (85 mL) was degassed with nitrogen for a period of 5 minutes. Potassium acetate (3.28 g, 33.47 mmol), 4,4,4',4',5,5,5',5'-octamethyl-2,2'-bi(1,3,2-dioxaborolane) (3.12 g, 12.27 mmol), (1,1'-Bis(diphenylphosphino)ferrocene)-dichloropalladium(II) (DCM adduct) (0.551 g, 0.67 mmol) and 1,1'-Bis(diphenylphosphino)ferrocene (0.375 g, 0.67 mmol) were added. The resulting mixture was stirred at 85° C. under nitrogen for 17 hours. The reaction mixture was concentrated and diluted with EtOAc (200 mL), and then mixture was filtered through celite. The filtrate was washed with saturated brine, the organic layer was dried over MgSO₄, filtered and evaporated to afford crude product. The crude product was purified by flash silica chromatography, elution gradient 0 to 20% EtOAc in isohexane. Pure fractions were evaporated to dryness to afford the title compound (2.68 g, 64.5%) as a white solid.

¹H NMR (400 MHz, CDCl₃) δ 1.02-1.13 (2H, m), 1.31-1.33 (1H, m), 1.33 (12H, s), 1.40-1.52 (2H, m), 1.59 (2H, q), 1.84-1.92 (4H, m), 2.36 (2H, t), 2.43-2.52 (1H, m), 3.68 (3H, s), 7.21 (2H, d), 7.73 (2H, d); m/z 372 (EI+) M⁺.

Intermediate 25-3: Methyl 3-((1r,4r)-4-(4-(trifluoromethylsulfonyloxy)phenyl)-cyclohexyl)propanoate

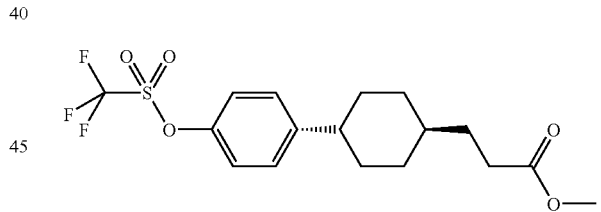

Triethylamine (2.59 mL, 18.57 mmol) was added to a stirred solution of Intermediate 25-4 (3.27 g, 12.46 mmol) and trifluoromethanesulphonic anhydride (2.56 mL, 15.58 mmol) in DCM (120 mL) cooled to 0° C., over a period of 5 minutes under nitrogen. The resulting red solution was stirred at 0° C. for 2 hours and then allowed to warm to ambient temperature overnight. The reaction mixture was diluted with DCM (100 mL), and washed sequentially with water (100 mL), saturated NaHCO₃ (100 mL), and saturated brine (100 mL). The organic layer was dried over MgSO₄, filtered and evaporated to afford crude product. The crude product was purified by flash silica chromatography, elution gradient 0 to 20% EtOAc in isohexane. Pure fractions were evaporated to dryness to afford the title compound (4.42 g, 90%) as a yellow oil.

¹H NMR (400 MHz, CDCl₃) δ 1.07-1.11 (2H, m), 1.29-1.35 (1H, m), 1.37-1.47 (2H, m), 1.58 (2H, q), 1.88-1.91 (4H, m), 2.36 (2H, t), 2.46-2.53 (1H, m), 3.68 (3H, s), 7.15-7.19 (2H, m), 7.23-7.27 (2H, m); m/z 394 (EI+) M⁺.

Intermediate 25-4: Methyl 3-((1r,4r)-4-(4-hydroxyphenyl)cyclohexyl)propanoate

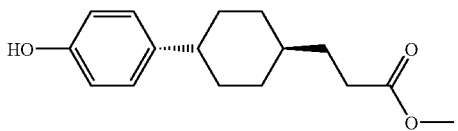

A solution of Intermediate 25-5 (3.82 g, 15.38 mmol) in MeOH (100 mL) and concentrated H$_2$SO$_4$ (1.0 mL) was stirred at 70° C. for 3 hours and allowed to cool to ambient temperature overnight. The reaction mixture was evaporated to dryness and redissolved in EtOAc (200 mL) and washed with saturated brine (2×150 mL). The organic layer was dried over MgSO$_4$, filtered and evaporated to afford crude product. The crude product was purified by flash silica chromatography, elution gradient 0 to 20% EtOAc in isohexane. Pure fractions were evaporated to dryness to afford the title compound (3.27 g, 81%) as a white solid.

$^1$H NMR (400 MHz, CDCl$_3$) δ 1.01-1.12 (2H, m), 1.26-1.33 (1H, m), 1.35-1.45 (2H, m), 1.58 (2H, q), 1.83-1.89 (4H, m), 2.36 (2H, t), 2.35-2.44 (1H, m), 3.68 (3H, s), 4.62 (1H, s), 6.73-6.77 (2H, m), 7.04-7.08 (2H, m); m/z 262 (EI+) M$^+$.

Intermediate 25-5: 3-((1r,4r)-4-(4-Hydroxyphenyl)cyclohexyl)propanoic acid

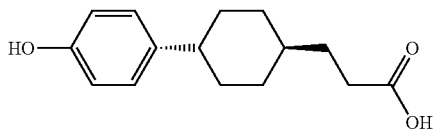

A solution of Intermediate 25-6 (5.49 g, 17.86 mmol) and sodium hydroxide (10.71 g, 267.88 mmol) in 1,2-propanediol (65 mL) and water (16 mL) was heated to 140° C. for 1 hour. The reaction mixture was allowed to cool to ambient temperature, adjusted to pH 2 with 2M HCl and the suspension was extracted into EtOAc (2×200 mL). The organic extracts were combined, washed with saturated brine (200 mL), dried over MgSO$_4$, filtered and evaporated to afford crude product. This was slurried in isohexane (120 mL), filtered and air dried to afford the title compound (3.87 g, 86%) as a white solid, which was used without further purification.

$^1$H NMR (400 MHz, DMSO) δ 0.95-1.05 (2H, m), 1.16-1.39 (3H, m), 1.44 (2H, q), 1.73-1.79 (4H, m), 2.23 (2H, t), 2.29-2.38 (1H, m), 6.62-6.66 (2H, m), 6.98 (2H, d), 9.03 (1H, s), 11.92 (1H, s); m/z 247 (M−H)$^-$.

Intermediate 25-6: 4-((1r,4r)-4-(2-Cyanoethyl)cyclohexyl)phenyl Methanesulfonate

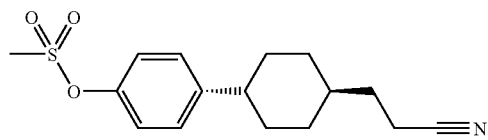

Sodium cyanide (1.669 g, 34.06 mmol) was added to a stirred solution of Intermediate 25-7 (8.55 g, 22.71 mmol) in DMF (153 mL). The resulting mixture was stirred at 80° C. for 3 h and then allowed to cool to ambient temperature. The reaction mixture was diluted with EtOAc (150 mL), and washed with saturated brine (2×250 mL). The organic layer was dried over MgSO$_4$, filtered and evaporated to afford desired product. This still contained DMF so it was re dissolved in EtOAc (150 mL), and washed with saturated brine (2×200 mL), the organic layer was dried over MgSO$_4$, filtered and evaporated to afford crude product. The crude product was purified by flash silica chromatography, elution gradient 30 to 60% EtOAc in isohexane. Pure fractions were evaporated to dryness to afford the title compound (4.08 g, 58.4%) as a white solid.

$^1$H NMR (400 MHz, CDCl$_3$) δ 1.06-1.16 (2H, m), 1.41-1.52 (3H, m), 1.54 (3H, s), 1.64 (2H, q), 1.89-1.95 (4H, m), 2.40 (2H, t), 2.47-2.53 (1H, m), 3.13 (3H, s), 7.18-7.24 (4H, m); m/z 307 (EI+) M$^+$.

Intermediate 25-7: 4-((1r,4r)-4-(2-(Methylsulfonyloxy)ethyl)cyclohexyl)phenyl methanesulfonate

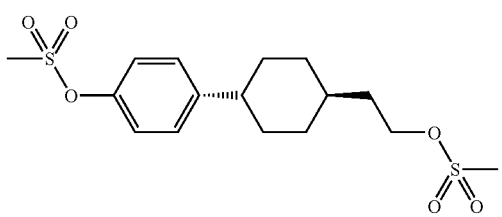

Methanesulphonyl chloride (6.56 mL, 84.58 mmol) was added to a stirred suspension of Intermediate 25-8 (8.47 g, 38.45 mmol) and triethylamine (11.79 mL, 84.58 mmol) in DCM (300 mL). The resulting solution was stirred at ambient temperature for 16 h. The reaction mixture was washed with saturated brine (100 mL), the organic layer was dried over MgSO$_4$, filtered and evaporated to afford crude product. The crude product was purified by flash silica chromatography, elution gradient 20 to 70% EtOAc in isohexane. Pure fractions were evaporated to dryness to afford the title compound (13.84 g, 96%) as a white solid.

$^1$H NMR (400 MHz, DMSO) δ 0.99-1.15 (2H, m), 1.32-1.51 (3H, m), 1.62 (2H, q), 1.75-1.87 (4H, m), 2.52-2.56 (1H, m), 3.16 (3H, s), 3.27 (3H, 3), 4.26 (1H, t), 7.22-7.26 (2H, m), 7.31-7.35 (2H, m); m/z 399 (M+Na)$^+$.

Intermediate 25-8: 4-((1r,4r)-4-(2-Hydroxyethyl)cyclohexyl)phenol

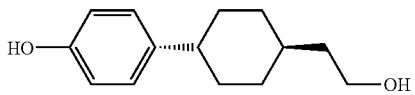

A 1M solution of lithium aluminum hydride in THF (80 mL, 79.75 mmol) was added dropwise to a stirred solution of methyl 2-((1r,4r)-4-(4-hydroxyphenyl)cyclohexyl)acetate (prepared according to WO 2004/047755) (12.3 g, 49.53 mmol, CAS 701232-67-9) in THF (280 mL) at 0° C. under nitrogen. A thick suspension formed so the mixture was removed from the cooling bath and stirred at ambient temperature for 1 h. The reaction mixture was cooled in 0° C. and carefully quenched with saturated NH$_4$Cl (75 mL), water (50 mL) and 2N HCl (50 mL). The mixture was filtered through celite, washing through with MeOH (150 mL) and EtOAc (2×250 mL). The filtrate was concentrated, the residue was diluted with EtOAc (300 mL), washed sequentially with 2N HCl (100 mL) and saturated brine (200 mL). The organic layer was dried over MgSO$_4$, filtered and evaporated to afford the title compound (10.37 g, 95%) as a white solid.

$^1$H NMR (400 MHz, DMSO) δ 0.97-1.06 (2H, m), 1.29-1.42 (5H, m), 1.71-1.79 (4H, m), 2.29-2.36 (1H, m), 3.42-3.47 (2H, m), 4.27 (1H, t), 6.64 (2H, d), 6.98 (2H, d), 9.03 (1H, s); m/z 220 (EI+) M$^+$.

Example 26

(1r,4r)-4-(4-(6-Carbamoyl-3,5-dimethylpyrazin-2-yl)-2-chlorophenoxy)cyclohexanecarboxylic acid

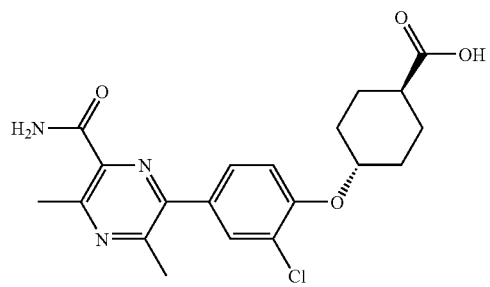

A solution of Intermediate 26-1 (561 mg, 1.22 mmol) in TFA (6.098 mL) allowed to stand at ambient temperature for 30 minutes. The reaction mixture was evaporated and ether was added to the residue to give a solid which was purified by recrystallisation from boiling absolute EtOH (~10 mL) to afford the title compound (293 mg, 59.5%) as a yellow solid.

$^1$H NMR (400 MHz, DMSO) δ 1.45-1.59 (4H, m), 1.93-2.00 (2H, m) 2.08-2.10 (2H, m), 2.28-2.34 (1H, m), 2.59 (3H, s), 2.73 (3H, s), 4.48-4.52 (1H, m), 7.32 (1H, d), 7.59 (1H, s), 7.63-7.66 (1H, m), 7.86 (1H, d), 8.05 (1H, s), 12.10 (1H, s); m/z 404 (M+H)$^+$.

Intermediate 26-1: (1r,4r)-tert-Butyl 4-(4-(6-carbamoyl-3,5-dimethylpyrazin-2-yl)-2-chlorophenoxy)cyclohexanecarboxylate

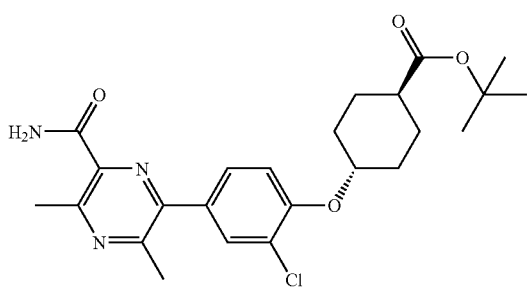

This compound was synthesised from Intermediate 26-2 using similar conditions as described in Intermediate 25-1 to give the title compound (561 mg, 71.5%) as a yellow solid.

$^1$H NMR (400 MHz, DMSO) δ 1.47 (9H, s), 1.54-1.65 (4H, m), 1.96-2.04 (2H, m), 2.12-2.17 (2H, m), 2.32-2.39 (1H, m), 2.66 (3H, s), 2.80 (3H, s), 4.53-4.60 (1H, m), 7.39 (1H, d), 7.66 (1H, s), 7.71 (1H, d), 7.92 (1H, s), 8.12 (1H, s); m/z 460 (M+H)$^+$.

Intermediate 26-2: (1r,4r)-tert-Butyl 4-(2-chloro-4-(4,4,5,5-tetramethyl-1,3,2-dioxaborolan-2-yl)phenoxy)cyclohexanecarboxylate

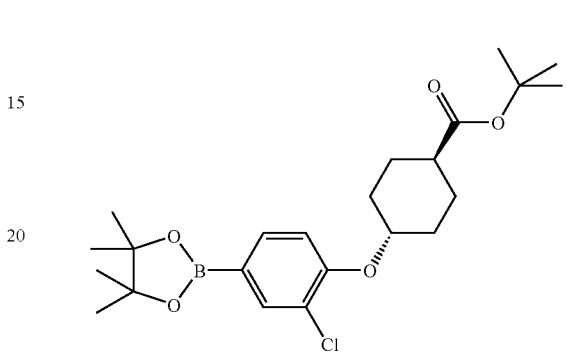

This compound was synthesised from Intermediate 26-3 using similar conditions as described in Intermediate 25-2 to give the title compound (4.23 g, 88%) as a colourless oil which solidified on standing.

$^1$H NMR (400 MHz, CDCl$_3$) δ 1.33 (12H, s), 1.45 (9H, s), 1.55-1.62 (4H, m), 2.03-2.08 (2H, m), 2.13-2.19 (2H, m), 2.24-2.31 (1H, m), 4.25-4.31 (1H, m), 6.92 (1H, d), 7.61 (1H, d), 7.79 (1H, s); m/z 436 (EI+) M$^+$.

Intermediate 26-3: (1r,4r)-tert-Butyl 4-(4-bromo-2-chlorophenoxy)cyclohexane-carboxylate

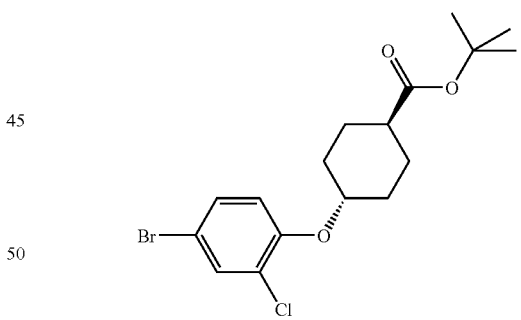

To a solution of Intermediate 26-4 (5.3 g, 26.46 mmol, CAS 931110-79-1), 4-bromo-2-chlorophenol (6.59 g, 31.76 mmol) and triphenylphosphine (8.33 g, 31.76 mmol) in THF (200 mL) was added diisopropyl azodicarboxylate (5.73 mL, 29.11 mmol). The solution was stirred at room temperature for 4 h. The reaction mixture was evaporated. The crude product was purified by flash silica chromatography, elution gradient 0 to 20% EtOAc in isohexane. Pure fractions were evaporated to dryness to afford the title compound (4.27 g, 41.4%) as a colourless oil.

$^1$H NMR (400 MHz, DMSO) δ 1.37-1.53 (13H, m), 1.88-2.03 (4H, m), 2.23-2.28 (1H, m), 4.35-4.39 (1H, m), 7.19 (1H, d), 7.42-7.44 (1H, m), 7.63 (1H, d); HPLC tR=3.65 min.

Intermediate 26-4: (1s,4s)-tert-Butyl 4-hydroxycyclohexanecarboxylate

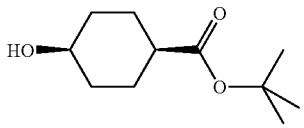

To a suspension of (1s,4s)-4-hydroxycyclohexanecarboxylic acid (5 g, 34.68 mmol, CAS 3685-22-1) in toluene (160 mL) at 90° C. was added N,N-Dimethylformamide di-tert-butyl acetal (16.63 mL, 69.36 mmol) in one portion. The resultant solution was stirred at 90° C. for 1 h. A further portion of N,N-Dimethylformamide di-tert-butyl acetal (16.63 mL, 69.36 mmol) was then added and the reaction mixture stirred for 30 min at 90° C. and then room temperature overnight. Further N,N-Dimethylformamide di-tert-butyl acetal (10 mL) added dropwise over 10 minutes, the reaction mixture was stirred at 70° C. for 1 h and then allowed to cool. The reaction mixture was washed with 2M NaOH (100 mL), brine (100 mL) and then evaporated to give the title compound (5.30 g, 76%) as an oil.

$^1$H NMR (400 MHz, DMSO) δ 1.36-1.39 (1H, m), 1.39 (9H, s), 1.41-1.51 (6H, m), 1.70-1.81 (2H, m), 2.19-2.25 (1H, m), 3.62 (1H, m), 4.32 (1H, d).

Example 27

(1s,4s)-4-(4-(6-Carbamoyl-3,5-dimethylpyrazin-2-yl)-2-chlorophenoxy)cyclohexanecarboxylic acid

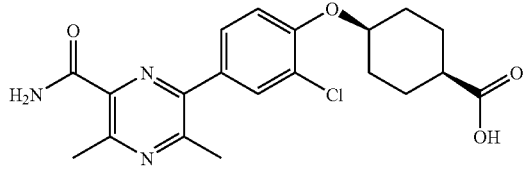

This compound was synthesised from Intermediate 27-1 using similar conditions as described in Example 21 to give the title compound (182 mg, 50.8%) as a white solid, which was crystallised from boiling absolute EtOH (~2 mL).

$^1$H NMR (400 MHz, DMSO) δ 1.67-1.74 (4H, m), 1.76-1.93 (4H, m), 2.35-2.41 (1H, m), 2.60 (3H, s), 2.73 (3H, s), 4.77 (1H, brs), 7.28 (1H, d), 7.59 (1H, s), 7.65 (1H, dd), 7.87 (1H, d), 8.05 (1H, s), 12.07 (1H, s); m/z 404 (M+H)$^+$.

Intermediate 27-1: (1s,4s)-Methyl 4-(4-(6-carbamoyl-3,5-dimethylpyrazin-2-yl)-2-chlorophenoxy)cyclohexanecarboxylate

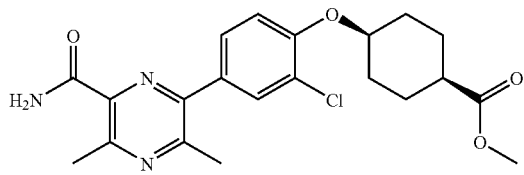

This compound was synthesised from Intermediate 27-2 and Intermediate 21-4 using similar conditions as described in Intermediate 25-1 to give the title compound (371 mg, 48.1%) as a white solid.

$^1$H NMR (400 MHz, DMSO) δ 1.68-1.75 (4H, m), 1.78-1.93 (4H, m), 2.52-2.54 (1H, m) 2.60 (3H, s), 2.73 (3H, s), 3.61 (3H, s), 4.76-4.79 (1H, m), 7.29 (1H, d), 7.59 (1H, s), 7.65 (1H, dd), 7.87 (1H, d), 8.05 (1H, s); m/z 418 (M+H)$^+$.

Intermediate 27-2: (1s,4s)-Methyl 4-(2-chloro-4-(4,4,5,5-tetramethyl-1,3,2-dioxaborolan-2-yl)phenoxy)cyclohexanecarboxylate

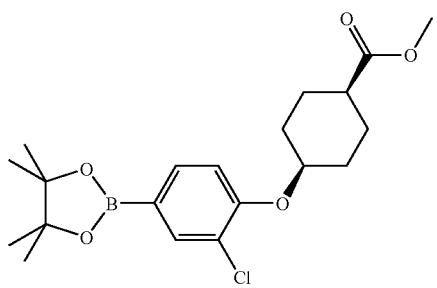

This compound was synthesised from Intermediate 27-3 using similar conditions as described in Intermediate 25-2 to give the title compound (4.73 g, 85%) as a pale yellow oil which solidified on standing.

$^1$H NMR (400 MHz, CDCl$_3$) δ 1.33 (12H, s), 1.60-1.68 (2H, m), 1.74-1.81 (2H, m), 1.98-2.09 (4H, m), 2.37-2.44 (1H, m), 3.69 (3H, s), 4.57-4.60 (1H, m), 6.90 (1H, d), 7.60-7.62 (1H, m), 7.80 (1H, d); m/z 394 (EI+) M$^+$.

Intermediate 27-3: (1s,4s)-methyl 4-(4-bromo-2-chlorophenoxy)cyclohexane-carboxylate

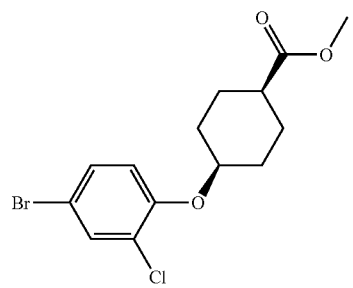

This compound was synthesised from (1r,4r)-methyl 4-hydroxycyclohexanecarboxylate (CAS 6125-57-1) and 4-bromo-2-chlorophenol using similar conditions as described in Intermediate 26-3 to give the title compound (4.88 g, 55.5%) as a colourless oil.

$^1$H NMR (400 MHz, DMSO) δ 1.62-1.86 (8H, m), 3.60 (3H, s), 4.66 (1H, m), 7.15 (1H, d), 7.42-7.45 (1H, m), 7.64 (1H, d) one CH obscured; HPLC tR=2.99 min.

Example 28

6-((1r,4s)-4-((2H-Tetrazol-5-yl)methyl)-2',3'-dihydrospiro[cyclohexane-1,1'-indene]-5'-yl)-3,5-dimethylpyrazine-2-carboxamide

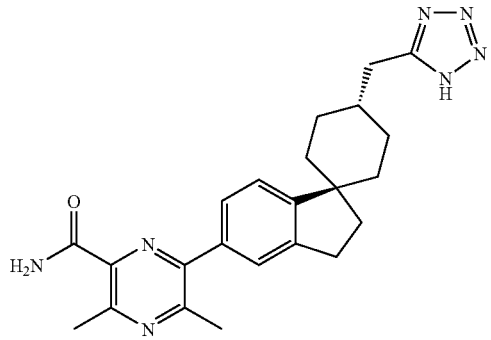

A solution of Intermediate 21-4 (197 mg, 1.06 mmol), Intermediate 28-1 (473 mg, 1.06 mmol) and tripotassium phosphate (449 mg, 2.11 mmol) in DME (10 mL), EtOH (6.25 mL) and water (2.5 mL) was degassed before addition of (1,1'-bis(diphenylphosphino)ferrocene)-dichloropalladium(II) (43.5 mg, 0.05 mmol). The reaction mixture was heated to 80° C., under nitrogen, and left to stir overnight for 5 hrs. The reaction mixture was allowed to cool to room temperature and then evaporated. The residue was acidified with 2N HCl (3 mL), diluted with water (20 mL) and extracted into EtOAc (4×50 mL). The organic extracts were combined, dried over MgSO$_4$, filtered and evaporated to afford crude product. The crude product was purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness to afford the title compound (51.9 mg, 11.76%) as a white solid.

$^1$H NMR (400 MHz, DMSO) δ 1.23-1.38 (2H, m), 1.58-1.73 (6H, m), 1.86-1.96 (1H, m), 2.04 (2H, t), 2.63 (3H, s), 2.79 (3H, s), 2.91 (2H, d), 2.97 (2H, t), 7.33 (1H, d), 7.55 (1H, d), 7.60 (1H, s), 7.62 (1H, s), 8.02 (1H, s); NH not seen; m/z 418 (M+H)$^+$.

Intermediate 28-1: 3-(5-(((1r,4s)-5'-(4,4,5,5-Tetramethyl-1,3,2-dioxaborolan-2-yl)-2',3'-dihydrospiro[cyclohexane-1,1'-indene]-4-yl)methyl)-2H-tetrazol-2-yl)propanenitrile

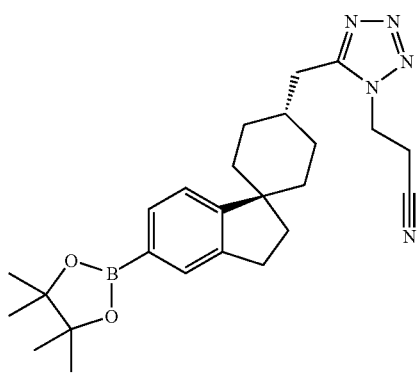

To a solution of triphenylphosphine (1.453 g, 5.54 mmol) and Intermediate 28-2 (900 mg, 2.13 mmol) in THF (25.400 mL) in an ice bath was added diisopropyl azodicarboxylate (1.133 mL, 5.75 mmol). The resulting yellow solution was allowed to stir at 0° C., after 2 minutes azidotrimethylsilane (0.820 mL, 6.18 mmol) was added dropwise. After 17 hours at ambient temperature further triphenylphosphine (1.453 g, 5.54 mmol), diisopropyl azodicarboxylate (1.133 mL, 5.75 mmol) and azidotrimethylsilane (0.820 mL, 6.18 mmol) were added and the suspension was stirred at ambient temperature for a further 24 hours. The reaction mixture was cooled in an ice bath and a solution of Sodium nitrite (162 mg, 2.34 mmol) in water (3 mL) was added and after 30 minutes a solution of ammonium cerium(IV) nitrate (1285 mg, 2.34 mmol) in water (10 mL) was added (CAUTION: Gas evolution). The reaction mixture was stirred for a further 45 minutes. The reaction mixture was poured into water (50 mL) and extracted with DCM (200 mL and 100 mL). The organic extracts were combined, dried over MgSO$_4$, filtered and evaporated to afford crude product.

The crude product was purified by flash silica chromatography, elution gradient 0 to 80% EtOAc in isohexane. Mixed fractions were evaporated to dryness to afford the title compound (487 mg, 51.1%) as a cream solid.

$^1$H NMR (400 MHz, DMSO) δ 1.20-1.38 (14H, m), 1.40-1.50 (2H, m), 1.53-1.70 (4H, m), 1.83-1.97 (3H, m), 2.82 (2H, t), 2.89 (2H, d), 3.18 (2H, t), 4.69 (2H, t), 7.16 (1H, d), 7.48 (1H, d), 7.49 (1H, s); m/z 448 (M+H)$^+$.

Intermediate 28-2: N-(2-Cyanoethyl)-2-((1r,4s)-5'-(4,4,5,5-tetramethyl-1,3,2-dioxaborolan-2-yl)-2',3'-dihydrospiro[cyclohexane-1,1'-indene]-4-yl)acetamide

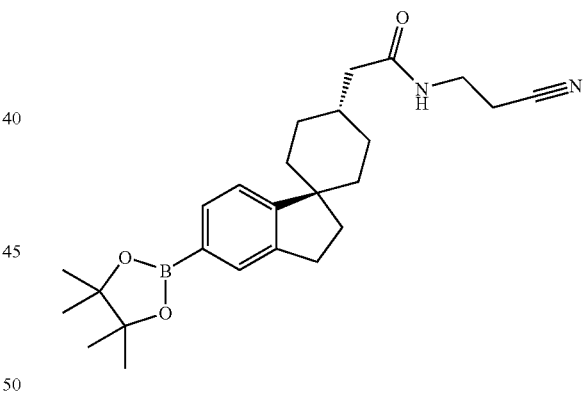

3-Aminopropionitrile (0.215 mL, 2.94 mmol) was added to a stirred solution of Intermediate 28-3 (725 mg, 1.96 mmol), N-ethyldiisopropylamine (1.023 mL, 5.87 mmol) and PyBROP (1.369 g, 2.94 mmol) in DCM (50 mL). The resulting solution was stirred at ambient temperature for 4 hours. The reaction mixture was evaporated to dryness and redissolved in EtOAc (125 mL), and washed sequentially with 2M HCl (75 mL) and saturated brine (75 mL). The organic layer was dried over MgSO$_4$, filtered and evaporated to afford crude product. The crude product was purified by flash silica chromatography, elution gradient 0 to 100% EtOAc in isohexane. Pure fractions were evaporated to dryness to afford the title compound (900 mg, 109%) as a white foam.

$^1$H NMR (400 MHz, DMSO) δ 1.09-1.20 (2H, m), 1.27 (12H, s), 1.42-1.46 (2H, m), 1.53-1.67 (4H, m), 1.72-1.79 (1H, m), 1.90 (2H, t), 2.03 (2H, d), 2.63 (2H, t), 2.81 (2H, t), 3.26-3.29 (2H, m), 7.17 (1H, d), 7.46 (1H, d), 7.48 (1H, s), 8.16 (1H, t); m/z 423 (M+H)$^+$.

Intermediate 28-3: 2-((1r,4s)-5'-(4,4,5,5-Tetramethyl-1,3,2-dioxaborolan-2-yl)-2',3'-dihydrospiro[cyclohexane-1,1'-indene]-4-yl)acetic acid

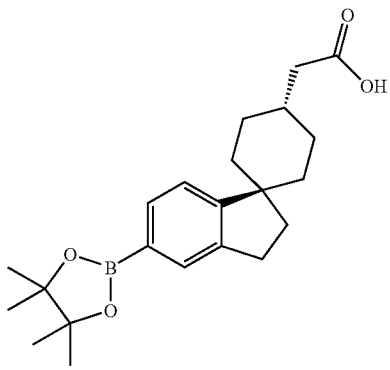

TFA (15.90 mL) was added to a stirred solution of Intermediate 29-3 (802 mg, 1.88 mmol) in DCM (15.90 mL) at 0° C. The resulting solution was stirred at 0° C. for 30 minutes, the reaction mixture was evaporated and the residue was azeotroped with toluene to afford the title compound (676 mg, 97%) as a white solid.

$^1$H NMR (400 MHz, CDCl$_3$) δ 1.21-1.28 (2H, m), 1.33 (12H, s), 1.56-1.70 (4H, m), 1.76-1.82 (2H, m), 1.85-1.93 (1H, m), 1.97 (2H, t), 2.31 (2H, d), 2.87 (2H, t), 7.15 (1H, d), 7.64-7.67 (2H, m); COOH not seen; m/z 370 (EI+) M$^+$.

Example 29

N: 2-((1s,4r)-5'-(6-Carbamoyl-3,5-dimethylpyrazin-2-yl)-2',3'-dihydrospiro[cyclohexane-1,1'-indene]-4-yl)acetic acid

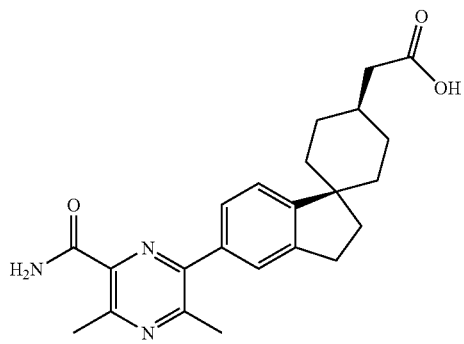

A solution of Intermediate 29-1 (0.748 g, 1.66 mmol) in TFA (8 mL) allowed to stand at room temperature for 0.5 h. The reaction mixture was evaporated to a solid. The crude product was purified by recrystallisation twice from MeOH to afford the title compound (0.201 g, 30.7%) as an off-white crystalline solid.

$^1$H NMR (400 MHz, DMSO) δ 1.40-1.56 (4H, m), 1.66-1.80 (4H, m), 1.96 (2H, t), 2.03 (1H, br s), 2.39 (2H, d), 2.58 (3H, s), 2.73 (3H, s), 2.89 (2H, t), 7.46-7.50 (2H, m), 7.54 (1H, s), 7.57 (1H, s), 7.97 (1H, s), 11.99 (1H, s); m/z 394 (M+H)$^+$.

Intermediate 29-1: N: tert-Butyl 2-((1s,4r)-5'-(6-carbamoyl-3,5-dimethylpyrazin-2-yl)-2',3'-dihydrospiro[cyclohexane-1,1'-indene]-4-yl)acetate

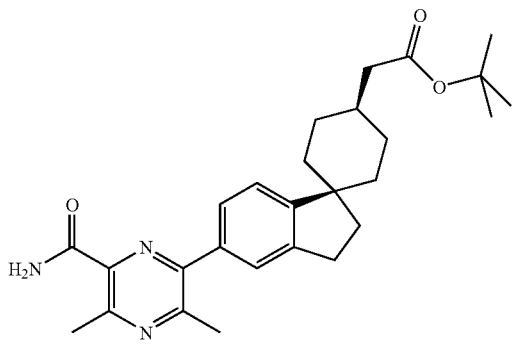

This compound was synthesised from Intermediate 29-2 using similar conditions as described in Intermediate 25-1 to give the title compound (0.748 g, 50.3%) as a solid which was a 2:1 mixture with the other diastereoisomer. m/z 450 (M+H)$^+$.

Intermediate 29-2: N: tert-Butyl 2-((1s,4r)-5'-(4,4,5,5-tetramethyl-1,3,2-dioxaborolan-2-yl)-2',3'-dihydrospiro[cyclohexane-1,1'-indene]-4-yl)acetate and Intermediate 29-3: tert-Butyl 2-((1r,4s)-5'-(4,4,5,5-tetramethyl-1,3,2-dioxaborolan-2-yl)-2',3'-dihydrospiro[cyclohexane-1,1'-indene]-4-yl)acetate Intermediate 29-2

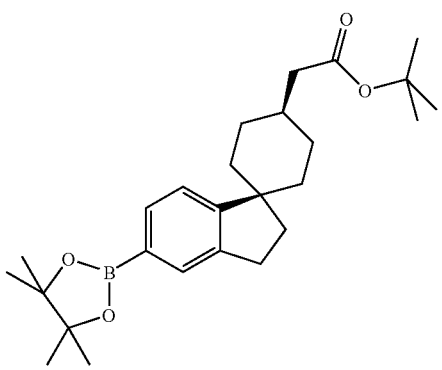

Intermediate 29-3

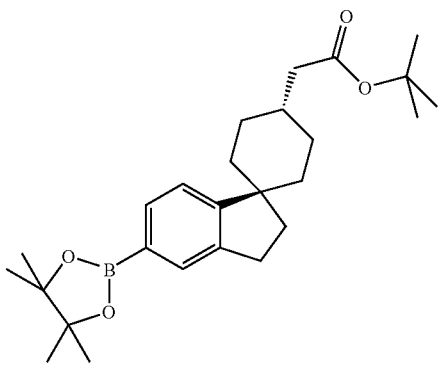

To a solution of Intermediate 29-4 (5.42 g, 12.77 mmol) in THF (125 mL), under nitrogen, was added 10% (w/w) palladium on carbon (1.4 g). The atmosphere was replaced with hydrogen and the reaction stirred at room temperature overnight. The reaction mixture was filtered and evaporated to a colourless oil. This was dissolved in methanol (ca. 20 mL) and cooled in a dry ice/acetone bath to produce a white solid. The suspension was allowed to warm and then evaporated to give the crude product as a white solid. This was recrystallised by dissolving in DCM (ca. 20 mL) adding methanol (ca. 20 mL) and cooling in a dry ice/acetone bath. The resultant suspension was filtered and the collected solid dried to give Intermediate 29-3 (2.290 g, 42.1%) as a white solid.

$^1$H NMR (400 MHz, DMSO) δ 1.17-1.21 (2H, m), 1.26 (12H, s), 1.40 (9H, s), 1.44-1.67 (7H, m), 1.90 (2H, t), 2.13 (2H, d), 2.81 (2H, t), 7.18 (1H, d), 7.46-7.48 (2H, m).

The mother liquors were evaporated to give Intermediate 29-2 (1.610 g, 29.6%) as a solid as a 2:1 mixture with the other diastereoisomer.

Intermediate 29-4: N: tert-Butyl 2-(5'-(4,4,5,5-tetramethyl-1,3,2-dioxaborolan-2-yl)-2',3'-dihydrospiro[cyclohexane-1,1'-indene]-4-ylidene)acetate

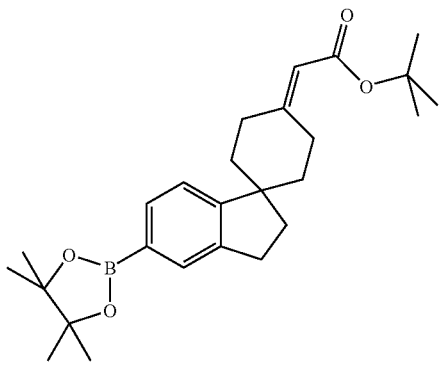

This compound was synthesised from Intermediate 29-5 using similar conditions as described in Intermediate 25-2 to give the title compound (5.42 g, 66.4%) as a solid.

$^1$H NMR (400 MHz, DMSO) δ 1.28 (12H, t), 1.42 (8H, s), 1.60-1.73 (4H, m), 2.04-2.13 (3H, m), 2.26 (1H, d), 2.31-2.36 (1H, m), 2.87 (2H, t), 3.66 (1H, d), 5.60 (1H, s), 7.17 (1H, d), 7.45-7.47 (1H, m), 7.50 (1H, s) one proton obscured; m/z 423 (M−H)$^−$.

Intermediate 29-5: N: tert-Butyl 2-(5'-bromo-2',3'-dihydrospiro[cyclohexane-1,1'-indene]-4-ylidene)acetate

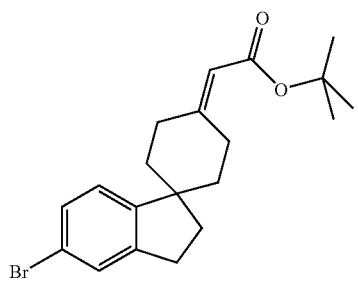

To a solution of tert-butyldiethylphosphonoacetate (8.80 mL, 37.47 mmol) in THF (100 mL) was added 60% w/w sodium hydride (1.498 g, 37.47 mmol). The reaction mixture was stirred at room temperature for 30 min. A solution of 5'-bromo-2',3'-dihydrospiro[cyclohexane-1,1'-inden]-4-one (prepared according to the procedure described in WO 2004/047755, CAS 701232-89-5) (8.716 g, 31.22 mmol) in THF (50 mL) was added and stirring continued at room temp for 1 hour. The reaction mixture was quenched with saturated brine (150 mL), extracted with EtOAc (2×200 mL), the organic layer was dried over Na$_2$SO$_4$, filtered and evaporated to afford the crude product as a brown oil (13.66 g). The crude oil was triturated with isohexane to give a solid which was collected by filtration and dried under vacuum to give the title compound (4.84 g, 41%) as a beige solid. A second crop of the title compound (2.42 g, 21%) was obtained from the filtrate.

$^1$H NMR (400 MHz, DMSO) δ 1.42 (9H, s), 1.59-1.69 (4H, m), 2.05-2.12 (3H, m), 2.24-2.35 (2H, m), 2.88 (2H, t), 3.66 (1H, d), 5.60 (1H, s), 7.14 (1H, d), 7.27-7.30 (1H, m), 7.38 (1H, t).

Example 30

2-((1r,4s)-5'-(6-Carbamoyl-3,5-dimethylpyrazin-2-yl)-2',3'-dihydrospiro[cyclohexane-1,1'-inden]-4-yl)acetic acid

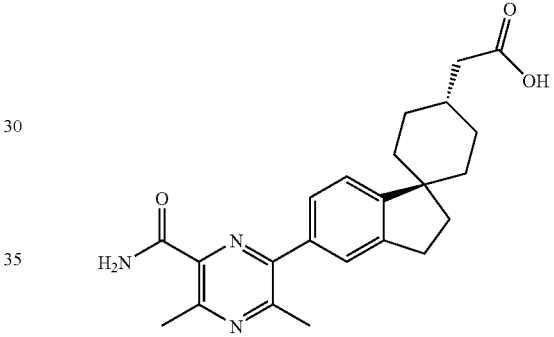

A solution of Intermediate 30-1 (1.16 g, 2.58 mmol) in TFA (12 mL) was allowed to stand at RT for 0.5 h. The reaction mixture was evaporated to a solid. The crude product was purified by recrystallisation from MeOH to afford the title compound (0.648 g, 63.8%) as a white crystalline solid.

$^1$H NMR (300 MHz, DMSO) δ 1.14-1.27 (2H, m), 1.51-1.80 (7H, m), 1.98 (2H, t), 2.17 (2H, d), 2.58 (3H, s), 2.73 (3H, s), 2.90 (2H, t), 7.30 (1H, d), 7.50 (1H, d), 7.54 (1H, s), 7.62 (1H, s), 8.01 (1H, s), 12.05 (1H, s); m/z 394 (M+H)$^+$.

Intermediate 30-1: tert-Butyl 2-((1r,4s)-5'-(6-carbamoyl-3,5-dimethylpyrazin-2-yl)-2',3'-dihydrospiro[cyclohexane-1,1'-inden]-4-yl)acetate

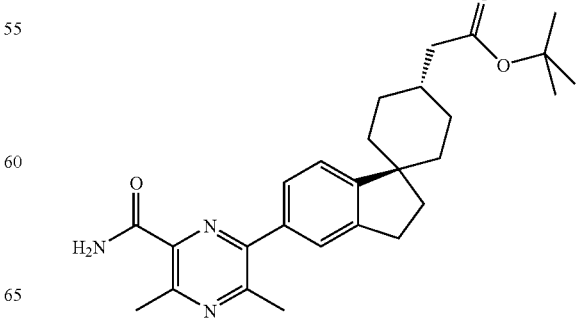

This compound was synthesised from Intermediate 29-3 using similar conditions as described in Intermediate 25-1 to give the title compound (1.260 g, 89%) as a solid.

$^1$H NMR (400 MHz, DMSO) δ 1.20-1.23 (2H, m), 1.41 (9H, s), 1.51-1.69 (7H, m), 1.97 (2H, t), 2.14 (2H, d), 2.57 (3H, s), 2.73 (3H, s), 2.90 (2H, t), 7.29 (1H, d), 7.47-7.57 (2H, m), 7.53 (1H, s), 7.96 (1H, s); m/z 450 (M+H)$^+$.

Example 31

(1r,4s)-5'-(6-Carbamoyl-3,5-dimethylpyrazin-2-yl)-2',3'-dihydrospiro[cyclohexane-1,1'-indene]-4-carboxylic acid

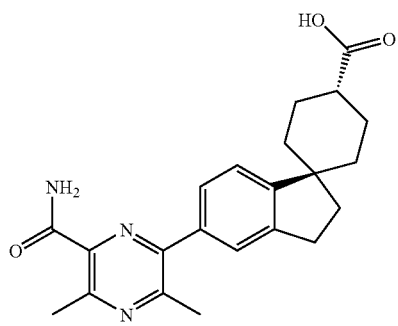

4M HCl in dioxane (10 mL, 0.43 mmol) was added to Intermediate 31-1 (188 mg, 0.43 mmol) in DCM (5 mL). The resulting solution was stirred for 16 hours. The resulting mixture was evaporated to dryness and the residue was slurried with ether then filtered to afford the title compound (158 mg, 96%) as a pale yellow solid.

$^1$H NMR (400 MHz, DMSO) δ 1.48-1.73 (6H, m), 1.85-1.93 (2H, m), 2.00 (2H, t), 2.28-2.36 (1H, m), 2.58 (3H, s), 2.73 (3H, s), 2.91 (2H, t), 7.29 (1H, d), 7.50 (1H, d), 7.56 (3H, d), 7.98 (1H, s); m/z 380 (M+H)$^+$.

Intermediate 31-1: (1r,4s)-tert-Butyl 5'-(6-carbamoyl-3,5-dimethylpyrazin-2-yl)-2',3'-dihydrospiro[cyclohexane-1,1'-indene]-4-carboxylate

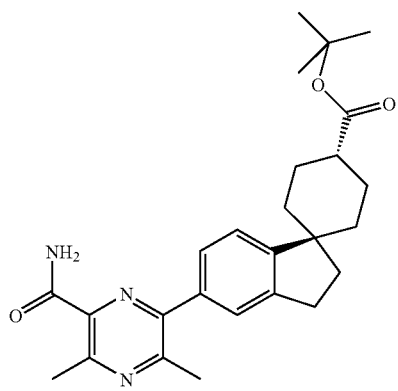

This compound was synthesised from Intermediate 31-2 and Intermediate 21-4 using similar conditions as described in Intermediate 25-1 to give the title compound (188 mg, 32.0%) as a solid.

$^1$H NMR (400 MHz, CDCl$_3$) δ 1.40 (9H, s), 1.54-1.68 (6H, m), 1.86-1.96 (2H, m), 2.02 (2H, t), 2.16-2.28 (1H, m), 2.60 (3H, s), 2.82-2.95 (5H, m), 5.40 (1H, s), 7.15 (1H, d), 7.30 (1H, d), 7.33 (1H, dd), 7.72 (1H, s); m/z 436 (M+H)$^+$.

Intermediate 31-2: (1r,4s)-tert-Butyl 5'-(4,4,5,5-tetramethyl-1,3,2-dioxaborolan-2-yl)-2',3'-dihydrospiro[cyclohexane-1,1'-indene]-4-carboxylate

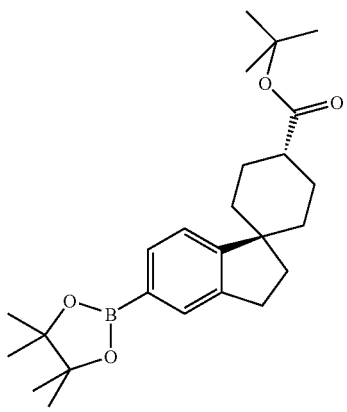

This compound was synthesised from Intermediate 31-3 using similar conditions as described in Intermediate 25-2 to give the title compound (3.13 g, 73.7%) as a white solid.

$^1$H NMR (400 MHz, CDCl$_3$) δ 1.26 (12H, s), 1.39 (19H, s), 1.50 (2H, d), 1.50-1.60 (6H, m), 1.80-1.90 (2H, m), 1.93 (2H, t), 2.15-2.25 (1H, m), 2.81 (2H, t), 7.07 (1H, d), 7.59 (1H, dd), 7.59 (1H, s).

Intermediate 31-3: (1r,4s)-tert-Butyl 5'-bromo-2',3'-dihydrospiro[cyclohexane-1,1'-indene]-4-carboxylate

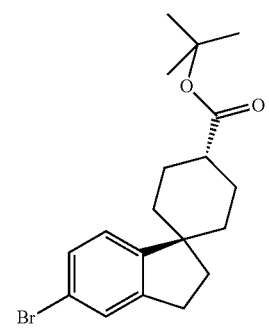

To a solution of Intermediate 31-4 (3.47 g, 11.22 mmol) in tert-butanol (100 mL) was added DMAP (0.411 g, 3.37 mmol) and di-tert-butyl dicarbonate (14.70 g, 67.34 mmol) (effervescence). The resulting solution was stirred at ambient temperature for 16 hours. Saturated NaHCO$_3$ (100 mL) was added and the reaction stirred for 30 minutes before adding EtOAc (400 mL). The organic layer was separated and washed with water (200 mL) then saturated brine (200 mL) and evaporated to afford crude product. The crude product was purified by flash silica chromatography, elution gradient 0 to 10% EtOAc in isohexane. Pure fractions were evaporated to dryness to afford the title compound (3.76 g, 92%) as a colourless oil.

¹H NMR (400 MHz, CDCl₃) δ 1.46 (9H, s), 1.52-1.67 (6H, m), 1.90-1.97 (2H, m), 1.98-2.03 (2H, m), 2.20-2.30 (1H, m), 2.86 (2H, t), 6.96 (1H, d), 7.28 (1H, dt), 7.32 (1H, d).

Intermediate 31-4: (1r,4s)-5'-Bromo-2',3'-dihydrospiro[cyclohexane-1,1'-indene]-4-carboxylic acid

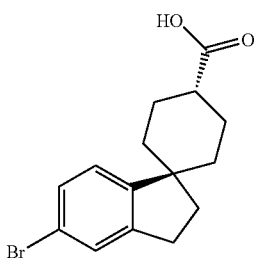

Oxone (6.98 g, 11.36 mmol) was added to Intermediate 31-5 (3.33 g, 11.36 mmol), in DMF (70 mL). The resulting suspension was stirred for 16 hours. The reaction mixture was diluted with EtOAc (300 mL), and washed sequentially with water (3×150 mL) and saturated brine (150 mL). The organic layer was evaporated to afford the title compound (3.51 g, 100%).

¹H NMR (400 MHz, DMSO) δ 1.30-1.73 (6H, m), 1.80-2.00 (4H, m), 2.20-2.32 (1H, m), 2.83 (2H, t), 7.12 (1H, d), 7.31 (1H, dt), 7.36 (1H, t), 12.03 (1H, s); m/z 309 M-H⁻.

Intermediate 31-5: (1r,4s)-5'-Bromo-2',3'-dihydrospiro[cyclohexane-1,1'-indene]-4-carbaldehyde
and Intermediate 31-6: (1s,4r)-5'-Bromo-2',3'-dihydrospiro[cyclohexane-1,1'-indene]-4-carbaldehyde Intermediate 31-5

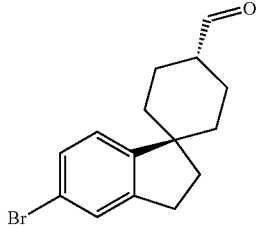

Intermediate 31-6

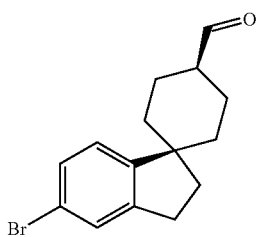

(Methoxymethyl)triphenylphosphonium chloride (20.76 g, 60.55 mmol) was added to a stirred suspension of potassium tert-butoxide (6.79 g, 60.55 mmol) in 1,4-dioxane (113 mL) at ambient temperature, over a period of 10 minutes under nitrogen. The resulting red solution was stirred at ambient temperature for 2 hours and then a solution of 5'-bromo-2',3'-dihydrospiro[cyclohexane-1,1'-inden]-4-one (prepared according to the procedure described in WO 2004/047755, CAS 701232-89-5) (7.35 g, 26.33 mmol) in 1,4-dioxane (63.4 mL) was added over a period of 10 minutes under nitrogen. The resulting solution was stirred at ambient temperature for 1 hour and then heated at 70° C. for 16 hours. The reaction mixture was poured into water (200 mL), extracted with EtOAc (2×200 mL), the organic layer was washed with saturated brine (200 mL) and evaporated to afford a black oil. To the crude oil was added EtOAc and isohexane (1:3, 200 mL) to give a solid which was collected by filtration, washed with EtOAc and isohexane (75 mL). The filtrate was evaporated to afford a solid residue, which was added to 90% acetic acid in water (200 mL, 3493.64 mmol). The resulting solution was stirred at 70° C. for 16 hours, the mixture was allowed to cool, evaporated to dryness and the crude product was purified by flash silica chromatography, elution gradient 0 to 15% EtOAc in isohexane. Pure fractions were evaporated to dryness to afford Intermediate 31-5 (3.33 g, 43.1%) and Intermediate 31-6 (1.17 g, 15%) as colourless gums.

Intermediate 31-5:

¹H NMR (400 MHz, CDCl₃) δ 1.36-1.67 (6H, m), 1.84-2.00 (4H, m), 2.19-2.29 (1H, m), 2.80 (2H, t), 6.92 (1H, m), 7.22 (1H, m), 7.23 (1H, dd), 9.61 (1H, d); m/z (EI+) 292 M⁺.

Intermediate 31-6:

¹H NMR (400 MHz, CDCl₃) δ 1.35-1.60 (4H, m), 1.68-1.80 (2H, m), 1.93 (2H, t), 2.09 (2H, dt), 2.37-2.44 (1H, m), 2.75-2.85 (2H, m), 6.90 (1H, d), 7.19 (1H, d), 7.24 (1H, d), 9.72 (1H, s); m/z 292 (EI+) M⁺.

Example 32

(1s,4r)-5'-(6-Carbamoyl-3,5-dimethylpyrazin-2-yl)-2',3'-dihydrospiro[cyclohexane-1,1'-indene]-4-carboxylic acid

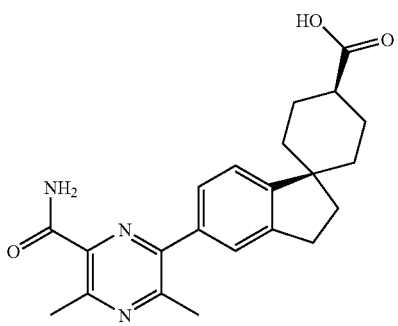

This compound was synthesised from Intermediate 32-1 using similar conditions as described in Example 31 to give the title compound (176 mg, 59.9%) as a pale yellow solid.

¹H NMR (400 MHz, DMSO) δ 1.45 (2H, dd), 1.72 (3H, dd), 1.77 (1H, m), 1.96 (1H, s), 1.99 (3H, t), 2.58 (4H, s), 2.73

(3H, s), 2.90 (2H, t), 7.25 (1H, d), 7.49 (1H, dd), 7.55 (1H, d), 7.57 (1H, s), 7.97 (1H, s); m/z 380 (M+H)+.

Intermediate 32-1: (1s,4r)-tert-Butyl 5'-(6-carbamoyl-3,5-dimethylpyrazin-2-yl)-2',3'-dihydrospiro[cyclohexane-1,1'-indene]-4-carboxylate

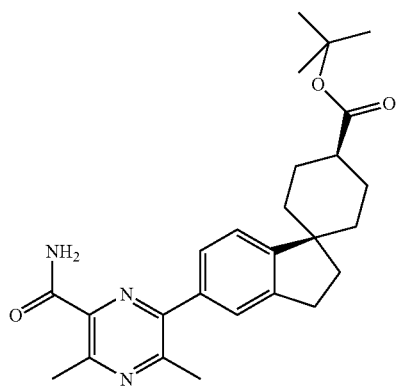

This compound was synthesised from Intermediate 32-2 and Intermediate 21-4 using similar conditions as described in Intermediate 25-1 to give the title compound (342 mg, 58.2%) as a solid.

¹H NMR (400 MHz, CDCl₃) δ 1.40-1.50 (2H, m), 1.44 (9H, s), 1.65-1.75 (2H, m), 1.75-1.85 (2H, m), 1.95-2.08 (4H, m), 2.45-2.51 (1H, m), 2.60 (3H, s), 2.85-2.93 (5H, m), 5.39 (1H, s), 7.26-7.35 (3H, m), 7.73 (1H, s); m/z 436 (M+H)+.

Intermediate 32-2: (1s,4r)-tert-Butyl 5'-(4,4,5,5-tetramethyl-1,3,2-dioxaborolan-2-yl)-2',3'-dihydrospiro[cyclohexane-1,1'-indene]-4-carboxylate

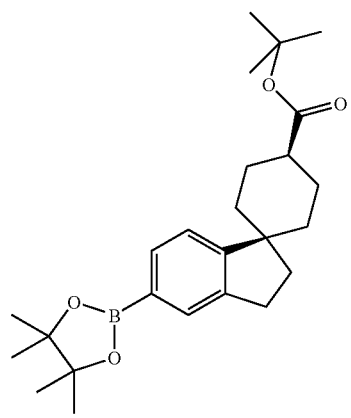

This compound was synthesised from Intermediate 32-3 using similar conditions as described in Intermediate 25-2 to give the title compound (0.935 g, 62.3%) as a colourless oil which solidified on standing.

¹H NMR (400 MHz, CDCl₃) δ 1.32 (12H, s), 1.44-1.47 (2H, m), 1.50 (9H, s), 1.67-1.86 (4H, m), 1.96 (2H, t), 2.01-2.09 (2H, m), 2.48-2.53 (1H, m), 2.83-2.90 (2H, m), 7.25 (1H, d), 7.63 (1H, d), 7.67 (1H, s); m/z 412 (EI+) M+.

Intermediate 32-3: (1s,4r)-tert-Butyl 5'-bromo-2',3'-dihydrospiro[cyclohexane-1,1'-indene]-4-carboxylate

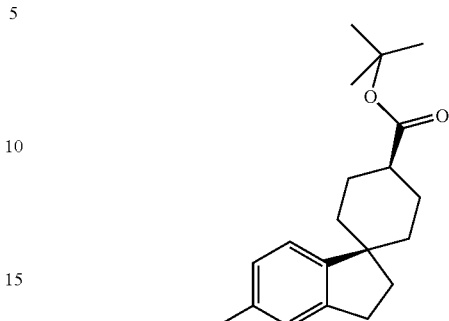

This compound was synthesised from Intermediate 32-4 using similar conditions as described in Intermediate 31-3 to give the title compound (1.330 g, 89%) as a colourless oil.

¹H NMR (400 MHz, CDCl₃) δ 1.42-1.46 (2H, m), 1.49 (9H, s), 1.67-1.81 (4H, m), 1.96 (2H, t), 2.00-2.06 (2H, m), 2.48-2.53 (1H, m), 2.85 (2H, t), 7.08 (1H, d), 7.26-7.28 (1H, m), 7.32 (1H, s); m/z 364 (EI+) M+.

Intermediate 32-4: (1s,4r)-5'-Bromo-2',3'-dihydrospiro[cyclohexane-1,1'-indene]-4-carboxylic acid

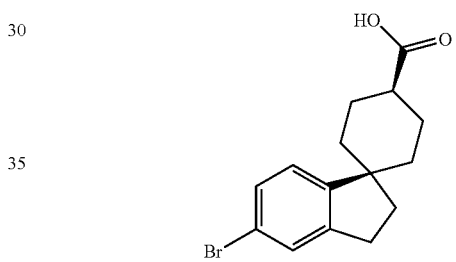

This compound was synthesised from Intermediate 31-6 using similar conditions as described in Intermediate 31-4 to give the title compound (1.27 g, 100%) as a solid.

¹H NMR (400 MHz, DMSO) δ 1.35-1.44 (2H, m), 1.60-1.73 (4H, m), 1.85-2.00 (4H, m), 2.53 (1H, q), 2.82 (2H, t), 7.08 (1H, d), 7.30 (1H, dt), 7.37 (1H, t), 12.12 (1H, s); m/z 309 (M−H)−.

Example 33

2-(1-(4-(6-Carbamoyl-3,5-dimethylpyrazin-2-yl)phenyl)piperidin-4-yl)acetic acid

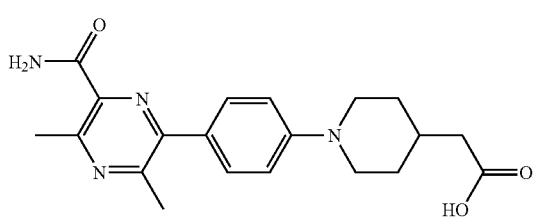

Powdered potassium hydroxide (44.5 mg, 0.79 mmol) was added in one portion to Intermediate 33-1 (60 mg, 0.16 mmol) in tert-butanol (5 mL). The resulting pale yellow suspension was stirred at 40° C. for 30 minutes. The reaction mixture was quenched with acetic acid (0.073 mL, 1.27 mmol) in EtOH (10.0 mL) and the resulting solution stirred for a further 10 minutes before being evaporated to dryness. The resulting solid was partitioned between water (20 mL) and EtOAc (20 mL). The aqueous layer showed a pH=6. The organic layer was separated and the aqueous re-extracted with EtOAc (2×25 mL). The combined organics were washed with brine (15 mL), dried over MgSO₄ and evaporated in vacuo to give crude product. This was recrystallised from hot EtOH (6 mL) to give a yellow solid which was washed with ethylacetate (5 mL) and dried under vacuum at room temperature to give the title compound (41.0 mg, 70.2%) as a yellow solid.

¹H NMR (400 MHz, DMSO) δ 1.28 (2H, m), 1.76 (2H, m), 1.86 (1H, m), 2.15 (2H, d), 2.60 (3H, s), 2.71 (3H, s), 2.76 (2H, d), 3.79 (2H, d), 7.00 (2H, d), 7.55 (1H, s), 7.60 (2H, d), 7.96 (1H, s); m/z 369 (M+H)⁺.

Intermediate 33-1: ethyl 2-(1-(4-(6-cyano-3,5-dimethylpyrazin-2-yl)phenyl)piperidin-4-yl)acetate

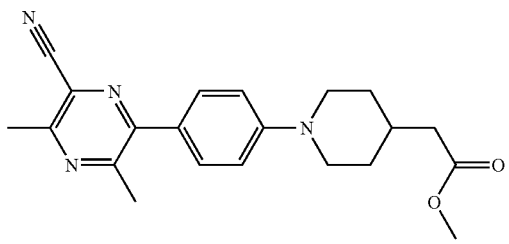

Pyridine (0.050 mL, 0.62 mmol) was added dropwise to Intermediate 33-2 (78 mg, 0.31 mmol), ethyl 2-(piperidin-4-yl)acetate (79 mg, 0.46 mmol) and Copper(II) acetate (56.0 mg, 0.31 mmol) in anhydrous DCM (10 mL) The resulting blue solution was stirred at 25° C. for 16 hours. The reaction mixture was diluted with DCM (25 mL), and washed with a 20% aqueous EDTA solution (25 mL). The organic layer was evaporated to afford crude product. The crude product was purified by flash silica chromatography, elution gradient 0 to 70% EtOAc in isohexane. Pure fractions were evaporated to dryness to afford the title compound (53.0 mg, 45.4%) as a pale yellow solid.

¹H NMR (400 MHz, DMSO) δ 1.20 (5H, m), 1.69 (2H, d), 1.84 (1H, m), 2.22 (2H, m), 2.61 (6H, s), 2.71 (2H, m), 3.77 (2H, d), 4.02 (2H, m), 6.97 (2H, m), 7.47 (2H, m); m/z 379 (M+H)⁺.

Intermediate 33-2: 4-(6-Cyano-3,5-dimethylpyrazin-2-yl)phenylboronic acid

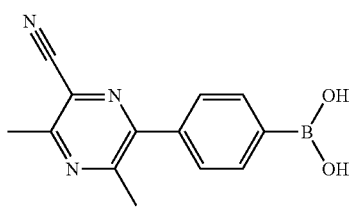

Sodium periodate (5.02 g, 23.45 mmol) was added in one portion to Intermediate 33-3 (2.62 g, 7.82 mmol) in THF (80 mL) and water (20 mL) and the cloudy suspension was stirred at room temperature for 30 minutes. 1M HCl (5.47 mL, 5.47 mmol) was added and the reaction mixture was stirred at room temperature for 2 hours. The THF was evaporated under reduced pressure, the reaction mixture was diluted with water (100 mL) and extracted with ethyl acetate (2×100 mL). The combined extracts were washed with water (2×30 mL) and brine (30 mL), dried over sodium sulfate, concentrated to dryness by rotary evaporation to give the title compound (1.980 g, 100%).

¹H NMR (400 MHz, DMSO) δ 2.62 (3H, s), 2.70 (3H, s), 7.60 (2H, d), 7.92 (2H, d), 8.16 (2H, s); m/z 254 (M+H)⁺.

Intermediate 33-3: 3,5-Dimethyl-6-(4-(4,4,5,5-tetramethyl-1,3,2-dioxaborolan-2-yl)phenyl)pyrazine-2-carbonitrile

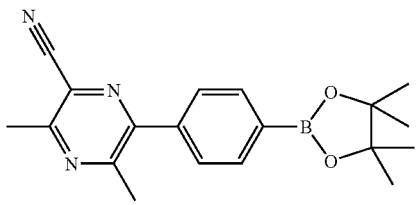

This compound was synthesised from Intermediate 33-4 using similar conditions as described in Intermediate 25-2 to give the title compound (70.0 mg, 50.4%) as a white crystalline solid.

¹H NMR (400 MHz, DMSO) δ 1.39 (12H, s), 2.68 (3H, s), 2.77 (3H, s), 7.73 (2H, d), 7.88 (2H, d); HPLC tR=2.85 min.

Intermediate 33-4: 4-(6-Cyano-3,5-dimethylpyrazin-2-yl)phenyl trifluoromethanesulfonate

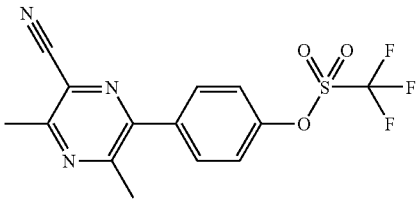

Trifluoromethanesulphonic anhydride (27.3 mL, 166.57 mmol) was added to a stirred solution of Intermediate 33-5 (10.13 g, 41.64 mmol) in DCM (400 mL) cooled to 0° C., over a period of 20 minutes under nitrogen. The resulting slurry was then allowed to warm to ambient temperature overnight under a nitrogen atmosphere. Triethylamine (46.4 mL, 333.14 mmol) was added dropwise over 10 minutes (under ice bath cooling, keeping temperature between 5-110° C.) and the resulting solution stirred at 30° C. for 3 hours under nitrogen. The reaction mixture was diluted with DCM (200 mL), and washed sequentially with water (200 mL), saturated NaHCO₃ (200 mL), and saturated brine (100 mL). The organic layer was dried over MgSO₄, filtered and evaporated to afford crude product. The crude product was purified by flash silica chromatography, elution gradient 0 to 40% EtOAc in isohexane. Pure fractions were evaporated to dryness to the title compound (9.87 g, 66.3%) as a yellow oil.

¹H NMR (400 MHz, DMSO) δ 2.68 (3H, s), 2.78 (3H, s), 7.74 (2H, d), 7.93 (2H, d); m/z=mass ion not seen; HPLC tR=2.84 min.

Intermediate 33-5: 6-(4-Hydroxyphenyl)-3,5-dimethylpyrazine-2-carboxamide

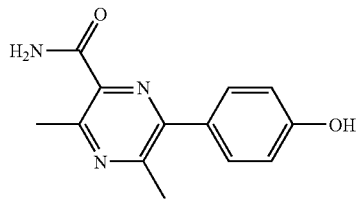

This compound was synthesised from Intermediate 21-4 and 4-(4,4,5,5-tetramethyl-1,3,2-dioxaborolan-2-yl)phenol (CAS 269409-70-3) using similar conditions as described in Intermediate 25-1 to give the title compound (10.13 g, 97%) as an orange solid.

¹H NMR (400 MHz, DMSO) δ 2.58 (3H, s), 2.71 (3H, s), 6.87 (2H, d), 7.56-7.60 (3H, m), 7.95 (1H, s), 9.73 (1H, s); m/z 244 (M+H)⁺.

The following examples were synthesised using similar conditions as described in Example 33 to give the desired compounds 34-39.

| Example | Structure | ¹H NMR (400 MHz, DMSO) δ | m/z (M + H)⁺ |
|---|---|---|---|
| 34 | 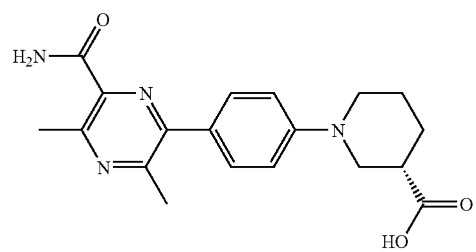 | 1.58 (2H, m), 1.72 (1H, m), 1.92 (1H, m), 2.53 (1H, m), 2.60 (3H, s), 2.72 (3H, s), 2.90 (1H, m), 3.04 (1H, m), 3.58 (1H, m), 3.76 (1H, m), 7.02 (2H, d), 7.56 (1H, s), 7.62 (2H, d), 7.96 (1H, s) | 355 |
| 35 | 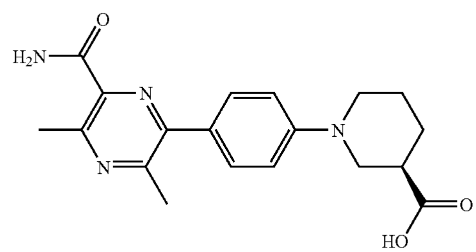 | 1.66 (2H, m), 1.80 (1H, m), 2.00 (1H, m), 2.61 (1H, m), 2.67 (3H, s), 2.78 (3H, s), 2.98 (1H, t), 3.14 (1H, t), 3.65 (1H, d), 3.83 (1H, d), 7.10 (2H, d), 7.63 (1H, s), 7.69 (2H, d), 8.02 (1H, s) | 355 |
| 36 | 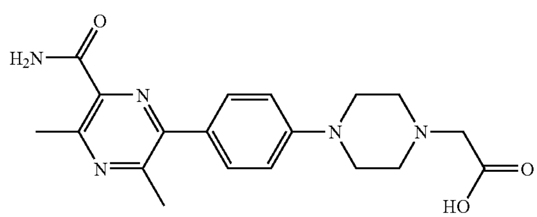 | 2.60 (3H, s), 2.71 (7H, m), 3.20 (2H, s), 3.27 (4H, m), 7.03 (2H, d), 7.56 (1H, s), 7.63 (2H, d), 7.96 (1H, s) | 370 |
| 37 | 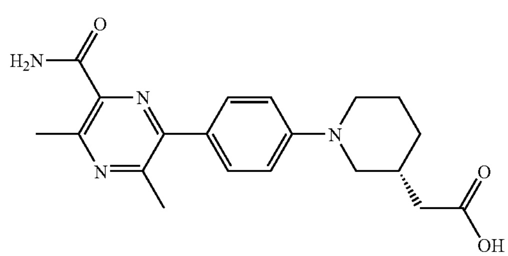 | 1.20 (1H, m), 1.55 (1H, m), 1.69 (1H, m), 1.81 (1H, m), 1.98 (1H, m), 2.17 (1H, m), 2.28 (1H, m), 2.60 (4H, m), 2.71 (3H, s), 2.81 (1H, t), 3.73 (2H, t), 7.00 (2H, d), 7.56 (1H, s), 7.61 (2H, d), 7.96 (1H, s), 12.11 (1H, s) | 369 |
| 38 | 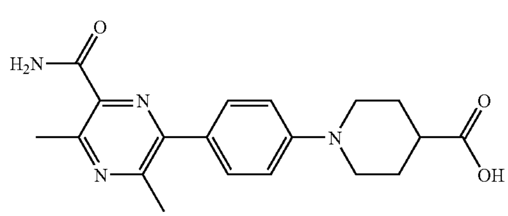 | 1.64 (2H, m), 1.90 (2H, m), 2.45 (1H, m), 2.60 (3H, s), 2.71 (3H, s), 2.87 (2H, t), 3.76 (2H, d), 7.03 (2H, d), 7.56 (1H, s), 7.61 (2H, d), 7.96 (1H, s), 12.19 (1H, s) | 355 |
| 39 | 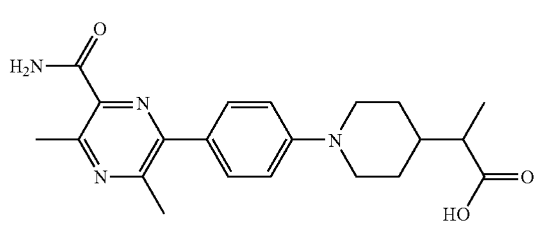 | 1.12 (3H, d), 1.39 (2H, m), 1.75 (3H, m), 2.27 (1H, m), 2.66 (3H, s), 2.77 (5H, m), 3.91 (2H, m), 7.08 (2H, d), 7.62 (1H, s), 7.67 (2H, d), 8.02 (1H, s), 12.14 (1H, s) | 383 |

Example 40

2-(1-(4-(6-Carbamoyl-3,5-dimethylpyrazin-2-yl)phenyl)pyrrolidin-3-yl)acetic acid

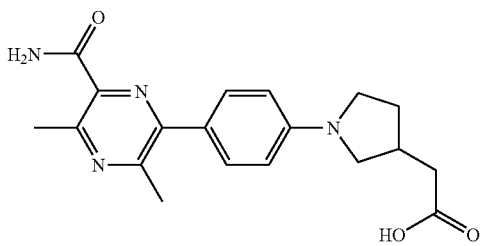

Powdered potassium hydroxide (122 mg, 2.17 mmol) was added in one portion to Intermediate 40-1 (170 mg, 0.43 mmol) in tert-butanol (5 mL). The resulting yellow suspension was stirred at 40° C. for 90 minutes. The reaction mixture was quenched with acetic acid (0.198 mL, 3.47 mmol) in EtOH (10.0 mL) and the resulting solution stirred for a further 10 minutes before being evaporated to dryness. The resulting solid was partitioned between water (20 mL) and EtOAc (20 mL). The aqueous layer showed a pH=6. The organic layer was separated and evaporated to dryness to afford crude product (185 mg). The crude product was dissolved in DCM (5.00 mL) and TFA (1.0 mL, 12.99 mmol) was added. The brown solution was stirred at room temperature for 2 hours. The reaction mixture was purified by ion exchange chromatography, using an SCX column. The column was eluted with DCM (100 mL) followed by MeOH (100 mL) and then the desired product was eluted from the column using 0.35M $NH_3$/MeOH (100 mL) and fractions containing the product were evaporated to dryness to afford crude product as a yellow solid (110 mg). This product was purified by preparative HPLC (Waters XBridge Prep C18 OBD column, 5μ silica, 50 mm diameter, 150 mm length), using decreasingly polar mixtures of water (containing 0.1% formic acid) and MeOH as eluents. Fractions containing the desired compound were evaporated to dryness to afford the title compound (76 mg, 49.5%) as a yellow solid.

$^1$H NMR (400 MHz, DMSO) δ 1.65 (1H, m), 2.13 (1H, m), 2.38 (2H, m), 2.55 (4H, m), 2.65 (3H, s), 2.93 (1H, t), 3.26 (1H, m), 3.33 (1H, m), 3.47 (1H, m), 6.55 (2H, d), 7.50 (1H, s), 7.56 (2H, d), 7.89 (1H, s), 12.13 (1H, s); m/z 355 (M+H)$^+$.

Example 41

(1R,5S,6r)-3-(4-(6-Carbamoyl-3,5-dimethylpyrazin-2-yl)phenyl)-3-azabicyclo[3.1.0]hexane-6-carboxylic acid

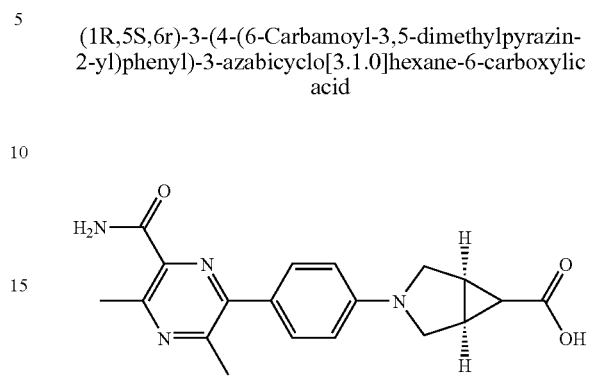

Powdered potassium hydroxide (101 mg, 1.79 mmol) was added in one portion to Intermediate 41-1 (175 mg, 0.45 mmol) in tert-butanol (4 mL) at 40° C. under nitrogen. The resulting suspension was stirred at 40° C. for 6 hours. A thick precipitate formed so the reaction was quenched with acetic acid (0.205 mL, 3.59 mmol) in EtOH (10 mL) and the resulting solution stirred for a further 10 minutes before being evaporated to dryness. The crude material was treated with a 5% HCl in methanol solution (10 mL), and stirred overnight. The mixture was then treated with powdered potassium hydroxide (101 mg, 1.79 mmol) in tert-butanol. The resulting mixture was stirred at 40° C. for 2 hours, before being quenched with acetic acid (0.205 mL, 3.59 mmol) in EtOH (5 mL) and evaporated to a gum. The crude product was purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness to afford the title compound (66.5 mg, 42.1%) as a yellow solid.

$^1$H NMR (400 MHz, DMSO) δ 1.51 (1H, t), 2.23-2.26 (2H, m), 2.66 (3H, s), 2.77 (3H, s), 3.39 (2H, d), 3.72 (2H, d), 6.71 (2H, d), 7.62 (1H, s), 7.66 (2H, d), 8.01 (1H, s,) COOH not seen; m/z 353 (M+H)$^+$.

The following compounds were synthesised from Intermediate 33-2 and the appropriate amine using similar conditions as described in Intermediate 33-1 to give the desired Intermediates 34-1 to 40-1.

| Intermediate | Structure | $^1$H NMR (400 MHz, DMSO) δ | m/z (M + H)$^+$ |
|---|---|---|---|
| 34-1 | 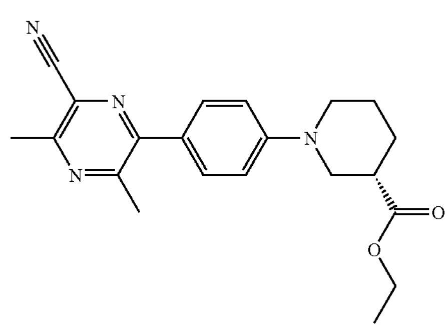 | 1.27 (3H, t), 1.71 (3H, m), 1.99 (1H, m), 2.70 (7H, m), 3.04 (1H, m), 3.23 (1H, m), 3.64 (1H, d), 3.83 (1H, d), 4.16 (2H, q), 7.10 (2H, d), 7.61 (2H, d). | 365 |

-continued

| Intermediate | Structure | ¹H NMR (400 MHz, DMSO) δ | m/z (M + H)⁺ |
|---|---|---|---|
| 35-1 | 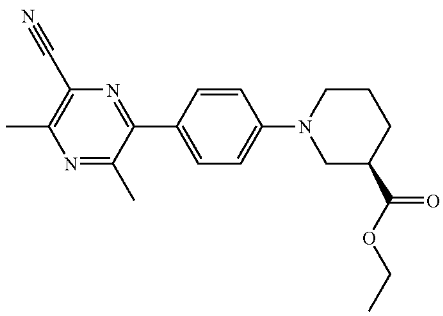 | 1.14 (3H, t), 1.59 (3H, m), 1.87 (1H, m), 2.58 (7H, m), 2.92 (1H, t), 3.10 (1H, t), 3.52 (1H, d), 3.71 (1H, d), 4.04 (2H, q), 6.98 (2H, d), 7.49 (2H, d). | 365 |
| 36-1 | 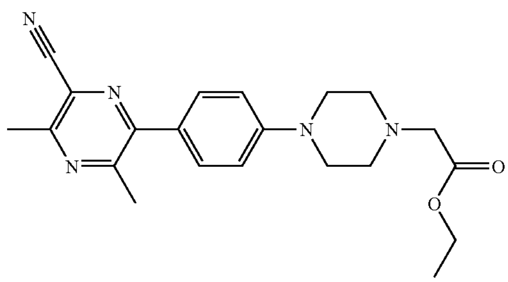 | 2.60 (3H, s), 2.71 (7H, m), 3.20 (2H, s), 3.27 (4H, m), 7.03 (2H, d), 7.56 (1H, s), 7.63 (2H, d), 7.96 (1H, s). | 370 |
| 37-1 | 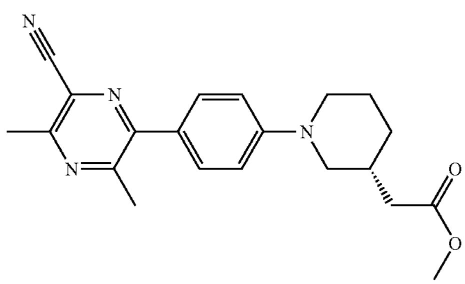 | 1.23 (1H, m), 1.55 (1H, m), 1.69 (1H, m), 1.79 (1H, m), 2.00 (1H, m), 2.28 (1H, m), 2.38 (1H, m), 2.63 (7H, m), 2.83 (1H, m), 3.62 (3H, s), 3.74 (2H, m), 7.01 (2H, d), 7.53 (2H, d). | 365 |
| 38-1 | 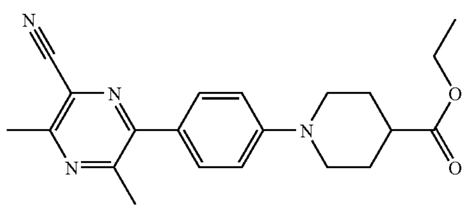 | 1.13 (3H, t), 1.60 (2H, m), 1.86 (2H, m), 2.51 (1H, m), 2.59 (3H, s), 2.61 (3H, s), 2.84 (2H, t), 3.72 (2H, d), 4.03 (2H, q), 6.98 (2H, d), 7.48 (2H, d). | 365 |
| 39-1ᵃ | | 1.07 (3H, d), 1.18 (3H, t), 1.31 (2H, m), 1.68 (3H, m), 2.30 (1H, m), 2.65 (3H, s), 2.66 (3H, s), 2.73 (2H, m), 3.87 (2H, t), 4.07 (2H, m), 7.02 (2H, d), 7.52 (2H, d). | 393 |

-continued

| Intermediate | Structure | $^1$H NMR (400 MHz, DMSO) δ | m/z (M + H)$^+$ |
|---|---|---|---|
| 40-1 | 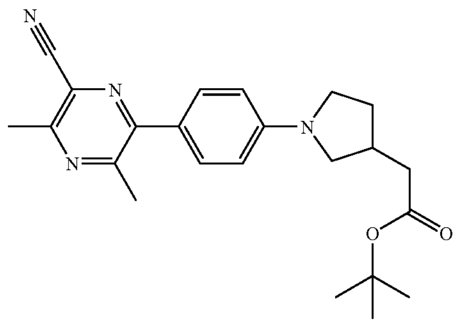 | 1.39 (1H, m), 1.42 (9H, s), 1.69 (1H, m), 2.16 (1H, m), 2.40 (2H, m), 2.59 (1H, m), 2.65 (6H, s), 2.96 (1H, t), 3.37 (1H, m), 3.50 (1H, m), 6.61 (2H, d), 7.53 (2H, d). | 393 |
| 41-1$^a$ | | 1.41 (9H, s), 1.42-1.45 (1H, m), 2.17-2.19 (2H, m), 2.64 (3H, s), 2.65 (3H, s), 3.27 (2H, d), 3.66 (2H, d), 6.64 (2H, d), 7.51 (2H, d). | 391 |

Note:
39-1$^a$ ethyl 2-(piperidin-4-yl)propanoate, CAS 141060-27-7 was prepared according to the procedure described in WO 2008042925.
41-1$^a$ (1R,5S,6r)-tert-butyl 3-azabicyclo[3.1.0]hexane-6-carboxylate, CAS 681424-89-5 (prepared according to the procedure described in WO 2004033451).

Example 42

2-((1r,4r)-4-(4-(6-Carbamoyl-3,5-dimethylpyrazin-2-yl)phenyl)cyclohexyl)-2-methylpropanoic acid

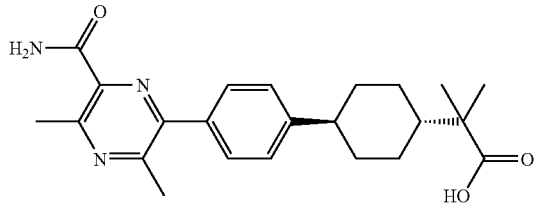

Powdered potassium hydroxide (193 mg, 3.44 mmol) was added in one portion to Intermediate 42-1 (470 mg, 1.15 mmol) in tert-butanol (20 mL) at 40° C. under nitrogen. The resulting suspension was stirred at 40° C. for 2 hours. The reaction was incomplete so the temperature was increased to 100° C. and the reaction mixture was stirred for a further 16 hours. The reaction was quenched with acetic acid (0.329 mL, 5.74 mmol) in EtOH (10 mL) and the resulting solution stirred for a further 20 minutes before being evaporated to dryness. The resulting solid was partitioned between water (50 mL) and EtOAc (50 mL). The aqueous layer was acidified with 2M HCl (5 mL) was added and the organic layer was separated and the aqueous re-extracted with EtOAc (50 mL). The combined organics were washed with saturated brine (50 mL) and evaporated in vacuo to give crude solid product. This was recrystallised from hot EtOH (15 mL) and washed with ether (10 mL) and dried under vacuum at room temperature to give the title compound (90 mg, 19.83%) as a pink solid.
$^1$H NMR (400.13 MHz, DMSO) δ 1.06 (6H, s), 1.15-1.30 (2H, m), 1.43-1.56 (2H, m), 1.60-1.80 (3H, m), 1.80-1.95 (2H, m), 2.40-2.60 (1H, m), 2.58 (3H, s), 2.73 (3H, s), 3.29 (3H, s), 7.36 (2H, d), 7.57 (1H, s), 7.64 (2H, d), 7.97 (1H, s), 12.03 (1H, s); m/z 396 (M+H)$^+$.

Intermediate 42-1: Methyl 2-((1r,4r)-4-(4-(6-carbamoyl-3,5-dimethylpyrazin-2-yl)phenyl)cyclohexyl)-2-methylpropanoate

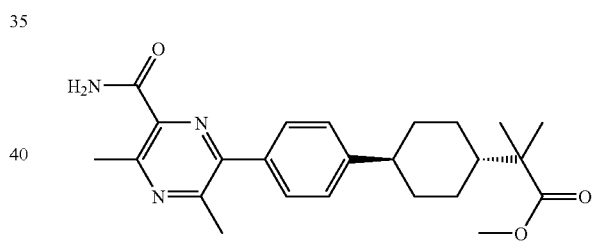

This compound was synthesised from Intermediate 42-2 and Intermediate 21-4 using similar conditions as described in Intermediate 25-1 to give the title compound (494 mg, 44.8%).
$^1$H NMR (400 MHz, CDCl$_3$) δ 1.10 (6H, s), 1.12-1.28 (2H, m), 1.40-1.53 (2H, m), 1.60-1.73 (3H, m), 1.90-2.00 (2H, m), 2.43-2.52 (1H, m), 2.60 (3H, s), 2.91 (3H, s), 3.62 (3H, s), 5.42 (1H, s), 7.25 (2H, d), 7.44 (2H, dt), 7.72 (1H, s); m/z 410 (M+H)$^+$.

Intermediate 42-2: Methyl 2-methyl-2-((1r,4r)-4-(4-(4,4,5,5-tetramethyl-1,3,2-dioxaborolan-2-yl)phenyl)cyclohexyl)propanoate

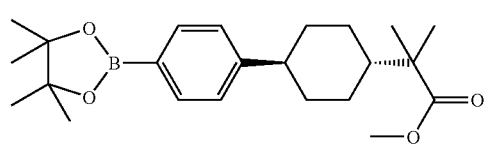

To a solution of diisopropylamine (4.83 mL, 34.17 mmol) in THF (50 mL) under nitrogen, cooled to −70° C. was added butyllithium (21.35 mL, 34.17 mmol) dropwise while maintaining the temperature between −70 and −60° C. After 30 minutes Intermediate 42-3 (3.18 g, 8.54 mmol) in THF (20 mL) was added and the mixture was allowed to warm to ~20° C. over 90 minutes. The solution was cooled to −65° C., methyl iodide (2.129 mL, 34.17 mmol) was added and the reaction allowed to stir for 1 hour and then allowed to warm to −30° C. The reaction was quenched with saturated ammonium chloride (100 mL), extracted with EtOAc (200 mL), the organic phase separated, washed with water (100 mL) and saturated brine (100 mL). The organic layer was dried over MgSO$_4$, filtered and evaporated to afford crude product (2.99 g). The crude product was purified by flash silica chromatography, elution gradient 0 to 10% EtOAc in isohexane. Pure fractions were evaporated to dryness to afford the title compound (1.830 g, 55.5%) as a white solid.

$^1$H NMR (400 MHz, CDCl$_3$) δ 1.15 (6H, s), 1.15-1.28 (2H, m), 1.33 (12H, s), 1.49 (2H, dd), 1.65-1.75 (3H, m), 1.90-1.98 (2H, m), 2.42-2.51 (1H, m), 3.68 (3H, d), 7.21 (2H, d), 7.74 (2H, dd); m/z (EI+) 386 M$^+$.

Intermediate 42-3: Methyl 2-((1r,4r)-4-(4-(4,4,5,5-tetramethyl-1,3,2-dioxaborolan-2-yl)phenyl)cyclohexyl)propanoate

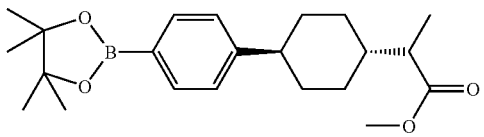

Lithium bis(trimethylsilyl)amide (16.75 mL, 16.75 mmol) was added to methyl 2-((1r,4r)-4-(4-(4,4,5,5-tetramethyl-1,3,2-dioxaborolan-2-yl)phenyl)cyclohexyl)acetate (CAS 701232-69-1) (prepared according to the procedure described in WO 2004047755) (5 g, 13.96 mmol) in THF (50 mL) at 0° C. under nitrogen. The resulting solution was stirred at 0° C. for 30 minutes and then methyl iodide (1.304 mL, 20.93 mmol) was added and the reaction stirred for 30 minutes. The reaction was quenched with saturated ammonium chloride (50 mL), extracted with EtOAc (100 mL), the organic phase separated, washed with water (50 mL) and saturated brine (50 mL). The organic layer was dried over MgSO$_4$, filtered and evaporated to afford crude product. The crude product was purified by flash silica chromatography, elution gradient 0 to 10% EtOAc in isohexane. Pure fractions were evaporated to dryness to afford the title compound (3.38 g, 65.1%) as a white solid.

$^1$H NMR (400 MHz, CDCl$_3$) δ 1.08-1.30 (5H, m), 1.33 (12H, s), 1.40-1.70 (3H, m), 1.70-1.97 (4H, m), 2.31 (1H, t), 2.43-2.53 (1H, m), 3.68 (3H, m), 7.21 (2H, d), 7.74 (2H, d); m/z 395 (M+Na)$^+$.

Example 43

2-((1r,4r)-4-(4-(6-Carbamoyl-3,5-dimethylpyrazin-2-yl)-2-fluorophenyl)cyclohexyl)acetic acid

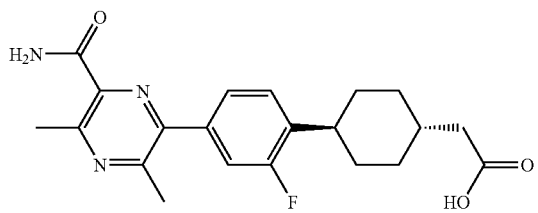

This compound was synthesised from Intermediate 43-1 using similar conditions as described in Example 21. Except the crude product was purified by crystallisation from boiling EtOH (6 mL) to afford the title compound (89 mg, 43.6%).

$^1$H NMR (400 MHz, DMSO) δ 1.09-1.22 (3H, m), 1.53-1.61 (2H, m), 1.72-1.89 (4H, m), 2.14-2.16 (2H, m), 2.60 (3H, s), 2.73 (3H, s), 2.79-2.87 (1H, m), 7.43-7.48 (1H, m), 7.53 (1H, d), 7.56-7.60 (2H, m), 8.04 (1H, s), 12.11 (1H, s); m/z 386 (M+H)$^+$.

Intermediate 43-1: Ethyl 2-((1r,4r)-4-(4-(6-Carbamoyl-3,5-dimethylpyrazin-2-yl)-2-fluorophenyl)cyclohexyl)acetate

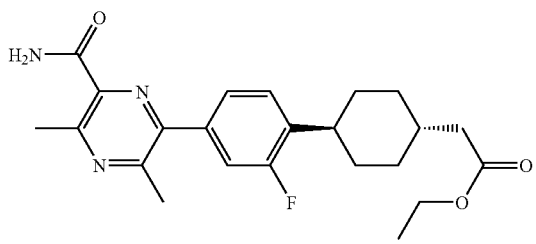

This compound was synthesised from Intermediate 43-2 and Intermediate 21-4 using similar conditions as described in Intermediate 21-1 to give the title compound (0.219 g, 23.90%) as a colourless oil.

$^1$H NMR (400 MHz, CDCl$_3$) δ 1.21 (3H, t), 1.54-1.64 (2H, m), 1.87-1.98 (7H, m), 2.26 (2H, d), 2.67 (3H, s), 2.86-2.94 (1H, m), 2.98 (3H, s), 4.13-4.18 (2H, m), 5.91 (1H, s), 7.24-7.36 (3H, m), 7.78 (1H, s); m/z 414 (M+H)$^+$.

Intermediate 43-2: Ethyl 2-((1r,4r)-4-(2-fluoro-4-(4,4,5,5-tetramethyl-1,3,2-dioxaborolan-2-yl)phenyl)cyclohexyl)acetate

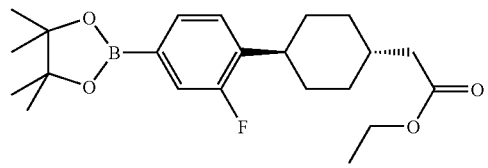

This compound was synthesised from Intermediate 43-3 using similar conditions as described in Intermediate 25-2 to give the title compound (0.865 g, 43.8%) as a white crystalline solid.

$^1$H NMR (400 MHz, CDCl$_3$) δ 1.09-1.17 (2H, m), 1.21 (3H, t), 1.26 (2H, s), 1.46 (12H, s), 1.48-1.54 (2H, m), 1.78-1.87 (4H, m), 2.73-2.81 (1H, m), 3.42 (1H, d), 4.05-4.11 (2H, m), 7.11 (1H, d), 7.14 (1H, d), 7.19-7.21 (1H, m).

Intermediate 43-3: Ethyl 2-((1r,4r)-4-(2-fluoro-4-(trifluoromethylsulfonyloxy)-phenyl)cyclohexyl)acetate

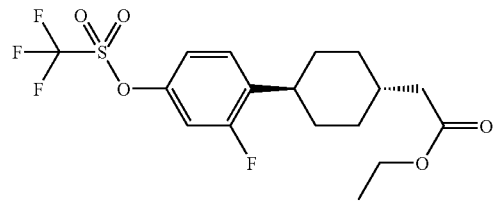

This compound was synthesised from Intermediate 43-4 using similar conditions as described in Intermediate 25-4 to give the title compound (2.087 g, 62.2%) as a yellow oil.
¹H NMR (400 MHz, CDCl₃) δ 1.14-1.25 (2H, m), 1.27 (3H, t), 1.46-1.56 (3H, m), 1.83-1.94 (4H, m), 2.24 (2H, d), 2.79-2.87 (1H, m), 4.12-4.17 (2H, m), 6.96-6.99 (1H, m), 7.01-7.05 (1H, m), 7.27-7.31 (1H, m); m/z 411 (M−H)⁻.

Intermediate 43-4: Ethyl 2-((1r,4r)-4-(2-fluoro-4-hydroxyphenyl)-cyclohexyl)acetate and Intermediate 43-5: Ethyl 2-((1s,4s)-4-(2-fluoro-4-hydroxyphenyl)-cyclohexyl)acetate

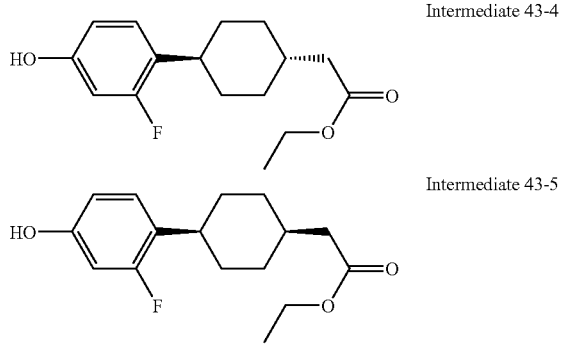

Intermediate 43-4

Intermediate 43-5

Intermediate 43-6 (6.29 g, 22.60 mmol) and palladium on carbon (10%) (0.6 g, 0.56 mmol) in EtOH (200 mL) was evacuated with hydrogen (4 cycles) and then stirred under a balloon of hydrogen at ambient temperature for 2 hours. The reaction mixture was filtered and evaporated to give a colourless oil. The crude product was purified by flash silica chromatography, elution gradient 10 to 20% EtOAc in isohexane. Pure fractions were evaporated to dryness to afford the desired product as a mixture of cis and trans isomers as a colourless oil which was further purified by preparative chiral-HPLC on a Chiralcel OJ column, eluting isocratically with 10% IPA in isohexane as eluent. The fractions containing the desired compounds were evaporated to dryness to afford Intermediate 43-4 (2.28 g, 36%) as a white solid and Intermediate 43-5 (3.08 g, 48.6%) as a pale yellow gum.
Intermediate 43-4
¹H NMR (400 MHz, CDCl₃) δ 1.11-1.24 (2H, m), 1.26 (3H, t), 1.42-1.53 (2H, m), 1.80-1.89 (5H, m), 2.23 (2H, d), 2.69-2.76 (1H, m), 4.14 (2H, q), 4.82 (1H, s), 6.50-6.57 (2H, m), 7.04 (1H, t); m/z (EI+) 280 M⁺.
Intermediate 43-5
¹H NMR (400 MHz, CDCl₃) δ 1.27 (3H, t), 1.59-1.76 (8H, m), 2.29-2.36 (1H, m), 2.45 (2H, d), 2.75-2.83 (1H, m), 4.15 (2H, q), 4.94 (1H, s), 6.51-6.57 (2H, m), 7.08 (1H, t); m/z (EI+) 280 M⁺.

Intermediate 43-6: Ethyl 2-(4-(2-fluoro-4-hydroxyphenyl)cyclohex-3-enyl)acetate

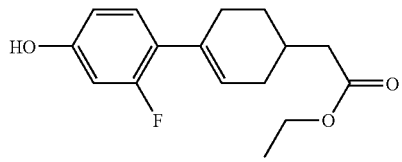

A solution of Intermediate 43-7 (18.48 g, 62.82 mmol) in DMF (100 mL) was added to a stirred suspension of 4-bromo-3-fluorophenol (10 g, 52.36 mmol), potassium carbonate (21.71 g, 157.07 mmol) and [1,1-Bis(diphenylphosphino) ferrocene]dichloropalladium(II) (1.163 g, 1.41 mmol) in DMF (100 mL) at ambient temperature. The resulting suspension was stirred at 80° C. under nitrogen for 2 hours. The reaction was incomplete so the temperature was increased to 100° C. and the reaction mixture was stirred for a further 30 minutes and then further [1,1-Bis(diphenylphosphino)ferrocene]dichloropalladium(II) (1.163 g, 1.41 mmol) was added and the suspension was stirred at 100° C. for a further 45 minutes and then further [1,1-Bis(diphenylphosphino)ferrocene]dichloropalladium(II) (400 mg, 0.487 mmol) was added and the suspension was stirred at 100° C. for a further 45 minutes. The reaction mixture was evaporated to dryness and redissolved in EtOAc (200 mL) and 2M HCl (250 mL) was cautiously added. The aqueous layer was further extracted with EtOAc (3×200 mL) and the organic extracts were combined, washed saturated brine (300 mL), dried over MgSO₄, filtered and evaporated to afford crude product. The crude product was purified by flash silica chromatography, elution gradient 0 to 20% EtOAc in isohexane. Pure fractions were evaporated to dryness to afford the title compound (6.34 g, 43.5%) as a pale yellow oil.
¹H NMR (400 MHz, CDCl₃) δ 1.27 (3H, t), 1.41-1.50 (1H, m), 1.85-1.95 (2H, m), 2.14-2.21 (1H, m), 2.32 (2H, d), 2.32-2.48 (3H, m), 4.16 (2H, q), 4.98 (1H, s), 5.81 (1H, s), 6.51-6.56 (2H, m), 7.05-7.09 (1H, m); m/z 277 (M−H)⁻.

Intermediate 43-7: Ethyl 2-(4-(4,4,5,5-tetramethyl-1,3,2-dioxaborolan-2-yl)cyclohex-3-enyl)acetate

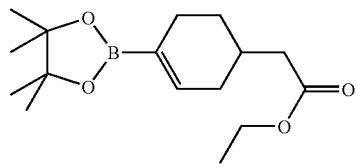

This compound was synthesised from Intermediate 43-8 using similar conditions as described in Intermediate 25-2 to give the title compound (10.4 g, 71%) as a colourless oil.
¹H NMR (300 MHz, CDCl₃) δ1.24-1.28 (18H, m), 1.77-1.80 (2H, m), 2.18-2.27 (2H, m), 2.20-2.24 (2H, m), 4.09-4.16 (2H, m), 6.51 (1H, d)

Intermediate 43-8: Ethyl 2-(4-(trifluoromethylsulfonyloxy)cyclohex-3-enyl)acetate

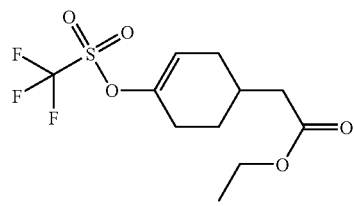

Trifluoromethanesulfonic anhydride (11.9 mL, 70.86 mmol) was added portionwise to a solution of 2,6-di-tert-butyl-4-methylpyridine (18.19 g, 88.58 mmol) in DCM (250 mL). A solution of ethyl 2-(4-oxocyclohexyl)acetate (10.88 g, 59.05 mmol, CAS 58012-34-3) in DCM (100 mL) was then added dropwise and the reaction mixture was allowed to stir open to air and at room temperature overnight. The reaction mixture was washed with water, saturated Na$_2$CO$_3$, saturated brine, dried over MgSO$_4$ and evaporated to afford crude product. The crude product was purified by flash silica chromatography, elution gradient 0 to 10% EtOAc in isohexane. Pure fractions were evaporated to dryness to afford the title compound (16.05 g, 86%) as a yellow oil.

$^1$H NMR (300 MHz, CDCl$_3$) δ 1.22-1.29 (3H, m), 1.39-1.51 (1H, m), 1.76-1.85 (2H, m), 2.07-2.23 (4H, m), 2.29 (2H, d), 4.09-4.18 (2H, m), 4.96 (1H, s).

Example 44

2-((1s,4s)-4-(4-(6-Carbamoyl-3,5-dimethylpyrazin-2-yl)-2-fluorophenyl)cyclohexyl)acetic acid

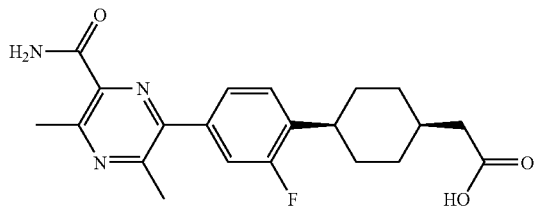

This compound was synthesized from Intermediate 44-1 using similar conditions as described in Example 21 to give the title compound (252 mg, 71%) as a white solid.

$^1$H NMR (400 MHz, DMSO) δ 1.65 (8H, m), 2.22 (1H, m), 2.41 (2H, d), 2.60 (3H, s), 2.74 (3H, s), 2.88 (1H, m), 7.53 (4H, m), 8.05 (1H, s), 12.03 (1H, s); m/z 386 (M+H)$^+$.

Intermediate 44-1: Ethyl 2-((1s,4s)-4-(4-(6-carbamoyl-3,5-dimethylpyrazin-2-yl)-2-fluorophenyl)cyclohexyl)acetate

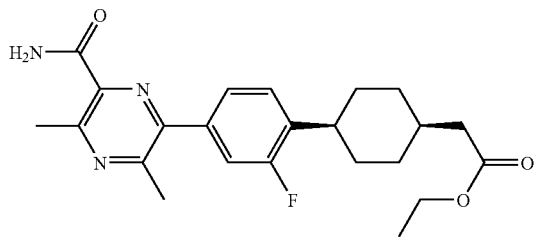

This compound was synthesized from Intermediate 44-2 and Intermediate 21-4 using similar conditions as described in Intermediate 21-1 to give the title compound (453 mg, 68%) as a pale yellow solid.

$^1$H NMR (400 MHz, CDCl$_3$) δ 1.28 (3H, t), 1.74 (8H, m), 2.39 (1H, m), 2.48 (2H, d), 2.68 (3H, s), 2.97 (4H, m), 4.16 (2H, q), 5.51 (1H, s), 7.26 (1H, m), 7.32 (1H, m), 7.38 (1H, t), 7.75 (1H, s); m/z 414 (M+H)$^+$.

Intermediate 44-2: Ethyl 2-((1s,4s)-4-(2-fluoro-4-(4,4,5,5-tetramethyl-1,3,2-dioxaborolan-2-yl)phenyl)cyclohexyl)acetate

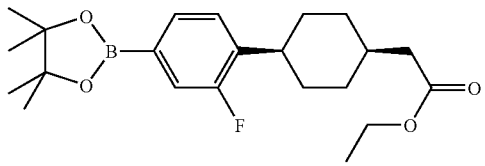

This compound was synthesized from Intermediate 44-3 using similar conditions as described in Intermediate 25-2 to give the title compound (1.45 g, 61%) as a white solid.

$^1$H NMR (400 MHz, CDCl$_3$) δ 1.27 (3H, t), 1.32 (12H, s), 1.67 (8H, m), 2.35 (1H, m), 2.46 (2H, d), 2.89 (1H, m), 4.14 (2H, q), 7.25 (1H, t), 7.42 (1H, d), 7.52 (1H, d); m/z (ES+) (M+H)+=No mass ion; HPLC tR=3.62 min.

Intermediate 44-3: Ethyl 2-((1s,4s)-4-(2-fluoro-4-(trifluoromethylsulfonyloxy)-phenyl)cyclohexyl)acetate

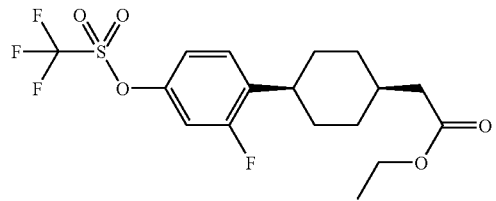

This compound was synthesized from Intermediate 43-5 using similar conditions as described in Intermediate 25-4 to give the title compound (2.53 g, 86%) as a yellow oil.

$^1$H NMR (400 MHz, DMSO) δ 1.12 (3H, t), 1.55 (8H, m), 2.15 (1H, m), 2.41 (2H, d), 2.77 (1H, m), 4.00 (3H, q), 7.24 (1H, m), 7.43 (1H, m), 7.56 (1H, t); m/z (ES−) 411 (M−H)$^−$.

Example 45

((1r,4r)-4-(4-(6-Carbamoyl-3,5-dimethylpyrazin-2-yl)-2-chlorophenyl)cyclohexyl)acetic acid

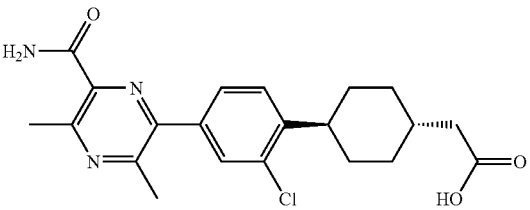

This compound was synthesised from Intermediate 45-1 using similar conditions as described in Example 21. Except the crude product was recrystallised from hot EtOH (15 mL) to give a solid which was washed with Ether (10 mL) and dried under vacuum at room temperature to give the title compound (313 mg, 80%).

$^1$H NMR (400 MHz, DMSO) δ 1.12-1.23 (2H, m), 1.49-1.60 (2H, m), 1.76-1.90 (5H, m), 2.18 (2H, d), 2.60 (3H, s), 2.75 (3H, s), 2.91-3.00 (1H, m), 7.52 (1H, d), 7.65 (1H, s), 7.67-7.70 (1H, m), 7.84 (1H, d), 8.10 (1H, s), 12.09 (1H, s); m/z 402 (M+H)$^+$.

Intermediate 45-1: Ethyl 2-((1r,4r)-4-(4-(6-Carbamoyl-3,5-dimethylpyrazin-2-yl)-2-chlorophenyl)cyclohexyl)acetate

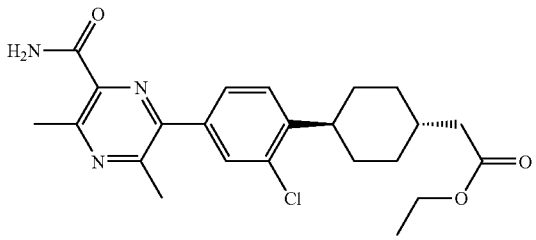

This compound was synthesized from Intermediate 45-2 and Intermediate 21-4 using similar conditions as described in Intermediate 21-1 to give the title compound (482 mg, 91%) as a yellow solid.

¹H NMR (400 MHz, CDCl₃) δ 1.21 (3H, t), 1.40-1.47 (1H, m), 1.84-1.94 (4H, m), 2.20 (2H, d), 2.60 (3H, s), 2.91 (3H, s), 2.94-3.02 (1H, m), 3.42 (4H, d), 4.06-4.11 (2H, m), 5.40 (1H, s), 7.29-7.32 (1H, m), 7.36-7.38 (1H, m), 7.51 (1H, d), 7.67 (1H, s); m/z 430 (M+H)⁺.

Intermediate 45-2: Ethyl 2-((1r,4r)-4-(2-Chloro-4-(4,4,5,5-tetramethyl-1,3,2-dioxaborolan-2-yl)phenyl)cyclohexyl)acetate

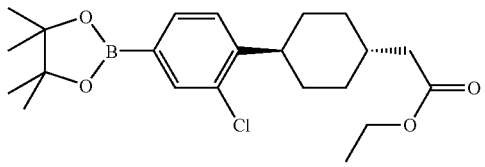

This compound was synthesized from Intermediate 45-3 using similar conditions as described in Intermediate 25-2 to give the title compound (1.046 g, 70.7%) as a colourless oil which crystallised on standing.

¹H NMR (400 MHz, CDCl₃) δ 0.76-0.87 (4H, m), 1.20 (3H, t), 1.35-1.44 (1H, m), 1.48 (12H, s), 1.80-1.86 (4H, m), 2.18 (2H, d), 2.89-2.97 (1H, m), 4.05-4.10 (2H, m), 7.18 (1H, d), 7.56 (1H, d), 7.70 (1H, d); m/z 430 (M+Na)⁺.

Intermediate 45-3: Ethyl 2-((1r,4r)-4-(2-Chloro-4-(trifluoromethyl-sulfonyloxy)phenyl)cyclohexyl)acetate

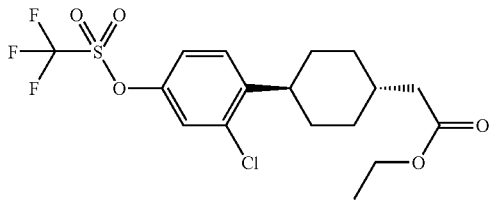

This compound was synthesized from Intermediate 45-4 using similar conditions as described in Intermediate 25-4 to give the title compound (1.560 g, 85%) as a yellow oil.

¹H NMR (400 MHz, CDCl₃) δ 1.18-1.29 (4H, m), 1.39-1.49 (2H, m), 1.88-1.95 (4H, m), 2.25 (2H, d), 2.93-3.01 (1H, m), 3.49 (2H, d), 4.12-4.18 (2H, m), 7.14-7.17 (1H, m), 7.29 (1H, d), 7.32 (1H, d); m/z 427 (M−H)⁻.

Intermediate 45-4: Ethyl 2-((1r,4r)-4-(2-chloro-4-hydroxyphenyl)-cyclohexyl)acetate and Intermediate 45-5: Ethyl 2-((1s,4s)-4-(2-chloro-4-hydroxyphenyl)cyclohexyl)acetate Intermediate 45-4

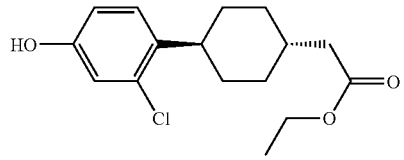

Intermediate 45-5

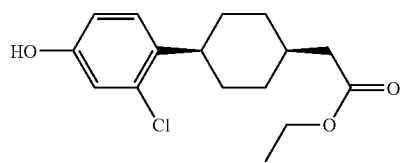

These compounds were synthesized from Intermediate 45-6 using similar conditions as described in Intermediate 43-4 and 43-5, except after silica chromatography the crude product was purified by preparative HPLC (Phenomenex Gemini C18 110A (axia) column, 5μ silica, 21 mm diameter, 150 mm length), using decreasingly polar mixtures of water (containing 0.1% formic acid) and MeCN as eluents. Fractions containing the desired compound were evaporated to dryness to afford crude product as a mixture of isomers (5.78 g, 49.9%) as a colourless oil. The oil was purified by preparative chiral-HPLC on a Merck 50 mm 20 μm Chiralcel OJ column, eluting isocratically with 70% isohexane in IPA (modified with AcOH/Et₃N) as eluent. The fractions containing the desired compound were evaporated to dryness to afford Intermediate 45-4 (1.264 g, 21.87%) as a white solid and Intermediate 45-5 (3.52 g, 60.9%) as white solid.

Intermediate 45-4:
¹H NMR (400 MHz, CDCl₃) δ 1.13-1.24 (2H, m), 1.27 (3H, t), 1.34-1.45 (2H, m), 1.80-1.91 (5H, m), 2.24 (2H, d), 2.84-2.92 (1H, m), 4.12-4.18 (2H, m), 6.70-6.73 (1H, m), 6.86 (1H, d), 7.08 (1H, d) phenol OH not seen; m/z (ES−) (M−H)−=295, 297

Intermediate 45-5:
¹H NMR (400 MHz, CDCl₃) δ 1.27 (3H, t), 1.46-1.58 (3H, m), 1.65-1.78 (5H, m), 2.33-2.40 (1H, m), 2.47 (2H, d), 2.89-2.96 (1H, m), 4.13-4.18 (2H, m), 6.70-6.73 (1H, m), 6.86 (1H, d), 7.12 (1H, d) phenol OH not seen; m/z (ES−) (M−H)−=295, 297

Intermediate 45-6: Ethyl 2-(4-(2-chloro-4-hydroxyphenyl)cyclohex-3-enyl)acetate

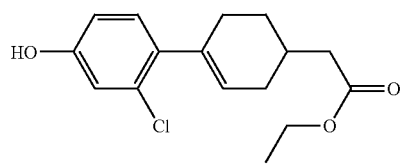

Example 46

2-((1s,4s)-4-(4-(6-Carbamoyl-3,5-dimethylpyrazin-2-yl)-2-chlorophenyl)cyclohexyl)acetic acid

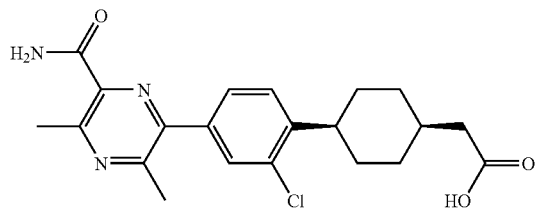

This compound was synthesized from Intermediate 46-1 using similar conditions as described in Example 21 to give the title compound (184 mg, 44%) as a white solid.

$^1$H NMR (400 MHz, DMSO) δ 1.65 (8H, m), 2.24 (1H, m), 2.44 (2H, d), 2.59 (3H, s), 2.73 (3H, s), 2.99 (1H, m), 7.58 (2H, m), 7.67 (1H, d), 7.81 (1H, s), 8.05 (1H, s), 12.01 (1H, s); m/z 402 (M+H)$^+$.

Intermediate 46-1: Ethyl 2-((1s,4s)-4-(4-(6-carbamoyl-3,5-dimethylpyrazin-2-yl)-2-chlorophenyl)cyclohexyl)acetate

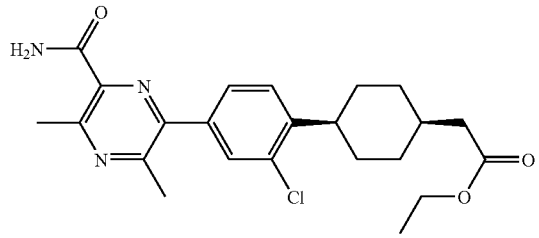

This compound was synthesized from Intermediate 46-2 and Intermediate 21-4 using similar conditions as described in Intermediate 21-1 to give the title compound (365 mg, 78%) as a colourless gum.

$^1$H NMR (400 MHz, CDCl$_3$) δ 1.28 (3H, t), 1.67 (2H, m), 1.78 (6H, m), 2.42 (1H, m), 2.50 (2H, d), 2.67 (3H, s), 2.98 (3H, s), 3.10 (1H, m), 4.16 (2H, m), 5.53 (1H, s), 7.43 (2H, m), 7.59 (1H, d), 7.75 (1H, s); m/z 430 (M+H)$^+$.

Intermediate 46-2: Ethyl 2-((1s,4s)-4-(2-Chloro-4-(4,5,5-tetramethyl-1,3,2-dioxaborolan-2-yl)phenyl)cyclohexyl)acetate

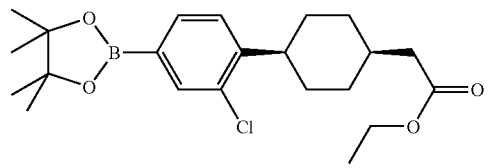

This compound was synthesized from Intermediate 46-3 using similar conditions as described in Intermediate 25-2 to give the title compound (1.19 g, 62%) as a colourless oil.

$^1$H NMR (400 MHz, CDCl$_3$) δ 1.27 (3H, t), 1.33 (12H, s), 1.59 (2H, m), 1.72 (6H, m), 2.39 (1H, m), 2.47 (2H, d), 3.05 (1H, m), 4.15 (2H, q), 7.28 (1H, t), 7.64 (1H, d), 7.77 (1H, s); m/z 430 (M+Na)$^+$.

Intermediate 46-3: Ethyl 2-((1s,4s)-4-(2-chloro-4-(trifluoromethyl-sulfonyloxy)phenyl)cyclohexyl)acetate

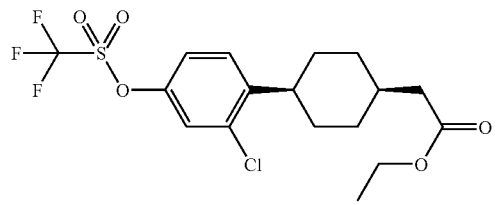

This compound was synthesized from Intermediate 45-5 using similar conditions as described in Intermediate 25-4 to give the title compound (2.051 g, 71.0%) as a colourless oil.

$^1$H NMR (400 MHz, CDCl$_3$) δ 1.26 (3H, t), 1.56 (2H, m), 1.73 (6H, m), 2.40 (1H, m), 2.46 (2H, d), 3.02 (1H, t), 4.16 (1H, q), 7.16 (1H, m), 7.30 (1H, d), 7.37 (1H, d); m/z 427 (M−H)$^−$.

Example 47

6-(4-((1r,4r)-4-((1H-Tetrazol-5-yl)methyl)cyclohexyl)phenyl)-3,5-dimethylpyrazine-2-carboxamide

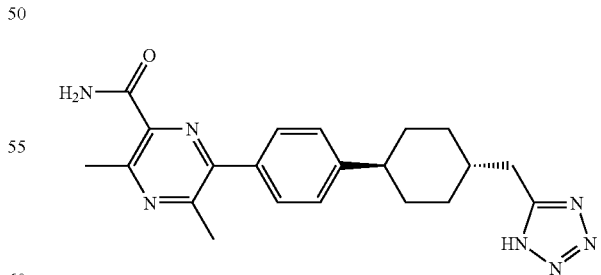

This compound was synthesised from Intermediate 47-1 using similar conditions as described in Example 28 to give the title compound (220 mg, 41.7%) as a white solid. The material was recrystallised from hot Methanol, filtered off and washed with ether before drying under vacuum to give the title compound (223 mg, 42.3%).

¹H NMR (300 MHz, DMSO) δ 1.13-1.27 (2H, m), 1.43-1.56 (2H, m), 1.74-1.88 (5H, m), 2.53-2.57 (1H, m), 2.58 (3H, s), 2.74 (3H, s), 2.84 (2H, d), 7.35 (2H, d), 7.58 (1H, s), 7.65 (2H, d), 7.97 (1H, s), 16.00 (1H, s); m/z 392 (M+H)⁺.

Intermediate 47-1: 3-(5-(((1r,4r)-4-(4-(4,4,5,5-Tetramethyl-1,3,2-dioxaborolan-2-yl)phenyl)cyclohexyl)methyl)-1H-tetrazol-1-yl)propanenitrile

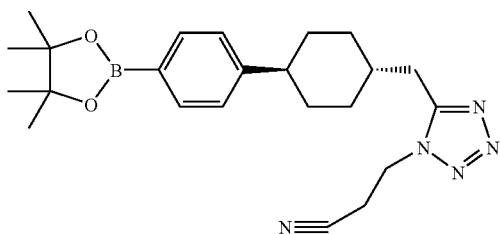

This compound was synthesised from Intermediate 47-2 using similar conditions as described in Intermediate 28-1 to give the title compound (1.960 g, 59.9%) contaminated with triphenyphosphine oxide (3 mol %).

¹H NMR (400 MHz, DMSO) δ 0.96-1.05 (2H, m), 1.06 (12H, s), 1.19-1.30 (2H, m), 1.54-1.64 (5H, m), 2.67 (2H, d), 2.97 (2H, t), 3.07 (1H, s), 4.47 (2H, t), 7.02 (2H, d), 7.37 (2H, d); HPLC tR=2.81.

Intermediate 47-2: N-(2-Cyanoethyl)-2-((1r,4r)-4-(4-(4,4,5,5-tetramethyl-1,3,2-dioxaborolan-2-yl)phenyl)cyclohexyl)acetamide

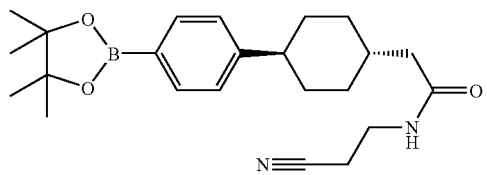

This compound was synthesised from Intermediate 47-3 using similar conditions as described in Intermediate 28-2 to give the title compound (3.08 g, 77%).

¹H NMR (400 MHz, DMSO) δ 1.03-1.13 (2H, m), 1.27 (12H, s), 1.37-1.47 (2H, m), 1.71-1.80 (5H, m), 2.02 (2H, d), 2.63 (2H, t), 7.22 (2H, d), 7.58 (2H, d), 8.16 (1H, t), 3×CH obscured by solvent.

Intermediate 47-3: 2-((1r,4r)-4-(4-(4,4,5,5-Tetramethyl-1,3,2-dioxaborolan-2-yl)phenyl)cyclohexyl)acetic acid

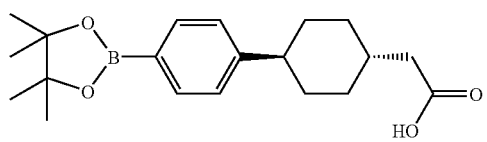

Methyl 2-((1r,4r)-4-(4-(4,4,5,5-tetramethyl-1,3,2-dioxaborolan-2-yl)phenyl)cyclohexyl)acetate (CAS 701232-69-1, prepared according to the procedure described in WO 2004/047755) (3.6 g, 10.05 mmol) was dissolved in a solution of sodium hydroxide (1.326 g, 33.16 mmol) in methanol (36 mL) and water (4.00 mL). The reaction mixture was split in two and heated to 120° C. for 30 min in a microwave. The reaction mixtures were combined, acidified with 2M HCl and evaporated. The crude product was taken onto the next step without purification.

¹H NMR (400 MHz, DMSO) δ 1.08-1.12 (2H, m), 1.27 (12H, s), 1.42-1.46 (2H, m), 1.74-1.82 (5H, m), 2.13 (2H, d), 7.22 (2H, d), 7.58 (2H, d) one CH and COOH not seen.

Example 48

4'-(6-Carbamoyl-3,5-dimethylpyrazin-2-yl)biphenyl-4-carboxylic acid

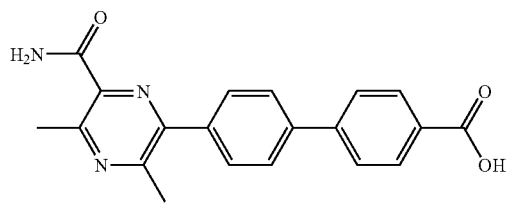

This compound was synthesised from Intermediate 48-1 using similar conditions as described in Example 21 to give the title compound (42.2 mg, 74.5%) as an off white solid.

¹H NMR (400 MHz, DMSO) δ 2.58 (3H, s), 2.70 (3H, s), 3.57 (2H, s), 7.32 (2H, d), 7.55 (1H, s), 7.64 (2H, d), 7.73 (2H, d), 7.78 (2H, d), 7.96 (1H, s), 12.29 (1H, s); m/z 362 (M+H)⁺.

Intermediate 48-1: Methyl 4'-(6-cyano-3,5-dimethylpyrazin-2-yl)biphenyl-4-carboxylate

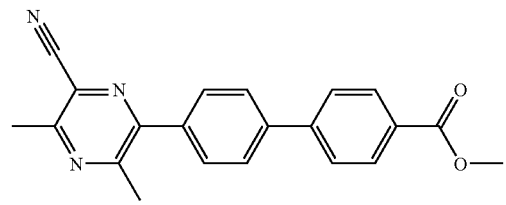

This compound was synthesised from Intermediate 33-3 and methyl 4-bromobenzoate using similar conditions as described in Intermediate 21-1 to give the title compound (124 mg, 72.1%) as a white solid.

¹H NMR (400 MHz, DMSO) δ 2.68 (3H, s), 2.72 (3H, s), 3.89 (3H, s), 7.80 (2H, d), 7.89-7.93 (4H, m), 8.07 (2H, d); HPLC tR=2.92 min.

The following examples were synthesised from Intermediates 49-1- to 53-1 using similar conditions as described in Example 21 to give the desired compounds.

| Example | Structure | $^1$H NMR (400 MHz, DMSO) δ | m/z (M + H)$^+$ |
|---|---|---|---|
| 49 | 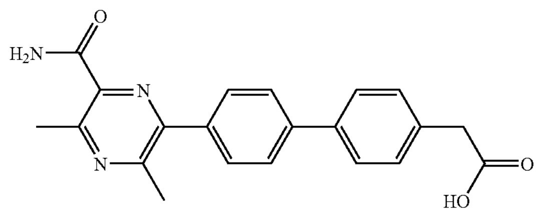 | 2.64 (3H, s), 2.76 (3H, s), 3.63 (2H, s), 7.38 (2H, d), 7.61 (1H, s), 7.70 (2H, d), 7.79 (2H, d), 7.84 (2H, d), 8.02 (1H, s), 12.33 (1H, s). | 362 |
| 50 | 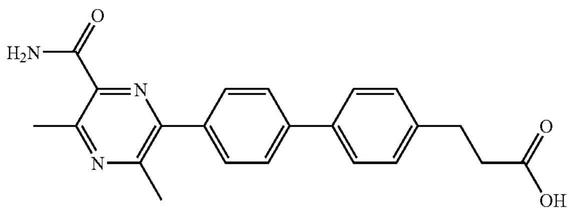 | 2.55 (2H, t), 2.64 (3H, s), 2.75 (3H, s), 2.87 (2H, t), 7.35 (2H, d), 7.61 (1H, s), 7.65 (2H, d), 7.77 (2H, d), 7.83 (2H, d), 8.02 (1H, s), COOH not seen. | 376 |
| 51 | 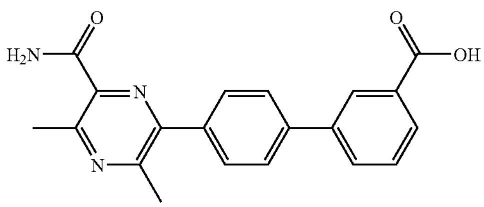 | 2.65 (3H, s), 2.76 (3H, s), 7.35 (1H, t), 7.61 (2H, d), 7.77 (2H, d), 7.82-7.86 (3H, m), 8.05 (1H, s), 8.19 (1H, s), COOH not seen. | 348 |
| 52 | 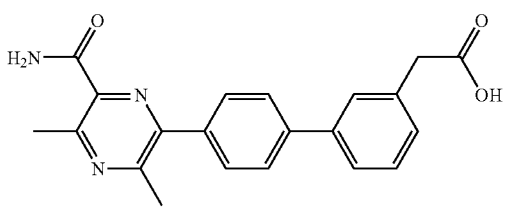 | 2.71 (3H, s), 2.82 (3H, s), 3.74 (2H, s), 7.36 (1H, d), 7.51 (1H, t), 7.69 (3H, d), 7.85 (2H, d), 7.92 (2H, d), 8.09 (1H, s), 12.43 (1H, s). | 362 |
| 53 | 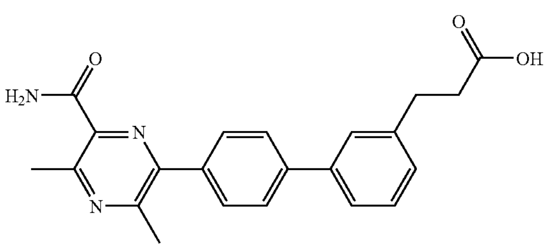 | 2.61 (2H, t), 2.64 (3H, s), 2.76 (3H, s), 2.92 (2H, t), 7.26 (1H, d), 7.40 (1H, t), 7.56 (1H, d), 7.60-7.63 (2H, m), 7.79 (2H, d), 7.84 (2H, d), 8.02 (1H, s), 12.12 (1H, s). | 376 |

The following Intermediates were synthesised from Intermediate 33-3 and the appropriate aryl bromide or triflate using similar conditions as described in Intermediate 21-1 to give the desired compounds.

| Intermediate | Structure | $^1$H NMR (400 MHz, DMSO) δ | m/z (M + H)$^+$ |
|---|---|---|---|
| 49-1$^a$ | | 2.75 (3H, s), 2.79 (3H, s), 3.70 (3H, s), 3.81 (2H, s), 7.46 (2H, d), 7.78 (2H, d), 7.82 (2H, d), 7.89 (2H, d) | HPLC tR = 2.83 min |

-continued

| Intermediate | Structure | ¹H NMR (400 MHz, DMSO) δ | m/z (M + H)⁺ |
|---|---|---|---|
| 50-1[b] | 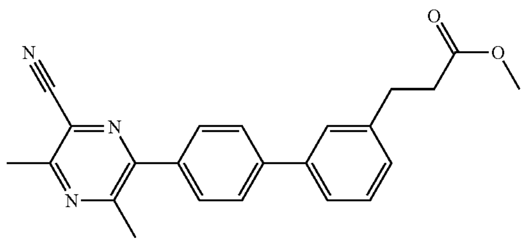 | 2.73-2.77 (5H, m), 2.78 (3H, s), 2.98 (2H, t), 3.35 (3H, s), 7.42 (2H, d), 7.74 (2H, d), 7.81 (2H, d), 7.87 (2H, d) | HPLC tR = 2.97 min. |
| 51-1[c] | 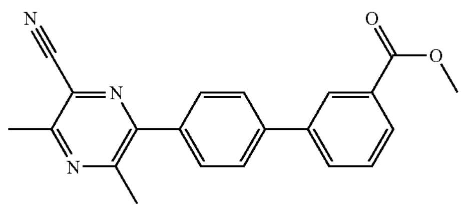 | 2.75 (3H, s), 2.79 (3H, s), 3.97 (3H, s), 7.74 (1H, t), 7.86 (2H, d), 7.95 (2H, d), 8.05-8.08 (1H, m), 8.10-8.13 (1H, m), 8.34 (1H, t). | HPLC tR = 2.93 min. |
| 52-1[d] | 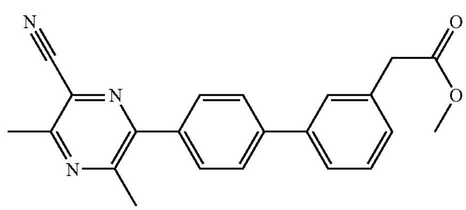 | 2.75 (3H, s), 2.79 (3H, s), 3.70 (3H, s), 3.85 (2H, s), 7.38 (1H, d), 7.52 (1H, t), 7.70-7.73 (2H, m), 7.83 (2H, d), 7.88 (2H, d). | 358 |
| 53-1[e] | 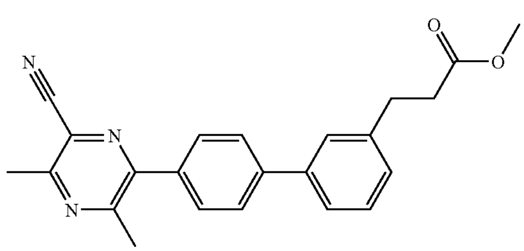 | 2.74 (3H, s), 2.76-2.80 (5H, m), 3.02 (2H, t), 3.66 (3H, s), 7.34 (1H, d), 7.48 (1H, t), 7.64 (1H, d), 7.68-7.69 (1H, m), 7.82 (2H, d), 7.89 (2H, d). | 372 |

Note:
49-1[a] methyl 2-(4-bromophenyl)acetate, CAS 41841-16-1 was made according to the procedure described by E. E. Knaus at al, Bioorg. Med. Chem., 2005, 13, 4694-4703.
50-1[b] methyl 3-(4-(trifluoromethylsulfonyloxy)phenyl)propanoate, CAS 475272-11-8. was made according to the procedure described in WO 2002089738.
51-1[c] methyl 3-bromobenzoate, CAS 618-89-3.
52-1[d] methyl 2-(3-bromophenyl)acetate, CAS 150529-73-0.
53-1[e] methyl 3-(3-bromophenyl)propanoate, CAS 151583-29-8 was made according to the procedure described in WO 2007089667.

The following Examples 54-56 were synthesised from Intermediates 54-1 to 56-1 using similar conditions as described in Example 26 and Examples 57 to 63 were synthesised from Intermediates 57-1 to 63-1 using similar conditions as described in Example 21. All crude products were purified by preparative HPLC (Waters XBridge Prep C18 OBD column, 5μ silica, 50 mm diameter, 150 mm length), using decreasingly polar mixtures of water (containing 0.1% formic acid) and MeCN as eluents. Fractions containing the desired compound were evaporated to dryness to afford the desired products.

| Example | Structure | ¹H NMR (400 MHz, DMSO) δ | m/z (M + H)⁺ |
|---|---|---|---|
| 54 | 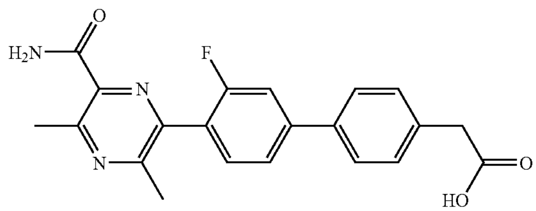 | 2.45 (3H, s), 2.75 (3H, s), 3.62 (2H, s), 7.38 (2H, d), 7.60 (1H, s), 7.66-7.68 (3H, m), 7.73 (2H, d), 7.96 (1H, s), 12.33 (1H, s) | 380 |
| 55 | 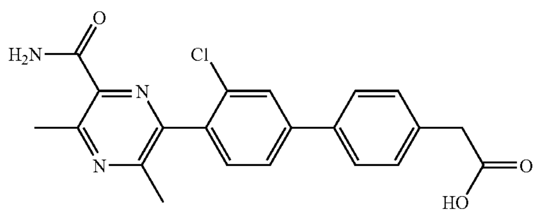 | 2.40 (3H, s), 2.78 (3H, s), 3.64 (2H, s), 7.39 (2H, d), 7.60-7.62 (2H, m), 7.73 (2H, d), 7.78 - 7.81 (1H, m), 7.90 (1H, d), 7.92 (1H, s), 12.35 (1H, s) | 396 |
| 56 | 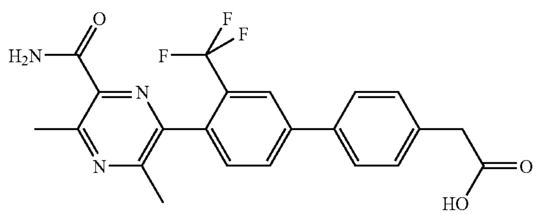 | 2.41 (3H, s), 2.87 (3H, s), 3.72 (2H, s), 7.49 (2H, d), 7.65 (1H, s), 7.75 (1H, d), 7.84 (3H, d), 8.17 (2H, t), COOH not seen. | 430 |
| 57 | 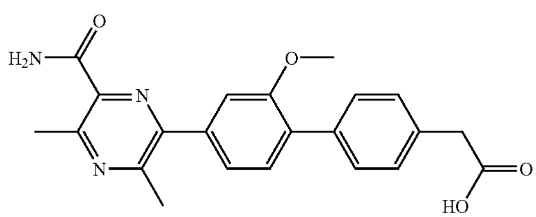 | 2.65 (3H, s), 2.76 (3H, s), 3.60 (2H, s), 3.83 (3H, s), 7.31 (2H, d), 7.34-7.43 (3H, m), 7.47 (2H, d), 7.60 (1H, s), 8.05 (1H, s), COOH not seen. | 392 |
| 58 | 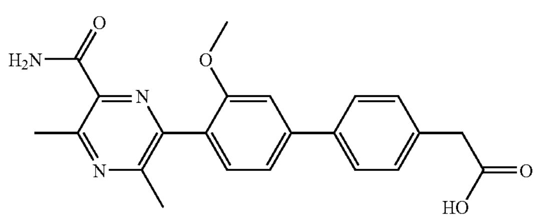 | 2.37 (3H, s), 2.75 (3H, s), 3.63 (2H, s), 3.87 (3H, s), 7.35-7.40 (4H, m), 7.45 (1H, d), 7.55 (1H, s), 7.72 (2H, d), 7.91 (1H, s), 12.34 (1H, s). | 392 |
| 59 | 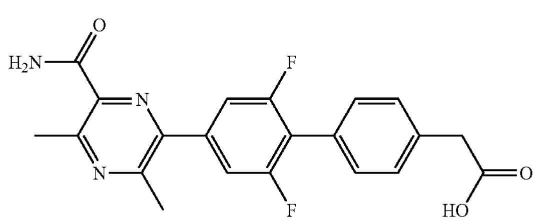 | 2.75 (3H, s), 2.84 (3H, s), 3.72 (2H, s), 7.48 (2H, d), 7.53 (2H, d), 7.70 (1H, s), 7.74-7.80 (2H, m), 8.20 (1H, s), 12.47 (1H, s) | 398 |
| 60 | 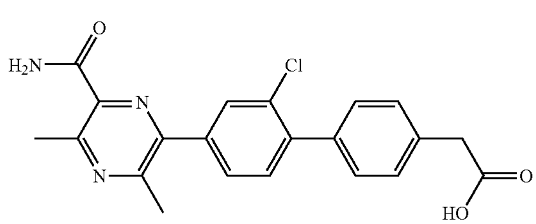 | 2.59 (3H, s), 2.71 (3H, s), 3.59 (2H, s), 7.32-7.34 (2H, m), 7.39-7.41 (2H, m), 7.48 (1H, d), 7.57 (1H, s), 7.73-7.75 (1H, m), 7.92 (1H, d), 8.04 (1H, s), 12.31 (1H, s). | 396 |

-continued

| Example | Structure | ¹H NMR (400 MHz, DMSO) δ | m/z (M + H)⁺ |
|---|---|---|---|
| 61 | 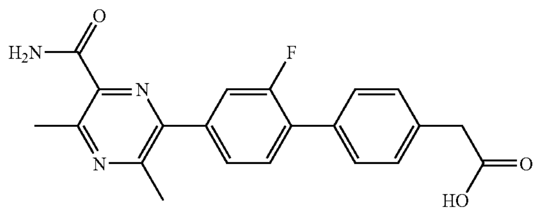 | 2.68 (3H, s), 2.78 (3H, s), 3.66 (2H, s), 7.42 (2H, d), 7.59 (2H, dd), 7.64 (1H, m), 7.69 (2H, dd), 7.80 (1H, dd), 8.10 (1H, s), 12.40 (1H, s). | 380 |
| 62 | 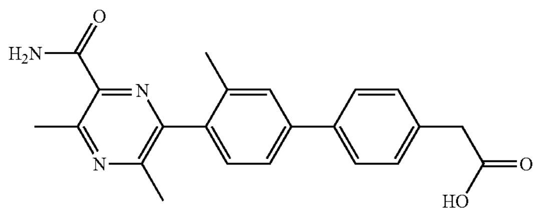 | 2.15 (3H, s), 2.37 (3H, s), 2.77 (3H, s), 3.62 (2H, s), 7.37 (3H, m), 7.54 (1H, s), 7.58 (1H, d), 7.67 (3H, m), 7.90 (1H, s), 12.34 (1H, s). | 376 |
| 63 | 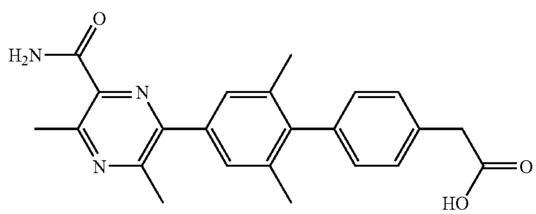 | 2.04 (6H, s), 2.63 (3H, s), 2.75 (3H, s), 3.63 (2H, s), 7.14 (2H, d), 7.37 (2H, d), 7.47 (2H, s), 7.60 (1H, s), 8.00 (1H, s), 12.33 (1H, s). | 390 |

The following Intermediates 54-1 to 63-1 were synthesised from Intermediates 54-2 to 63-2 and Intermediate 21-4 using similar conditions as described in Intermediate 21-1 to afford the desired compounds.

| Intermediate | Structure | ¹H NMR (400 MHz, DMSO) δ | m/z (M + H)⁺ |
|---|---|---|---|
| 54-1 | 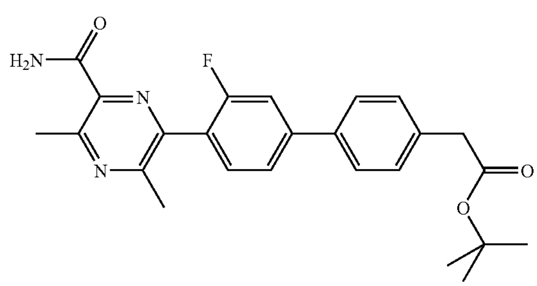 | 1.48 (9H, s), 2.53 (3H, s), 2.83 (3H, s), 3.69 (2H, s), 7.45 (2H, d), 7.69 (1H, s), 7.74-7.78 (3H, m), 7.82 (2H, d), 8.05 (1H, s) | 436 |
| 55-1 | 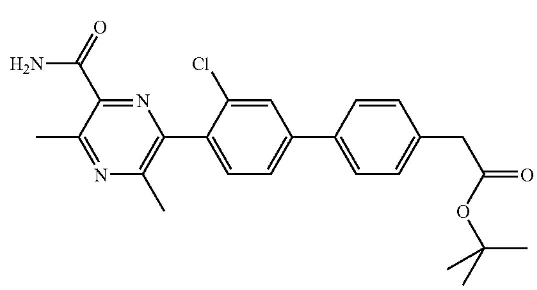 | 1.42 (9H, s), 2.40 (3H, s), 2.78 (3H, s ), 3.63 (2H, s), 7.38 (2H, d), 7.59-7.62 (2H, m), 7.74 (2H, d), 7.78-7.81 (1H, m), 7.90-7.91 (2H, m) | 452 |

| Intermediate | Structure | $^1$H NMR (400 MHz, DMSO) δ | m/z (M + H)$^+$ |
|---|---|---|---|
| 56-1 | 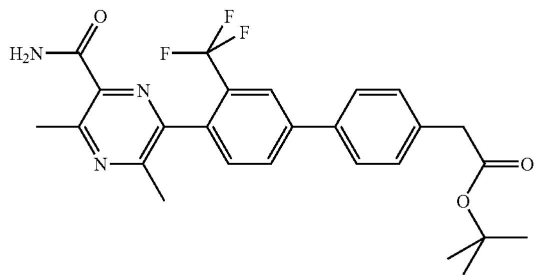 | 1.42 (9H, s), 2.34 (3H, s), 2.80 (3H, s), 3.64 (2H, s), 7.41 (2H, d), 7.59 (1H, s), 7.68 (1H, d), 7.75 (1H, s), 7.79 (2H, d), 8.09-8.11 (2H, m) | 486 |
| 57-1 | 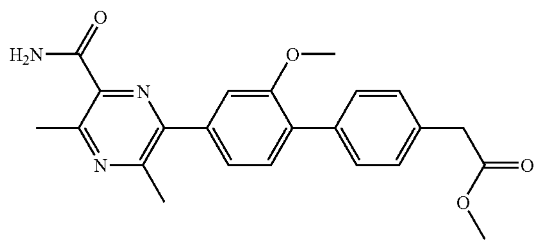 | 2.65 (3H, s), 2.77 (3H, s), 3.64 (3H, s), 3.72 (2H, s), 3.84 (3H, s), 7.31 (2H, d), 7.36-7.42 (3H, m), 7.49 (2H, d), 7.61 (1H, s), 8.05 (1H, s) | 406 |
| 58-1 | 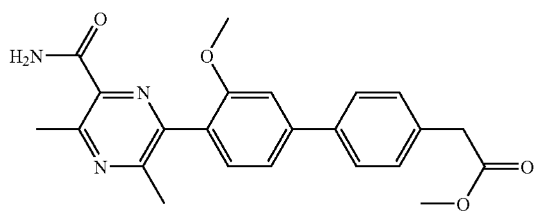 | 2.37 (3H, s), 2.75 (3H, s), 3.64 (3H, s), 3.75 (2H, s), 3.87 (3H, s), 7.36-7.40 (4H, m), 7.45 (1H, d), 7.55 (1H, s), 7.73 (2H, d), 7.90 (1H, s) | 406 |
| 59-1 | 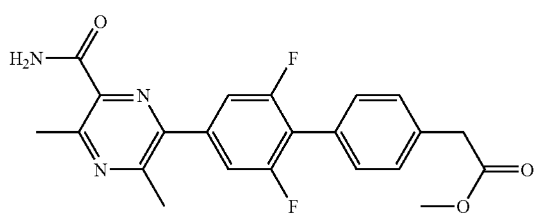 | 2.75 (3H, s), 2.84 (3H, s), 3.72 (3H, s), 3.84 (2H, s), 7.49 (2H, d), 7.55 (2H, d), 7.71 (1H, s), 7.75-7.80 (2H, m), 8.20 (1H, s). | 412 |
| 60-1 | 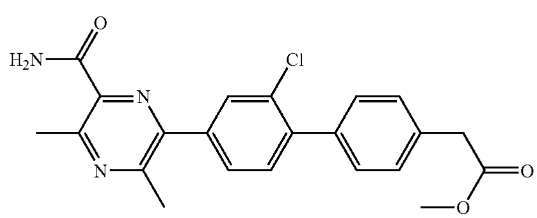 | 2.71 (3H, s), 2.83 (3H, s), 3.72 (3H, s), 3.95 (2H, s), 7.46 (2H, d), 7.52-7.54 (2H, m), 7.60 (1H, d), 7.69 (1H, s), 7.85-7.87 (1H, m), 8.05 (1H, d), 8.16 (1H, s). | 410 |
| 61-1 | 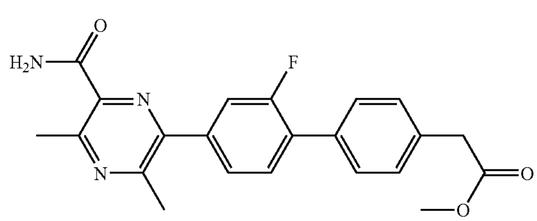 | (CDCl$_3$) δ 2.65 (3H, s), 2.93 (3H, s), 3.63 (2H, s), 3.66 (3H, s), 5.58 (1H, s), 7.31-7.39 (4H, m), 7.46-7.53 (3H, m), 7.69 (1H, s). | 394 |

-continued

| Intermediate | Structure | ¹H NMR (400 MHz, DMSO) δ | m/z (M + H)⁺ |
|---|---|---|---|
| 62-1 | 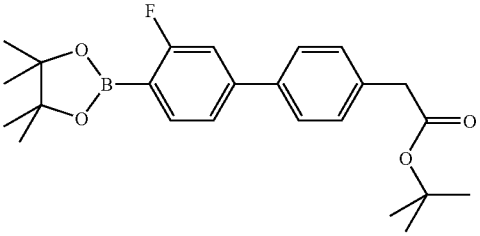 | 2.16 (3H, s), 2.36 (3H, s), 2.78 (3H, s), 3.64 (3H, s), 3.74 (2H, s), 7.38 (3H, d), 7.55 (1H, s), 7.59 (1H, d), 7.67 (3H, m), 7.90 (1H, s). | 390 |
| 63-1 | 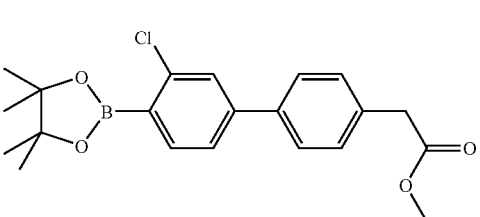 | 2.05 (6H, s), 2.63 (3H, s), 2.75 (3H, s), 3.66 (3H, s), 3.76 (2H, s), 7.15 (2H, d), 7.38 (2H, d), 7.47 (2H, s), 7.60 (1H, s), 8.00 (1H, s). | 404 |

The following Intermediates 54-2 to 63-2 were synthesised from Intermediates 54-3 to 63-3 using similar conditions as described in Intermediate 25-2 to afford the desired compounds.

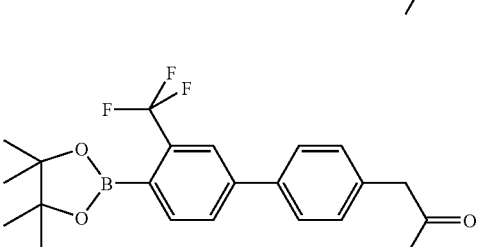

| Intermediate | Structure | ¹H NMR (400 MHz) | m/z |
|---|---|---|---|
| 54-2 | 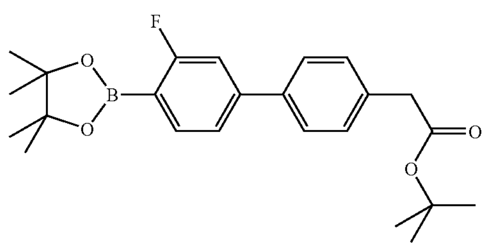 | (CDCl₃) δ 1.38 (12H, s), 1.45 (9H, s), 3.56 (2H, s), 7.24-7.27 (1H, m), 7.33-7.38 (3H, m), 7.55 (2H, d), 7.77-7.80 (1H, m) | 412 M⁺· (EI+) |
| 55-2 | 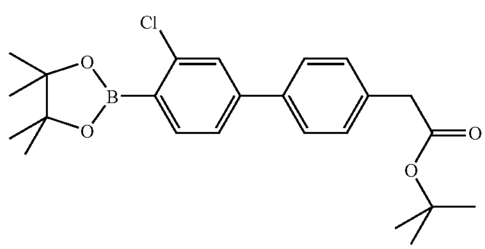 | (CDCl₃) δ 1.39 (12H, s), 1.45 (9H, s), 3.56 (2H, s), 7.34 (2H, d), 7.43-7.45 (1H, m), 7.53 (2H, d), 7.58 (1H, s), 7.75 (1H, d) | 428 M⁺· (EI+) |
| 56-2 | 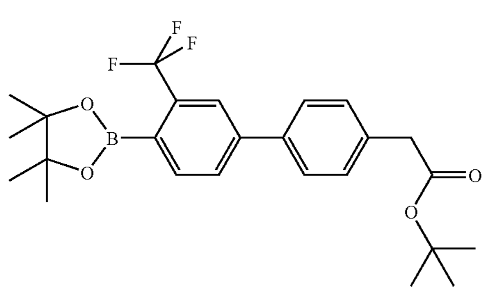 | (CDCl₃) δ 1.38 (12H, s), 1.46 (9H, s), 3.57 (2H, s), 7.37 (2H, d), 7.56 (2H, d), 7.72 (1H, d), 7.80 (1H, d), 7.87 (1H, s) | 462 M⁺· (EI+) |

-continued

| Intermediate | Structure | ¹H NMR (400 MHz) | m/z |
|---|---|---|---|
| 57-2 | 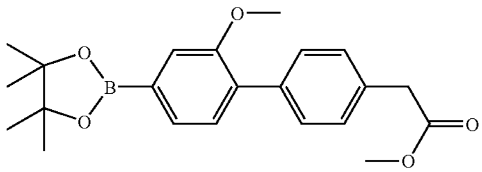 | (CDCl₃) δ 1.36 (12H, s), 3.65 (2H, s), 3.71 (3H, s), 3.85 (3H, s), 7.31-7.33 (3H, m), 7.39 (1H, s), 7.47-7.51 (3H, m) | 382 M⁺· (EI+) |
| 58-2 | 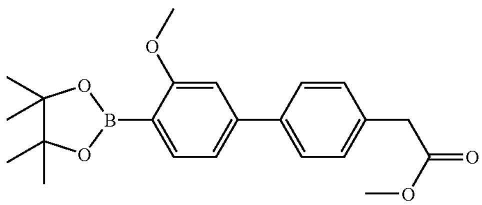 | (DMSO) δ 1.34 (12H, s), 3.35 (3H, s), 3.80 (2H, s), 3.89 (3H, s), 7.24 (1H, d), 7.26-7.28 (1H, m), 7.43 (2H, d), 7.67 (1H, d), 7.72 (2H, d) | mass ion not seen; HPLC tR = 3.01 min. |
| 59-2 | 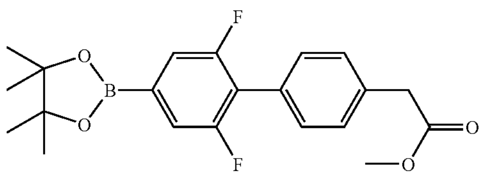 | (DMSO) δ 1.38 (12H, s), 3.70 (3H, s), 3.82 (2H, s), 7.40 (2H, d), 7.46 (4H, s) | mass ion not seen; HPLC tR = 3.30 min. |
| 60-2 | 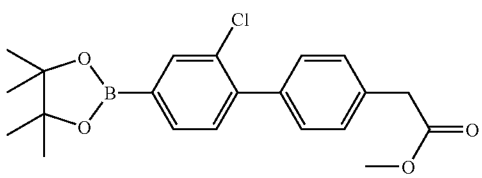 | (DMSO) δ 1.31 (12H, s), 3.64 (3H, s), 3.75 (2H, s), 7.35-7.41 (4H, m), 7.42 (1H, d), 7.65-7.67 (1H, m), 7.72 (1H, d). | mass ion not seen; HPLC tR = 3.42 min. |
| 61-2 | 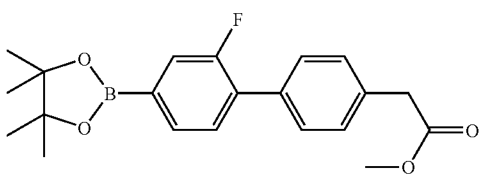 | (DMSO) δ 1.31 (12H, s), 3.63 (3H, s), 3.74 (2H, s), 7.36-7.46 (3H, m), 7.52 (2H, dd), 7.55 (2H, d). | 388 M + Na⁺ |
| 62-2 | 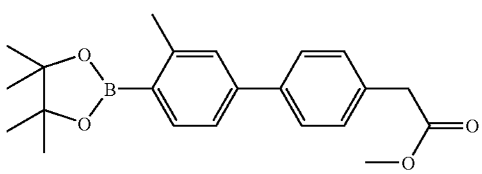 | (DMSO) δ 1.30 (12H, s), 2.52 (3H, s), 3.62 (3H, s), 3.72 (2H, s), 7.26 (1H, m), 7.40 (3H, m), 7.62 (2H, d), 7.70 (1H, d). | no mass ion seen; HPLC tR = 3.44 min |
| 63-2 | 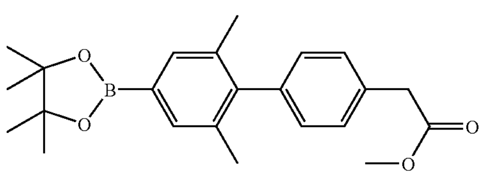 | (DMSO) δ 1.28 (12H, s), 1.94 (6H, s), 3.64 (3H, s), 3.74 (2H, s), 7.06 (2H, d), 7.34 (2H, d), 7.41 (2H, s). | no mass ion seen; HPLC tR = 3.39 min. |

The following Intermediates 54-3 to 63-3 were synthesised from Intermediates 54-4 to 63-4 either using similar conditions as described in Intermediate 25-4 (Method A) or by Method B (the procedure described by A. Bengtson, A. Hallberg and M. Larhed, *Org. Lett.*, 2002, 4, 1231-1233) to afford the desired compounds.

Representative example of Method B:

Intermediate 54-3: tert-Butyl 2-(3'-fluoro-4'-(trifluoromethylsulfonyl-oxy)biphenyl-4-yl)acetate Intermediate 54-4 (637 mg, 2.11 mmol), 1,1,1-trifluoro-N-phenyl-N-(trifluoromethylsulfonyl)methanesulfonamide (753 mg, 2.11 mmol) and potassium carbonate (874 mg, 6.32 mmol) were suspended in THF (11 mL) and sealed into a microwave tube. The reaction was heated to 120° C. for 6 minutes in the microwave reactor and cooled to RT. The suspension was filtered, the solid was washed with EtOAc (20 mL) and the filtrate was evaporated to afford crude product.

The crude product was purified by flash silica chromatography, elution gradient 0 to 10% EtOAc in isohexane. Pure fractions were evaporated to dryness to afford the title compound (690 mg, 75%) as a colourless oil.

| Intermediate | Structure | $^1$H NMR (400 MHz) | m/z (M − H)$^-$ |
|---|---|---|---|
| 54-3 | 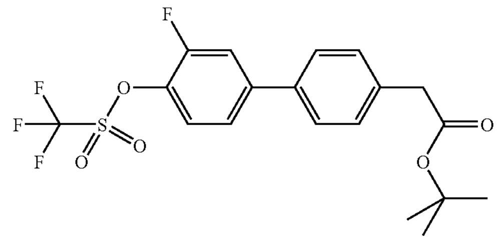 | (CDCl$_3$) δ 1.46 (9H, s), 3.58 (2H, s), 7.35-7.39 (4H, m), 7.43-7.51 (3H, m) | 433 |
| 55-3 | 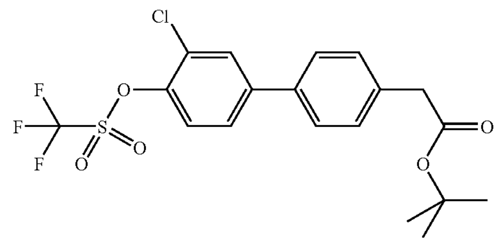 | (CDCl$_3$) δ 1.46 (9H, s), 3.57 (2H, s), 7.36-7.41 (3H, m), 7.48-7.53 (3H, m), 7.71 (1H, s) | 449 |
| 56-3 | 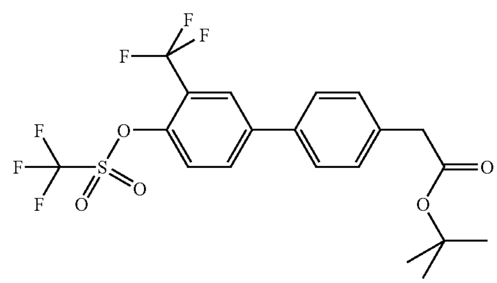 | (CDCl$_3$) δ 1.46 (9H, s), 3.59 (2H, s), 7.40 (2H, d), 7.52 (2H, d), 7.56 (1H, d), 7.80-7.83 (1H, m), 7.92 (1H, d) | 483 |
| 57-3 | 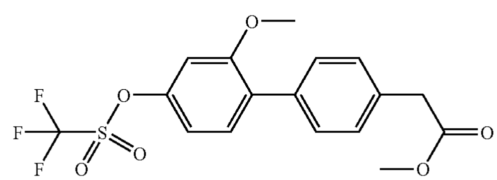 | (CDCl$_3$) δ 3.67 (2H, s), 3.72 (3H, s), 3.83 (3H, s), 6.85 (1H, d), 6.92-6.95 (1H, m), 7.33-7.35 (3H, m), 7.44 (2H, d) | 404 |
| 58-3 | 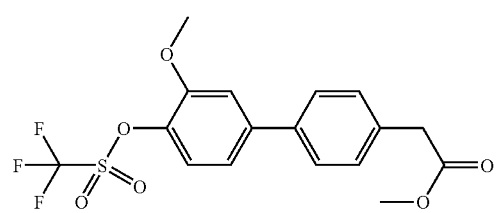 | (DMSO) δ 3.63 (3H, s), 3.74 (2H, s), 3.99 (3H, s), 7.30-7.33 (1H, m), 7.38 (2H, d), 7.48 (1H, d), 7.52 (1H, d), 7.69 (2H, d) | 409 |
| 59-3 | 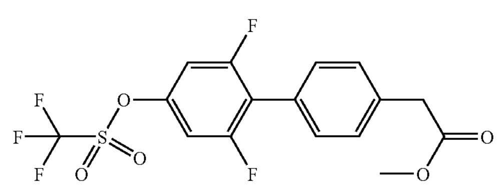 | (DMSO) δ 3.70 (3H, s), 3.83 (2H, s), 7.46-7.52 (4H, m), 7.74 (2H, d). | 409 |

| Intermediate | Structure | ¹H NMR (400 MHz) | m/z (M − H)⁻ |
|---|---|---|---|
| 60-3 | 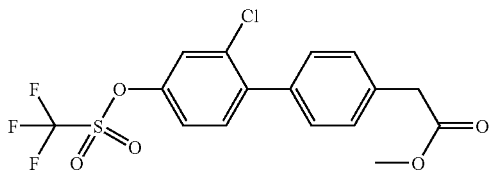 | (DMSO) δ 3.71 (3H, s), 3.82 (2H, s), 7.43-7.50 (4H, m), 7.64-7.69 (2H, m), 7.95 (1H, d). | mass ion not seen; HPLC tR = 3.14 min. |
| 61-3 | 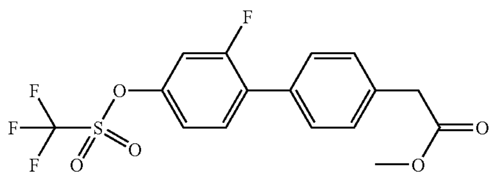 | (DMSO) δ 3.63 (3H, s), 3.75 (2H, s), 7.41 (2H, dd), 7.53 (2H, dt), 7.72 (1H, d), 7.73 (1H, t). | 391 |
| 62-3 | 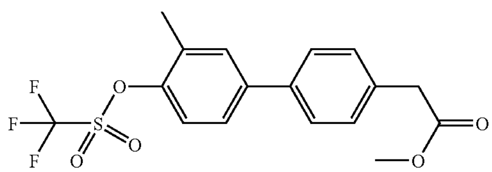 | (DMSO) δ 2.40 (3H, s), 3.63 (3H, s), 3.73 (2H, s), 7.27 (1H, m), 7.40 (3H, m), 7.65 (2H, m), 7.77 (1H, s). | 387 |
| 63-3 | 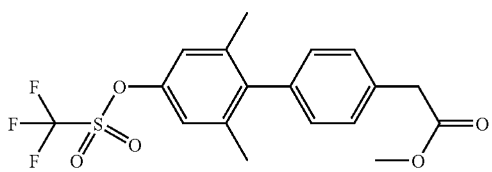 | (DMSO) δ 2.01 (6H, s), 3.64 (3H, s), 3.73 (2H, s), 7.12 (2H, d), 7.26 (2H, s), 7.37 (2H, d). | 401 |

Notes:
Method A 58-3, 59-3, 60-3;
Method B 54-3, 55-3, 56-3, 57-3, 61-3, 62-3, 63-3

The following Intermediates 54-4 to 63-4 were synthesised from either Intermediate 54-5 or 54-7 and the appropriate bromophenol using similar conditions as described in Intermediate 21-1 to afford the desired compounds.

| Intermediate | Structure | ¹H NMR (400 MHz) | m/z (M − H)⁻ |
|---|---|---|---|
| 54-4[a] | 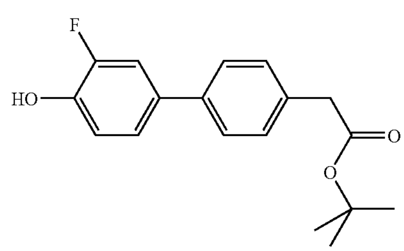 | (CDCl₃) δ 1.45 (9H, s), 3.55 (2H, s), 5.11 (1H, d), 7.04 (1H, t), 7.24-7.27 (1H, m), 7.28-7.33 (3H, m), 7.46 (2H, d). | 301 |
| 55-4[b] | 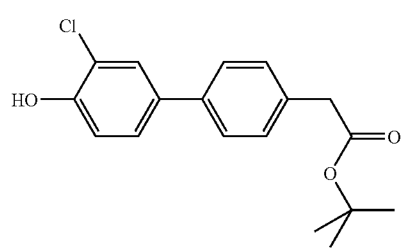 | (CDCl₃) δ 1.45 (9H, s), 3.55 (2H, s), 5.54 (1H, s), 7.07 (1H, d), 7.31-7.33 (2H, m), 7.38-7.41 (1H, m), 7.45-7.47 (2H, m), 7.54 (1H, d). | 317 |

-continued

| Intermediate | Structure | ¹H NMR (400 MHz) | m/z (M − H)⁻ |
|---|---|---|---|
| 56-4[c] | 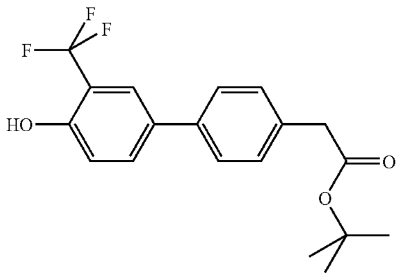 | (CDCl₃) δ 1.45 (9H, s), 3.55 (2H, s), 5.11 (1H, d), 7.04 (1H, t), 7.24-7.27 (1H, m), 7.28-7.33 (3H, m), 7.46 (2H, d) | 351 |
| 57-4[d] | 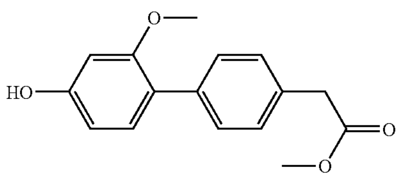 | (CDCl₃) δ 3.65 (2H, s), 3.71 (3H, s), 3.78 (3H, s), 4.88 (1H, s), 6.45-6.47 (1H, m), 6.51 (1H, s), 7.15 (1H, d), 7.29 (2H, d), 7.44 (2H, d) | 271 |
| 58-4[e] | 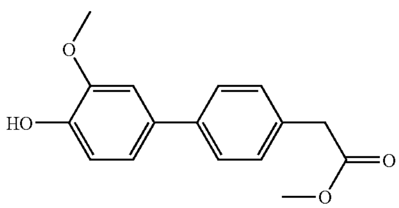 | (DMSO) δ 3.69 (3H, s), 3.75 (2H, s), 3.91 (3H, s), 6.90 (1H, d), 7.11-7.13 (1H, m), 7.23 (1H, d), 7.35 (2H, d), 7.61 (2H, d), 9.10 (1H, s). | mass ion not seen; HPLC tR = 2.20 min. |
| 59-4[f] | 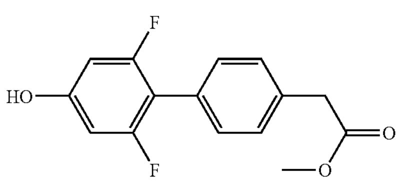 | (DMSO) δ 3.38 (3H, s), 3.47 (2H, s), 6.28-6.34 (2H, m), 7.05-7.10 (4H, m), 10.18 (1H, s). | 277 |
| 60-4[g] | 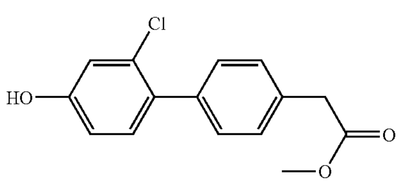 | (DMSO) δ 3.63 (3H, s), 3.71 (2H, s), 6.80-6.83 (1H, m), 6.92 (1H, d), 7.20 (1H, d), 7.28-7.33 (4H, m), 9.93 (1H, s). | 275 |
| 61-4[h] | 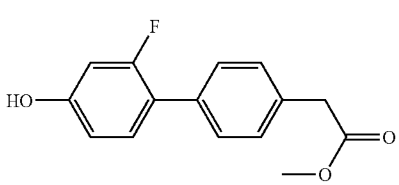 | (DMSO) δ 3.62 (3H, s), 3.70 (2H, s), 6.65 (1H, dd), 6.70 (1H, dd), 7.30 (1H, d), 7.32 (2H, dd), 7.41 (2H, dd), 9.96 (1H, s). | 259 |
| 62-4[i] | 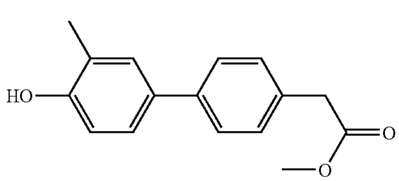 | (DMSO) δ 2.18 (3H, s), 3.62 (3H, s), 3.67 (2H, s), 6.83 (1H, d), 7.27 (3H, d), 7.36 (1H, s), 7.50 (2H, d), 9.35 (1H, s). | no mass ion seen HPLC tR = 2.28 min. |

| Intermediate | Structure | ¹H NMR (400 MHz) | m/z (M − H)⁻ |
|---|---|---|---|
| 63-4ʲ | (structure) | (DMSO) δ 1.87 (6H, s), 3.64 (3H, s), 3.71 (2H, s), 6.50 (2H, s), 7.03 (2H, d), 7.29 (2H, d), 9.12 (1H, s). | no mass ion seen HPLC tR = 2.31 min. |

Notes:
54-4ᵃ 4-Bromo-2-fluorophenol and Intermediate 54-5
55-4ᵇ 4-Bromo-2-chlorophenol and Intermediate 54-5.
56-4ᶜ 4-Bromo-2-(trifluoromethyl)benzenol and Intermediate 54-5.
57-4ᵈ 4-Bromo-3-methoxyphenol and Intermediate 54-5.
58-4ᵉ 4-Bromo-2-methoxyphenol and Intermediate 54-7.
59-4ᶠ 4-Bromo-3,5-Difluorophenol and Intermediate 54-7.
60-4ᵍ 4-Bromo-3-chlorophenol and Intermediate 54-7.
61-4ʰ 4-Bromo-3-fluorophenol and Intermediate 54-7.
62-4ⁱ 4-Bromo-2-methylphenol and Intermediate 54-7.
63-4ʲ 4-Bromo-3,5-dimethylphenol and Intermediate 54-7.

Intermediate 54-5: tert-Butyl 2-(4-(4,4,5,5-tetramethyl-1,3,2-dioxaborolan-2-yl)phenyl)acetate

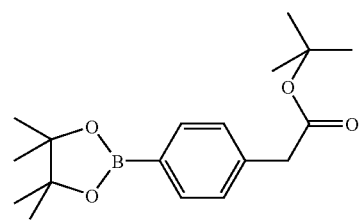

This compound was synthesised from Intermediate 54-6 using similar conditions as described in Intermediate 25-2 to give the title compound (8.37 g, 69.3%) as a pale yellow oil.

¹H NMR (400 MHz, CDCl₃) δ 1.34 (12H, s), 1.42 (9H, s), 3.53 (2H, s), 7.27 (2H, d), 7.75 (2H, d); m/z (EI+) 318 M⁺.

Intermediate 54-6: tert-Butyl 2-(4-bromophenyl)acetate CAS 33155-58-7

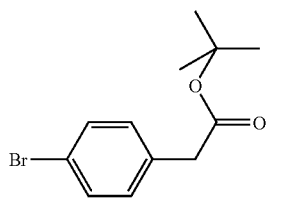

N,N-Dimethylformamide di-tert-butyl acetal (29.8 mL, 124.44 mmol) was added portionwise over 10 minutes to a stirred solution of 4-bromophenylacetic acid (13.38 g, 62.22 mmol) in toluene (400 mL) at 85° C. The resulting solution was stirred at 85° C. for 4 hours and allowed to cool to ambient temperature. The reaction mixture was evaporated afford crude product which was purified by flash silica chromatography, elution gradient 0 to 20% EtOAc in isohexane. Pure fractions were evaporated to dryness to afford the title compound (10.29 g, 61.0%) as a colourless oil.

¹H NMR (400 MHz, CDCl₃) δ 1.43 (9H, s), 3.46 (2H, s), 7.14 (2H, d), 7.44 (2H, d); m/z (EI+) 270 M⁺.

Intermediate 54-7: Methyl 2-(4-(4,4,5,5-tetramethyl-1,3,2-dioxaborolan-2-yl)phenyl)acetate (CAS 454185-98-9)

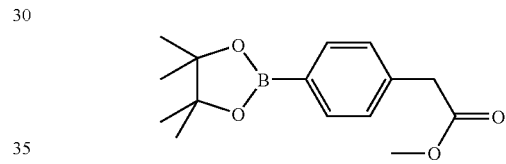

This compound was synthesised from methyl 2-(4-bromophenyl)acetate (CAS 41841-16-1 made according to the procedure described by E. E. Knaus at al, Bioorg. Med. Chem., 2005, 13, 4694-4703) using similar conditions as described in Intermediate 25-2 to afford the title compound (2.140 g, 100%) as a white solid.

¹H NMR (400 MHz, CDCl₃) δ 1.34 (12H, s), 3.64 (2H, s), 3.68 (3H, s), 7.28 (2H, d), 7.77 (2H, d); m/z (EI+) 276 M⁺.

Example 64

2-((1r,4r)-4-(4-(6-Carbamoyl-5-methylpyrazin-2-yl)phenyl)cyclohexyl)acetic acid

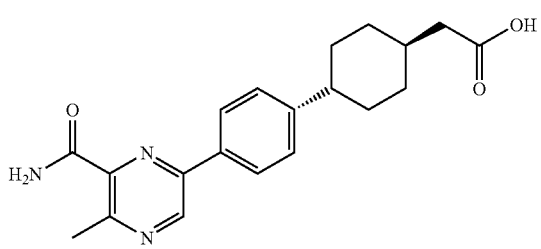

This compound was synthesised from Intermediate 64-1 using similar conditions as described in Example 21 to afford the title compound (120 mg, 64.3%) as a white solid.

¹H NMR (400 MHz, DMSO) δ 1.10-1.18 (2H, m), 1.49-1.53 (2H, m), 1.84 (4H, d), 2.15 (2H, d), 2.31-2.33 (1H, m), 2.65-2.67 (1H, m), 2.75 (3H, s), 7.38 (2H, d), 7.70 (1H, s), 8.14 (2H, d), 8.22 (1H, s), 9.18 (1H, s), 11.97 (1H, s); m/z 395 (M+H)⁺.

Intermediate 64-1: Methyl 2-((1r,4r)-4-(4-(6-Carbamoyl-5-methylpyrazin-2-yl)phenyl)cyclohexyl)acetate

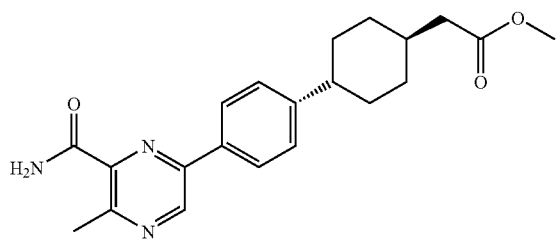

This compound was synthesised from Intermediate 64-2 and methyl 2-((1r,4r)-4-(4-(4,4,5,5-tetramethyl-1,3,2-dioxaborolan-2-yl)phenyl)cyclohexyl)acetate (CAS 701232-69-1: see also Intermediate 64-8) using similar conditions as described in Intermediate 21-1 to afford the title compound (194 mg, 83%) as a white solid.
¹H NMR (400 MHz, CDCl₃) δ 1.15 (3H, m), 1.60 (2H, m) 1.87 (4H, s), 2.20-2.22 (2H, m), 2.40-2.50 (1H, m) 2.94 (3H, s), 3.63 (3H, s), 5.5 (1H, s), 7.29 (2H, d), 7.80 (1H, s), 7.85 (2H, d), 8.95 (1H, s); m/z 368 (M+H)⁺.

Intermediate 64-2: 6-Chloro-3-methylpyrazine-2-carboxamide

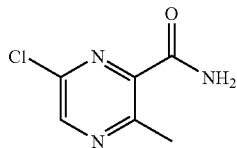

This compound was synthesised from Intermediate 64-3 using similar conditions as described in Intermediate 21-4 to afford the title compound (109 mg, 83%) as a white solid.
¹H NMR (400 MHz, CDCl₃) δ 2.89 (3H, s), 5.45-5.55 (1H, s), 7.45-7.55 (1H, s), 8.56 (1H, s).

Intermediate 64-3: Methyl 6-chloro-3-methylpyrazine-2-carboxylate

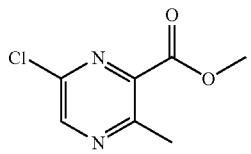

A suspension of Intermediate 64-4 (314 mg, 1.87 mmol) and Phosphorus oxychloride (2.088 mL, 22.40 mmol) stirred at 90° C. for 70 minutes. The reaction mixture was added dropwise to water (20 mL) over 2-3 hours while maintaining the temperature below 40° C. (external cooling required). The mixture was extracted with DCM (5×50 mL), the organic layer was dried over MgSO₄, filtered and evaporated to afford a yellow oil. This was then purified by flash silica chromatography, elution gradient 0 to 20% EtOAc in isohexane. Pure fractions were evaporated to dryness to afford the title compound (142 mg, 40.8%) as a white solid.
¹H NMR (400 MHz, CDCl₃) δ 2.76 (3H, s), 3.94 (3H, s), 8.56 (1H, s); m/z 187 (M+H)⁺.

Intermediate 64-4: Methyl 6-hydroxy-3-methylpyrazine-2-carboxylate

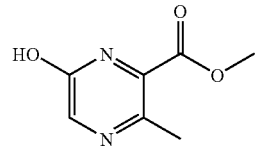

A solution of Intermediate 64-5 (1.3 g, 5.79 mmol) in pyridine (58.5 mL) was stirred at 60° C. for 90 minutes. The reaction mixture was evaporated to afford crude product. The crude product was purified by flash silica chromatography, elution gradient 50 to 80% EtOAc in isohexane. Pure fractions were evaporated to dryness to afford the title compound (0.340 g, 34.9%) as a yellow solid.
¹H NMR (400 MHz, CDCl₃) δ 2.59 (3H, s), 3.94 (3H, s), 8.27 (1H, s); m/z 169 (M+H)⁺.

Intermediate 64-5: (S)-Methyl 2-(2-aminoacetamido)-3-oxobutanoate Hydrochloric Acid salt

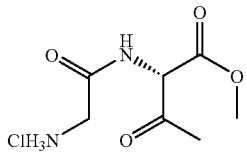

A 4M solution of Hydrogen chloride (7.98 mL, 31.91 mmol) in dioxane was added to Intermediate 64-6 (2.3 g, 7.98 mmol). The resulting solution was stirred at ambient temperature for 4 hours. The reaction mixture was evaporated to afford the title compound (1.790 g, 119%) as a cream solid, which was used without further purification. m/z 189 (M+H)⁺.

Intermediate 64-6: (S)-Methyl 2-(2-(tert-butoxycarbonylamino)acetamido)-3-oxobutanoate

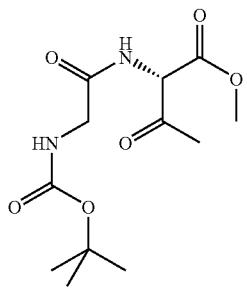

A solution of Intermediate 64-7 (12.9 g, 44.43 mmol) in DCM (72 mL) was added to a stirred suspension of pyridinium chlorochromate (22.99 g, 106.64 mmol) in DCM (43 mL) at 0° C., over a period of 15 minutes under air. The resulting mixture was stirred at ambient temperature for 24 hours. The reaction mixture was evaporated to dryness and ether (400 mL) and water (300 mL) were added. The suspension was filtered through celite and the flask was rinsed with ether (4×300 mL) and water (3×200 mL). The washings were filtered through celite and the organic layers were combined, washed with saturated brine (200 mL), The aqueous phase was re extracted with EtOAc (2×500 mL), the organic layers were combined dried over MgSO$_4$, filtered and evaporated to afford 5.5 g of crude product. The crude product was purified by flash silica chromatography, elution gradient 50 to 80% EtOAc in isohexane. Pure fractions were evaporated to dryness to afford the title compound (18.29%) as a yellow oil.

$^1$H NMR (400 MHz, CDCl$_3$) δ 1.39 (9H, d), 1.97-2.01 (3H, m), 2.31 (2H, s), 3.68 (1H, t), 3.75 (3H, s), 3.76-3.82 (3H, m), 4.05 (2H, q), 5.19 (1H, d).

Intermediate 64-7: Methyl 2-(2-(tert-butoxycarbonylamino)acetamido)-3-hydroxybutanoate

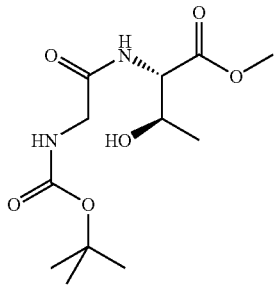

HATU (46.9 g, 123.30 mmol) was added to a stirred solution of 2-(tert-butoxycarbonylamino)acetic acid (18 g, 102.75 mmol) DMA (230 mL) at ambient temperature. After 5 minutes a solution of (2S,3R)-methyl 2-amino-3-hydroxybutanoate hydrochloride (17.43 g, 102.75 mmol) and DIPEA (71.8 mL, 411.00 mmol) in DMA (230 mL) was added and the resulting solution was stirred at ambient temperature for 20 hours, The reaction mixture was diluted with EtOAc (300 mL), and washed with 1N citric acid (300 mL), salt was added to the aqueous layer which was re extracted with EtOAc (4×400 mL). The organic extracts were combined, washed with saturated NaHCO$_3$ (200 mL), dried over MgSO$_4$, filtered and evaporated to afford crude product. The crude product was purified by flash silica chromatography, elution gradient 50 to 100% EtOAc in isohexane. Pure fractions were evaporated to dryness to afford the title compound (12.97 g, 43.5%) as a yellow glass which formed a solid on standing.

$^1$H NMR (400 MHz, CDCl$_3$) δ 1.16 (3H, t), 1.38 (9H, d), 3.70 (3H, s), 3.80-3.81 (2H, m), 4.25-4.28 (1H, m), 4.51-4.54 (1H, m), 5.36 (1H, s), 6.96 (1H, d); m/z 291 (M+H)$^+$.

Intermediate 64-8: Methyl 2-((1r,4r)-4-(4-(4,4,5,5-tetramethyl-1,3,2-dioxaborolan-2-yl)phenyl)cyclohexyl)acetate

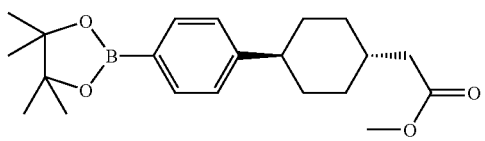

Trimethylphosphonoacetate (1.05X-1.06X) was added dropwise to a suspended solution of t-BuOK (0.70X-0.71X) in 2-MeTHF (10 vol) at 5-10° C. The resulting solution was stirred at 15-20° C. for 3.5-4.0 hours. The reaction mixture was cooled to 5-10° C. and DIPEA (0.81-0.82X) was added to the reaction at 10-15° C. 4-(4-Hydroxyphenyl)cyclohexanone (1.0X) was added in portions to the above reaction mixture at 10-15° C. and the resulting solution was stirred at 15-20° C. for 3-6 hours and then sampled for HPLC analysis. NH4Cl-sol (5.0X-6.0X) was added to the reaction mixture at 0-15° C., and the reaction was quenched. The organic layer was separated and the aqueous layer was extracted with 2-MeTHF (2.5X-3.0X). The two organic extracts were combined and washed with NaHSO$_3$ aq. and then NaCl-solution (2.5X-3.0X) twice. The organic layer was concentrated to 2~3 vol and n-heptane was added to give a suspended solution, and the above mixture was concentrated to below 3% of 2-MeTHF residue to give a suspended solution. The mixture was cooled to 0~5° C., stirred for 1.0-2.0 h, filtered and the cake washed with n-heptane (2 vol X2). Dry in vacuum at below 45° C. to give the desired phenoxyacrylate product.

AcOH (0.05X) and Toluene (20 vol) were added to a pressure reactor, then the above phenoxyacrylate (1.0X) was added to the mixture. The reactor was carefully inertised, then 10% Pd/C (0.15X) was added to the reaction mixture under nitrogen protection. The agitation was slowed down and the nitrogen-atmosphere was exchanged by hydrogen three times, and hydrogenation was performed at 1200 mbar at 25-28° C. The resulting solution was stirred at 25-28° C. for 14-18 h. HPLC showed conversion of >98%. The reaction mixture was filtered, and the cake was washed with EtOH (1.5X×2), then the filtrate was concentrated in vacuo to 2-3 vol, n-heptane (10 vol) was added to precipitate, then concentrated until toluene residue <1.0%, cooled to 0-5° C., filtered, the cake was dried in vacuo to dryness. The crude product was dissolved in EtOH:H$_2$O=2:1 (1.09X of crude product) by heating to reflux and stirred at this temperature for ~5 min, then cooled slowly to 20° C. over 3 h and stirred at 20° C. for 1 h, followed by cooling slowly to 0~5° C. over 90 min and stirred at 0~5° C. for 1 h. After filtering the filter cake was washed with cold EtOH:H$_2$O=2:1 (0.18X×2 of crude product, 0~5° C.). The filter cake was dried in vacuo at 45-50° C. for 24 h to give the pure trans-ester product.

The above trans ester (1.0X) was dissolved in anhydrous CH$_2$Cl$_2$ (12 vol), NMM (0.57X, 1.4 eq) was added dropwise to the mixture under N$_2$. The resulting solution was cooled to −10~0° C. and stirred for 10 min, then Tf$_2$O (1.36X, 1.2 eq) was added dropwise at −10~0° C. (N.B. CF$_3$SO$_2$Cl can be appropriately used in place of triflic anhydride Tf$_2$O). The resulting solution was stirred at −10~0° C. for 30 min, warmed to 0~10° C. and stirred for 30 min. (sampled for HPLC analysis, conversion was >98%). 10% citric acid solution (10.0X) was added dropwise to the mixture. The mixture was stirred for 10 min, the organic layer was separated, washed with 10% citric acid (10.0X) and brine (10.0X), dried with anhydrous MgSO$_4$ (0.5X) for 2 hrs, filtered and concentrated to remove CH$_2$Cl$_2$. Heptane (10X) was added and concentrated to remove the residual CH$_2$Cl$_2$ (expectation <1.0%), then the suspension in heptane was concentrated to 1.5~2.0 vol, the mixture was cooled to 0~5° C. and stirred for 30~60 min at 0~5° C. After filtering the cake was dried under vacuum at 30~40° C. to give the desired triflate as a white solid.

Pinacoldiboron ester (0.8X, 1.2 eq), TBAF (0.13X, 0.2 eq) and KOAc (0.38X, 1.5 eq) were dissolved in CH$_3$CN (5 vol), then PCy$_3$ (1.5% X, 0.02 eq) and PdCl$_2$ (0.47% X, 0.01 eq) were added. The mixture was degassed with nitrogen. A solution of the triflate (1.0X, 1.0 eq) in CH₃CN (7 vol) was added to the mixture at 20-25° C. Then the resulting solution was heated to reflux and stirred for 16 hrs (overnight-sampled for HPLC analysis, conversion was >98%). The mixture was filtered via a pad of 20 um cellulose, activated carbon (0.2X) was added to the filtrate and the resulting solution was heated to reflux for 2~3 hrs. The mixture was cooled to 40~50° C. and then filtered and the filtrate was concentrated to dryness. The residue solid was dissolved in EtOAc, and the EtOAc solution was washed with water (10 vol), 1N HCl (10 vol) and brine (10 vol). The organic layer was separated and concentrated to 1~2 vol, then heptane (5~6 vol) was added to the solution and concentrated until EtOAc was removed (EtOAc/Heptane=0-1%), heptane (5~6 vol) was added to the resulting solution and heated to 50~60° C. for 30 min. There were two layers (a clear upper heptane layer and a yellowish bottom layer). The heptane layer was separated, heptane (5~6 vol) was added to the yellowish bottom layer and heated to 50~60° C. for 30 min, and the heptane layer was separated again. The heptane layers were combined and filtered via silica gel. The filtrate was concentrated to 1~1.5 vol and the precipitate was filtered and dried in vacuo to give the desired boronate ester as a white solid.

Example 65

Methyl trans-4-{4-[6-(aminocarbonyl)-3-methylpyrazin-2-yl]phenyl}-cyclohexanecarboxylate

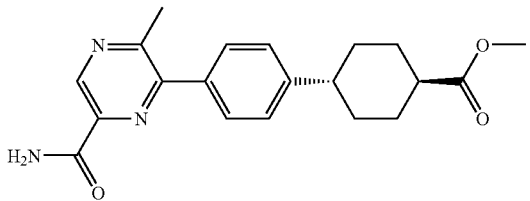

Ethyl chloroformate (245 μl, 2.54 mmol) was added dropwise to a stirred solution of 6-{4-[trans-4-(methoxycarbonyl) cyclohexyl]phenyl}-5-methylpyrazine-2-carboxylic acid (Intermediate 65-1, 751 mg, 2.12 mmol) and N-methylmorpholine (350 μl, 3.18 mmol) in DCM (20 mL) at 0° C. Ammonia (5 mL of a 7M solution in MeOH) was added. The reaction mixture was allowed to warm up over 1 h then was concentrated and the residue was purified by chromatography eluting with 0-10% MeOH/DCM to give the title compound (226 mg, 30%) as a solid; ¹H NMR δ 9.00 (1H, s), 8.08 (1H, s), 7.74 (1H, s), 7.70 (2H, d), 7.40 (2H, d), 3.63 (3H, s), 2.70-2.55 (1H, m), 2.67 (3H, s), 2.50-2.35 (1H, m), 2.10-1.98 (2H, m), 1.96-1.83 (2H, m), 1.65-1.43 (4H, m); MS 354.

Intermediate 65-1: 6-{4-[trans-4-(Methoxycarbonyl) cyclohexyl]phenyl}-5-methylpyrazine-2-carboxylic acid

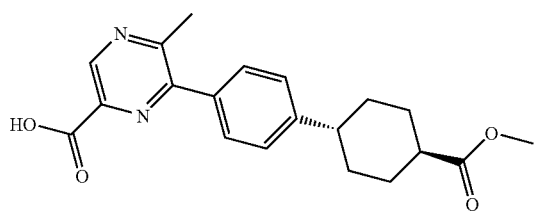

Diaminopropionic acid hydrochloride (496 mg, 3.52 mmol) was added to a stirred solution of methyl trans-4-(4-pyruvoylphenyl)cyclohexanecarboxylate (Intermediate 65-2, 844 mg, 2.93 mmol) and triethylamine (1.6 mL, 11.72 mmol) in MeOH (6 mL). After 48 h the reaction mixture was concentrated and the residue was triturated with ether to give the title compound (751 mg, 72%) as a solid that was used without further purification; ¹H NMR δ 9.04 (1H, s), 7.62 (2H, d), 7.40 (2H, d), 3.64 (3H, obs. s), 2.70-2.55 (1H, m), 2.66 (3H, s), 2.50-2.36 (1H, m), 2.08-1.96 (2H, m), 1.95-1.85 (2H, m), 1.65-1.45 (4H, m); MS 355.

Intermediate 65-2: Methyl trans-4-(4-pyruvoylphenyl)cyclohexanecarboxylate

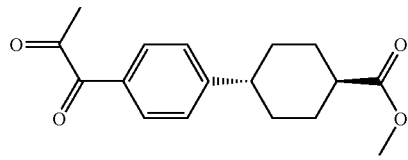

1,1,1-tris(Acetoxy)-1,1-dihydro-1,2-benziodoxol-3-(1H)-one (5.14 g, 12.12 mmol) was added to a stirred solution of methyl trans-4-(4-lactoylphenyl)cyclohexanecarboxylate (Intermediate 65-3, 1.758 g, 6.06 mmol) in DCM (25 mL). The mixture was stirred for 1 h, hexanes (50 mL) was added and the mixture was filtered through a pad of diatomaceous earth. Volatile material was removed by evaporation to give the title compound (1.55 g, 88%) as a solid that was used without further purification; ¹H NMR δ 7.88 (2H, d), 7.45 (2H, d), 3.63 (3H, s), 2.70-2.57 (1H, m), 2.50 (3H, s), 2.48-2.36 (1H, m), 2.08-1.94 (2H, m), 1.90-1.80 (2H, m), 1.60-1.40 (4H, m); MS 311 (M+Na)⁺.

Intermediate 65-3: Methyl trans-4-(4-lactoylphenyl)cyclohexanecarboxylate

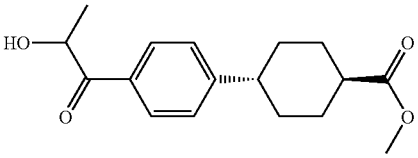

Sodium hydroxide (370 mg, 9.25 mmol) in water (2 mL) was added to a stirred solution of methyl trans-4-[4-(2-bromopropanoyl)phenyl]cyclohexanecarboxylate (prepared as described in Patent Application WO2004/047755) (3.264 g, 9.25 mmol) in DMF (10 mL). The mixture was stirred for 40 minutes then extracted with ether (5×20 mL). The extracts were combined, dried and concentrated. The crude product was purified by flash column chromatography eluting with 20-40% EtOAc/hexanes to give the title compound (1.76 g, 66%) as a solid; ¹H NMR δ 7.94 (2H, d), 7.39 (2H, d), 5.29 (1H, d), 5.08-4.98 (1H, m), 3.62 (3H, s), 2.68-2.54 (1H, m), 2.48-2.35 (1H, m), 2.08-1.94 (2H, m), 1.90-1.79 (2H, m), 1.60-1.40 (4H, m), 1.28 (3H, s); MS 313 (M+Na)⁺.

Example 66 trans-4-{4-[6-(Aminocarbonyl)-3-methylpyrazin-2-yl]phenyl}cyclo-hexanecarboxylic acid

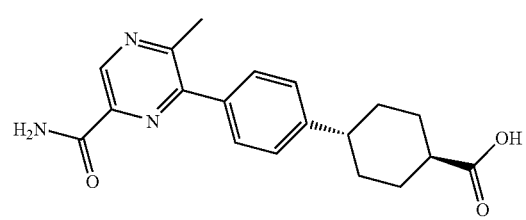

Lithium hydroxide monohydrate (42 mg, 1.00 mmol) was added to a stirred solution of methyl trans-4-{4-[6-(aminocarbonyl)-3-methylpyrazin-2-yl]phenyl}-cyclohexanecarboxylate (Example 65, 71 mg, 0.20 mmol) in MeOH (2 mL), THF (1 mL) and water (0.5 mL). After 16 h the reaction mixture was concentrated in vacuo and purified by reverse phase HPLC (150 mm×21 mm Phenomenex Column packed with Luna 10u C18 silica, eluting with 5-95% acetonitrile/water) to give the title compound as a yellow solid (6 mg, 9%); $^1$H NMR δ 9.01 (1H, s), 8.08 (1H, s), 7.73 (1H, s), 7.70 (2H, d), 7.40 (2H, d), 2.70-2.50 (1H, m), 2.65 (3H, s), 2.37-2.25 (1H, m), 2.10-2.00 (2H, m), 1.95-1.85 (2H, m), 1.65-1.40 (4H, m); MS 340.

Examples 67 to 70

Other compounds which have been made by processes analogous to those described herein are 2-(4'-(6-carbamoyl-3,5-dimethylpyrazin-2-yl)-2'-methylbiphenyl-4-yl)acetic acid; 2-(4-(4-(6-carbamoyl-3,5-dimethylpyrazin-2-yl)naphthalen-1-yl)phenyl)acetic acid; 2-(4'-(6-carbamoyl-3,5-dimethylpyrazin-2-yl)-2'-cyanobiphenyl-4-yl)acetic acid and 2-(4'-(6-carbamoyl-3,5-dimethylpyrazin-2-yl)-3',5'-difluorobiphenyl-4-yl)acetic acid.

Alternative Preparations

Intermediate 1-4: Ethyl 6-chloro-3,5-dimethylpyrazine-2-carboxylate

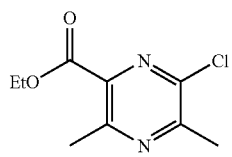

A suspension of Intermediate 1-5 (268 g, 1365.93 mmol) in phosphorus oxychloride (1273 mL, 13659.31 mmol) was heated at 90° C. under nitrogen for 1 hour then cooled to ambient temperature. The reaction was cautiously added to water (6 L) with vigorous stirring keeping the temperature between 17° C. and 20° C. The mixture was then extracted with DCM (5×2.5 L), washed with water, saturated brine and dried over MgSO$_4$ and evaporated to afford crude product. The crude product was purified by flash silica chromatography, elution gradient 0 to 25% EtOAc in isohexane. Pure fractions were evaporated to dryness to afford the title compound (227 g, 77%) as a yellow oil which solidified on standing.

$^1$H NMR (400 MHz, CDCl$_3$) δ 1.43 (3H, t), 2.68 (3H, s), 2.77 (3H, s), 4.46 (2H, q); m/z 215 (M+H)$^+$.

Intermediate 1-5: Ethyl 6-hydroxy-3,5-dimethylpyrazine-2-carboxylate

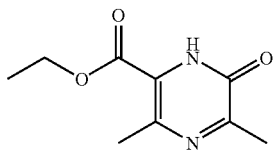

A solution of 2M Hydrochloric acid in 1,4-dioxane (1177 mL, 4709.97 mmol) was added to Intermediate 1-6 (745 g, 2354.99 mmol) and stirred at room temperature for 15 minutes then warmed to 40° C. for a further 40 minutes. Pyridine (6500 mL) was then slowly added and then the reaction was heated to 80° C. for 2 hours in the presence of air. The reaction was then allowed to cool to ambient temperature and evaporated to dryness to afford a viscous oil. This was suspended in DCM (2.5 L) and washed water (1.5 L). The DCM was then dried over MgSO$_4$, filtered and concentrated to afford an orange semi-solid, which was triturated with 1:1 EtOAc/iso-hexane (250 mL) to afford ethyl 6-hydroxy-3,5-dimethyl-1,4-dihydropyrazine-2-carboxylate (127 g, 27.1%) as a cream solid. The mother liquors were then purified by flash silica chromatography (gradient from 20% ethyl acetate/iso-hexane to 80% ethyl acetate/iso-hexane). Fractions containing the desired product were concentrated and the residue was triturated with a small volume of 1:1 EtOAc/iso-hexane to afford the title compound (9.00 g, 1.948%). Manganese dioxide (150 g) was added to a suspension of ethyl 6-hydroxy-3,5-dimethyl-4,5-dihydropyrazine-2-carboxylate (121 g, 610.44 mmol) in DCM (1.8 L) at ambient temperature giving rise to a 2° C. exotherm. The reaction was stirred for 10 minutes then warmed to 35° C. for 1 hour. The reaction was incomplete so an additional 115 g of Manganese dioxide was added and the reaction stirred for 1 hour at 35° C. then stirred to cool to ambient temperature. The reaction was filtered through a short bed of silica and washed through with 2 L of 1:1 EtOAc/iso-hexane and finally 2×2 L EtOAc. The fractions were then combined and reduce in-vacuo to give an orange solid, which was slurried in 300 mL of 1:1 EtOAc/iso-hexane, filtered and washed with iso-hexane to afford the title compound (87 g, 72.6%) as an orange solid.

$^1$H NMR (400 MHz, DMSO) δ 1.31 (3H, t), 2.35 (3H, s), 2.50 (3H, s), 4.31 (2H, q), 11.93 (1H, s); m/z 197 (M+H)$^+$.

Intermediate 1-6 can also be prepared by the following procedure:

Intermediate 1-6: Ethyl 2-(2-(tert-butoxycarbonylamino)propanamido)-3-oxobutanoate

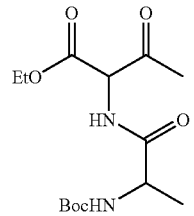

A solution of 4-methylmorpholine (900 g) in THF (15 L) was added to 2-(tert-butoxycarbonylamino)propanoic acid (1690 g, 8933.17 mmol). The mixture was cooled to −25° C. and isobutyl chloroformate (1.164 L, 8933.17 mmol) was added. After 20 minutes the second equivalent of 4-methylmorpholine (900 g) was added followed by ethyl 2-amino-3-oxobutanoate Tosylate salt (see J-P. Genet et al, *Eur. J. Org. Chem.*, 2004, 3017-3026) (2700 g, 8507.78 mmol) suspended in THF (2.5 L). The mixture was stirred at −25° C. for 30 minutes and then left to warm to ambient temperature overnight. The reaction was quenched with water (15 L), extracted with EtOAc (3×5 L) and the combined extracts washed with 50% saturated brine (5 L). The organic layer was dried over MgSO$_4$, filtered and evaporated to afford crude product. The crude product was purified by flash silica chromatography, elution gradient 50 to 80% EtOAc in isohexane. Pure fractions were evaporated to dryness to afford ethyl 2-(2-(tert-butoxycarbonylamino)propanamido)-3-oxobutanoate (1850 g, 68.7%).

Example 1

2-((1r,4r)-4-(4-(6-carbamoyl-3,5-dimethylpyrazin-2-yl)phenyl)cyclohexyl)acetic acid

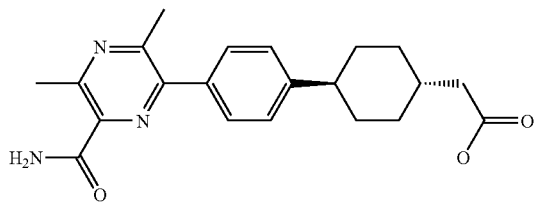

Powdered potassium hydroxide (2.81 g, 50.10 mmol) was added in one portion to Intermediate 1-8 (6.37 g, 16.70 mmol) in tert-butanol (150 mL) at 40° C. under nitrogen. The resulting suspension was stirred at 40° C. for 20 minutes. A thick precipitate formed so the reaction was quenched with acetic acid (4.78 mL, 83.49 mmol) in ethanol (100.0 mL) and the resulting solution stirred for a further 20 minutes before being evaporated to dryness. The resulting solid was partitioned between water (500 mL) and EtOAc (500 mL). The aqueous layer showed a pH=4~5. The organic layer was separated and the aqueous re-extracted with EtOAc (2×250 mL). The combined organics were washed with brine (100 mL), dried over MgSO$_4$ and evaporated in vacuo to give crude product. This was recrystallised from hot ethanol (250 mL) to give a yellow solid which was washed with ether (100 mL) and dried under vacuum at room temperature to give the title compound (4.82 g, 79%).

[$^1$H NMR (400.132 MHz, DMSO) δ 1.09-1.19 (2H, m), 1.46-1.57 (2H, m), 1.70-1.78 (1H, m), 1.81-1.87 (4H, m), 2.15 (2H, d), 2.58 (3H, s), 2.73 (3H, s), 3.29 (1H, s), 7.36 (2H, d), 7.57 (1H, s), 7.64 (2H, d), 7.98 (1H, s), 11.98 (1H, s)].

A melting point with an onset value of approximately 225° C. has been determined for {trans-4-[4-(6-Carbamoyl-3,5-dimethylpyrazin-2-yl)phenyl]cyclohexyl}acetic acid.

Intermediate 1-8: methyl 2-((1s,4s)-4-(4-(6-carbamoyl-3,5-dimethylpyrazin-2-yl)phenyl)cyclohexyl) acetate

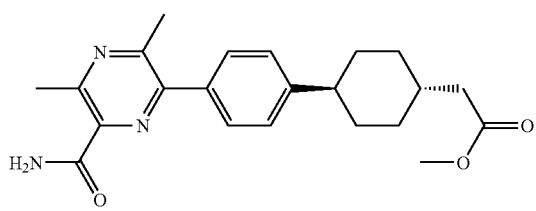

A solution of 6-chloro-3,5-dimethylpyrazine-2-carboxamide (see Intermediate 21-4) (3.15 g, 16.97 mmol), methyl 2-((1s,4s)-4-(4-(4,4,5,5-tetramethyl-1,3,2-dioxaborolan-2-yl)phenyl)cyclohexyl)acetate (see Intermediate 64-8) (6.08 g, 16.97 mmol) and tripotassium phosphate (4.32 g, 20.37 mmol) in DME (120 mL), ethanol (75 mL) and water (30.0 mL) were degassed before addition of (1,1'-bis(diphenylphosphino)ferrocene)-dichloropalladium(II) (0.698 g, 0.85 mmol). The reaction mixture was heated to 80° C., under nitrogen, and left to stir overnight for 16 hrs. The reaction mixture was allowed to cool to room temperature and then evaporated. The crude product was partitioned between water (250 mL) and EtOAc (250 mL). The catalyst was filtered off from the biphasic mixture. The organic phase was separated and washed with brine (100 mL), dried (Na$_2$SO$_4$) and evaporated. The crude product was purified by flash silica chromatography, elution gradient 5 to 90% EtOAc in isohexane on 330 g silicyle column. Pure fractions were evaporated to dryness to afford the title compound (6.47 g, 100%) as a yellow solid.

[$^1$H NMR (400.132 MHz, DMSO) δ 1.10-1.21 (2H, m), 1.46-1.56 (2H, m), 1.73-1.86 (5H, m), 2.25 (2H, d), 2.58 (3H, s), 2.73 (3H, s), 3.28 (1H, s), 3.60 (3H, s), 7.35 (2H, d), 7.58 (1H, s), 7.64 (2H, d), 7.97 (1H, s); HPLC tR=2.53 min.]

The invention claimed is:

1. A compound of formula (I)

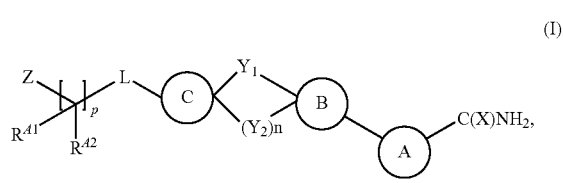

wherein
X is O;
Ring A is 2,6-pyrazinediyl substituted by two methyl groups;
Ring B is 1,4-phenylene;
Y$_1$ is a direct bond;
n is 0;
Ring C is 1,4-cyclohexanediyl;
L is a direct bond;
p is 1;
R$^{A1}$ and R$^{A2}$ are each hydrogen; and
Z is carboxy,
or a pharmaceutically-acceptable salt thereof.

2. The compound {trans-4[4-(6-carbamoyl-3,5-dimethylpyrazin-2-yl)phenyl]cyclohexyl}acetic acid as claimed in claim 1, of formula

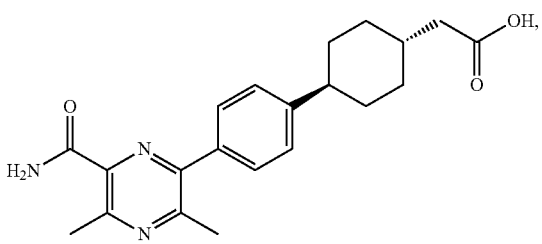

or a pharmaceutically-acceptable salt thereof.

3. The compound {trans-4-[4-(6-carbamoyl-3,5-dimethylpyrazin-2-yl)phenyl]cyclohexyl}acetic acid as claimed in claim 1, of formula

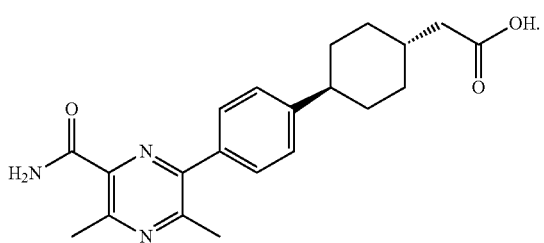

4. The compound {cis-4-[4-(6-carbamoyl-3,5-dimethylpyrazin-2-yl)phenyl]cyclohexyl}acetic acid of formula (I) as claimed in claim 1, or a pharmaceutically-acceptable salt thereof.

5. The compound {cis-4-[4-(6-carbamoyl-3,5-dimethylpyrazin-2-yl)phenyl]cyclohexyl}acetic acid of formula (I) as claimed in claim 1.

6. A pharmaceutical formulation comprising a compound as claimed in claim 1, or a pharmaceutically-acceptable salt thereof, in admixture with a pharmaceutically-acceptable excipient or carrier.

7. A pharmaceutical formulation comprising a compound as claimed in claim 2, or a pharmaceutically-acceptable salt thereof, in admixture with a pharmaceutically-acceptable excipient or carrier.

8. A pharmaceutical formulation comprising a compound as claimed in claim 3, in admixture with a pharmaceutically-acceptable excipient or carrier.

9. A pharmaceutical formulation comprising a compound as claimed in claim 4, or a pharmaceutically-acceptable salt thereof, in admixture with a pharmaceutically-acceptable excipient or carrier.

10. A pharmaceutical formulation comprising a compound as claimed in claim 5, in admixture with a pharmaceutically-acceptable excipient or carrier.

* * * * *